United States Patent
Valamehr et al.

(10) Patent No.: US 11,072,781 B2
(45) Date of Patent: Jul. 27, 2021

(54) GENOMIC ENGINEERING OF PLURIPOTENT CELLS

(71) Applicant: Fate Therapeutics, Inc., San Diego, CA (US)

(72) Inventors: Bahram Valamehr, San Diego, CA (US); Ramzey Abujarour, San Diego, CA (US); Tom Tong Lee, San Diego, CA (US); Weijie Lan, San Diego, CA (US); Raedun Clarke, San Diego, CA (US); Ryan Bjordahl, San Diego, CA (US)

(73) Assignee: FATE THERAPEUTICS, INC., San Diego, CA (US)

(*) Notice: Subject to any disclaimer, the term of this patent is extended or adjusted under 35 U.S.C. 154(b) by 0 days.

(21) Appl. No.: 16/379,668

(22) Filed: Apr. 9, 2019

(65) Prior Publication Data

US 2019/0271005 A1 Sep. 5, 2019

Related U.S. Application Data

(60) Division of application No. 15/818,649, filed on Nov. 20, 2017, now Pat. No. 10,287,606, which is a continuation of application No. PCT/US2016/060699, filed on Nov. 4, 2016.

(60) Provisional application No. 62/366,503, filed on Jul. 25, 2016, provisional application No. 62/337,258, filed on May 16, 2016, provisional application No. 62/251,032, filed on Nov. 4, 2015.

(51) Int. Cl.

| | |
|---|---|
| *C12N 5/00* | (2006.01) |
| *C12N 5/074* | (2010.01) |
| *C12N 15/90* | (2006.01) |
| *C12N 5/0783* | (2010.01) |
| *A61P 35/02* | (2006.01) |
| *C07K 16/28* | (2006.01) |
| *A61P 35/00* | (2006.01) |
| *C12N 5/078* | (2010.01) |
| *C12N 15/85* | (2006.01) |
| *A61K 35/17* | (2015.01) |
| *C07K 14/705* | (2006.01) |
| *C07K 14/725* | (2006.01) |
| *C12N 9/22* | (2006.01) |
| *C12N 15/11* | (2006.01) |
| *C12N 15/113* | (2010.01) |
| *A61K 35/12* | (2015.01) |

(52) U.S. Cl.
CPC ............ *C12N 5/0696* (2013.01); *A61K 35/17* (2013.01); *A61P 35/00* (2018.01); *A61P 35/02* (2018.01); *C07K 14/7051* (2013.01); *C07K 14/70503* (2013.01); *C07K 16/2803* (2013.01); *C12N 5/0634* (2013.01); *C12N 5/0636* (2013.01); *C12N 9/22* (2013.01); *C12N 15/11* (2013.01); *C12N 15/85* (2013.01); *C12N 15/907* (2013.01); *A61K 2035/124* (2013.01); *C07K 2319/33* (2013.01); *C12N 15/1138* (2013.01); *C12N 15/90* (2013.01); *C12N 2310/20* (2017.05); *C12N 2501/25* (2013.01); *C12N 2501/505* (2013.01); *C12N 2501/51* (2013.01); *C12N 2501/515* (2013.01); *C12N 2501/599* (2013.01); *C12N 2501/998* (2013.01); *C12N 2506/03* (2013.01); *C12N 2506/11* (2013.01); *C12N 2510/00* (2013.01); *C12N 2800/107* (2013.01); *C12N 2800/80* (2013.01); *C12N 2830/00* (2013.01)

(58) Field of Classification Search
CPC .... C12N 15/85; C12N 15/90; C12N 2510/00; C12N 2506/03; C12N 5/0696
See application file for complete search history.

(56) References Cited

U.S. PATENT DOCUMENTS

| | | |
|---|---|---|
| 5,780,300 A | 7/1998 | Artavanis-Tsakonas et al. |
| 5,858,358 A | 1/1999 | June et al. |
| 5,883,223 A | 3/1999 | Gray |
| 5,942,435 A | 8/1999 | Wheeler |
| 6,140,081 A | 10/2000 | Barbas |
| 6,352,694 B1 | 3/2002 | June et al. |
| 6,453,242 B1 | 9/2002 | Eisenberg et al. |
| 6,534,055 B1 | 3/2003 | June et al. |
| 6,534,261 B1 | 3/2003 | Cox et al. |
| 6,534,476 B2 | 3/2003 | Miyazono et al. |
| 6,689,744 B2 | 2/2004 | Gao et al. |
| 6,692,964 B1 | 2/2004 | June et al. |

(Continued)

FOREIGN PATENT DOCUMENTS

| | | |
|---|---|---|
| EP | 1 992 360 A1 | 11/2008 |
| EP | 2 606 884 A1 | 6/2013 |

(Continued)

OTHER PUBLICATIONS

Birch et al., "Suspension culture of mammalian cells," Bioprocess Technol., 10:251-270 (1990).
Brentjens et al., "Genetically targeted T cells eradicate systemic acute lymphoblastic leukemia xenografts," Clin. Cancer Res., 13(18Pt 1):5426-5435 (2007).
Brentjens et al., "Treatment of chronic lymphocytic leukemia with genetically targeted autologous T cells: case report of an unforeseen adverse event in a phase I clinical trial," Mol. Ther., 18(4):666-668 (2010).

(Continued)

*Primary Examiner* — Marcia S Noble
(74) *Attorney, Agent, or Firm* — Mintz, Levin, Cohn, Ferris, Glovsky and Popeo, P.C.

(57) ABSTRACT

Provided are methods and compositions for obtaining genome-engineered iPSCs, and derivative cells with stable and functional genome editing at selected sites. Also provided are cell populations or clonal cell lines derived from genome-engineered iPSCs, which comprise targeted integration of one or more exogenous polynucleotides, and/or in/dels in one or more selected endogenous genes.

18 Claims, 67 Drawing Sheets

Specification includes a Sequence Listing.

(56) References Cited

U.S. PATENT DOCUMENTS

| | | | |
|---|---|---|---|
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,888,121 B2 | 2/2011 | Urnov et al. | |
| 7,972,854 B2 | 7/2011 | Miller et al. | |
| 8,044,201 B2 | 10/2011 | Xu et al. | |
| 8,168,428 B2 | 5/2012 | Zon et al. | |
| 8,389,282 B2 | 3/2013 | Sadelain et al. | |
| 8,652,845 B2 | 2/2014 | Niwa et al. | |
| 9,220,728 B2 | 12/2015 | Sadelain et al. | |
| 9,382,531 B2 | 7/2016 | Slukvin et al. | |
| 9,452,186 B2 | 9/2016 | Shoemaker et al. | |
| 9,889,160 B2 | 2/2018 | Jantz et al. | |
| 10,287,606 B2 | 5/2019 | Valamehr et al. | |
| 10,464,989 B2* | 11/2019 | Walcheck | A61K 38/1774 |
| 10,626,372 B1 | 4/2020 | Valamehr et al. | |
| 10,858,628 B2 | 12/2020 | Valamehr et al. | |
| 2004/0067583 A1 | 4/2004 | Bernstein et al. | |
| 2004/0101519 A1 | 5/2004 | June et al. | |
| 2005/0119203 A1 | 6/2005 | Steinbrecher et al. | |
| 2006/0034810 A1 | 2/2006 | Riley et al. | |
| 2006/0121005 A1 | 6/2006 | Berenson et al. | |
| 2011/0027235 A1 | 2/2011 | Gregory et al. | |
| 2011/0027886 A1 | 2/2011 | Han et al. | |
| 2011/0145940 A1 | 6/2011 | Voytas et al. | |
| 2012/0009676 A1 | 1/2012 | Mack | |
| 2012/0039911 A1 | 2/2012 | Park et al. | |
| 2012/0129211 A1 | 5/2012 | Kaltman et al. | |
| 2012/0202291 A1 | 8/2012 | Chen et al. | |
| 2012/0264218 A1 | 10/2012 | Lin et al. | |
| 2013/0071414 A1 | 3/2013 | Dotti et al. | |
| 2013/0078226 A1 | 3/2013 | Nakauchi et al. | |
| 2013/0280222 A1 | 10/2013 | Kay et al. | |
| 2014/0155468 A1 | 6/2014 | Gregory et al. | |
| 2014/0171148 A1 | 6/2014 | Hilbrink et al. | |
| 2014/0273211 A1 | 9/2014 | Slukvin | |
| 2014/0349402 A1 | 11/2014 | Cooper et al. | |
| 2014/0369973 A1 | 12/2014 | Bernstein et al. | |
| 2015/0140665 A1 | 5/2015 | Calos et al. | |
| 2015/0174169 A1 | 6/2015 | Genovese et al. | |
| 2015/0342993 A1 | 12/2015 | Kloss et al. | |
| 2015/0376296 A1 | 12/2015 | Fedorov et al. | |
| 2016/0009813 A1 | 1/2016 | Themeli et al. | |
| 2017/0020922 A1 | 1/2017 | Wagner et al. | |
| 2017/0073643 A1 | 3/2017 | Valamehr et al. | |
| 2018/0008640 A1 | 1/2018 | Feng et al. | |
| 2018/0072992 A1 | 3/2018 | Valamehr et al. | |
| 2018/0112180 A1 | 4/2018 | Robbins et al. | |
| 2018/0155717 A1 | 6/2018 | Valamehr et al. | |
| 2018/0320137 A1 | 11/2018 | Valamehr et al. | |
| 2019/0071636 A1 | 3/2019 | Eto et al. | |
| 2019/0119638 A1* | 4/2019 | Sadelain | C12N 15/86 |
| 2020/0095604 A1 | 3/2020 | Valamehr et al. | |
| 2020/0248142 A1 | 8/2020 | Valamehr et al. | |

FOREIGN PATENT DOCUMENTS

| | | |
|---|---|---|
| EP | 2853590 A1 | 4/2015 |
| EP | 2853590 B1 | 4/2015 |
| WO | WO 1998/53058 A1 | 11/1998 |
| WO | WO 1998/53059 A1 | 11/1998 |
| WO | WO 1998/53060 A1 | 11/1998 |
| WO | WO 1999/001426 A1 | 1/1999 |
| WO | WO 2002/006213 A2 | 1/2002 |
| WO | WO 2002/016536 A1 | 2/2002 |
| WO | WO 2003/016496 A2 | 2/2003 |
| WO | WO 2003/077914 A1 | 9/2003 |
| WO | WO 2005/051301 A2 | 6/2005 |
| WO | WO 2005/117994 A2 | 12/2005 |
| WO | WO 2007/044084 A2 | 4/2007 |
| WO | WO 2008/006583 A1 | 1/2008 |
| WO | WO 2008/094597 A2 | 8/2008 |
| WO | WO 2009/091826 A2 | 7/2009 |
| WO | WO 2009/091826 A3 | 7/2009 |
| WO | WO 2009/091826 A9 | 7/2009 |
| WO | WO 2009/097140 A1 | 8/2009 |
| WO | WO-2010/096746 A1 | 8/2010 |
| WO | WO-2010/099539 A1 | 9/2010 |
| WO | WO-2011/096482 A1 | 8/2011 |
| WO | WO 2011/115308 A1 | 9/2011 |
| WO | WO 2011/159726 A2 | 12/2011 |
| WO | WO 2012/012667 A2 | 1/2012 |
| WO | WO 2012/021845 A2 | 2/2012 |
| WO | WO 2012/087965 A2 | 6/2012 |
| WO | WO-2013/009825 A1 | 1/2013 |
| WO | WO-2013/074916 A1 | 5/2013 |
| WO | WO 2013/075222 A1 | 5/2013 |
| WO | WO 2013/086029 A1 | 6/2013 |
| WO | WO-2013/126794 A1 | 8/2013 |
| WO | WO 2013/158292 A1 | 10/2013 |
| WO | WO 2013/163171 A1 | 10/2013 |
| WO | WO-2013/176197 A1 | 11/2013 |
| WO | WO 2013/176916 A1 | 11/2013 |
| WO | WO 2014/011540 A1 | 1/2014 |
| WO | WO 2014/062138 A1 | 4/2014 |
| WO | WO 2014/152603 A1 | 9/2014 |
| WO | WO 2014/165131 A1 | 10/2014 |
| WO | WO-2014/165825 A2 | 10/2014 |
| WO | WO-2014/165825 A3 | 10/2014 |
| WO | WO 2016/123100 A1 | 8/2016 |
| WO | WO 2016/123117 A1 | 8/2016 |
| WO | WO 2017/078807 A1 | 5/2017 |
| WO | WO 2017/079673 A1 | 5/2017 |
| WO | WO 2017/180989 A2 | 10/2017 |

OTHER PUBLICATIONS

Brown et al., "Derivation of induced pluripotent stem cells from human peripheral blood T lymphocytes," PLoSOne, 5(6):e11373 (2010).

Chang et al., "Transforming growth factor-beta signaling in breast cancer", Frontiers in Bioscience, 12: 4393-4401 (2007).

Choi et al., "Identification of the hemogenic endothelial progenitor and its direct precursor in human pluripotent stem cell differentiation cultures," Cell Rep., 2(3):553-567 (2012).

Cui et al., "Selective inhibition of TGF-β responsive genes by Smad-interacting peptide aptamers from FoxH1, Lef1 and CBP", Oncogene, 24: 3864-3874 (2005).

Dacosta et al., "SB-505124 is a selective inhibitor of transforming growth factor-beta type I receptors ALK4, ALK5, and ALK7," Mol. Pharmacol., 65(3):744-752 (2004).

De Gouville and Huet, "Inhibition of ALK5 as a new approach to treat liver fibrotic diseases", Drug News Perspective, 19(2): 85-90 (2006).

Figueiredo et al., "Class-, gene-, and group-specific HLA silencing by lentiviral shRNA delivery," J. Mol. Med., 84(5):425-437 (2006).

French et al., "Human induced pluripotent stem cell-derived B lymphocytes express sIgM and can be generated via a hemogenic endothelium intermediate," Stem Cells and Development, 24(9):1082-1095 (2015).

Gellibert et al., "Discovery of 4-{4- [3 -(Pyridin-2-yl)-1H-pyrazol-4-yl]pyridin-2-yl}-N-(tetrahydro-2H-pyran-4-yl)benzamide (GW788388): A Potent, Selective, and Orally Active Transforming Growth Factor-β Type I Receptor Inhibitor", Journal Medicinal Chemistry, 49(7): 2210-2221 (2006).

Gong et al., "Cancer patient T cells genetically targeted to prostate-specific membrane antigen specifically lyse prostate cancer cells and release cytokines in response to prostate-specific membrane antigen," Neoplasia, 1(2):123-127 (1999).

Hu et al., "Large-scale mammalian cell culture," Curr. Opin. Biotechnol., 8(2):148-153 (1997).

(56) References Cited

OTHER PUBLICATIONS

Huang et al., "Pivotal role for glycogen synthase kinase-3 in hematopoietic stem cell homeostasis in mice," J. Clin. Invest., 119(12):3519-3529 (2009).
Inman et al., "SB-431542 is a potent and specific inhibitor of transforming growth factor-β Superfamily Type I Activin Receptor-Like Kinase (ALK) Receptors ALK4, ALK5, and ALK7", Molecular Pharmacology, 62(1): 65-74 (2002).
Kaminska, et al., "TGF beta signalling and its role in tumour pathogenesis", Acta Biochimica Polonica, 52(2): 329-337 (2005).
Kennedy et al., "T lymphocyte potential marks the emergence of definitive hematopoietic progenitors in human pluripotent stem cell differentiation cultures," Cell Rep., 2(6):1722-1735 (2012).
Kim, et al., "Pharmacokinetics and tissue distribution of 3-((5-(6-methylpyridin-2-yl)-4-(quinoxalin-6-yl)-1H-imidazol-2-yl)methyl)benzamide; a novel ALK5 inhibitor and a potential anti-fibrosis drug", Xenobiotica, 38(3): 325-339 (2008).
Kitano, "Serum-free media," in Animal Cell Bioreactors, eds. Ho and Wang, Butterworth-Heinemann, Stoneham, MA, Chapter 4, pp. 73-106 (1991).
Knorr et al., "Clinical-scale derivation of natural killer cells from human pluripotent stem cells for cancer therapy," Stem Cells Transl. Med., 2(4):274-283 (2013).
Knorr et al., "Engineering Human Pluripotent Stem Cells for Enhanced Lymphocyte Development and Function A Dissertation Submitted to the Faculty of the Graduate School of the University of Minnesota By," Oct. 2012, Retrieved from the Internet: URL:http://conservancy.umn.edu/bitstream/handle/11299/142741/Knorr_umn_0130E_13251.pdf?sequence=1 &isAllowed=y [retrieved on Oct. 5, 2015].
Knorr et al., "Pluripotent stem cell-derived natural killer cells for cancer therapy," Transl. Res., 156(3):147-154 (2010).
Lian et al., "Efficient differentiation of human pluripotent stem cells to endothelial progenitors via small-molecule activation of WNT signaling," Stem Cell Reports, 3(5):804-816 (2014).
Maher et al., "Human T-lymphocyte cytotoxicity and proliferation directed by a single chimeric TCRzeta /CD28 receptor," Nat. Biotechnol., 20(1):70-75 (2002).
Nishimura et al., "Generation of rejuvenated antigen-specific T cells by reprogramming to pluripotency and redifferentiation," Cell Stem Cell, 12(1):114-126 (2013).
Papapetrou et al., "Genomic safe harbors permit high β-globin transgene expression in thalassemia induced pluripotent stem cells," Nat. Biotechnol., 29(1):73-78 (2011).
Poirot et al., "Multiplex genome-edited T-cell manufacturing platform for "off-the-shelf" adoptive T-cell immunotherapies," Cancer Res., 75(18):3853-3864 (2015).
Rathjen et al., "Properties and uses of embryonic stem cells: prospects for application to human biology and gene therapy," Reprod. Feral. Dev., 10:31-47 (1998).
Robertston, "Derivation and maintenance of embryonic stem cell cultures," Methods Mol. Biol., 75:173-184 (1997).
Sadelain et al., "The promise and potential pitfalls of chimeric antigen receptors," Curr. Opin. Immunol., 21(2):215-223 (2009).
Schmitt et al., "Induction of T cell development and establishment of T cell competence from embryonic stem cells differentiated in vitro," Nat. Immunol., 5(4):410-417 (2004).
Schmitt et al., "Induction of T cell development from hematopoietic progenitor cells by delta-like-1 in vitro," Immunity, 17(6):749-756 (2002).
Shimanuki et al., "Modulation of the functional binding sites for TGF-beta on the type II receptor leads to suppression of TGF-beta signaling", Oncogene, 26: 3311-3320 (2007).
Spier, "Large-scale mammalian cell culture: methods, applications and products," Curr. Opin. Biotechnol., 2(3):375-379 (1991).
Suzuki et al., "A novel small-molecule inhibitor of transforming growth factor beta type I receptor kinase (SM16) inhibits murine mesothelioma tumor growth in vivo and prevents tumor recurrence after surgical resection", Cancer Research, 67(5): 2351-2359 (2007).
Tojo, et al., "The ALK-5 inhibitor A-83-01 inhibits Smad signaling and epithelia-to-mesenchymal transition by transforming growth factor-β," Cancer Sci, 96(11): 791-800 (2005).
Torikai et al., "A foundation for universal T-cell based immunotherapy: T cell engineered to express a CD19-specific chimeric-antigen-receptor and eliminate expression of endogenous TCR," Blood, 119(24):5697-5705 (2012).
Valamehr et al., "A novel platform to enable the high-throughput derivation and characterization of feeder-free human iPSCs," Sci. Rep., 2:213 (2012).
Valamehr et al., "Platform for induction and maintenance of transgene-free hiPSCs resembling ground state pluripotent stem cells," Stem Cell Reports, 2:366-381 (2014).
Wang et al., "WNT and BMP signaling are both required for hematopoietic cell development from human ES cells," Stem Cell Res., 3(2-3):113-125 (2009).
Wiles, "Embryonic stem cell differentiation in vitro," Methods Enzymol., 225:900-918 (1993).
Wrzesinski, et al., "Transforming growth factor-beta and the immune response: implications for anticancer therapy", Clinical Cancer Research, 13(18): 5262-5270 (2007).
Yamane et al., "Expression of AA4.1 marks lymphohematopoietic progenitors in early mouse development," Proc. Natl. Acad. Sci. USA, 106(22):8953-8958 (2009).
Zhao et al., "Inhibition of transforming growth factor-betal-induced signaling and epithelial-to-mesenchymal transition by the Smad-binding peptide aptamer Trx-SARA", Molecular Biology of the Cell, 17(9): 3819-3831 (2006).
Chiang et al., "Differentiation of an embryonic stem cell to hemogenic endothelium by defined factors: essential role of bone morphogenetic protein 4," Development, 138(13):2833-2843 (2011).
Joo et al., "ROCK suppression promotes differentiation and expansion of endothelial cells from embryonic stem cell-derived Flk1(+) mesodermal precursor cells," Blood, 120(13):2733-2744 (2012).
Krawetz et al., "Inhibition of Rho kinase regulates specification of early differentiation events in P19 embryonal carcinoma stem cell," PLoS One, 6(11):e26484 (2011).
Pearson et al., "The stepwise specification of embryonic stem cells to hematopoietic fate is driven by sequential exposure to Bmp4, activin A, bFGF and VEGF," Development, 135:1525-1535 (2008).
Vijayaragavan et al., "Noncanonical Wnt signaling orchestrates early developmental events toward hematopoietic cell fate from human embryonic stem cells," Cell Stem Cell, 4:248-262 (2009).
Ameri et al., "FGF2 specifies hESC-derived definitive endoderm into foregut/midgut cell lineages in a concentration-dependent manner," Stem Cells,28(1):45-56 (2010).
Ansari et al., "The programmed death-1 (PD-1) pathway regulates autoimmune diabetes in nonobese diabetic (NOD) mice," J. Exp. Med., 198(1):63-69 (2003).
Beilhack et al., "Purified allogeneic hematopoietic stem cell transplantation blocks diabetes pathogenesis in NOD mice," Diabetes, 52:59-68 (2003).
Brevini et al., "No shortcuts to pig embryonic stem cells," Theriogenology, 74(4):544-550 (2010).
D'Addio et al., "Autologous nonmyeloablative hematopoietic stem cell transplantation in new-onset type 1 diabetes: a multicenter analysis," Diabetes, 63:3041-3046 (2014).
Eiselleova et al., "A complex role for FGF-2 in self-renewal, survival, and adhesion of human embryonic stem cells," Stem Cells, 27(8):1847-1857 (2009).
Eyquem, J. et al. (Mar. 2, 2017, e-published Feb. 22, 2017). "Targeting a CAR to the TRAC locus with CRISPR/Cas9 enhances tumour rejection," Nature 543(7643):113-117.
Fiorina et al., "Targeting the CXCR4-CXCL12 axis mobilizes autologous hematopoietic stem cells and prolongs islet allograft survival via programmed death ligand 1," J. Immunol., 186:121-131 (2011).
Hoggatt et al., "Prostaglandin E2 enhances hematopoietic stem cell homing, survival, and proliferation," Blood, 113(22):5444-5455 (2009).

(56) References Cited

OTHER PUBLICATIONS

Macleod, D.T. et al. (Apr. 5, 2017, e-published Feb. 23, 2017). "Integration of a CD19 CAR into the TCR Alpha Chain Locus Streamlines Production of Allogeneic Gene-Edited CAR T Cells," Mol Ther 25(4):949-961.
Menon et al., "Lymphoid regeneration from gene-corrected SCID-X1 subject-derived iPSCs," Cell Stem Cell, 16(4):367-372 (2015).
Munoz et al., "Conventional pluripotency markers are unspecific for bovine embryonic-derived cell-lines," Theriogenology, 69(9):1159-1164 (2008).
Munoz et al., "Constraints to progress in embryonic stem cells from domestic species," Stem Cell Rev. Rep., 5:6-9 (2009).
Ozkaynak et al., "Programmed death-1 targeting can promote allograft survival," J. Immunol., 169:6546-6553 (2002).
Paris et al., "Equine embryos and embryonic stem cells: defining reliable markers of pluripotency," Theriogenology, 74:516-524 (2010).
Rahman et al., "Rescue of DNA-PK Signaling and T-Cell Differentiation by Targeted Genome Editing in a prkdc Deficient iPSC Disease Model," PLoS Genet., 11(5):e1005239 (2015).
Riella et al., "Role of the PD-1 pathway in the immune response," Am. J. Transplant., 12:2575-2587 (2012).
Smith, C. et al. (Mar. 2015, e-published Nov. 24, 2014). "Efficient and allele-specific genome editing of disease loci in human iPSCs," Mol Ther 23(3):570-577.
Song et al., "Improved hematopoietic differentiation efficiency of gene-corrected beta-thalassemia induced pluripotent stem cells by CRISPR/Cas9 system," Stem Cells Dev., 24(9):1053-1065 (2015).
Themeli, M. et al. (Oct. 2013, e-published Aug. 11, 2013). "Generation of tumor-targeted human T lymphocytes from induced pluripotent stem cells for cancer therapy," Nat Biotechnol 31(10):928-933.
Themeli, M. et al. (Apr. 2, 2015). "New cell sources for T cell engineering and adoptive immunotherapy," Cell Stem Cell 16(4):357-366.
Vodyanik et al., "Leukosialin (CD43) defines hematopoietic progenitors in human embryonic stem cell differentiation cultures," Blood, 108:2095-2105 (2006).
Voltarelli et al., "Autologous nonmyeloablative hematopoietic stem cell transplantation in newly diagnosed type 1 diabetes mellitus," JAMA, 297(14):1568-1576 (2007).
Xu et al., "BMP4 initiates human embryonic stem cell differentiation to trophoblast," Nat. Biotechnol., 20:1261-1264 (2002).
Zhao et al., "Inhibition of transforming growth factor-beta1-induced signaling and epithelial-to-mesenchymal transition by the Smad-binding peptide aptamer Trx-SARA", Molecular Biology of the Cell, 17(9): 3819-3831 (2006).
Zheng et al., "Ex vivo expanded hematopoietic stem cells overcome the MHC barrier in allogeneic transplantation," Cell Stem Cell, 9:119-130 (2011).
Bykovskaia, S.N. et al. (Oct. 1999). "The generation of human dendritic and NK cells from hemopoietic progenitors induced by interleukin-15," J Leukoc Biol 66(4):659-666.
Li, W. et al. (Dec. 2009). "Generation of human-induced pluripotent stem cells in the absence of exogenous Sox2," Stem Cells 27(12):2992-3000.
Nazareth, E.J. et al. (Dec. 2010, e-published Oct. 20, 2013). "High-throughput fingerprinting of human pluripotent stem cell fate responses and lineage bias," Nat Methods 10(12):1225-1231.
Ninomiya, H. et al. (Jan. 2015, e-published Aug. 15, 2014). "Improved efficiency of definitive endoderm induction from human induced pluripotent stem cells in feeder and serum-free culture system," In Vitro Cell Dev Biol Anim 51(1):1-8.
Ogorevc, J. et al. (Feb. 19, 2016). "Cellular reprogramming in farm animals: an overview of iPSC generation in the mammalian farm animal species," J Anim Sci Biotechnol 7:10.
Paterson, Y.Z. et al. (Jan. 2018, e-published Jul. 5, 2017). "Characterization of companion animal pluripotent stem cells," Cytometry A 93(1):137-148.
Tsutsui, H. et al. (Jan. 2011). "An optimized small molecule inhibitor cocktail supports long-term maintenance of human embryonic stem cells," Nat Commun 2:167.
Valamehr, B. et al. (Sep. 2011). "Developing defined culture systems for human pluripotent stem cells," Regen Med 6(5):623-634.
Chen, W. et al. (Jun. 2014). "Generation of the SCN1A epilepsy mutation in hiPS cells using the TALEN technique," Scientific Reports 4:5404, pp. 1-7.
Dravid, G. (Nov.-Dec. 2005, e-published Jul. 7, 2005). "Defining the role of Wnt/β-catenin signaling in the survival, proliferation, and self-renewal of human embryonic stem cells," Stem Cells 23(10):1489-1501.
Ducy, P. et al. (Jun. 2000). "The family of bone morphogenetic proteins," Kidney Int 57(6):2207-2214.
Hoffman, L.M. et al. (Jun. 2005). "Characterization and culture of human embryonic stem cells," Nat Biotechnol 23(6):699-708.
Kumar, D. et al. (Mar. 26, 2015,). "Induced Pluripotent Stem Cells: Mechanisms, Achievements and Perspectives in Farm Animals," World J Stem Cells 7(2):315-328.
Lu, Y. Et al. (Aug. 2012). "Livestock Induced Pluripotent Stem Cells," Reprod Domest Anim 47(Suppl 4):72-76.
Meijer, L. et al. (Sep. 2004). "Pharmacological inhibitors of glycogen synthase kinase 3," Trends Pharmacol Sci 25(9):471-480.
Mikels, A.J. et al. (Dec. 4, 2006). "Wnts as ligands: processing, secretion and reception," Oncogene 25(57):7461-7468.
Sato, T. et al. (Nov. 2007). "High-level expression of CD109 is frequently detected in lung squamous cell carcinomas," Pathology International 57(11):719-724.
Shimasaki, S. et al. (Feb. 2004). "The bone morphogenetic protein system in mammalian reproduction," Endocr Rev 25(1):72-101.
Verfaillie, C.M. et al. (2002). "Stem cells: hype and reality," Hematology Am Soc Hematol Educ Program 369-391.

\* cited by examiner

| Clone | MFI |
|---|---|
| CAG-C5 | 1500 |
| CAG-C8 | 1328 |
| CAG-C12 | 1145 |
| CAG-C38 | 858 |

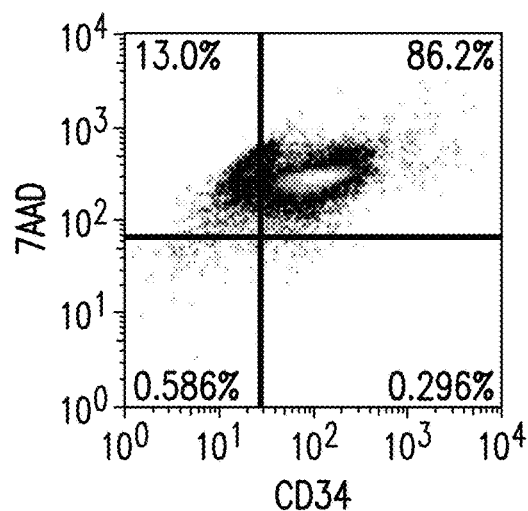
FIG. 6E
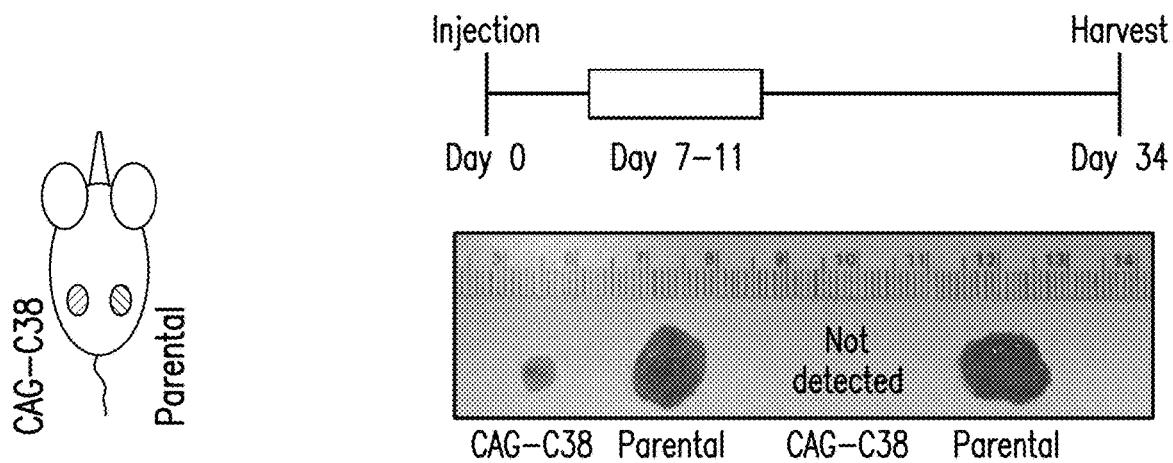
FIG. 7A
FIG. 7B

US 11,072,781 B2

GENOMIC ENGINEERING OF PLURIPOTENT CELLS

RELATED APPLICATION

This application is a divisional application of U.S. patent application Ser. No. 15/818,649, filed on Nov. 20, 2017, now U.S. Pat. No. 10,287,606, issued on May 14, 2019, which is a continuation of International Patent Application No. PCT/US2016/060699, which was filed Nov. 4, 2016, and which claims priority to U.S. Provisional Application Ser. No. 62/251,032, filed Nov. 4, 2015; U.S. Provisional Application Ser. No. 62/337,258, filed May 16, 2016; and U.S. Provisional Application Ser. No. 62/366,503, filed Jul. 25, 2016, the disclosures of which are hereby incorporated by reference in their entireties.

This application includes a Sequence Listing submitted via EFS-Web as an ASCII text file named 13601-229-999_ST25.txt, created Apr. 8, 2019, and being 17,191 bytes in size, which is hereby incorporated by reference in its entirety.

FIELD OF THE INVENTION

The present disclosure is broadly concerned with the field of genetic editing and genomic engineering of stem cells. More particularly, the present disclosure is concerned with the use of genetic modulation of clonal pluripotent stem cells with molecular strategies that target specific loci and ensure continuous retaining and/or functioning of edited genetic material.

BACKGROUND OF THE INVENTION

As the field of human induced pluripotent stem cell (hiPSC) research continues to advance, and as the clinical investigation of genetically-engineered hiPSC-derived cellular therapeutics begins to emerge, safety concerns relating to the administration of genetically-altered cells must be addressed and mitigated. To address these safety issues, a number of strategies including recombinant peptides, monoclonal antibodies, small molecule-modulated enzyme activity and gene-specific modifications have been explored to facilitate the selective elimination of aberrant cells. In general, previous studies have employed viral vectors, such as lentivirus, and short promoters to stably introduce suicide genes, including herpes complex virus thymidine kinase or inducible caspase-9 (iCasp9), into human cells. However, the use of viral vectors can lead to random integration events which can disrupt or activate disease-related genes, potentially causing deleterious effects. Other problems in the currently used methods include, but not limited to, low insertion rate; random insertions; mutations; high insertion copy numbers; and laborious cell sorting to select against heterogeneous population of cells with varied copy number insertions due to random insertions. In addition, for iPSC genome engineering, many artificial promoters and genome regions are prone to epigenetic gene expression silencing in both pluripotent and differentiated states, resulting in the promoters or the inserted genes becoming unresponsive with events such as cell expansion, passaging, reprogramming, differentiation, and/or dedifferentiation. Thus, it is of great importance to identify optimal genome editing strategy, integration sites, promoters, and other factors in order to maintain responses of inserted functional modalities without compromising safety, especially when developing genetically-engineered immune cells for therapeutic use.

SUMMARY OF THE INVENTION

It is an object of the present invention to provide methods and compositions to generate single cell derived iPSC clonal lines, or derivative cells therefrom, comprising one or several genetic modifications at selected sites, which include polynucleotides insertion, deletion, and substitution, and which modifications are retained and remain functional in subsequently derived cells after differentiation, dedifferentiation, reprogramming, expansion, passaging and/or transplantation.

It is an object of the present invention to generate single cell derived iPSC clonal lines comprising one or several genetic modifications at selected sites through reprogramming non-pluripotent cells comprising the same genetic modifications, including targeted integration and/or targeted in/dels. Specifically, it is an object of the present invention to reprogram non-pluripotent cells before genome-engineering of the reprogrammed cells, as such iPSCs or less differentiated cells are obtained first for the subsequent genome editing. It is also an object of the present invention to reprogram non-pluripotent cells after genome-engineering of the non-pluripotent cells, as such genome engineered non-pluripotent cells are obtained first for the subsequent cell reprogramming. It is a further object of the present invention to reprogram non-pluripotent cells concurrently with genome-engineering of the non-pluripotent cells, as such no intermediate cells are isolated from, or for, either reprogramming or genome-engineering, and the two processes take place simultaneously in the single pool of cells.

It is an object of the present invention to generate iPSC (or less differentiated cells) derived non-pluripotent cells including, but not limited to, CD34 cells, hemogenic endothelium cells, HSCs (hematopoietic stem and progenitor cells), hematopoietic multipotent progenitor cells, T cell progenitors, NK cell progenitors, T cells, NKT cells, NK cells, and B cells comprising one or several genetic modifications at selected sites through differentiating iPSCs or less differentiated cells comprising the same genetic modifications at the same selected sites. Specifically, it is an object of the present invention to differentiate less differentiated cells including progenitor and pluripotent cells after genome-engineering of the less differentiated cells, as such genome engineered less differentiated cells are obtained first for the subsequent cell differentiation. It is a further object of the present invention to differentiate less differentiated cells concurrently with genome-engineering of the less differentiated cells, as such no intermediate cells are isolated from, or for, either differentiation or genome-engineering, and the two processes take place simultaneously in the single pool of cells.

One aspect of the present invention provides a construct comprising: (1) one or more exogenous polynucleotides of interest operatively linked to one or more exogenous promoters comprised in the construct, or to an endogenous promoter comprised in a selected site upon integration; and (2) a pair of homology arms specific to the selected site and flanking the exogenous polynucleotides of interest, for targeted integration of the exogenous polynucleotides at the selected site in iPSCs; and in subsequently expanded iPSCs, differentiated cells derived from the iPSCs, and/or dedifferentiated cells derived therefrom, those one or more exogenous polynucleotides remain integrated and functional. In some embodiments, the one or more exogenous polynucleotides are linked to each other by a linker sequence. In some embodiments, the linker sequence encodes a self-cleaving peptide. In some embodiments, the linker sequence provides an Internal Ribosome Entry Sequence (IRES). In some other embodiments, the above constructs further comprise at least one polynucleotide encoding a marker. In other embodiments, the construct comprises a polynucleotide encoding a marker that is driven by the endogenous promoter at the selected site. In some embodiments, the selected site is a safe harbor locus, highly expressive locus, temporally expressed locus, or a gene locus for interruption. In some embodiments, the safe harbor locus may be AAVS1, CCR5, ROSA26, collagen, HTRP, H11, beta-2 microglobulin, GAPDH, TCR or RUNX1, or loci meeting the criteria of a genome safe harbor as defined herein. In some embodiments, a gene locus for interruption comprising TAP1, TAP2 or tapasin, or other genes of interest whose interruption is relevant to desirable cell function or properties, for example, NLRC5, PD1, LAG3, TIM3, RFXANK, CIITA, RFX5, RFXAP, and any gene in the chromosome 6p21 region.

In some embodiments of the construct above, at least one of the exogenous polynucleotides operatively linked to an exogenous promoter comprising CMV, EF1α, PGK, CAG UBC, or other constitutive, inducible, temporal-, tissue-, or cell type-specific promoters. In one embodiment, the exogenous promoter comprised in the construct is CAG In some other embodiments, the one or more polynucleotides encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival of the iPSCs or derivative cells thereof integrated with the construct. In some particular embodiments, the one or more polynucleotides encode safety switch proteins comprising caspase, thymidine kinase, cytosine deaminase, modified EGFR, B-cell CD20, or any combinations thereof. In some embodiments, the caspase may be caspase 9, caspase 3, or caspase 7. In some other embodiments, the polynucleotides encoding safety switch protein is operatively linked to CAG in the construct.

One aspect of the present invention provides a method of generating genome-engineered iPSCs, which iPSCs comprise at least one targeted genomic editing at one or more selected sites in genome, the method comprising (I), (II) or (III):

(I): genetically engineering iPSCs by one or both of (i) and (ii), in any order: (i) introducing into iPSCs one or more construct of claim 1 to allow targeted integration at selected site; (ii) (a) introducing into iPSCs one or more double strand break at the selected sites using one or more endonuclease capable of selected site recognition; and (b) culturing the iPSCs of step (I)(ii)(a) to allow endogenous DNA repair to generate targeted in/dels at the selected sites; thereby obtaining genome-engineered iPSCs comprising at least one functional targeted genomic editing, and wherein the genome-engineered iPSCs are capable of being differentiated into partially differentiated cells or fully-differentiated cells (II): genetically engineering reprogramming non-pluripotent cells to obtain the genome-engineered iPSCs comprising: (i) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate reprogramming of the non-pluripotent cells; and (ii) introducing into the reprogramming non-pluripotent cells of step (II)(i) one or both of (a) and (b), in any order: (a) one or more construct of claim 1 to allow targeted integration at a selected site; (b) one or more double strand break at a selected site using at least one endonuclease capable of selected site recognition, wherein the cells of step (II)(ii)(b) are cultured to allow endogenous DNA repair to generate targeted in/dels at the selected sites; thereby obtaining genome-engineered iPSCs comprising at least one functional targeted genomic editing, and wherein the genome-engineered iPSCs are capable of being differentiated into partially differentiated cells or fully-differentiated cells.

(III): genetically engineering non-pluripotent cells for reprogramming to obtain genome-engineered iPSCs comprising (i) and (ii): (i) introducing into non-pluripotent cells one or both of (a) and (b), in any order: (a) one or more construct of claim 1 to allow targeted integration at a selected site; (b) one or more double strand break at a selected site using at least one endonuclease capable of selected site recognition, wherein the cells of step (III)(i)(b) are cultured to allow endogenous DNA repair to generate targeted in/dels at the selected sites; and (ii) contacting the cells of step (III)(i) with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted editing at selected sites; thereby obtaining genome-engineered iPSCs comprising at least one functional targeted genomic editing, and wherein the genome-engineered iPSCs are capable of being differentiated into partially differentiated cells or fully-differentiated cells.

In one embodiment of the above method, the at least one targeted genomic editing at one or more selected sites comprises insertion of one or more exogenous polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the genome-engineered iPSCs or derivative cells thereof. In some embodiments, the exogenous polynucleotides for insertion are operatively linked to (1) one or more exogenous promoters comprising CMV, EF1α, PGK, CAG UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, GAPDH, TCR or RUNX1, or other locus meeting the criteria of a genome safe harbor. In some embodiments, the genome-engineered iPSCs generated using the above method comprise one or more different exogenous polynucleotides encoding protein comprising caspase, thymidine kinase, cytosine deaminase, modified EGFR, or B-cell CD20, wherein when the genome-engineered iPSCs comprise two or more suicide genes, the suicide genes are integrated in different safe harbor locus comprising AAVS1, CCR5, ROSA26, collagen, HTRP, H11, H11, beta-2 microglobulin, GAPDH, TCR or RUNX1.

In some other embodiments, the genome-engineered iPSCs generated using the method provided herein comprise in/del at one or more endogenous genes associated with targeting modality, receptors, signaling molecules, transcription factors, drug target candidates, immune response regulation and modulation, or proteins suppressing engraftment, trafficking, homing, viability, self-renewal, persistence, and/ or survival of the iPSCs or derivative cells thereof. In some embodiments, the endogenous gene for disruption comprises at least one of B2M, TAP1, TAP2, Tapasin, NLRC5, PD1, LAG3, TIM3, RFXANK, CIITA, RFX5, RFXAP, and any gene in the chromosome 6p21 region.

In yet some other embodiments, the genome-engineered iPSCs generated using the method provided herein comprise a caspase encoding exogenous polynucleotide at AAVS1 locus, and a thymidine kinase encoding exogenous polynucleotide at H11 locus.

In still some other embodiments, approach (I), (II) and/or (III) further comprises: contacting the genome-engineered iPSCs with a small molecule composition comprising a MEK inhibitor, a GSK3 inhibitor and a ROCK inhibitor, to maintain the pluripotency of the genomic-engineered iPSCs. In one embodiments, the obtained genome engineered iPSCs comprising at least one targeted genomic editing are functional, are differentiation potent, and are capable of differentiating into non-pluripotent cells comprising the same functional genomic editing.

Another aspect of the present invention provides genome-engineered iPSCs generated from any one of the methods depicted above. In one embodiment, the genome-engineered iPSCs generated comprise one or more exogenous polynucleotides introduced using the constructs provided above, and the exogenous polynucleotide is integrated at one or more selected sites in the iPSCs. In one embodiment, the genome-engineered iPSCs generated comprise one or more in/dels comprised in an endogenous gene associated with targeting modalities; receptors; signaling molecules; transcription factors; drug target candidates; immune response regulation and modulation; and proteins suppressing engraftment, trafficking, homing, viability, self-renewal, persistence, and/or survival of the iPSCs or derivative cells thereof. In one embodiment, the endogenous gene comprises one or more of B2M, TAP1, TAP2, Tapasin, NLRC5, PD1, LAG3, TIM3, RFXANK, CIITA, RFX5, RFXAP, and any gene in the chromosome 6p21 region. In some other embodiments, the genome-engineered iPSCs comprise deletion or reduced expression in at least one of B2M, TAP1, TAP2, Tapasin, NLRC5, PD1, LAG3, TIM3, RFXANK, CIITA, RFX5, RFXAP and any gene in the chromosome 6p21 region. In some other embodiments, the genome-engineered iPSCs comprise introduced or increased expression in at least one of HLA-E, HLA-G, CD16, 41BBL, CD3, CD4, CD8, CD47, CD113, CD137, CD80, PDL1, A2AR, CAR, TCR, Fc receptor, an engager, and surface triggering receptor for coupling with bi-, multi-specific or universal engagers. In some embodiments, the introduced or increased expression is via integrated or non-integrated method for introducing exogenous protein encoding polynucleotides. In some embodiments, the genome-engineered iPSCs are HLA class I and/or class II deficient. In some embodiment, the genome-engineered iPSCs comprise B2M null or low, TAP1 null or low, and/or TAP2 null or low. In some embodiments, the genome-engineered iPSCs comprise integrated or non-integrated exogenous polynucleotide encoding one or more of HLA-E, HLA-G, CD16, 41BBL and PDL1 proteins; or wherein the genome-engineered iPSCs comprise introduced expression of one or more of HLA-E, HLA-G, CD16, 41BBL and PDL1 proteins. In some embodiments, said introduced expression is an increased expression from either non-expressed or lowly expressed genes comprised in said cells. In some embodiments, the non-integrated exogenous polynucleotides are introduced using sendai virus, episomal, or plasmid.

In some other embodiments, the genome-engineered iPSCs comprise at least one exogenous polynucleotide encodes high affinity CD16 receptor; at least one exogenous polynucleotide encodes non-cleavable CD16 receptor; at least one exogenous polynucleotide encodes high affinity and non-cleavable CD16 receptor (hnCD16); at least one exogenous polynucleotide encodes non-cleavable HLA-E; or at least one exogenous polynucleotide encodes non-cleavable HLA-G In some embodiments, the iPSC comprises one or more exogenous polynucleotides encoding proteins comprising safety switch proteins; targeting modalities; receptors; signaling molecules; transcription factors; pharmaceutically active proteins or peptides; drug target candidates; or proteins promoting engraftment, trafficking, homing, viability, self-renewal, persistence, and/or survival of the iPSCs or derivative cells thereof.

In yet some other embodiments, the exogenous polynucleotides comprised in the one or more constructs are operatively linked to (1) one or more exogenous promoters comprising CMV, EF1α, PGK, CAG UBC, or other constitutive, inducible, temporal-, tissue-, or cell type-specific promoters; or (2) one or more endogenous promoters comprised in selected sites comprising AAVS1, CCR5, ROSA26, collagen, HTRP, H11, beta-2 microglobulin, GAPDH, TCR or RUNX1 upon integration. In some other embodiments, the iPSCs comprise at least one exogenous polynucleotide that encodes a safety switch protein comprising caspase, thymidine kinase, cytosine deaminase, modified EGFR, or B-cell CD20. In some particular embodiments, the iPSCs comprise at least two same or different safety switch protein encoding exogenous polynucleotides are integrated in the same safe harbor locus comprising AAVS1, CCR5, ROSA26, collagen, HTRP, H11, beta-2 microglobulin, GAPDH, TCR or RUNX1, or other locus meeting the criteria of a genome safe harbor. In one embodiment, the iPSCs comprise two same or different safety switch protein encoding exogenous polynucleotides integrated in different safe harbor loci comprising AAVS1, CCR5, ROSA26, collagen, HTRP, H11, beta-2 microglobulin, GAPDH, TCR or RUNX1 or other locus meeting the criteria of a genome safe harbor. In one particular embodiment, the iPSCs comprise two same or different safety switch protein encoding exogenous polynucleotides integrated in different safe harbor loci comprising AAVS1, CCR5, ROSA26, collagen, HTRP, H11, beta-2 microglobulin, GAPDH, TCR or RUNX1 or other locus meeting the criteria of a genome safe harbor.

In some embodiments, the genome-engineered iPSCs generated using the provided method have improved persistency, increased resistance to immune cells, increased immune-resistance, or increased resistance to T and/or NK cells in comparison to iPSCs without the same genomic engineering; wherein the genome-engineered iPSCs maintain pluripotency; and wherein the genome-engineered iPSCs maintain differentiation potential to non-pluripotent cells having the same functional genomic engineering. In one embodiment, the genome-engineered iPSCs generated are capable of differentiating into partially differentiated cells or fully-differentiated cells, and wherein the partially differentiated cells or fully-differentiated cells comprise at least one targeted genomic editing comprised in the iPSCs. In one embodiment, the generated genome-engineered iPSCs are capable of differentiating into hematopoietic lineage cells, including mesodermal cells, CD34 cells, hemogenic endothelium cells, hematopoietic stem and progenitor cells, hematopoietic multipotent progenitor cells, T cell progenitors, NK cell progenitors; T cells, NKT cells, NK cells, or B cells.

Another aspect of the invention provides genome-engineered iPSCs comprising (i) B2M null or low; (ii) TAP1 null or low; (iii) TAP2 null or low; (iv) Tapasin null or low; (v) introduced expression of HLA-E or non-cleavable HLA-E; (vi) introduced expression of HLA-G or non-cleavable HLA-G; (vii) introduced expression of PDL1; (viii) high affinity non-cleavable CD16 (hnCD16); (ix) a Fc receptor; (x) a T cell receptor (TCR); (xi) a chimeric antigen receptor (CAR); (xii) one or more suicide genes expressing safety switch protein; (xiii) a bi-, multi-specific or universal engagers, or any combinations thereof. In some embodiment, the genome-engineered iPSCs are B2M null, TAP1 null, TAP2 null, or Tapasin null. In some embodiment, the genome-engineered iPSCs are B2M null, with introduced expression of one or more of HLA-E, HLA-Q PDL1, and hnCD16. In some embodiment, the genome-engineered iPSCs are B2M null, with introduced expression of one or more of HLA-E, HLA-Q PDL1, hnCD16, and a CAR. In some embodiment, the genome-engineered iPSCs are B2M null, with introduced expression of one or more of HLA-E, HLA-Q PDL1, hnCD16, a CAR, and at least one safety switch protein. In some embodiments, said introduced expression is an increased expression from either non-expressed or lowly expressed genes comprised in said cells. In some other embodiments, said introduced expression is an exogenous expression. In some embodiments, the TCR, CAR, engager, Fc receptor, or suicide gene is inducible. In some embodiments, the genome-engineered iPSCs have improved persistency, increased resistance to immune cells, increased resistance to T and/or NK cells, or increased immune-resistance in comparison to iPSCs without the same genomic engineering; wherein the genome-engineered iPSCs maintain pluripotency; and wherein the genome-engineered iPSCs maintain differentiation potential to non-pluripotent cells having the same functional genomic engineering.

Further provided are modified HLA deficient iPSCs, which are HLA class I and/or II deficient and further comprise (1) one or more of exogenous HLA-E, HLA-G CD16, 41BBL, CD47, CD113, and PDL1; or (2) introduced expression of one or more of HLA-E, HLA-G, CD16, 41BBL, CD47, CD113, and PDL1 proteins; and optionally (3) one or more of a TCR, a CAR, an engager, an Fc receptor, and a single or dual safety switch proteins. In some embodiments, said introduced expression is an increased expression from either non-expressed or lowly expressed genes comprised in said cells. In one embodiment, the TCR, CAR, engager, Fc receptor, or suicide gene comprised in the modified HLA deficient iPSCs is inducible. In some embodiments, the modified HLA deficient iPSCs have improved persistency, increased resistance to immune cells, increased resistance to T and/or NK cells, or increased immune-resistance in comparison to iPSCs without the same genomic engineering; wherein the modified HLA deficient iPSCs maintain pluripotency; and wherein the modified HLA deficient iPSCs maintain differentiation potential to non-pluripotent cells that are HLA deficient and have the same functional genomic engineering.

Still another aspect of the invention provides a method of generating genome-engineered non-pluripotent cells derived from genome-engineered iPSCs, which comprises (i) obtaining genome-engineered iPSCs or modified HLA deficient iPSCs as provided above, wherein the iPSC comprises at least one functional genomic editing; and (ii) differentiating the genome-engineered iPSCs or modified HLA deficient iPSCs to obtain derived non-pluripotent cells comprising the same functional targeted genomic editing comprised in the genome-engineered iPSCs. In some embodiments, the differentiating step does not require embryoid body formation. In some embodiments, the differentiation is feeder free, stromal free, or serum-free. In some embodiments, the derived non-pluripotent cells comprise hematopoietic lineage cells. In some embodiments, the derived non-pluripotent cells comprise mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells.

An additional aspect of this invention provides a method of generating genome-engineered non-pluripotent cells from iPSCs, the method comprising (i) subjecting iPSCs under the condition sufficient for initiating lineage specific differentiation; and (ii) genetically engineering the differentiating cells of step (i) to obtain the genome-engineered non-pluripotent cells by one or both of (a) and (b), in any order: (a) introducing into the differentiating cells of step (i) one or more construct of claim 1 to allow targeted integration at selected site; (b) (1) introducing into the differentiating cells of step (i) one or more double strand break at the selected sites using one or more endonuclease capable of selected site recognition; and (2) culturing the cells from step (ii)(b)(1) to allow endogenous DNA repair to generate targeted in/dels at the selected sites; thereby obtaining genome-engineered non-pluripotent cells comprising one or more functional targeted editing in one or more selected sites. In some embodiments, the genome-engineered non-pluripotent cells comprise hematopoietic lineage cells. In some other embodiments, the genome-engineered non-pluripotent cells comprise mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells.

The present invention further provides iPSC derived genome-engineered non-pluripotent cells generated using the above general method, and the generated non-pluripotent cells comprise one or more functional targeted genomic editing. In one embodiment, the iPSC derived genome-engineered non-pluripotent cells comprise mesodermal cells, hemogenic endothelium cells, CD34 cells, hematopoietic stem and progenitor cells, hematopoietic multipotent progenitor cells, T cell progenitors, NK cell progenitors, T cells, NKT cells, NK cells, or B cells. In some embodiments, the iPSC derived genome-engineered non-pluripotent cells comprise one or more exogenous polynucleotides encoding proteins comprising safety switch proteins; targeting modalities; receptors; signaling molecules; transcription factors; pharmaceutically active proteins or peptides; drug target candidates; or proteins promoting engraftment, trafficking, homing, viability, self-renewal, persistence, and/or survival of the non-pluripotent cells. In yet some other embodiments, the iPSC derived genome-engineered non-pluripotent cells comprise one or more in/dels comprised in an endogenous gene associated with targeting modalities; receptors; signaling molecules; transcription factors; drug target candidates; immune response regulation and modulation; and proteins suppressing engraftment, trafficking, homing, viability, self-renewal, persistence, and/or survival of the non-pluripotent cells. In some specific embodiments, the iPSC derived genome-engineered non-pluripotent cells comprise the endogenous gene having one or more in/dels, and the endogenous gene comprises B2M, TAP1, TAP2, Tapasin, NLRC5, PD1, LAG3, TIM3, RFXANK, CIITA, RFX5, RFXAP, or any gene in the chromosome 6p21 region. In some embodiments, the derived genome-engineered non-pluripotent cells comprise deletion or reduced expression in at least one of B2M, TAP1, TAP2, Tapasin, NLRC5, PD1, LAG3, TIM3, RFXANK, CIITA, RFX5, RFXAP, and any gene in the chromosome 6p21 region. In some other embodiments, the derived genome-engineered non-pluripotent cells comprise introduced or increased expression in at least one of HLA-E, HLA-G, CD16, 41BBL, CD3, CD4, CD8, CD47, CD113, CD131, CD137, CD80, PDL1, A2AR, CAR, TCR, Fc receptor, an engager, and a surface triggering receptor for coupling with bi- or multi-specific, or universal engagers.

In yet some other embodiments, the iPSC derived genome-engineered non-pluripotent cells of any of the claims 54-60, wherein the non-pluripotent cells comprise: (i) at least two exogenous polynucleotides each integrated in the same safe harbor locus, and wherein the exogenous polynucleotides encode the same or different safety switch proteins; or (ii) at least two exogenous polynucleotides each integrated in different safe harbor locus, and wherein the exogenous polynucleotides encode the same or different safety switch proteins. In some embodiments of the iPSC derived genome-engineered non-pluripotent cells, the exogenous polynucleotide encoding a safety switch protein is selected from caspase, thymidine kinase, cytosine deaminase, modified EGFR, B-cell CD20, and any combinations thereof. In some embodiments of the iPSC derived genome-engineered non-pluripotent cells, the safe harbor locus comprise AAVS1, CCR5, ROSA26, collagen, HTRP, H11, beta-2 microglobulin, GAPDH, TCR or RUNX1, or other locus meeting the criteria of a genome safe harbor. In some embodiments, the iPSC derived genome-engineered non-pluripotent cells are capable of being reprogrammed to iPSCs, and wherein the iPSCs comprise the same functional exogenous polynucleotides comprised in the non-pluripotent cells. In some embodiments of the iPSC derived genome-engineered non-pluripotent cells, the iPSCs reprogrammed therefrom are capable of being differentiated into partially differentiated cells or fully-differentiated cells. In still some embodiments, the iPSC derived genome-engineered non-pluripotent cells are capable of being transdifferentiated to non-pluripotent cells of a different fate.

An additional aspect of the present invention provides iPSC derived genome-engineered hematopoietic lineage cells, which comprise (i) B2M null or low; (ii) TAP1 null or low; (iii) TAP2 null or low; (iv) Tapasin null or low; (v) introduced expression of HLA-E or non-cleavable HLA-E; (vi) introduced expression of HLA-G or non-cleavable HLA-G; (vii) introduced expression of PDL1; (viii) high affinity non-cleavable CD16 (hnCD16); (ix) a Fc receptor; (x) a T cell receptor (TCR); (xi) a chimeric antigen receptor (CAR); (xii) one or more suicide genes expressing safety switch protein; (xiii) a bi-, multi-specific or universal engagers, or any combinations thereof. In some embodiment, the iPSC derived genome-engineered hematopoietic lineage cells are B2M null, TAP1 null, TAP2 null, or Tapasin null. In some embodiment, the iPSC derived genome-engineered hematopoietic lineage cells are B2M null, with introduced expression of one or more of HLA-E, HLA-Q PDL1, and hnCD16. In some embodiment, the iPSC derived genome-engineered hematopoietic lineage cells are B2M null, with introduced expression of one or more of HLA-E, HLA-G PDL1, hnCD16, and a CAR. In some embodiment, the iPSC derived genome-engineered hematopoietic lineage cells are B2M null, with introduced expression of one or more of HLA-E, HLA-Q PDL1, hnCD16, a CAR, and at least one safety switch protein. In some embodiments, said introduced expression is an increased expression from either non-expressed or lowly expressed genes comprised in said cells. In some other embodiments, said introduced expression is an exogenous expression. In some embodiments, the TCR, CAR, engager, Fc receptor, or suicide gene comprised in the iPSC derived genome-engineered hematopoietic lineage cells is inducible. In some embodiments, the iPSC derived genome-engineered hematopoietic lineage cells have improved persistency, increased resistance to immune cells, increased resistance to T and/or NK cells, or increased immune-resistance; and the genome-engineered hematopoietic lineage cells that are less differentiated maintain differentiation potential to more differentiated hematopoietic lineage cells having the same functional genomic engineering.

The present invention further provides a composition comprising iPSC derived hematopoietic cells, which comprises (a) iPSC derived genome-engineered CD34 cells; (b) iPSC derived genome-engineered hematopoietic stem and progenitor cells; (c) iPSC derived genome-engineered hematopoietic multipotent progenitor cells; (d) iPSC derived genome-engineered T cell progenitors; (e) iPSC derived genome-engineered NK cell progenitors; (f) iPSC derived genome-engineered T cell; (g) iPSC derived genome-engineered NK cell, as described above, and any combinations thereof.

Further provided are genome-engineered hematopoietic lineage cells comprising (i) B2M null or low; (ii) TAP1 null or low; (iii) TAP2 null or low; (iv) Tapasin null or low; (v) introduced expression of HLA-E or non-cleavable HLA-E; (vi) introduced expression of HLA-G or non-cleavable HLA-G; (vii) introduced expression of PDL1; (viii) high affinity non-cleavable CD16 (hnCD16); (ix) a Fc receptor; (x) a T cell receptor (TCR); (xi) a chimeric antigen receptor (CAR); (xii) one or more suicide genes expressing safety switch protein; (xiii) a bi-, multi-specific or universal engagers, or any combinations thereof. In some embodiment, the genome-engineered hematopoietic lineage cells are B2M null, TAP1 null, TAP2 null, or Tapasin null. In some embodiment, the genome-engineered hematopoietic lineage cells are B2M null, with introduced expression of one or more of HLA-E, HLA-G PDL1, and hnCD16. In some embodiment, the genome-engineered hematopoietic lineage cells are B2M null, with introduced expression of one or more of HLA-E, HLA-G PDL1, hnCD16, and a CAR. In some embodiment, the genome-engineered hematopoietic lineage cells are B2M null, with introduced expression of one or more of HLA-E, HLA-Q PDL1, hnCD16, a CAR, and at least one safety switch protein. In some embodiments, said introduced expression is an increased expression from either non-expressed or lowly expressed genes comprised in said cells. In some other embodiments, said introduced expression is an exogenous expression. In some embodiments, the TCR, CAR or suicide gene comprised in the genome-engineered hematopoietic lineage cells is inducible. In some embodiments, the genome-engineered hematopoietic lineage cells have improved persistency, increased resistance to immune cells, increased resistance to T and/or NK cells, or increased immune-resistance; and the genome-engineered hematopoietic lineage cells that are less differentiated maintain differentiation potential to more differentiated hematopoietic lineage cells having the same functional genomic engineering.

Additionally provided are modified HLA deficient hematopoietic lineage cells, which are HLA class I and/or II deficient, and which further comprise (1) one or more of exogenous HLA-E, HLA-G, CD16, 41BBL, CD47, CD113, and PDL1; or (2) introduced expression of one or more of HLA-E, HLA-G, CD16, 41BBL, CD47, CD113, and PDL1 proteins; and optionally (3) one or more of a TCR, a CAR, an engager, an Fc receptor, and a single or dual safety switch proteins. In some embodiments, said introduced expression is an increased expression from either non-expressed or lowly expressed genes comprised in said cells. In some embodiments, the TCR, CAR, engager, Fc receptor, or suicide gene comprised in the modified HLA deficient hematopoietic lineage cells is inducible. In some embodiments, modified HLA deficient hematopoietic lineage cells as provided herein have improved persistency, increased resistance to immune cells, increased resistance to T and/or NK cells, or increased immune-resistance; wherein the modified HLA deficient hematopoietic lineage cells that are less differentiated maintain differentiation potential to more differentiated hematopoietic lineage cells having the same functional genomic engineering.

Another aspect of the present invention provides a composition for obtaining genome-engineered iPSCs, the composition comprising: (i) genome-engineered non-pluripotent cells as provided herein, which cells comprise at least one targeted genomic editing at one or more selected sites in the genome; (ii) one or more reprogramming factors; and optionally, (iii) a small molecule composition comprising a TGFβ receptor/ALK inhibitor, a MEK inhibitor, a GSK3 inhibitor and/or a ROCK inhibitor, wherein the composition is useful for obtaining iPSCs comprising the same targeted genomic editing comprised in the genome-engineered non-pluripotent cells. In some embodiments, the at least one targeted genomic editing of the above cells at one or more selected sites comprises insertion of one or more exogenous polynucleotides encoding safety switch proteins, targeting modalities, receptors, signaling molecules, transcription factors, pharmaceutically active proteins or peptides, drug target candidates, or proteins promoting engraftment, trafficking, homing, viability, self-renewal, self-renewal, persistence, and/or survival of the non-pluripotent cells and the iPSCs reprogrammed thereof.

In some embodiments of the composition, said one or more exogenous polynucleotides are operatively linked to (1) one or more exogenous promoters comprising CMV, EF1α, PGK, CAG UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, GAPDH, TCR or RUNX1. In some embodiments of the composition, the one or more exogenous polynucleotides are operatively linked to one or more endogenous promoters comprised in selected insertion sites comprising AAVS1, CCR5, ROSA26, collagen, HTRP, H11, beta-2 microglobulin, GAPDH, TCR or RUNX1. In yet some other embodiments of the composition, the genome-engineered non-pluripotent cells comprise one or more exogenous polynucleotides encoding safety switch proteins comprising caspase, thymidine kinase, cytosine deaminase, modified EGFR, B-cell CD20, or any combinations thereof. In some embodiments of the composition, the genome-engineered non-pluripotent cells comprise two or more same or different safety switch protein encoding exogenous polynucleotides integrated in different safe harbor loci comprising AAVS1, CCR5, ROSA26, collagen, HTRP, H11, beta-2 microglobulin, GAPDH, TCR or RUNX1, or other locus meeting the criteria of a genome safe harbor. In one particular embodiments of the composition, the genome-engineered non-pluripotent cells comprise a caspase encoding polynucleotide at AAVS1 locus, and a thymidine kinase encoding polynucleotide at H11 locus. In some other embodiments of the composition, the genome-engineered non-pluripotent cells comprise one or more in/dels comprised in an endogenous gene associated with targeting modalities; receptors; signaling molecules; transcription factors; drug target candidates; immune response regulation and modulation; and proteins suppressing engraftment, trafficking, homing, viability, self-renewal, persistence, and/or survival of the non-pluripotent cells and the iPSCs therefrom.

In some embodiments of the composition, the one or more endogenous gene for disruption with in/del is selected from B2M, TAP1, TAP2, Tapasin, NLRC5, PD1, LAG3, TIM3, RFXANK, CIITA, RFX5, RFXAP, and any gene in the chromosome 6p21 region. In some embodiments of the composition, the genome-engineered non-pluripotent cells comprise deletion or reduced expression in at least one of B2M, TAP1, TAP2, Tapasin, NLRC5, PD1, LAG3, TIM3, RFXANK, CIITA, RFX5, RFXAP, and any gene in the chromosome 6p21 region. In some other embodiments of the composition, the the genome-engineered non-pluripotent cells comprise introduced or increased expression in at least one of HLA-E, HLA-G, CD16, 41BBL, CD3, CD4, CD8, CD47, CD113, CD131, CD137, CD80, PDL1, A2AR, CAR, TCR, Fc receptor, an engager, and surface triggering receptor for coupling with bi- or multi-specific or universal engagers. In some embodiments of the composition, said introduced or increased expression is via integrated or non-integrated method for introducing exogenous protein encoding polynucleotides. In some embodiments, the non-integrated exogenous polynucleotides are introduced using sendai virus, or episomal, or plasmids. In one embodiment of the composition, said genome-engineered non-pluripotent cells are HLA class I and/or class II deficient. In one embodiment, said genome-engineered non-pluripotent cells comprise B2M null or low, TAP1 null or low, TAP2 null or low, and/or Tapasin null or low. In some other embodiments of the composition, said genome-engineered non-pluripotent cells comprise integrated or non-integrated exogenous polynucleotide encoding one or more of HLA-E, HLA-G, CD16, 41BBL and PDL1 proteins. In some embodiments, the non-integrated exogenous polynucleotides are introduced using sendai virus, or episomal, or plasmids. In some embodiments, the genome-engineered non-pluripotent cells comprise introduced expression of one or more of HLA-E, HLA-G, CD16, 41BBL and PDL1 proteins, wherein said introduced expression is an increased expression from either non-expressed or lowly expressed genes comprised in said cells. In some embodiments of the composition, the genomic-engineered non-pluripotent cells comprise at least one exogenous polynucleotide encodes high affinity CD16 receptor; at least one exogenous polynucleotide encodes non-cleavable CD16 receptor; at least one exogenous polynucleotide encodes high affinity and non-cleavable CD16 receptor (hnCD16); at least one exogenous polynucleotide encodes non-cleavable HLA-E; or at least one exogenous polynucleotide encodes non-cleavable HLA-G In yet some other embodiments of the composition, the genomic-engineered non-pluripotent cells comprise mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells. In some embodiments of the composition, the genomic-engineered non-pluripotent cells have improved persistency, increased resistance to immune cells, or increased immune-resistance; or wherein the genomic-engineered non-pluripotent cells have increased resistance to T and/or NK cells.

Yet another aspect of the present invention provides a composition for obtaining genome-engineered iPSCs, the composition comprising: (i) non-pluripotent cells; (ii) one or more constructs for targeted editing at one or more selected loci; (iii) one or more reprogramming factors; and optionally, (iv) a small molecule composition comprising a TGFβ receptor/ALK inhibitor, a MEK inhibitor, a GSK3 inhibitor and/or a ROCK inhibitor, wherein the composition is useful for obtaining iPSCs comprising targeted genomic editing, and thereby the genome-engineered iPSCs have improved persistency, increased resistance to immune cells, or increased immune-resistance; or wherein the genome-engineered iPSCs have increased resistance to T and/or NK cells.

In some embodiments, the composition above further comprises one or more endonuclease capable of selected site recognition for introducing double strand break at selected sites; and/or a construct comprising one or more exogenous polynucleotides encoding safety switch proteins, targeting modality, receptors, signaling molecules, transcription factors, pharmaceutically active proteins and peptides, drug target candidates, or proteins promoting engraftment, trafficking, homing, viability, self-renewal, persistence, and/or survival of the non-pluripotent cell reprogrammed iPSCs or derivative cells thereof. In some embodiments, said one or more exogenous polynucleotides is operatively linked to (1) one or more exogenous promoters comprising CMV, EF1α, PGK, CAG UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, GAPDH, TCR or RUNX1. In some embodiments of the composition, the obtained genome-engineered iPSCs comprise one or more exogenous polynucleotide encoding safety switch proteins comprising caspase, thymidine kinase, cytosine deaminase, modified EGFR, B-cell CD20, or any combinations thereof. In some other embodiments, the obtained genome-engineered iPSCs comprise two or more same or different safety switch protein encoding exogenous polynucleotides integrated in different safe harbor loci comprising AAVS1, CCR5, ROSA26, collagen, HTRP, H11, beta-2 microglobulin, GAPDH, TCR or RUNX1, or other locus meeting the criteria of a genome safe harbor.

In some other embodiments, the obtained genome-engineered iPSCs comprise a caspase encoding exogenous polynucleotide at AAVS1 locus, and a thymidine kinase encoding exogenous polynucleotide at H11 locus. In yet some other embodiments, the obtained genome-engineered iPSCs comprise one or more in/dels comprised in an endogenous gene associated with targeting modalities; receptors; signaling molecules; transcription factors; drug target candidates; immune response regulation and modulation; and proteins suppressing engraftment, trafficking, homing, viability, self-renewal, persistence, and/or survival of the iPSCs or derivative cells thereof. In some embodiments, the obtained genome-engineered iPSCs comprising one or more in/dels comprises one or more of B2M, TAP1, TAP2, Tapasin, NLRC5, PD1, LAG3, TIM3, RFXANK, CIITA, RFX5, RFXAP, and any gene in the chromosome 6p21 region.

In one embodiment, the non-pluripotent cells of the composition comprise mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells. In another embodiment, the composition further comprises a small molecule composition comprising a MEK inhibitor, a GSK3 inhibitor and a ROCK inhibitor for maintaining pluripotency of the obtained genome-engineered iPSCs.

An additional aspect of the invention comprises a composition for maintaining the pluripotency of genome-engineered iPSCs, and the composition comprises (i) genome-engineered iPSCs, and (ii) a small molecule composition comprising a MEK inhibitor, a GSK3 inhibitor and a ROCK inhibitor. In some embodiments, the genome-engineered iPSCs are obtained from reprogramming genome-engineered non-pluripotent cells, wherein the obtained iPSCs comprise the same targeted integration and/or in/del at selected sites in the genome-engineered non-pluripotent cells. In some embodiments, the genome-engineered iPSCs are obtained from genomically engineering a clonal iPSC or a pool of iPSCs by introducing one or more targeted integration and/or in/del at one or more selected sites. In some other embodiments, the genome-engineered iPSCs are obtained from genome engineering by introducing one or more targeted integration and/or in/del at one or more selected sites to a pool of reprogramming non-pluripotent cells in contact with one or more reprogramming factors and optionally a small molecule composition comprising a TGFβ receptor/ALK inhibitor, a MEK inhibitor, a GSK3 inhibitor and/or a ROCK inhibitor.

Said genome-engineered iPSCs of the composition comprise one or more exogenous polynucleotides encoding safety switch proteins, targeting modality, receptors, signaling molecules, transcription factors, pharmaceutically active proteins and peptides, drug target candidates, or proteins promoting engraftment, trafficking, homing, viability, self-renewal, persistence, and/or survival of the non-pluripotent cell reprogrammed iPSCs or derivative cells thereof, and/or in/dels at one or more endogenous genes associated with targeting modality, receptors, signaling molecules, transcription factors, drug target candidates, immune response regulation and modulation, or proteins suppressing engraftment, trafficking, homing, viability, self-renewal, persistence, and/or survival of the non-pluripotent cell reprogrammed iPSCs or derivative cells thereof. In some embodiments, said one or more exogenous polynucleotides is operatively linked to (1) one or more exogenous promoters comprising CMV, EF1α, PGK, CAG UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, GAPDH, TCR or RUNX1. In some embodiments, the composition further comprises one or more endonuclease capable of selected site recognition for introducing double strand break at selected sites.

In some embodiments, said genome-engineered iPSCs of the composition comprise one or more exogenous polynucleotides encoding safety switch proteins selected from caspase, thymidine kinase, cytosine deaminase, modified EGFR, B-cell CD20, and any combinations thereof. In some embodiments, said genome-engineered iPSCs comprise two or more same or different safety switch protein encoding exogenous polynucleotides integrated in different safe harbor loci comprising AAVS1, CCR5, ROSA26, collagen, HTRP, H11, H11, beta-2 microglobulin, GAPDH, TCR or RUNX1, or other locus meeting the criteria of a genome safe harbor. In some embodiments, said genome-engineered iPSCs comprise a caspase encoding gene at AAVS1 locus, and a thymidine kinase encoding gene at H11 locus. In some embodiments, said genome-engineered iPSCs comprise one or more in/dels comprises B2M, TAP1, TAP2, Tapasin, NLRC5, PD1, LAG3, TIM3, RFXANK, CIITA, RFX5, RFXAP, and any gene in the chromosome 6p21 region. In some embodiments, said genome-engineered iPSCs comprise deletion or reduced expression in at least one of B2M, TAP1, TAP2, Tapasin, NLRC5, PD1, LAG3, TIM3, RFXANK, CIITA, RFX5, RFXAP, and any gene in the chromosome 6p21 region. In some embodiments, said genome-engineered iPSCs of the composition comprise introduced or increased expression in at least one of HLA-E, HLA-G, CD16, 41BBL, CD3, CD4, CD8, CD47, CD113, CD131, CD137, CD80, PDL1, A2AR, CAR, TCR, Fc receptor, an engager, and surface triggering receptor for coupling with bi- or multi-specific or universal engagers. In some embodiments, said genome-engineered iPSCs comprise introduced or increased expression via integrated or non-integrated method for introducing exogenous protein encoding polynucleotides.

In some embodiments, said genome-engineered iPSCs of the composition are HLA class I and/or class II deficient. In some embodiments, said genome-engineered iPSCs of the composition comprise B2M null or low, TAP1 null or low and/or TAP2 null or low. In some embodiments, said genome-engineered iPSCs of the composition comprise integrated or non-integrated exogenous polynucleotide encoding one or more of HLA-E, HLA-G, CD16, 41BBL and PDL1 proteins; or wherein the genome-engineered iPSCs comprise introduced expression of one or more of HLA-E, HLA-G, CD16, 41BBL and PDL1 proteins. In some embodiments, said genome-engineered iPSCs of the composition comprise at least one exogenous polynucleotide encodes high affinity CD16 receptor; at least one exogenous polynucleotide encodes non-cleavable CD16 receptor; at least one exogenous polynucleotide encodes high affinity and non-cleavable CD16 receptor (hnCD16); at least one exogenous polynucleotide encodes non-cleavable HLA-E; or at least one exogenous polynucleotide encodes non-cleavable HLA-G.

In some embodiments, said genome-engineered iPSCs of the composition have improved persistency, increased resistance to immune cells, or increased immune-resistance; or wherein the genome-engineered iPSCs have increased resistance to T and/or NK cells. In some embodiments, said genome-engineered iPSCs of the composition have the potential to differentiate into non-pluripotent cells comprising hematopoietic lineage cells having the same functional targeted genomic editing. In some embodiments, said genome-engineered iPSCs of the composition have the potential to differentiate into mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells.

Additionally provided in the present invention is a pharmaceutical composition comprising (i) one or more populations of genome-engineered iPSCs, modified HLA deficient iPSCs, genome-engineered non-pluripotent cells, genome-engineered hematopoietic lineage cells, modified HLA deficient hematopoietic lineage cells as provided by the methods and composition as disclosed in this invention, or any combinations thereof; and (ii) a pharmaceutically acceptable medium. In some embodiments, said hematopoietic lineage cells mesodermal cells, CD34 cells, hemogenic endothelium cells, hematopoietic stem and progenitor cells, hematopoietic multipotent progenitor cells, T cell progenitors, NK cell progenitors, T cells, NKT cells, NK cells, or B cells.

Further provided is the therapeutic use of the above pharmaceutical composition by introducing the composition to a subject suitable for adoptive cell therapy, wherein the subject has an autoimmune disorder; a hematological malignancy; a solid tumor; cancer, or an infection associated with HIV, RSV, EBV, CMV, adenovirus, or BK polyomavirus.

Yet another aspect of the invention provides a method of manufacturing genome-engineered iPSCs derived non-pluripotent cells therefrom using the methods and compositions provided herein.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIGS. 6A-E are a graphic representation of induced suicide gene mediated killing of hiPSC clones at both pluripotent and differentiated states with CAG-driven iCasp9 targeted into AAVS1 locus. A. Twenty CAG-iCasp9 targeted hiPSC clones were treated with AP1903 (or DMSO control) for 24 hours, and then analyzed for GFP and 7AAD staining by flow cytometry. Flow cytometry plots from clones CAG-C5 and -C38 were also shown in this figure. B. One of fifteen CAG-iCasp9 targeted iPSC clones survived after AP1903 (10 nM) treatment. C. CAG-C5 live cell coverage kinetics on a 10 cm dish after AP1903 (10 nM) treatment. D. CAG-iCasp9 targeted hiPSC clones were induced to differentiate into endoderm, mesoderm or ectoderm cells and each was treated with AP1903, before allowed to recover and differentiating. The replicate wells before treatment and after recovery were stained with crystal violet and imaged. Images from CAG-C5 clone were shown as a representation. E. CAG-iCasp9 targeted hiPSC clones were induced to differentiate into CD34+ cells, which were treated with AP1903 for 48 hours and flow cytometry analyzed for cell death.

FIGS. 7A-E are a graphic representation of in vivo AP1903-induced regression of teratomas derived from iCasp9-iPSC clones. A. Illustration of subcutaneous injection positioning in the NSG mice studies. B. Image of teratomas harvested at day 34 after the parental hiPSC line and CAG-C38 clone were treated with AP1903 (i.p. 200 μg total) on days 7-11. C. Harvested teratomas were measured for volume. D. Harvested teratomas derived from parental hiPSC or CAG-C38 lines stained with Hematoxylin and Eosin. While parental hiPSC line displays majority of tri-lineage differentiated cell types, CAG-C38 appears to consist of mostly highly organized fat-like cells. E. Parental hiPSC line and CAG clones were injected at 4E6 cells and treated with AP1903 (i.p. 200 μg total) on days 40-46. All tumors were routinely measured for volume.

DETAILED DESCRIPTION OF THE INVENTION

Figure 1A:
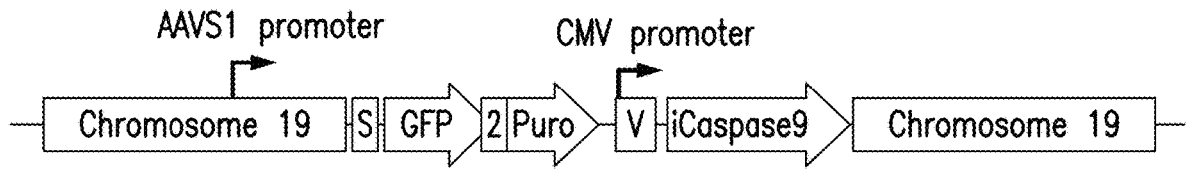
FIGS. 1A-G are a graphic representation of AAVS1 safe harbor targeted insertion of a CMV promoter driven iCasp9 suicide gene and cell response when the suicide gene was activated by AP1903. A. An illustration of a donor construct, AAVS1-G1.0, designed to target the AAVS1 locus. B. Flow cytometry for GFP expression in puromycin selected 293T cells transfected with ZFNs specific to AAVS1 locus and the donor construct. C. Puro-selected 293T cells were subjected to AP1903 (or DMSO control) treatment for 24 hrs. The treated cells were harvested and stained with 7AAD (stains membrane-compromised dying cells) and analyzed by flow cytometry. The 7AAD negative cells (presumably live cells) percentage were plotted for each treatment (n=2). Significant cell death was detected post AP1903 treatment. D. Junction PCR of genomic DNA from puro-selected 293T cells showed the targeted insertion of donor vectors into AAVS1 locus. E. hiPSCs were transfected with ZFNs specific to AAVS1 locus and a donor construct encompassing CMV-driven iCasp9 (AAVS1-G1.0). The puro-resistant cells were analyzed by flow cytometry for GFP expression. Three populations based on the GFP intensity were sorted and expanded for further analysis. F. Sorted and expanded GFP (neg), GFP (low) and GFP (hi) populations were subjected to AP1903 (or DMSO control) treatment for 24 hrs. The treated cells were harvested and stained with 7AAD and analyzed by flow cytometry. The 7AAD negative cells (live cells) percentage were plotted for each treatment. G. Junction PCR of genomic DNA from puro-selected and sorted hiPSCs showed the targeted insertion of donor vectors into AAVS1 locus in GFP (low) but not in GFP (neg) or GFP (hi) populations.

Genomic modification of stem cells, such as hESCs (embryonic stem cell) or iPSCs (induced pluripotent stem cells) include polynucleotide insertion, deletion and substitution. Exogenous gene expression in genome-engineered iPSCs often encounter problems such as gene silencing or reduced gene expression after prolonged clonal expansion of the original genome-engineered iPSCs, after cell differentiation, and in dedifferentiated cell types from the cells derived from the genome-engineered iPSCs. The present invention provides an efficient, reliable, and targeted approach for stably integrating one or more exogenous genes, including suicide genes and other functional modalities to iPSC, and maintaining functional responses of the gene in expanded iPSC and differentiated cells derived from the genome-engineered iPSC. In one embodiment the iPSC is a single cell derived clonal iPSC. In one embodiment, the present invention provides a genetically-encoded inducible "suicide" system suitable for targeted integration at one or more selected sites, which is responsive to specific non-toxic chemical inducer in iPSC, expanded iPSC, and differentiated cells derived therefrom. The invention thus represents an efficient, reliable, and targeted approach for eliminating administered cells without damaging surrounding cells and tissues, suitable for various cellular therapeutics. Further, the present invention also provides a method and system for obtaining a clonal iPSC integrated with multiple genetic modalities relating to reprogramming and dedifferentiation, iPSC differentiation, proteins promoting engraftment, trafficking, homing, migration, cytotoxicity, viability, maintenance, expansion, longevity, self-renewal, persistence, and/or survival of the iPSCs or derivative cells thereof, including but not limited to HSC (hematopoietic stem and progenitor cell), T cell progenitor cells, NK cell progenitor cells, T cells, NKT cells, NK cells. In addition, the present invention describes the identification of a mutation in the icaspase9 gene that renders it refractory to chemical induction and permits the escape from induced cell death, and approaches such as dual suicide genes safe guard system, or biallelic suicide gene insertions to overcome or prevent such escape.

Definitions

Unless defined otherwise, all technical and scientific terms used herein have the same meaning as commonly understood by those of ordinary skill in the art to which the invention belongs. For the purposes of the present invention, the following terms are defined below. The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or 1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta, i.e., are not totipotent.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, the term "mesoderm" refers to one of the three germinal layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34+ hematopoietic cells capable of giving rise to both mature myeloid and lymphoid cell types including T cells, NK cells and B cells. Hematopoietic cells also include various subsets of primitive hematopoietic cells that give rise to primitive erythrocytes, megakarocytes and macrophages.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

"CD4+ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL-2, IL-4 and IL-10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8+ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3− and CD56+, expressing NKG2C and CD57, and optionally, CD16, but lack expression of one or more of the following: PLZF, SYK, FceRγ, and EAT-2. In some embodiments, isolated subpopulations of CD56+NK cells comprise expression of CD16, NKG2C, CD57, NKG2D, NCR ligands, NKp30, NKp40, NKp46, activating and inhibitory KIRs, NKG2A and DNAM-1. CD56+ can be dim or bright expression.

As used herein, the term "NKT cells" or "natural killer T cells" refers to CD1 d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are currently recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or non-invariant type II NKT cells, display a more heterogeneous TCR αβ usage. Type I NKT cells are currently considered suitable for immunotherapy. Adaptive or invariant (type I) NKT cells can be identified with the expression of at least one or more of the following markers, TCR Vα24-Jα18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, tissue, biopsy. The term also includes a cell that is removed from at least one, some or all components as the cell is found in non-naturally occurring environments, for example, culture, cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cells, substantially pure cells and cells cultured in a medium that is non-naturally occurring. Isolated cells may be obtained from separating the desired cells, or populations thereof, from other substances or cells in the environment, or from removing one or more other cell populations or subpopulations from the environment. As used herein, the term "purify" or the like refers to increase purity. For example, the purity can be increased to at least 50%, 60%, 70%, 80%, 90%, 95%, 99%, or 100%.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

As used herein, the term "exogenous" in intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived cells" depending on the context. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSC using genomic editing. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

As used herein, the term "engager" refers to a molecule, e.g. a fusion polypeptide, which is capable of forming a link between an immune cell, e.g. a T cell, a NK cell, a NKT cell, a B cell, a macrophage, a neutrophil, and a tumor cell; and activating the immune cell. Examples of engagers include, but are not limited to, bi-specific T cell engagers (BiTEs), bi-specific killer cell engagers (BiKEs), tri-specific killer cell engagers, or multi-specific killer cell engagers, or universal engagers compatible with multiple immune cell types.

As used herein, the term "surface triggering receptor" refers to a receptor capable of triggering or initiating an immune response, e.g. a cytotoxic response. Surface triggering receptors may be engineered, and may be expressed on effector cells, e.g. a T cell, a NK cell, a NKT cell, a B cell, a macrophage, a neutrophil. In some embodiments, the surface triggering receptor facilitates bi- or multi-specific antibody engagement between the effector cells and specific target cell e.g. a tumor cell, independent of the effector cell's natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers having the same epitope recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some case, and to kill two or more types of tumors in some other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refer to proteins or peptides that are capable of achieving a biological and/or pharmaceutical effect on an organism. A pharmaceutically active protein has healing curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, the cellular signal transduction. Signal transduction refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes but not limited to i) antigen specificity as it related to a unique chimeric antigen receptor (CAR) or T cell receptor (TCR), ii) engager specificity as it related to monoclonal antibodies or bispecific engager, iii) targeting of transformed cell, iv) targeting of cancer stem cell, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in constrast to non-specific or non-selective binding.

The term "adoptive cell therapy" as used herein refers to a cell-based immunotherapy that, as used herein, relates to the transfusion of autologous or allogenic lymphocytes, identified as T or B cells, genetically modified or not, that have been expanded ex vivo prior to said transfusion.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. "Embryoid bodies" are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogeneous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cells proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are deemed as minimal as compared to all three germ layer differentiation in EB.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, "feeder cells" or "feeders" are terms describing cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium.

"Functional" as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level—successful knocked-in, knocked-out, knocked-down gene expression, transgenic or controlled gene expression such as inducible or temporal expression at a desired cell development stage, which is achieved through direct genomic editing or modification, or through "passing-on" via differentiation from or reprogramming of a starting cell that is initially genomically engineered; or (2) at the cell level-successful removal, adding, or altering a cell function/characteristics via (i) gene expression modification obtained in said cell through direct genomic editing, (ii) gene expression modification maintained in said cell through "passing-on" via differentiation from or reprogramming of a starting cell that is initially genomically engineered; (iii) down-stream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

"HLA deficient", including HLA-class I deficient, or HLA-class II deficient, or both, refers to cells that either lack, or no longer maintain, or have reduced level of surface expression of a complete MHC complex comprising a HLA class I protein heterodimer and/or a HLA class II heterodimer, such that the diminished or reduced level is less than the level naturally detectable by other cells or by synthetic methods. HLA class I deficiency can be achieved by functional deletion of any region of the HLA class I locus (chromosome 6p21), or deletion or reducing the expression level of HLA class-I associated genes including, not being limited to, beta-2 microglobulin (B2M) gene, TAP1 gene, TAP2 gene and Tapasin. HLA class II deficiency can be achieved by functional deletion or reduction of HLA-II associated genes including, not being limited to, RFXANK, CIITA, RFX5 and RFXAP. It was unclear, prior to this invention, whether HLA complex deficient or altered iPSCs have the capacity to enter development, mature and generate functional differentiated cells while retaining modulated activity. In addition, it was unclear, prior to this invention, whether HLA complex deficient differentiated cells can be reprogrammed to iPSCs and maintained as pluripotent stem cells while having the HLA complex deficiency. Unanticipated failures during cellular reprogramming, maintenance of pluripotency and differentiation may related to aspects including, but not limited to, development stage specific gene expression or lack thereof, requirements for HLA complex presentation, protein shedding of introduced surface expressing modalities, need for proper and efficient clonal reprogramming, and need for reconfiguration of differentiation protocols.

"Modified HLA deficient iPSC," as used herein, refers to HLA deficient iPSC that is further modified by introducing genes expressing proteins related but not limited to improved differentiation potential, antigen targeting, antigen presentation, antibody recognition, persistence, immune evasion, resistance to suppression, proliferation, costimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 41BB, DAP10, DAP12, CD24, CD3z, 41BBL, CD47, CD113, and PDL1. The cells that are "modified HLA deficient" also include cells other than iPSCs.

"Fc receptors," abbreviated FcR, are classified based on the type of antibody that they recognize. For example, those that bind the most common class of antibody, IgG are called Fc-gamma receptors (FcγR), those that bind IgA are called Fc-alpha receptors (FcαR) and those that bind IgE are called Fc-epsilon receptors (FcεR). The classes of FcR's are also distinguished by the cells that express them (macrophages, granulocytes, natural killer cells, T and B cells) and the signalling properties of each receptor. Fc-gamma receptors (FcγR) includes several members, FcγRI (CD64), FcγRIIA (CD32), FcγRIIB (CD32), FcγRIIIA (CD16a), FcγRIIIB (CD16b), which differ in their antibody affinities due to their different molecular structure CD16 has been identified as two isoforms, Fc receptors FcγRIIIa (CD16a) and FcγRIIIb (CD16b). CD16a is a transmembrane protein expressed by NK cells, which bindes monomeric IgG attached to target cells to activate NK cells and facilitate antibody-dependent cell-mediated cytotoxicity (ADCC). "High affinity CD16," "non-cleavable CD16," or "high affinity non-cleavable CD16," as used herein, refers to a variant of CD16. The wildtype CD16 has low affinity and is subject to extodomain shedding, a proteolytic cleavage process that regulates the cells surface density of various cell surface molecules on leukocytes upon NK cell activation. F176V and F158V are exemplary CD16 variants having high affinity; whereas S197P variant is an example of non-cleavable version of CD16.

I. Methods for Targeted Genome Editing at Selected Locus in iPSC Cells

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted at the insertion site during targeted editing, an endogenous gene comprising the affected sequence may be knocked-out or knocked-down due to the sequence deletion. Therefore, targeted editing may also be used to disrupt endogenous gene expression. Similarly used herein is the term "targeted integration," referring to a process involving insertion of one or more exogenous sequences, with or without deletion of an endogenous sequence at the insertion site. In comparison, randomly integrated genes are subject to position effects and silencing, making their expression unreliable and unpredictable. For example, centromeres and sub-telomeric regions are particularly prone to transgene silencing. Reciprocally, newly integrated genes may affect the surrounding endogenous genes and chromatin, potentially altering cell behavior or favoring cellular transformation. Therefore, inserting exogenous DNA in a pre-selected locus such as a safe harbor locus, or genomic safe harbor (GSH) is important for safety, efficiency, copy number control, and for reliable gene response control.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration."

Available endonucleases capable of introducing specific and targeted DSBs include, but not limited to, zinc-finger nucleases (ZFN), transcription activator-like effector nucleases (TALEN), RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases is also a promising tool for targeted integration.

ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a targeted Spo11 nuclease, a polypeptide comprising a Spo11 polypeptide having nuclease activity fused to a DNA binding domain, e.g. a zinc finger DNA binding domain, a TAL effector DNA binding domain, etc. that has specificity for a DNA sequence of interest. See, for example, U.S. Application No. 61/555,857, the disclosure of which is incorporated herein by reference.

Additional examples of targeted nucleases suitable for the present invention include, but not limited to Bxb1, phiC31, R4, PhiBT1, and Wβ/SPBc/TP901-1, whether used individually or in combination.

Other non-limiting examples of targeted nucleases include naturally occurring and recombinant nucleases, e.g. CRISPR/Cas9, restriction endonucleases, meganucleases homing endonucleases, and the like.

CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction.

DICE mediated insertion uses a pair of recombinases, for example, phiC31 and Bxb1, to provide unidirectional integration of an exogenous DNA that is tightly restricted to each enzymes' own small attB and attP recognition sites. Because these target att sites are not naturally present in mammalian genomes, they must be first introduced into the genome, at the desired integration site. See, for example, U.S. Application Publication No. 2015/0140665, the disclosure of which is incorporated herein by reference.

One aspect of the present invention provides a construct comprising one or more exogenous polynucleotides for targeted genome integration. In one embodiment, the construct further comprises a pair of homologous arm specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Promising sites for targeted integration include, but are not limited to, safe harbor loci, or genomic safe harbor (GSH), which are intragenic or extragenic regions of the human genome that, theoretically, are able to accommodate predictable expression of newly integrated DNA without adverse effects on the host cell or organism. A useful safe harbor must permit sufficient transgene expression to yield desired levels of the vector-encoded protein or non-coding RNA. A safe harbor also must not predispose cells to malignant transformation nor alter cellular functions. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed.

Suitable sites for human genome editing, or specifically, targeted integration, include, but are not limited to the adeno-associated virus site 1 (AAVS1), the chemokine (CC motif) receptor 5 (CCR5) gene locus and the human orthologue of the mouse ROSA26 locus. Additionally, the human orthologue of the mouse H11 locus may also be a suitable site for insertion using the composition and method of targeted integration disclosed herein. Further, collagen and HTRP gene loci may also be used as safe harbor for targeted integration. However, validation of each selected site has been shown to be necessary especially in stem cells for specific integration events, and optimization of insertion strategy including promoter election, exogenous gene sequence and arrangement, and construct design is often needed.

For targeted in/dels, the editing site is often comprised in an endogenous gene whose expression and/or function is intended to be disrupted. In one embodiments, the endogenous gene comprising a targeted in/del is associated with immune response regulation and modulation. In some other embodiments, the endogenous gene comprising a targeted in/del is associated with targeting modality, receptors, signaling molecules, transcription factors, drug target candidates, immune response regulation and modulation, or proteins suppressing engraftment, trafficking, homing, viability, self-renewal, persistence, and/or survival of stem cells and/or progenitor cells, and the derived cells therefrom.

As such, one aspect of the present invention provides a method of targeted integration in a selected locus including genome safe harbor or a preselected locus known or proven to be safe and well-regulated for continuous or temporal gene expression such as the B2M, TAP1, TAP2 or tapasin locus as provided herein. In one embodiment, the genome safe harbor for the method of targeted integration comprises one or more desired integration site comprising AAVS1, CCR5, ROSA26, collagen, HTRP, H11, beta-2 microglobulin, GAPDH, TCR or RUNX1, or other loci meeting the criteria of a genome safe harbor. In one embodiment, the method of targeted integration in a cell comprising introducing a construct comprising one or more exogenous polynucleotides to the cell, and introducing a construct comprising a pair of homologous arm specific to a desired integration site and one or more exogenous sequence, to enable site specific homologous recombination by the cell host enzymatic machinery, wherein the desired integration site comprises AAVS1, CCR5, ROSA26, collagen, HTRP, H11, beta-2 microglobulin, GAPDH, TCR or RUNX1, or other loci meeting the criteria of a genome safe harbor.

In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration, wherein the desired integration site comprises AAVS1, CCR5, ROSA26, collagen, HTRP, H11, beta-2 microglobulin, GAPDH, TCR or RUNX1, or other loci meeting the criteria of a genome safe harbor.

Further, as provided herein, the above method for targeted integration in a safe harbor is used to insert any polynucleotide of interest, for example, polynucleotides encoding safety switch proteins, targeting modality, receptors, signaling molecules, transcription factors, pharmaceutically active proteins and peptides, drug target candidates, and proteins promoting engraftment, trafficking, homing, viability, self-renewal, persistence, and/or survival of stem cells and/or progenitor cells. In some other embodiments, the construct comprising one or more exogenous polynucleotides further comprises one or more marker genes. In one embodiment, the exogenous polynucleotide in a construct of the invention is a suicide gene encoding safety switch proteins. Suitable suicide gene systems for induced cell death include, but not limited to Caspase 9 (or caspase 3 or 7) and AP1903; thymidine kinase (TK) and ganciclovir (GCV); cytosine deaminase (CD) and 5-fluorocytosine (5-FC). Additionally, some suicide gene systems are cell type specific, for example, the genetic modification of T lymphocytes with the B-cell molecule CD20 allows their elimination upon administration of mAb Rituximab. Further, modified EGFR containing epitope recognized by cetuximab can be used to deplete genetically engineered cells when the cells are exposed to cetuximab. As such, one aspect of the invention provides a method of targeted integration of one or more suicide genes encoding safety switch proteins selected from caspase 9 (caspase 3 or 7), thymidine kinase, cytosine deaminase, modified EGFR, and B-cell CD20.

In some embodiments, one or more exogenous polynucleotides integrated by the method herein are driven by operatively linked exogenous promoters comprised in the construct for targeted integration. The promoters may be inducible, or constructive, and may be temporal-, tissue- or cell type-specific. Suitable constructive promoters for methods of the invention include, but not limited to, cytomegalovirus (CMV), elongation factor 1α (EF1α), phosphoglycerate kinase (PGK), hybrid CMV enhancer/chicken (3-actin (CAG) and ubiquitin C (UBC) promoters. In one embodiment, the exogenous promoter is CAG The exogenous polynucleotides integrated by the method herein may be driven by endogenous promoters in the host genome, at the integration site. In one embodiment, the method of the invention is used for targeted integration of one or more exogenous polynucleotides at AAVS1 locus in the genome of a cell. In one embodiment, at least one integrated polynucleotide is driven by the endogenous AAVS1 promoter. In another embodiment, the method of the invention is used for targeted integration at ROSA26 locus in the genome of a cell. In one embodiment, at least one integrated polynucleotide is driven by the endogenous ROSA26 promoter. In still another embodiment, the method of the invention is used for targeted integration at H11 locus in the genome of a cell. In one embodiment, at least one integrated polynucleotide is driven by the endogenous H11 promoter. In another embodiment, the method of the invention is used for targeted integration at collagen locus in the genome of a cell. In one embodiment, at least one integrated polynucleotide is driven by the endogenous collagen promoter. In still another embodiment, the method of the invention is used for targeted integration at HTRP locus in the genome of a cell. In one embodiment, at least one integrated polynucleotide is driven by the endogenous HTRP promoter. Theoretically, only correct insertions at the desired location would enable gene expression of an exogenous gene driven by an endogenous promoter.

In some embodiments, the one or more exogenous polynucleotides comprised in the construct for the methods of targeted integration are driven by one promoter. In some embodiments, the construct comprises one or more linker sequences between two adjacent polynucleotides driven by the same promoter to provide greater physical separation between the moieties and maximize the accessibility to enzymatic machinery. The linker peptide of the linker sequences may consist of amino acids selected to make the physical separation between the moieties (exogenous polynucleotides, and/or the protein or peptide encoded therefrom) more flexible or more rigid depending on the relevant function. The linker sequence may be cleavable by a protease or cleavable chemically to yield separate moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the moiety with respect to another adjacent moiety for the moieties to function properly. The linker may also be a simple amino acid sequence of a sufficient length to prevent any steric hindrance between the moieties. In addition, the linker sequence may provide for post-translational modification including, but not limited to, e.g., phosphorylation sites, biotinylation sites, sulfation sites, γ-carboxylation sites, and the like. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a 2A linker sequence allows for two separate proteins to be produced from a single translation. Suitable linker sequences can be readily identified empirically. Additionally, suitable size and sequences of linker sequences also can be determined by conventional computer modeling techniques. In one embodiment, the linker sequence encodes a self-cleaving peptide. In one embodiment, the self-cleaving peptide is 2A. In some other embodiments, the linker sequence provides an Internal Ribosome Entry Sequence (IRES). In some embodiments, any two consecutive linker sequences are different.

The method of introducing into cells a construct comprising exogenous polynucleotides for targeted integration can be achieved using a method of gene transfer to cells known per se. In one embodiment, the construct comprises backbones of viral vectors such as adenovirus vector, adeno-associated virus vector, retrovirus vector, lentivirus vector, Sendai virus vector. In some embodiments, the plasmid vectors are used for delivering and/or expressing the exogenous polynucleotides to target cells (e.g., pA1-11, pXT1, pRc/CMV, pRc/RSV, pcDNAI/Neo) and the like. In some other embodiments, the episomal vector is used to deliver the exogenous polynucleotide to target cells. In some embodiments, recombinant adeno-associated viruses (rAAV) can be used for genetic engineering to introduce insertions, deletions or substitutions through homologous recombinations. Unlike lentiviruses, rAAVs do not integrate into the host genome. In addition, episomal rAAV vectors mediate homology-directed gene targeting at much higher rates compared to transfection of conventional targeting plasmids. In some embodiments, an AAV6 or AAV2 vector is used to introduce insertions, deletions or substitutions in a target site in the genome of iPSCs.

II. Method of Obtaining and Maintaining Genome-Engineered iPSCs

The present invention provides a method of obtaining and maintaining genome-engineered iPSCs comprising one or more targeted editing at one or more desired sites, wherein the targeted editing remain intact and functional in expanded genome-engineered iPSCs or the iPSCs derived non-pluripotent cells at the respective selected editing site. The targeted editing introduces into the genome iPSC insertions, deletions, and/or substitutions, i.e., targeted integration and/or in/dels at selected sites.

In particular embodiments, the genome-engineered iPSCs comprising one or more targeted editing at one or more selected sites are maintained, passaged and expanded as single cells for an extended period in the cell culture medium shown in Table 1 as Fate Maintenance Medium (FMM), wherein the iPSCs retain the targeted editing and functional modification at the selected site(s). The components of the medium may be present in the medium in amounts within an optimal range shown in Table 1. The iPSCs cultured in FMM have been shown to continue to maintain their undifferentiated, and ground or naïve, profile; genomic stability without the need for culture cleaning or selection; and are readily to give rise to all three somatic lineages, in vitro differentiation via embryoid bodies or monolayer (without formation of embryoid bodies); and in vivo differentiation by teratoma formation. See, for example, U.S. Application No. 61/947,979, the disclosure of which is incorporated herein by reference.

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum | Knockout Serum | Knockout Serum |
|  | N2 |  |
|  | B27 |  |
| Glutamine | Glutamine | Glutamine (1x) |
| Non-Essential Amino Acids | Non-Essential Amino Acids | Non-Essential Amino Acids |
| β-mercaptoethanol | β-mercaptoethanol | β-mercaptoethanol |
| bFGF (0.2-50 ng/mL) | bFGF (2-500 ng/mL) | bFGF (2-500 ng/mL) |
|  | LIF (0.2-50 ng/mL) | LIF (0.2-50 ng/mL) |
|  | Thiazovivin (0.1-25 μM) | Thiazovivin (0.1-25 μM) |
|  | PD0325901 (0.005-2 μM) | PD0325901 (0.005-2 μM) |
|  | CHIR99021 (0.02-5 μM) | CHIR99021 (0.02-5 μM) |
|  | SB431542 (0.04-10 μM) |  |
| In combination with MEF | Feeder-free, in combination with Matrigel ™ or Vitronectin ||

In some embodiments, the genome-engineered iPSCs comprising one or more targeted integration and/or in/dels are maintained, passaged and expanded in a medium comprising MEKi, GSKi, and ROCKi, and free of, or essentially free of, TGFβ receptor/ALK5 inhibitors, wherein the iPSCs retain the intact and functional targeted editing at the selected sites. In some embodiments, the site for targeted integration comprises AAVS1, CCR5, ROSA26, collagen, HTRP, H11, beta-2 microglobulin, GAPDH, TCR or RUNX1, or other loci meeting the criteria of a genome safe harbor. In some embodiments, the site for targeted in/dels is selected from endogenous gene associated with targeting modalities, receptors, signaling molecules, transcription factors, drug target candidates; immune response regulation and modulation; or proteins suppressing engraftment, trafficking, homing, viability, self-renewal, persistence, and/or survival of the iPSCs or derivative cells thereof. In some embodiments, the maintained, passaged and expanded genome-engineered iPSCs comprise one or more inducible suicide genes integrated at one or more desired integration sites comprising AAVS1, CCR5, ROSA26, collagen, HTRP, H11, beta-2 microglobulin, GAPDH, TCR or RUNX1, or other loci meeting the criteria of a genome safe harbor. In some other embodiments, the maintained, passaged and expanded genome-engineered iPSCs comprise polynucleotides encoding safety switch proteins, targeting modality, receptors, signaling molecules, transcription factors, pharmaceutically active proteins and peptides, drug target candidates, or proteins promoting engraftment, trafficking, homing, viability, self-renewal, persistence, and/or survival of stem cells and/or progenitor cells at the same or different desired integration site.

In some embodiments, the genome-engineered iPSC comprises one or more exogenous polynucleotides further comprises in/dels in one or more endogenous genes. In some embodiments, the in/del comprised in an endogenous gene results in disruption of gene expression. In some embodiments, the in/del comprised in an endogenous gene results in knock-out of the edited gene. In some embodiment, the in/del comprised in an endogenous gene results in knockdown of the edited gene. In some embodiments, the genome-engineered iPSC comprising one or more exogenous polynucleotides at selected site(s) may further comprise one or more targeted editing including in/dels at selected site(s). In some embodiments, the in/del is comprised in one or more endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, B2M, PD1, TAP1, TAP2, Tapasin, TCR genes. In one embodiment, the genome-engineered iPSC comprising one or more exogenous polynucleotides at selected site(s) further comprises a targeted editing in B2M (beta-2-microglobulin) encoding gene.

Another aspect of the invention provides a method of generating genome-engineered iPSCs through targeted editing of iPSCs; or through first generating genome-engineered non-pluripotent cells by targeted editing, and then reprogramming the selected/isolated genome-engineered non-pluripotent cells to obtain iPSCs comprising the same targeted editing as the non-pluripotent cells. A further aspect of the invention provides genome-engineering non-pluripotent cells which are concurrently undergoing reprogramming by introducing targeted integration and/or targeted in/dels to the cells, wherein the contacted non-pluripotent cells are under sufficient conditions for reprogramming, and wherein the conditions for reprogramming comprise contacting non-pluripotent cells with one or more reprogramming factors and small molecules. In various embodiments of the method for concurrent genome-engineering and reprogramming, the targeted integration and/or targeted in/dels may be introduced to the non-pluripotent cells prior to, or essentially concomitantly with, initiating reprogramming by contacting the non-pluripotent cells with one or more reprogramming factors and small molecules.

In some embodiments, to concurrently genome-engineer and reprogram non-pluripotent cells, the targeted integration and/or in/dels may also be introduced to the non-pluripotent cells after the multi-day process of reprogramming is initiated by contacting the non-pluripotent cells with one or more reprogramming factors and small molecules, and wherein the vectors carrying the constructs are introduced before the reprogramming cells present stable expression of one or more endogenous pluripotent genes including but not limited to SSEA4, Tra181 and CD30.

In some embodiments, the reprogramming is initiated by contacting the non-pluripotent cells with at least one reprogramming factor, and optionally a combination of a TGFβ receptor/ALK inhibitor, a MEK inhibitor, a GSK3 inhibitor and a ROCK inhibitor (FRM; Table 1). In some embodiments, the genome-engineered iPSCs through any methods above are further maintained and expanded using a mixture of comprising a combination of a MEK inhibitor, a GSK3 inhibitor and a ROCK inhibitor (FMM; Table 1).

In some embodiments of the method of generating genome-engineered iPSCs, the method comprises: genomic engineering an iPSC by introducing one or more targeted integration and/or in/dels into iPSCs to obtain genome-engineered iPSCs at selected sites. Alternatively, the method of generating genome-engineered iPSCs comprises: (a) introducing one or more targeted editing into non-pluripotent cells to obtain genome-engineered non-pluripotent cells comprising targeted integration and/or in/dels at selected sites, and (b) contacting the genome-engineered non-pluripotent cells with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted integration and/or in/dels at selected sites. Alternatively, the method of generating genome-engineered iPSCs comprises: (a) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate the reprogramming of the non-pluripotent cells; (b) introducing one or more targeted integration and/or in/dels into the reprogramming non-pluripotent cells for genome-engineering; and (c) obtaining clonal genome-engineered iPSCs comprising targeted integration and/or in/dels at selected sites.

The reprogramming factors are selected from the group consisting of OCT4, SOX2, NANOG KLF4, LIN28, C-MYC, ECAT1, UTF1, ESRRB, SV40LT, HESRG CDH1, TDGF1, DPPA4, DNMT3B, ZIC3, L1TD1, and any combinations thereof. The one or more reprogramming factors may be in a form of polypeptide. The reprogramming factors may also be in a form of polynucleotides, and thus are introduced to the non-pluripotent cells by vectors such as, a retrovirus, a Sendai virus, an adenovirus, an episome, and a mini-circle. In particular embodiments, the one or more polynucleotides encoding at least one reprogramming factor are introduced by a lentiviral vector. In some embodiments, the one or more polynucleotides introduced by an episomal vector. In various other embodiments, the one or more polynucleotides are introduced by a Sendai viral vector.

In some embodiments, the non-pluripotent cells are transferred with multiple constructs comprising different exogenous polynucleotides and/or different promoters by multiple vectors for targeted integration at the same or different selected sites. These exogenous polynucleotides may comprise a suicide gene, or a gene encoding targeting modality, receptors, signaling molecules, transcription factors, pharmaceutically active proteins and peptides, drug target candidates, or a gene encoding a protein promoting engraftment, trafficking, homing, viability, self-renewal, persistence, and/or survival of the iPSCs or derivative cells thereof. In some embodiments, the exogenous polynucleotides encode RNA, including but not limited to siRNA, shRNA, miRNA and antisense nucleic acids. These exogenous polynucleotides may be driven by one or more promoters selected form the group consisting of constitutive promoters, inducible promoters, temporal-specific promoters, and tissue or cell type specific promoters. Accordingly, the polynucleotides are expressible when under conditions that activate the promoter, for example, in the presence of an inducing agent or in a particular differentiated cell type. In some embodiments, the polynucleotides are expressed in iPSCs and/or in cells differentiated from the iPSCs. In one embodiment, one or more suicide gene is driven by a constitutive promoter, for example Capase-9 driven by CAG These constructs comprising different exogenous polynucleotides and/or different promoters can be transferred to non-pluripotent cells either simultaneously or consecutively. The non-pluripotent cells subjecting to targeted integration of multiple constructs can simultaneously contact the one or more reprogramming factors to initiate the reprogramming concurrently with the genomic engineering, thereby obtaining genome-engineered iPSCs comprising multiple targeted integration in the same pool of cells. As such, this robust method enables a concurrent reprogramming and engineering strategy to derive a clonal genomically engineered hiPSC with multiple modalities integrated to one or more selected target sites.

In some embodiments, the non-pluripotent cells are introduced with one or more in/dels at selected sites including one or more endogenous genes. In some embodiments, the non-pluripotent cells comprising one or more in/dels further comprises one or more targeted integrations described above. In some embodiments, the in/del comprised in an endogenous gene results in disruption of gene expression. In some embodiments, the in/del comprised in an endogenous gene results in knock-out of the edited gene. In some embodiment, the in/del comprised in an endogenous gene results in knock-down of the edited gene. In some embodiments, the genome-engineered iPSC comprising one or more exogenous polynucleotides at selected site(s) may further comprise one or more targeted editing including in/dels at selected site(s). In some embodiments, the in/del is comprised in one or more endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, B2M, PD1, TAP1, TAP2, Tapasin, TCR genes. In one embodiment, the genome-engineered iPSC comprising one or more exogenous polynucleotides at selected site(s) further comprises a targeted editing in B2M (beta-2-microglobulin) encoding gene.

III. A Method of Obtaining Genetically Engineered Non-Pluripotent Cells by Differentiating Genome-Engineered iPSC A further aspect of the present invention provides a method of in vivo differentiation of genome-engineered iPSC by teratoma formation, wherein the differentiated cells derived in vivo from the genome-engineered iPSCs retain the intact and functional targeted editing including targeted integration and/or in/dels at the desired site(s). In some embodiments, the differentiated cells derived in vivo from the genome-engineered iPSCs via teratoma comprise one or more inducible suicide genes integrated at one or more desired site comprising AAVS1, CCR5, ROSA26, collagen, HTRP H11, beta-2 microglobulin, GAPDH, TCR or RUNX1, or other loci meeting the criteria of a genome safe harbor. In some other embodiments, the differentiated cells derived in vivo from the genome-engineered iPSCs via teratoma comprise polynucleotides encoding targeting modality, or encoding proteins promoting trafficking, homing, viability, self-renewal, persistence, and/or survival of stem cells and/or progenitor cells. In some embodiments, the differentiated cells derived in vivo from the genome-engineered iPSCs via teratoma comprising one or more inducible suicide genes further comprises one or more in/dels in endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, B2M, PD1, TAP1, TAP2, Tapasin, TCR genes. In one embodiment, the genome-engineered iPSC comprising one or more exogenous polynucleotides at selected site(s) further comprises a targeted editing in B2M (beta-2-microglobulin) encoding gene.

In particular embodiments, the genome-engineered iPSCs comprising one or more targeted editing at selected site(s) as provided herein are used to derive hematopoietic cell lineages or any other specific cell types in vitro, wherein the derived non-pluripotent cells retain the functional targeted editing at the selected site(s). In one embodiment, the genome-engineered iPSC-derived cells include, but not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, and B cells, wherein these cells derived from the genome-engineered iPSCs retain the functional targeted editing at the desired site(s).

Applicable differentiation methods and compositions for obtaining iPSC-derived hematopoietic cell lineages include those depicted in, for example, International Application No. PCT/US2016/044122, the disclosure of which is incorporated herein by reference. As provided, the methods and compositions for generating hematopoietic cell lineages are through definitive hemogenic endothelium (HE) derived from pluripotent stem cells, including hiPSCs under serum-free, feeder-free, and/or stromal-free conditions and in a scalable and monolayer culturing platform without the need of EB formation. Cells that may be differentiated according to the provided methods range from pluripotent stem cells, to progenitor cells that are committed to a particular terminally differentiated cell and transdifferentiated cells, cells of various lineages directly transitioned to hematopoietic fate without going through a pluripotent intermediate. Similarly, the cells produced by differentiation of stem cells range from multipotent stem or progenitor cells to terminally differentiated stem cells, and all intervening hematopoietic cell lineages.

The methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

The provided monolayer differentiation platform facilitates differentiation towards definitive hemogenic endothelium resulting in the derivation of hematopoietic stem cells and differentiated progeny such as T, B, NKT and NK cells. The monolayer differentiation strategy combines enhanced differentiation efficiency with large-scale expansion enables the delivery of therapeutically relevant number of pluripotent stem cell-derived hematopoietic cells for various therapeutic applications. Further, the monolayer culturing using the methods provided herein leads to functional hematopoietic lineage cells that enable full range of in vitro differentiation, ex vivo modulation, and in vivo long term hematopoietic self-renewal, reconstitution and engraftment. As provided, the iPSC derived hematopoietic lineage cells include, but not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

The method for directing differentiation of pluripotent stem cells into cells of a definitive hematopoietic lineage, wherein the method comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSC are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies, and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−. In some embodiments, the definitive hemogenic endothelium cells are CD34+CXCR4−CD73−. In some embodiments, the definitive hemogenic endothelium cells are CD34+CD43−CD93−. In some embodiments, the definitive hemogenic endothelium cells are CD34+CD93−.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are CD34+CD45+CD7+. In some embodiments of the method, the pluripotent stem cell-derived T cell progenitors are CD45+CD7+.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are CD3–CD45+CD56+CD7+. In some embodiments, the pluripotent stem cell-derived NK cells are CD3–CD45+CD56+, and optionally further defined by NKp46+, CD57+ and CD16+.

Therefore, using the above differentiation methods, one may obtain one or more population of iPSC derived hematopoietic cells (i) CD34+HE cells (iCD34), using one or more culture medium selected from iMPP-A, iTC-A2, iTC-B2, iNK-A2, and iNK-B2; (ii) definitive hemogenic endothelium (iHE), using one or more culture medium selected from iMPP-A, iTC-A2, iTC-B2, iNK-A2, and iNK-B2; (iii) definitive HSCs, using one or more culture medium selected from iMPP-A, iTC-A2, iTC-B2, iNK-A2, and iNK-B2; (iv) multipotent progenitor cells (iMPP), using iMPP-A; (v) T cell progenitors (ipro-T), using one or more culture medium selected from iTC-A2, and iTC-B2; (vi) T cells (iTC), using iTC-B2; (vii) NK cell progenitors (ipro-NK), using one or more culture medium selected from iNK-A2, and iNK-B2; and/or (viii) NK cells (iNK), and iNK-B2. In some embodiments, the medium:
  a. iCD34-C comprises a ROCK inhibitor, one or more growth factors and cytokines selected from the group consisting of bFGF, VEGF, SCF, IL6, IL11, IGF, and EPO, and optionally, a Wnt pathway activator; and is free of TGFβ receptor/ALK inhibitor;
  b. iMPP-A comprises a BMP activator, a ROCK inhibitor, and one or more growth factors and cytokines selected from the group consisting of TPO, IL3, GMCSF, EPO, bFGF, VEGF, SCF, IL6, Flt3L and IL11;
  c. iTC-A2 comprises a ROCK inhibitor; one or more growth factors and cytokines selected from the group consisting of SCF, Flt3L, TPO, and IL7; and optionally, a BMP activator;
  d. iTC-B2 comprises one or more growth factors and cytokines selected from the group consisting of SCF, Flt3L, and IL7; wherein the composition is free of one or more of VEGF, bFGF, BMP activators, and ROCK inhibitors;
  e. iNK-A2 comprises a ROCK inhibitor, and one or more growth factors and cytokines selected from the group consisting of SCF, Flt3L, TPO, IL3, IL7, and IL15; and optionally, a BMP activator, and
  f. iNK-B2 comprises one or more growth factors and cytokines selected from the group consisting of SCF, Flt3L, IL7 and IL15.

In some embodiments, the genome-engineered iPSC-derived cells obtained from the above methods comprise one or more inducible suicide gene integrated at one or more desired integration sites comprising AAVS1, CCR5, ROSA26, collagen, HTRP, H11, beta-2 microglobulin, GAPDH, TCR or RUNX1, or other loci meeting the criteria of a genome safe harbor. In some other embodiments, the genome-engineered iPSC-derived cells comprise polynucleotides encoding safety switch proteins, targeting modality, receptors, signaling molecules, transcription factors, pharmaceutically active proteins and peptides, drug target candidates, or proteins promoting trafficking, homing, viability, self-renewal, persistence, and/or survival of stem cells and/or progenitor cells. In some embodiments, the genome-engineered iPSC-derived cells comprising one or more suicide genes further comprise one or more in/del comprised in one or more endogenous genes associated with immune response regulation and mediation, including, but not limited to, check point genes, endogenous T cell receptor genes, and MHC class I suppressor genes. In one embodiment, the genome-engineered iPSC-derived cells comprising one or more suicide genes further comprise an in/del in B2M gene, wherein the B2M is knocked out.

Additionally, applicable dedifferentiation methods and compositions for obtaining genomic-engineered hematopoietic cells of a first fate to genomic-engineered hematopoietic cells of a second fate include those depicted in, for example, International Publication No. WO2011/159726, the disclosure of which is incorporated herein by reference. The method and composition provided therein allows partially reprogramming a starting non-pluripotent cell to a non-pluripotent intermediate cell by limiting the expression of endogenous Nanog gene during reprogramming; and subjecting the non-pluripotent intermediate cell to conditions for differentiating the intermediate cell into a desired cell type.

IV. Compositions for Targeted Integration at Selected Loci to Incorporate Genes of Interest in iPSC Cells In view of the above, the present invention provides a construct for targeted integration of one or more exogenous polynucleotides into a genome of induced pluripotent stem cells (iPSCs) at a selected site, with or without deletion of any endogenous sequence at the site of integration. In one embodiment, the construct comprises at least one exogenous promoter operatively linked to one or more exogenous polynucleotides expressing one or more proteins of interest. In one embodiment, the construct is transferred to iPSCs by a vector for targeted integration. In another embodiment, the construct is transferred to non-pluripotent cells by a vector for targeted integration, and the non-pluripotent cells are then subjected to reprogramming to obtain genome-engineered iPSCs. By either approach, the construct remains integrated and the exogenous polynucleotides are functional in iPSC obtained from reprogramming or vector transferring, in subsequently expanded iPSCs, in differentiated cells derived from the iPSCs, and in dedifferentiated cells derived therefrom.

In some embodiments, the construct comprising at least one exogenous promoter operatively linked to one or more exogenous polynucleotides further comprises homology arms specific to a selected site, and the homology arms flank the promoter and exogenous polynucleotides of interest in the construct. This embodiment of the construct enable a nuclease-independent targeted integration strategy. In some embodiments the exogenous promoter is CAG In some embodiments, the one or more exogenous polynucleotides comprised in the construct having at least one exogenous promoter are linked to each other by a linker sequence. In some embodiments, the linker sequence encodes a self-cleaving peptide. In other embodiments, the linker sequence provides an Internal Ribosome Entry Sequence (IRES). In some embodiments, the one or more exogenous polynucleotides in the construct are polycistronic.

Some embodiments of the construct comprising one or more exogenous promoters and operatively linked one or more exogenous polynucleotides further comprises at least one polynucleotide encoding a marker. In some embodiments, the at least one polynucleotide encoding a marker is driven by an endogenous promoter at the selected site. In one embodiment, one polynucleotide encodes fluorescent protein. In another embodiment, one polynucleotide is a puromycin-resistance gene.

In some embodiments, the construct comprising operatively linked polynucleotides further comprises components enabling targeted integration at a safe harbor locus comprising AAVS1, CCR5, ROSA26, collagen, HTRP, H11, beta-2 microglobulin, GAPDH, TCR or RUNX1, or other loci meeting the criteria of a genome safe harbor. In some embodiments, the safe harbor locus is selected from the group consisting of AAVS1, CCR5, ROSA26, collagen, HTRP, H11, beta-2 microglobulin, GAPDH, TCR and RUNX1.

The construct comprising operatively linked polynucleotides may comprise one or more polynucleotides encoding safety switch proteins, targeting modality, receptors, signaling molecules, transcription factors, pharmaceutically active proteins and peptides, drug target candidates, or proteins promoting engraftment, trafficking, homing, viability, self-renewal, self-renewal, persistence, and/or survival of the genome-engineered iPSCs or derivative cells thereof. In some embodiments, the one or more polynucleotides are driven by the same promoter. In some embodiments, the one or more polynucleotides are driven by one or more different promoters selected form the group consisting of constitutive promoters, inducible promoters, temporal-specific promoters, and tissue or cell type specific promoters. In some embodiments, the one or more polynucleotides are integrated in the same selected safe harbor locus. In some embodiments, the one or more polynucleotides are integrated in different selected safe harbor loci. In one particular embodiment, one or more of the exogenous polynucleotides operatively linked to an exogenous or endogenous promoter encode one or more safety switch proteins. The safety switch proteins may be selected from the group consisting of caspase 9 (or caspase 3 or 7), thymidine kinase, cytosine deaminase, modified EGFR, and B-cell CD20. In one embodiment, the suicide gene comprised in the construct encodes caspase-9. In one embodiment, the suicide gene comprised in the construct encodes thymidine kinase. In some embodiments, the construct is for targeted integration at one of AAVS1, CCR5, ROSA26, collagen, HTRP, H11, beta-2 microglobulin, GAPDH, TCR or RUNX1, and other loci meeting the criteria of a genome safe harbor. In some embodiments, the construct is for targeted integration at AAVS1. In some embodiments, the construct is for targeted integration at ROSA26. In some embodiments, the construct is for targeted integration at H11.

The present invention also provides a genome-engineered iPSC which comprises one or more exogenous polynucleotides, and/or in/dels at selected site(s). In some embodiments, the genome-engineered iPSC is obtained through construct transferring by a vector to iPSCs, and/or editing using NHEJ. In some other embodiments, the genome-engineered iPSC is obtained from reprogramming non-pluripotent cells with targeted editing including targeted integration and/or in/dels. In yet some other embodiments, the genome-engineered iPSC is obtained from concurrently reprogramming and genome-engineering non-pluripotent cells using reprogramming factors, reprogramming small molecules, and/or vectors carrying the constructs for targeted integration of polynucleotides of interest.

In some embodiments, the genome-engineered iPSC comprises one or more exogenous polynucleotides encoding proteins selected from safety switch proteins, targeting modalities, receptors, signaling molecules, transcription factors, pharmaceutically active proteins and peptides, drug target candidates; or proteins promoting engraftment, trafficking, homing, viability, self-renewal, persistence, and/or survival of the iPSCs or derivative cells thereof. In some embodiments, the genome-engineered iPSC comprises in/dels in one or more endogenous genes encoding proteins associated with targeting modalities, receptors, signaling molecules, transcription factors, drug target candidates; immune response regulation and modulation; or proteins suppressing engraftment, trafficking, homing, viability, self-renewal, persistence, and/or survival of the iPSCs or derivative cells thereof. In some embodiments, the genome-engineered iPSC comprises one or more exogenous polynucleotides further comprises in/dels in one or more endogenous genes. In some embodiments, the in/del comprised in an endogenous gene results in disruption of gene expression. In some embodiments, the in/del comprised in an endogenous gene results in knock-out of the edited gene. In some embodiment, the in/del comprised in an endogenous gene results in knock-down of the edited gene. In some embodiments, the genome-engineered iPSC comprising one or more exogenous polynucleotides at selected site(s) may further comprise one or more targeted editing including in/dels at selected site(s). In some embodiments, the in/del is comprised in one or more endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, B2M, PD1, TAP1, TAP2, Tapasin, TCR genes. In one embodiment, the genome-engineered iPSC comprising one or more exogenous polynucleotides at selected site(s) further comprises a targeted editing in B2M (beta-2-microglobulin) encoding gene. In one embodiment, the genome-engineered iPSC comprising a targeted editing in B2M gene is B2M null or low, and HLA-I deficient.

In some embodiments, the genome-engineered iPSC comprises at least one suicide gene integrated in a selected site. In some embodiments, the genome-engineered iPSC comprises at least two suicide genes each integrated in same or different integration site. In some embodiments, the exogenous polynucleotides are driven by one or more promoters selected form the group consisting of constitutive promoters, inducible promoters, temporal-specific promoters, and tissue or cell type specific promoters. In some embodiments, the genome-engineered iPSC comprises one or more suicide genes at selected integration site(s) further comprises in/del(s) in one or more selected endogenous genes. As disclosed herein, the non-pluripotent cell with multiple targeted editing of desired modalities are suitable for reprogramming using the culture platform in Table 1 to obtain derived genome-engineered iPSCs. In some embodiments, the genomic engineering of non-pluripotent cells for targeted integration or in/dels takes place concurrently with the reprogramming of the non-pluripotent cells, and result in genome-engineered iPSCs in a robust, efficient, precise and reliable way.

The present invention further provides non-pluripotent cells derived from the genome-engineered iPSCs, wherein the genome-engineered iPSCs are obtained either through targeted editing of iPSCs, or through reprogramming genome-engineered non-pluripotent cells having site specific integration or in/dels consecutively (obtain reprogrammed iPSC first, and then conduct genome-engineering; or obtain genome-engineered non-pluripotent cells first, and then conduct reprogramming), or concurrently (reprogramming and genome-engineering the same pool of cells simultaneously). In some embodiments, the genome-engineered iPSC-derived non-pluripotent cells are progenitor cells or fully-differentiated cells. In some embodiments, the genome-engineered iPSC-derived cells are mesodermal cells, CD34 cells, hemogenic endothelium cells, hematopoietic stem or progenitor cells, hematopoietic multipotent progenitor cells, T cell progenitor, NK cell progenitor, T cells, NKT cells, NK cells, or B cells.

Also provided by the present invention is a composition for obtaining genome-engineered iPSCs. In one embodiment, the composition comprises genome-engineered non-pluripotent cells; one or more reprogramming factors; and a small molecule composition comprising a TGFβ receptor/ALK inhibitor, a MEK inhibitor, a GSK3 inhibitor and/or a ROCK inhibitor for reprogramming the genome-engineered non-pluripotent cells to genome-engineered iPSCs comprising the same targeted editing. In some embodiments of the above composition, the genome-engineered non-pluripotent cells for reprogramming comprise one or more polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the iPSCs or derivative cells thereof, wherein the one or more polynucleotides are driven by one or more promoters selected form the group consisting of constitutive promoters, inducible promoters, temporal-specific promoters, and tissue or cell type specific promoters. In some embodiments, the one or more polynucleotides are comprised in different constructs capable of targeted integration at the same or different selected sites. In some embodiments, the one or more selected sites comprise AAVS1, CCR5, ROSA26, collagen, HTRP, H11, beta-2 microglobulin, GAPDH, TCR or RUNX1, or other loci meeting the criteria of a genome safe harbor.

In some other embodiments, the composition for obtaining genome-engineered iPSCs comprises non-pluripotent cells, one or more site-specific endonuclease, one or more reprogramming factors; and a combination of a TGFβ receptor/ALK inhibitor, a MEK inhibitor, a GSK3 inhibitor and/or a ROCK inhibitor, and optionally one or more constructs comprising operatively linked polynucleotides flanked by homology arms for targeted integration, wherein the composition is useful for concurrent genome-engineering and reprogramming non-pluripotent cells to genome-engineered iPSCs comprising targeted integration, and/or in/dels at selected sites. In some embodiments, the different constructs and/or in/dels are introduced to the non-pluripotent cells simultaneously or consecutively with the reprogramming factors. In some embodiments, the different constructs and/or in/dels are introduced to the non-pluripotent cells during reprogramming, such that the genome engineering and reprogramming are simultaneous or concurrent.

In some other embodiments, the composition for obtaining genome-engineered iPSCs comprises non-pluripotent cells, one or more reprogramming factors; and a combination of a TGFβ receptor/ALK inhibitor, a MEK inhibitor, a GSK3 inhibitor and a ROCK inhibitor, and one or more constructs comprising operatively linked polynucleotides flanked by homology arms for targeted integration, wherein the composition is useful for concurrent genome-engineering and reprogramming non-pluripotent cells to genome-engineered iPSCs comprising targeted integration, and/or in/dels at selected sites. In some embodiments, the different constructs and/or in/dels are introduced to the non-pluripotent cells simultaneously or consecutively with the reprogramming factors. In some embodiments, the different constructs and/or in/dels are introduced to the non-pluripotent cells during reprogramming, such that the genome engineering and reprogramming are simultaneous or concurrent.

Further, a composition for maintaining genome-engineered iPSCs obtained from reprogramming genome-engineered non-pluripotent cells is also provided herein. In one embodiment, the composition comprises genome-engineered iPSCs reprogrammed from the genome-engineered non-pluripotent cells; and a combination of a MEK inhibitor, a GSK3 inhibitor and a ROCK inhibitor. In one embodiment, the iPSCs obtained from reprogramming retain pluripotency and the targeted editing during a long-term passaging and expansion.

Also provided is a composition comprising: genome-engineered iPSCs and a small molecule composition comprising a MEK inhibitor, a GSK3 inhibitor and a ROCK inhibitor, wherein the genome-engineered iPSCs are obtained from (a) reprogramming genome-engineered non-pluripotent cells, wherein the obtained iPSCs comprise the same targeted editing comprised in the genome-engineered non-pluripotent cells; or (b) genome engineering a clonal iPSC or a pool of iPSCs by introducing one or more targeted editing at selected sites; or (c) genome engineering by introducing one or more targeted editing at selected sites to a pool of reprogramming non-pluripotent cells in contact with one or more reprogramming factors and optionally a small molecule composition comprising a TGFβ receptor/ALK inhibitor, a MEK inhibitor, a GSK3 inhibitor and/or a ROCK inhibitor. In some embodiments, the genome-engineered iPSCs comprise one or more polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the non-pluripotent cell reprogrammed iPSCs or derivative cells thereof. In some embodiments, the genome-engineered iPSC comprises in/dels in one or more endogenous genes encoding proteins associated with targeting modalities, receptors, signaling molecules, transcription factors, drug target candidates; immune response regulation and modulation; or proteins suppressing engraftment, trafficking, homing, viability, self-renewal, persistence, and/or survival of the iPSCs or derivative cells thereof. In some embodiments, the genome-engineered iPSC comprises one or more exogenous polynucleotides further comprises in/dels in one or more endogenous genes.

V. Therapeutic Use of Genetically Engineered iPSCs and Derived Immune Cells with Functional Modalities Therefrom The present invention provides a composition comprising an isolated population or subpopulation of geneticallly engineered iPSCs and/or immune cells that have been derived from said iPSC using the methods and compositions as disclosed, wherein the immune cells are genetically engineered and are suitable for cell based adoptive therapies. In one embodiment, the isolated population or subpopulation of genetically engineered immune cell comprises iPSC derived HSC cells. In one embodiment, the isolated population or subpopulation of genetically engineered immune cell comprises iPSC derived HSC cells. In one embodiment, the isolated population or subpopulation of genetically engineered immune cell comprises iPSC derived proT or T cells. In one embodiment, the isolated population or subpopulation of genetically engineered immune cell comprises iPSC derived proNK or NK cells. In some embodiments, the iPSC derived genetically engineered immune cells are further modulated ex vivo for improved therapeutic potential. In one embodiment, an isolated population or subpopulation of genetically engineered immune cells that have been derived from iPSC comprises an increased number or ratio of naïve T cells, stem cell memory T cells, and/or central memory T cells. In one embodiment, the isolated population or subpopulation of genetically engineered immune cell that have been derived from iPSC comprises an increased number or ratio of type I NKT cells. In another embodiment, the isolated population or subpopulation of genetically engineered immune cell that have been derived from iPSC comprises an increased number or ratio of adaptive NK cells. In some embodiments, the isolated population or subpopulation of genetically engineered CD34 cells, HSC cells, T cells, or NK cells derived from iPSC are allogenic. In some other embodiments, the isolated population or subpopulation of genetically engineered CD34 cells, HSC cells, T cells, or NK cells derived from iPSC are autogenic.

In some embodiments, the iPSC for differentiation comprises genetic imprints conveying desirable therapeutic attributes in effector cells, which genetic imprints are retained and functional in the differentiated hematopoietic cells derived from said iPSC.

In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC derived hematopoietic lineage cells.

In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, 41BBL, CD3, CD4, CD8, CD47, CD113, CD131, CD137, CD80, PDL1, A2AR, CAR, TCR, Fc receptor, or surface triggering receptors for coupling with bi- or multi-specific or universal engagers.

In still some other embodiments, the hematopoietic lineage cells comprise the therapeutic attributes of the source specific immune cell relating to one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In some embodiments, the iPSC and its derivative hematopoietic cells comprise one or more of B2M null or low, HLA-E/Q PDL1, A2AR, CD47, LAG3 null or low, TIM3 null or low, TAP1 null or low, TAP2 null or low, Tapasin null or low, NLRC5 null or low, PD1 null or low, RFKANK null or low, CIITA null or low, RFX5 null or low and RFXAP null or low. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen.

In some embodiments, the iPSC and its derivative hematopoietic cells comprise one or more of hnCD16 (high-affinity non-cleavable CD16), HLA-E, HLA-Q 41BBL, CD3, CD4, CD8, CD47, CD113, CD131, CD137, CD80, PDL1, A2AR, CAR, or TCR. Such cells have improved immune effector ability.

In some embodiments, the iPSC and its derivative hematopoietic cells are antigen specific.

A variety of diseases may be ameliorated by introducing the immune cells of the invention to a subject suitable for adoptive cell therapy. Examples of diseases including various autoimmune disorders, including but not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis *nodosa*, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's); hematological malignancies, including but not limited to, acute and chronic leukemias, lymphomas, multiple myeloma and myelodysplastic syndromes; solid tumors, including but not limited to, tumor of the brain, prostate, breast, lung, colon, uterus, skin, liver, bone, pancreas, ovary, testes, bladder, kidney, head, neck, stomach, cervix, rectum, larynx, or esophagus; and infections, including but not limited to, HIV—(human immunodeficiency virus), RSV—(Respiratory Syncytial Virus), EBV—(Epstein-Barr virus), CMV—(cytomegalovirus), adenovirus- and BK polyomavirus-associated disorders.

Particular embodiments of the present invention are directed to methods of treating a subject in need thereof by administering to the subject a composition comprising any of the cells described herein. In particular embodiments, the terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of disease or injury. The treatment of ongoing disease, where the treatment stabilizes or reduces the undesirable clinical symptoms of the patient, is of particular interest.

In particular embodiments, the subject has a disease, condition, and/or an injury that can be treated, ameliorated, and/or improved by a cell therapy. Some embodiments contemplate that a subject in need of cell therapy is a subject with an injury, disease, or condition, whereby a cell therapy, e.g., a therapy in which a cellular material is administered to the subject, can treat, ameliorate, improve, and/or reduce the severity of at least one symptom associated with the injury, disease, or condition. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

According, the present invention further provides pharmaceutical compositions comprising the pluripotent cell derived hematopoietic lineage cells made by the methods and composition disclosed herein, wherein the pharmaceutical compositions further comprise a pharmaceutically acceptable medium. In one embodiment, the pharmaceutical composition comprises the pluripotent cell derived T cells made by the methods and composition disclosed herein. In one embodiment, the pharmaceutical composition comprises the pluripotent cell derived NK cells made by the methods and composition disclosed herein. In one embodiment, the pharmaceutical composition comprises the pluripotent cell derived CD34+HE cells made by the methods and composition disclosed herein. In one embodiment, the pharmaceutical composition comprises the pluripotent cell derived HSCs made by the methods and composition disclosed herein.

Additionally, the present invention provides therapeutic use of the above pharmaceutical compositions by introducing the composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

The isolated pluripotent stem cell derived hematopoietic lineage cells can have at least 50%, 60%, 70%, 80%, 90%, 95%, 98%, or 99% T cells, NK cells, NKT cells, proT cells, proNK cells, CD34+HE cells or HSCs. In some embodiments, the isolated pluripotent stem cell derived hematopoietic lineage cells has about 95% to about 100% T cells, NK cells, NKT cells, proT cells, proNK cells, CD34+HE cells or HSCs. In some embodiments, the present invention provides pharmaceutical compositions having purified T cells, NK cells, NKT cells, CD34+HE cells, proT cells, proNK cells, or HSCs, such as a composition having an isolated population of about 95% T cells, NK cells, NKT cells, proT cells, proNK cells, CD34+HE cells or HSCs to treat a subject in need of the cell therapy.

In some embodiments, the pharmaceutical composition includes an isolated population of pluripotent stem cell derived hematopoietic lineage cells, wherein population has less than about 0.1%, 0.5%, 1%, 2%, 5%, 10%, 15%, 20%, 25%, or 30% iPSC derived T cells, NK cells, NKT cells, proT cells, proNK cells, CD34+HE cells or HSCs. The isolated population of derived hematopoietic lineage cells in some embodiments can have more than about 0.1%, 0.5%, 1%, 2%, 5%, 10%, 15%, 20%, 25%, or 30% T cells, NK cells, NKT cells, proT cells, proNK cells, CD34+HE cells or HSCs. In other embodiments, the isolated population of derived hematopoietic lineage cells can have about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% T cells, NK cells, NKT cells, proT cells, proNK cells, CD34+HE cells or HSCs.

In particular embodiments, the derived hematopoietic lineage cells can have about 0.1%, about 1%, about 3%, about 5%, about 10%, about 15%, about 20%, about 25%, about 30%, about 35%, about 40%, about 45%, about 50%, about 60%, about 70%, about 80%, about 90%, about 95%, about 98%, about 99%, or about 100% T cells, NK cells, NKT cells, proT cells, proNK cells, CD34+HE cells or HSCs.

As a person of ordinary skill in the art would understand, both autologous and allogeneic immune cells can be used in cell therapies. Autologous cell therapies can have reduced infection, low probability for GvHD, and rapid immune reconstitution. Allogeneic cell therapies can have an immune mediated graft-versus-malignancy (GVM) effect, and low rate of relapse. Based on the specific conditions of the patients or subject in need of the cell therapy, a person of ordinary skill in the art would be able to determine which specific type of therapy to administer.

In particular embodiments, the derived hematopoietic lineage cells of the pharmaceutical composition of the invention are allogeneic to a subject. In particular embodiments, the derived hematopoietic lineage cells of the pharmaceutical formulation of the invention are autologous to a subject. For autologous transplantation, the isolated population of derived hematopoietic lineage cells are either complete or partial HLA-match with the patient. In another embodiment, the derived hematopoietic lineage cells are not HLA-matched to the subject.

In some embodiments, the number of derived hematopoietic lineage cells in the pharmaceutical composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In some embodiments, the number of derived hematopoietic lineage cells in the pharmaceutical composition is about $0.1 \times 10^5$ cells to about $10 \times 10^5$ cells; about $0.5 \times 10^6$ cells to about $5 \times 10^6$ cells; about $1 \times 10^6$ cells to about $3 \times 10^6$ cells; about $1.5 \times 10^6$ cells to about $2.5 \times 10^6$ cells; or about $2 \times 10^6$ cells to about $2.5 \times 10^6$ cells.

In some embodiments, the number of derived hematopoietic lineage cells in the pharmaceutical composition is about $1 \times 10^6$ cells to about $3 \times 10^6$ cells; about $1.0 \times 10^6$ cells to about $5 \times 10^6$ cells; about $1.0 \times 10^6$ cells to about $10 \times 10^6$ cells, about $10 \times 10^6$ cells to about $20 \times 10^6$ cells, about $10 \times 10^6$ cells to about $30 \times 10^6$ cells, or about $20 \times 10^6$ cells to about $30 \times 10^6$ cells.

In some other embodiments, the number of derived hematopoietic lineage cells in the pharmaceutical composition is about $1 \times 10^6$ cells to about $30 \times 10^6$ cells; about $1.0 \times 10^6$ cells to about $20 \times 10^6$ cells; about $1.0 \times 10^6$ cells to about $10 \times 10^6$ cells, about $2.0 \times 10^6$ cells to about $30 \times 10^6$ cells, about $2.0 \times 10^6$ cells to about $20 \times 10^6$ cells, or about $2.0 \times 10^6$ cells to about $10 \times 10^6$ cells.

In yet other embodiments, the number of derived hematopoietic lineage cells in the pharmaceutical composition is about $1 \times 10^6$ cells, about $2 \times 10^6$ cells, about $5 \times 10^6$ cells, about $7 \times 10^6$ cells, about $10 \times 10^6$ cells, about $15 \times 10^6$ cells, about $17 \times 10^6$ cells, about $20 \times 10^6$ cells about $25 \times 10^6$ cells, or about $30 \times 10^6$ cells.

In one embodiment, the number of derived hematopoietic lineage cells in the pharmaceutical composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

The derived genetically engineered hematopoietic lineage cells provided by the invention can be administration to a subject without being expanded ex vivo or in vitro prior to administration. In particular embodiments, an isolated population of derived genetically engineered hematopoietic lineage cells is modulated and treated ex vivo using one or more agent to obtain immune cells with improved therapeutic potential. The modulated population of derived genetically engineered hematopoietic lineage cells can be washed to remove the treatment agent(s), and the improved population is administered to a patient without further expansion of the population in vitro.

In other embodiments, the invention provides an isolated population of derived genetically engineered hematopoietic lineage cells that are expanded prior to modulation with one or more agents. The isolated population of derived hematopoietic lineage cells can be recombinantly produced to express TCR, CAR or other proteins using the method and composition provided herein.

For genetically engineered derived hematopoietic lineage cells that express recombinant TCR or CAR, whether prior to or after genetic modification of the cells, the cells can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In certain embodiments, the primary stimulatory signal and the co-stimulatory signal for the derived genetically engineered hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Patent Application Publication Nos. 20040101519 and 20060034810 for artificial antigen presenting cells (aAPCs) that are contemplated for use in activating and expanding T lymphocytes in the present invention.

The compositions comprising a population of derived hematopoietic lineage cells of the invention can be sterile, and can be suitable and ready for administration (i.e., can be administered without any further processing) to human patients. In some embodiments, the therapeutic composition is ready for infusion into a patient. A cell based composition that is ready for administration means that the composition does not require any further treatment or manipulations prior to transplant or administration to a subject.

The sterile, therapeutically acceptable compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, 17th ed. 1985, the disclosure of which is hereby incorporated by reference in its entirety).

In particular embodiments, therapeutic cell compositions having an isolated population of derived genetically engineered hematopoietic lineage cells also have a pharmaceutically acceptable cell culture medium. A therapeutic composition comprising a population of derived genetically engineered hematopoietic lineage cells as disclosed herein can be administered separately by enteral or parenteral administration methods or in combination with other suitable compounds to effect the desired treatment goals.

The pharmaceutically acceptable carrier and/or diluent must be of sufficiently high purity and of sufficiently low toxicity to render it suitable for administration to the human subject being treated. It further should maintain or increase the stability of the therapeutic composition.

Such carrier solutions also can contain buffers, diluents and other suitable additives. A buffer refers to a solution or liquid whose chemical makeup neutralizes acids or bases without a significant change in PH. Examples of buffers envisioned by the invention include, but are not limited to, Dulbecco's phosphate buffered saline (PBS), Ringer's solution, 5% dextrose in water (D5W), normal/physiologic saline (0.9% NaCl).

These pharmaceutically acceptable carriers and/or diluents can be present in amounts sufficient to maintain a PH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the PH of the therapeutic composition is in the range from about 4 to about 10. Alternatively, the PH of the therapeutic composition is in the range from about 5 to about 9, from about 6 to about 9, or from about 6.5 to about 8. In another embodiment, the therapeutic composition includes a buffer having a PH in one of said PH ranges. In another embodiment, the therapeutic composition has a PH of about 7. Alternatively, the therapeutic composition has a PH in a range from about 6.8 to about 7.4. In still another embodiment, the therapeutic composition has a PH of about 7.4.

The sterile composition of the invention can be a sterile solution or suspension in a nontoxic pharmaceutically acceptable medium. Suspension can refer to non-adherent conditions in which cells are not attached to a solid support.

For example, cells maintained in suspension can be stirred and are not adhered to a support, such as a culture dish.

A suspension is a dispersion (mixture) in which a finely-divided species is combined with another species, with the former being so finely divided and mixed that it doesn't rapidly settle out. A suspension can be prepared using a vehicle such as a liquid medium, including a solution. In some embodiments, the therapeutic composition of the invention is a suspension, where the stem and/or progenitor cells are dispersed within an acceptable liquid medium or solution, e.g., saline or serum-free medium, and are not attached to a solid support. In everyday life, the most common suspensions are those of solids in liquid water. Among the acceptable diluents, e.g., vehicles and solvents, that can be employed are water, Ringer's solution, isotonic sodium chloride (saline) solution, and serum-free cell culture medium. In some embodiments, hypertonic solutions are employed in making suspensions. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions can contain substances which increase the viscosity of the suspension and include, for example, sodium carboxymethyl cellulose, sorbitol and/or dextran. In some embodiments, the infusion solution is isotonic to subject tissues. In some embodiments, the infusion solution is hypertonic to subject tissues.

The pharmaceutically acceptable carrier, diluents, and other components comprising the administration-ready pharmaceutical composition of the invention are derived from U.S. Pharmaceutical grade reagents that will permit the therapeutic composition to be used in clinical regimens. Typically, these finished reagents, including any medium, solution, or other pharmaceutically acceptable carriers and/or diluents, are sterilized in a manner conventional in the art, such as filter sterilized, and are tested for various undesired contaminants, such as *mycoplasma*, endotoxin, or virus contamination, prior to use. The pharmaceutically acceptable carrier in one embodiment is substantially free of natural proteins of human or animal origin, and suitable for storing the population of cells of the pharmaceutical composition, including hematopoietic stem and progenitor cells. The pharmaceutical composition is intended to be administered into a human patient, and thus is substantially free of cell culture components such as bovine serum albumin, horse serum, and fetal bovine serum.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the derived hematopoietic lineage cells of the invention are suitable for use as a pharmaceutical cell culture medium. In particular embodiments, the pharmaceutically acceptable cell culture medium is a serum free, and/or feeder free medium.

The pharmaceutical composition can have serum-free medium suitable for storing the modulated isolated population of derived hematopoietic lineage cells. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein.

One having ordinary skill in the art would appreciate that the above examples of media are illustrative and in no way limit the formulation of media suitable for use in the present invention and that there are many suitable media known and available to those in the art.

The pharmaceutical composition is substantially free of *mycoplasma*, endotoxin, and microbial contamination. In particular embodiments, the therapeutic composition contains less than about 10, 5, 4, 3, 2, 1, 0.1, or 0.05 µg/ml bovine serum albumin.

With respect to *mycoplasma* and microbial contamination, "substantially free" as used herein means a negative reading for the generally accepted tests known to those skilled in the art. For example, *mycoplasma* contamination is determined by subculturing a sample of the therapeutic composition in broth medium and distributed over agar plates on day 1, 3, 7, and 14 at 37° C. with appropriate positive and negative controls. The sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The sample is considered satisfactory if the agar and/or the broth media procedure and the indicator cell culture procedure show no evidence of *mycoplasma* contamination.

An organic solvent or a suitable organic solvent relates generally to carbon containing liquids or gases that dissolve a solid, liquid, or gaseous solute, resulting in a solution. A suitable organic solvent is one that is appropriate for ex vivo administration to, or incubation with, mammalian cells, and can also be appropriate for in vivo administration to a subject, such as by having minimal toxicity or other inhibitory effects under ex vivo conditions (e.g., cell culture) or in vivo at a selected concentration for the time of incubation or administration. A suitable organic solvent should also be appropriate for storage stability and handling of the agents described herein.

Examples of suitable organic solvents include, but are not limited to, dimethyl sulfoxide (DMSO), N,N-dimethylformamide (DMF), dimethoxyethane (DME), and dimethylacetamide, including mixtures or combinations thereof. In certain embodiments, a composition or organic solvent is substantially free of methyl acetate, meaning that there should be no more than trace amounts of methyl acetate in the composition or solvent, and preferably undetectable amounts (e.g., as measured by high pressure liquid chromatography (HPLC), gas chromatography (GC), etc.).

A vessel or composition that is endotoxin free means that the vessel or composition contains at most trace amounts (i.e., amounts having no adverse physiological effects to a subject) of endotoxin, or undetectable amounts of endotoxin. Cells being "substantially free of endotoxin" means that there is less endotoxin per dose of cells than is allowed by the FDA for a biologic, which is a total endotoxin of 5 EU/kg body weight per day, which for an average 70 kg person is 350 EU per total dose of cells.

In one embodiment, the endotoxin free vessel and/or compositions is at least 95%, at least 96%, at least 97%, at least 98%, at least 99%, or 100% endotoxin free. Endotoxins are toxins associated with certain bacteria, typically gram-negative bacteria, although endotoxins can be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts can cause adverse effects in humans. Endotoxins can be removed from vessels using methods known in the art, for example, vessels can be cleaned in HEPA filtered washing equipment with endotoxin-free water, depyrogenated at 250° C., and clean-packaged in HEPA filtered workstations located inside a class 100/10 clean room (e.g., a class 100 clean room, contains no more than 100 particles bigger than half a micron in a cubic foot of air).

EXAMPLES

The following examples are offered by way of illustration and not by way of limitation.

Example 1—Materials and Methods

To effectively select and test suicide systems under the control of various promoters in combination with different safe harbor loci integration strategies, a proprietary hiPSC platform of the applicant was used, which enables single cell passaging and high-throughput, 96-well plate-based flow cytometry sorting, to allow for the derivation of clonal hiPSCs with single or multiple genetic modulations.

hiPSC Maintenance in Small Molecule Culture:

hiPSCs were routinely passaged as single cells once confluency of the culture reached 75%-90%. For single-cell dissociation, hiPSCs were washed once with PBS (Mediatech) and treated with Accutase (Millipore) for 3-5 min at 37° C. followed with pipetting to ensure single-cell dissociation. The single-cell suspension was then mixed in equal volume with conventional medium, centrifuged at 225×g for 4 min, resuspended in FMM, and plated on Matrigel-coated surface. Passages were typically 1:6-1:8, transferred tissue culture plates previously coated with Matrigel for 2-4 hr in 37° C. and fed every 2-3 days with FMM. Cell cultures were maintained in a humidified incubator set at 37° C. and 5% CO2.

Human iPSC Genome Editing with ZFN, CRISPR for Targeted Insertion of iCasp9 into Genome Safe Harbors:

For ZFN mediated genome editing, 2 million iPSCs were transfected with mixture of 2.5 ug ZFN-L (FTV893; SEQ ID NOs:2 and 4), 2.5 ug ZFN-R (FTV894; SEQ ID NOs:3 and 5) and 5 ug AAVS1 iCasp9 donor construct (FTV895, FTV930, FTV921, FTV931, FTV932, FTV952 or FTV953; iCaspase9 SEQ ID NOs: 7 and 8) plasmid DNA. For CRISPR mediated genome editing, 2 million iPSCs were transfected with mixture of 5 ug ROSA26-gRNA/Cas9 (FTV922; SEQ ID NO:6) and 5 ug ROSA26 iCasp9 donor construct (FTV955 or FTV956). Transfection was done using Neon transfection system (Life Technologies) using parameters 1500V, 10 ms, 3 pulses. On day 2 or 3 after transfection, transfection efficiency was measured using flow cytometry if the plasmids contains artificial promoter-driver GFP and/or RFP expression cassette. On day 4 after transfection, puromycin was added to the medium at concentration of 0.1 ug/ml for the first 7 days and 0.2 ug/ml after 7 days to select the targeted cells. During the puromycin selection, the cells were passaged onto fresh matrigel-coated wells on day 10. On day 16 or later of puromycin selection, the surviving cells were analyzed by flow cytometry for GFP+iPS cell percentage.

Bulk Sort and Clonal Sort of Genome-Edited iPSCs:

iPSCs targeted with AAVS1 EF1α or CAG promoter-driven iCasp9-2A-GFP mediated by ZFN were bulk sorted and clonal sorted of GFP+SSEA4+TRA181+iPSCs after 20 days of puromycin selection. Single cell dissociated targeted iPSC pools were resuspended in chilled staining buffer containing Hanks' Balanced Salt Solution (MediaTech), 4% fetal bovine serum (Invitrogen), 1× penicillin/streptomycin (Mediatech) and 10 mM Hepes (Mediatech); made fresh for optimal performance. Conjugated primary antibodies, including SSEA4-PE, TRA181-Alexa Fluor-647 (BD Biosciences), were added to the cell solution and incubated on ice for 15 min. All antibodies were used at 7 µL in 100 µL staining buffer per million cells. The solution was washed once in staining buffer, spun down at 225 g for 4 min and resuspended in staining buffer containing 10 µM Thiazovivn and maintained on ice for flow cytometry sorting. Flow cytometry sorting was performed on FACS Aria II (BD Biosciences). For bulk sort, GFP+SSEA4+TRA181+ cells were gated and sorted into 15 ml canonical tubes filled with 7 ml FMM. For clonal sort, the sorted cells were directly ejected into 96-well plates using the 100 µM nozzle, at concentrations of 3 events per well. Each well was prefilled with 200 µL FMM supplemented with 5 µg/mL fibronectin and 1× penicillin/streptomycin (Mediatech) and previously coated overnight with 5× Matrigel. 5× Matrigel precoating includes adding one aliquot of Matrigel into 5 mL of DMEM/F12, then incubated overnight at 4° C. to allow for proper resuspension and finally added to 96-well plates at 50 µL per well followed by overnight incubation at 37° C. The 5× Matrigel is aspirated immediately before the addition of media to each well. Upon completion of the sort, 96-well plates were centrifuged for 1-2 min at 225 g prior to incubation. The plates were left undisturbed for seven days. On the seventh day, 150 µL of medium was removed from each well and replaced with 100 µL FMM. Wells were refed with an additional 100 µL FMM on day 10 post sort. Colony formation was detected as early as day 2 and most colonies were expanded between days 7-10 post sort. In the first passage, wells were washed with PBS and dissociated with 30 µL Accutase for approximately 10 min at 37° C. The need for extended Accutase treatment reflects the compactness of colonies that have sat idle in culture for prolonged duration. After cells are seen to be dissociating, 200 µL of FMM is added to each well and pipetted several times to break up the colony. The dissociated colony is transferred to another well of a 96-well plate previously coated with 5× Matrigel and then centrifuged for 2 min at 225 g prior to incubation. This 1:1 passage is conducted to spread out the early colony prior to expansion. Subsequent passages were done routinely with Accutase treatment for 3-5 min and expansion of 1:4-1:8 upon 75-90% confluency into larger wells previously coated with 1× Matrigel in FMM. Each clonal cell lines was analyzed for GFP fluorescence level and TRA1-81 expression level. Clonal lines with near 100% GFP+ and TRA1-81+ were selected for further PCR screening and analysis. Flow cytometry analysis was performed on Guava EasyCyte 8 HT (Millipore) and analyzed using Flowjo (FlowJo, LLC).

In Vitro Inducible Killing of iCasp9-Integrated iPSCs:

The chemical inducer of dimerization (CID; AP1903) was purchased from Medchemexpress (Monmouth Junction, N.J.). Twenty-four hours after CID exposure, the cells were harvested and stained with 7-amino actinomycin D (7-AAD) according to the manufacturer's instruction (BD Biosciences). The percentage of 7-AAD positive cells were quantified as dead cells by flow cytometry (Guava, EMD Millipore, Billerica, Mass.) and analyzed with flowjo software.

To test if the AP1903 induced complete cell death of iCasp9-targeted iPSC clones, we treated 3 wells of each targeted iPSC clone with AP1903 for 48 hours and then washed the wells twice with PBS before adding fresh iPSC medium. The wells were allowed to recover with refreshing medium every 2 days for total 5 days. Then the wells were stained with Alkaline Phosphatase staining reagent (Sigma).

In Vitro Tri-Lineage Directed Differentiation of iCasp9 Targeted Clones and Inducible Killing:

For directed monolayer tri-lineage differentiation, hiPSCs were seeded on Matrigel coated wells in FMM (for example, 200K cells/well for endoderm, 50K cells/well for ectoderm, 10K and 50K cells/well for mesoderm) the day before starting differentiation. Four replicate wells were set up for each lineage differentiation. For endoderm differentiation, FMM media was replaced with endoderm induction media: RPMI-1640, Ascorbic Acid (50 µg/ml), Monothioglycerol (450 µM), 1× Glutamine, Knockout Serum Replacement (0.20%), Activin A (100 ng/ml), CHIR99021 (Biovision) (3 µM), 1× penicillin/streptomycin. Following 2 days, replace with media: RPMI-1640, Ascorbic Acid (50 µg/ml), Monothioglycerol (450 µM), 1× Glutamine, Knockout Serum Replacement (0.50%), bFGF (5 ng/ml), Activin A (100 ng/ml), 1× penicillin/streptomycin. One well was fixed on day 3 and stained for Sox17 (R&D Systems). One well was stained with crystal violet on day 3. Two other wells were treated with AP1903 for 48 hours, then washed and replenished with fresh differentiation medium and continued culture for 5 days before stained with crystal violet. For mesoderm differentiation, media was replaced with DMEM/F12 (Mediatech) supplemented with ITS, 10 ng/ml bFGF, 20 µM Forskolin and 3 µM CHIR99021. Media was changed every other day and one well fixed on the 4th day and stained for αSMA (Sigma). One well was stained with crystal violet on day 4. Two other wells were treated with AP1903 for 48 hours, then washed and replenished with fresh differentiation medium and continued culture for 5 days before stained with crystal violet. For ectoderm differentiation, FMM media was replaced with neural induction media: DMEM/F12 (Mediatech) supplemented with 1×B27 media additive (Life Technologies), 1×N2 media additive (Life Technologies), 10 µM SB431542 and 100 nM LDN-193189. Media was changed every other day and one well fixed on the 7th day and stained for Nestin (Abcam). One well was stained with crystal violet on day 7. Two other wells were treated with AP1903 for 48 hours, then washed and replenished with fresh differentiation medium and continued culture for 5 days before stained with crystal violet.

Crystal Violet Staining:

0.5% Crystal violet solution were made by dissolving 0.5 g of crystal violet stain (Sigma) in 100 mL deionized water. Filter and store at room temperature. For staining, wash cells 2 times with PBS. Replace with PBS containing 4% paraformaldehyde for 15 minutes at room temperature. Rinse twice with PBS. Stain with 0.1% crystal violet (prepared in 10% ethanol) 15 minutes at room temperature. Pour off the CV. Gently wash the cells with deionized water from a wash bottle until the water no longer runs dark. Withdraw the deionized water and let the stained cells dry before taking pictures.

In Vivo Inducible Killing of Teratomas Derived from iCasp9-Integrated iPSCs:

All mice were housed in applicant's facility. All experimental protocols involving mice were approved by applicant's Institutional Animal Care and Use Committee. All mice used in this study were 7-10 week-old female NSG mice (NOD/SCID/$\gamma^{null}$, the Jackson Laboratory). For the teratoma assay, 200 µl consisting of 1-2×10$^6$ iPSCs in 50% FMM medium and 50% Matrigel was subcutaneously introduced into the dorso-lateral area. Each mouse received two cell injections on both sides, with iCasp9-integrated iPSCs injected on the left side and unmodified parental iPSC line injected on the right side. To initiate in vivo killing at the indicated time points, the mice were administered daily with AP1903 (125 µg/mouse) through intraperitoneal (i.p.) injection for 5 or 7 days. The mice were monitored for teratoma formation and volume measurements were initiated on week 3 or as indicated. Teratomas were collected at indicated time points and processed for histology or molecular assays. AP1903 stock was prepared in DMSO (25 µg/ml). For a single i.p. injection, 5 µl stock solution was added to 200 µl PBS, followed by sonication in a water bath for 10 minutes. For histology, teratomas were harvested in PBS, fixed overnight at room temperature in 4% paraformaldehyde and maintained thereafter in 70% ethanol at room temperature for processing. Samples were submitted to UCSD Histology Core Facility for sectioning and hematoxylin and eosin staining. Sections were examined, interpreted and photographed using a Nikon Eclipse TS100 microscope equipped with a Nikon DS-Fi1 camera.

In Vivo Visualization of Inducible Killing of Engrafted Luciferase-Expressing iPSCs:

To visualize AP1903-induced killing in vivo, iCasp9-integrated iPSCs and unmodified parental iPSCs were infected with a lentivirus containing a polycistronic cassette composed of a Firefly luciferase gene and RFP linked by IRES and expressed under the control of EF1α (Biosettia). The infected cells were sorted for RFP+ cells and were injected as above. 2×10$^6$ iCasp9-integrated iPSCs were injected subcutaneously on the left side of NSG mice and same number of parental iPSCs injected on the right side. AP1903 i.p. injections were administered on the indicated days. Starting immediately after iPSCs implantation (day 0), engraftment and teratoma volumes were monitored weekly using the Xenogen IVIS imaging system. For imaging, mice were injected intraperitoneally with D-luciferin (4 mg/mouse, Thermo Fisher) and bioluminescence recorded 10 min after. Analysis was done using the Xenogen Living Image software.

Example 2—AAVS1 Safe Harbor Targeted iCasp9 Suicide Gene Regulated by CMV Promoter Elicits Variable Response when Activated by AP1903

To conduct high-throughput analyses of proper integration and expression strategies in iPSCs, an iCasp9 suicide gene platform was selected, where rapid caspase-9 mediated cell death can be induced by small molecule chemical inducers of dimerization such as AP1903. Note that for the small molecule induction to demonstrate efficacy at each stage of development towards the final product, the iCasp9 gene will need to be continuously expressed in every stage of pluripotent stem cell maintenance and differentiation. In a single hiPSC per well manner, in order to efficiently and precisely integrate and maintain various suicide gene expression cassettes in safe harbor loci including, but not limited to, AAVS1, ROSA26, and H11 loci. Several integration vectors, each containing a suicide gene expression cassette downstream of various exogenous and endogenous promoters, including endogenous AAVS1 or ROSA26, cytomegalovirus (CMV), elongation factor 1α (EF1α), phosphoglycerate kinase (PGK), hybrid CMV enhancer/chicken β-actin (CAG) and ubiquitin C (UBC) promoters, were tested to systematically analyze and compare the activity of different suicide systems in both hiPSCs and hiPSC-derived differentiated cells.

Figure 1B:
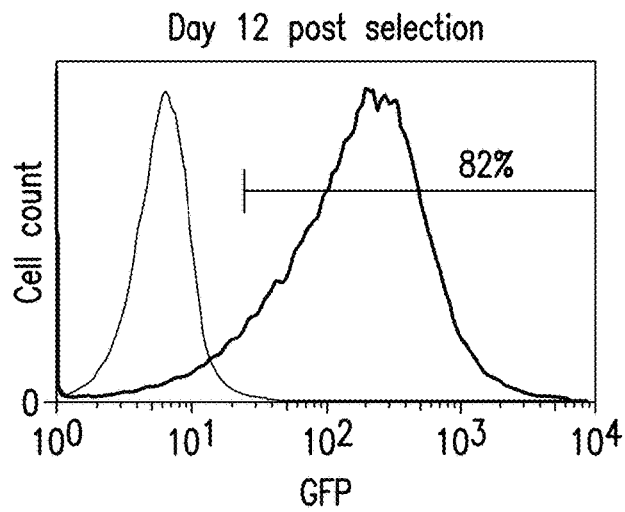
Figure 1C:
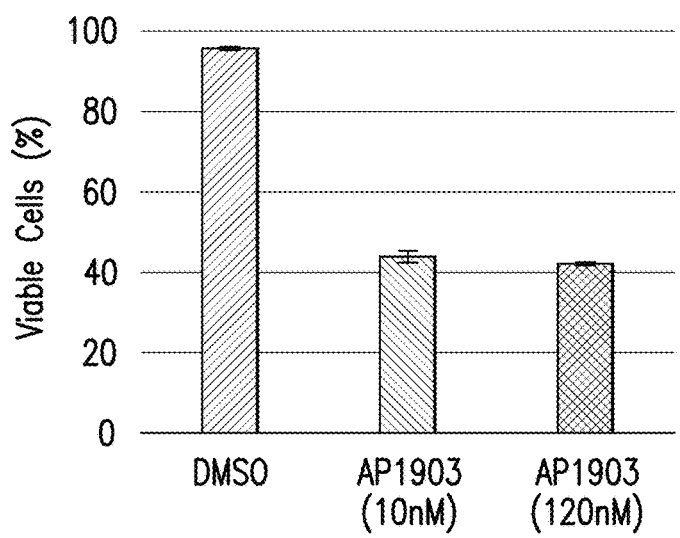
Figure 1D:
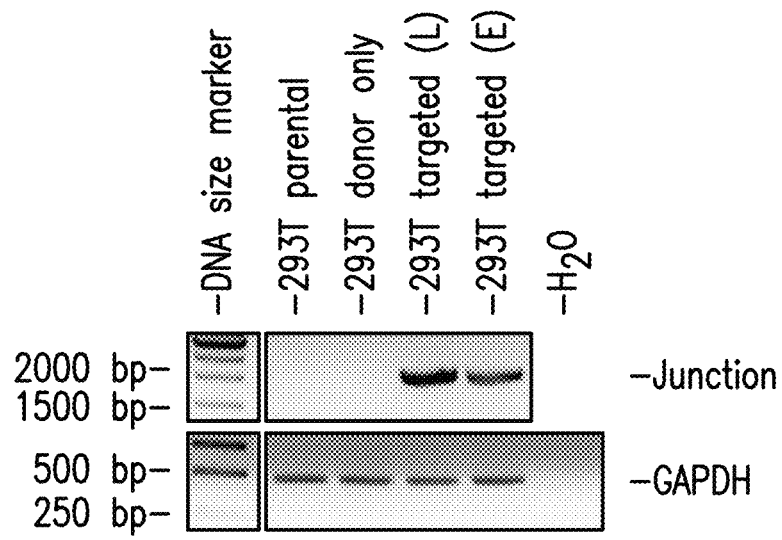

A donor construct encompassing CMV-driven iCasp9 (AAVS1-G1.0) was designed to target the AAVS1 locus (FIG. 1A) and to integrate the Casp9 suicide gene to 293T cells. The donor construct also comprise GFP and puromycin genes, the expression of which are driven by AAVS1 endogenous promoter once the targeted insertion takes place (FIG. 1A). 293T cells were transfected with ZFNs specific to AAVS1 locus and the donor construct AAVS1-G1.0. Three days after transfection, the puromycin selection was started and continued for 12 days. The puro-selected population was analyzed by flow cytometry for GFP expression, and a range of GFP expression levels were observed. It was observed that about 82% of the puro-selected cell population expressed GFP (FIG. 1B). Next, the puro-selected 293T cells were subjected to 10 nM or 120 nM AP1903 (DMSO was used as control) treatments for 24 hrs. The treated cells were then harvested and stained with 7AAD, which selectively stains membrane-compromised dying cells, and analyzed by flow cytometry. The 7AAD negative cells (presumably live cells) percentage were plotted for each treatment (DMSO at control; AP1903 10 nM; and AP1903 120 nM) (n=2). Significant cell death was detected post AP1903 treatment under both concentrations (FIG. 1C). The dosage of AP1903 did not seem to have an effect on the dying cell rate. The targeted insertion of donor vectors into AAVS1 locus in the puro-selected 293T cells was further verified using Junction PCR of genomic DNA from these puro-selected 293T cells (FIG. 1D) with the presence of PCR amplification products specific to the junction formed by donor vector insertion.

Figure 1E:
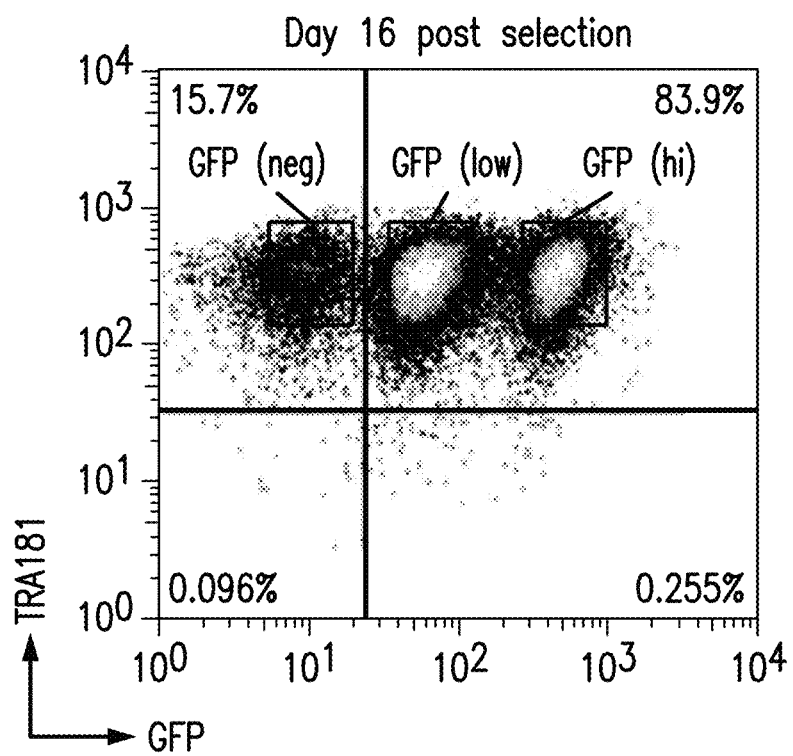
Figure 1F:
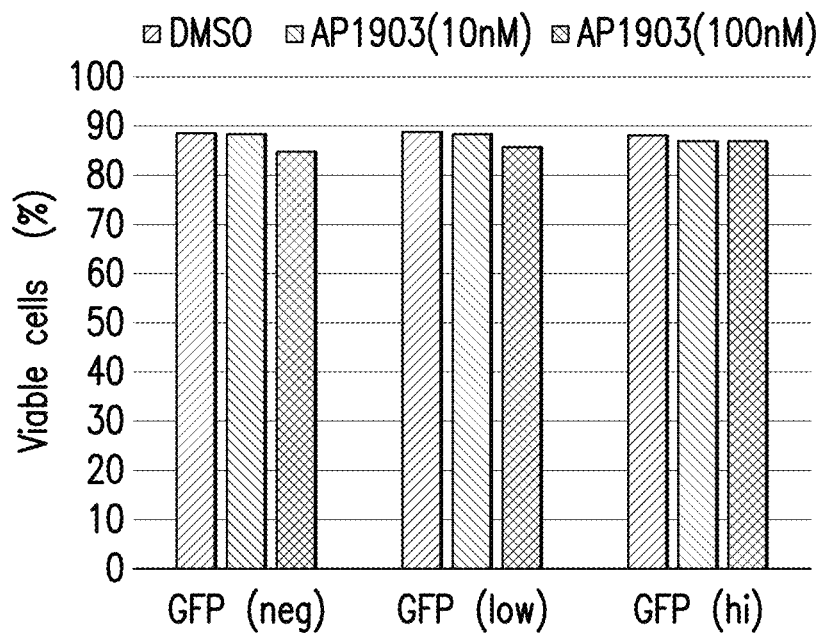
Figure 1G:
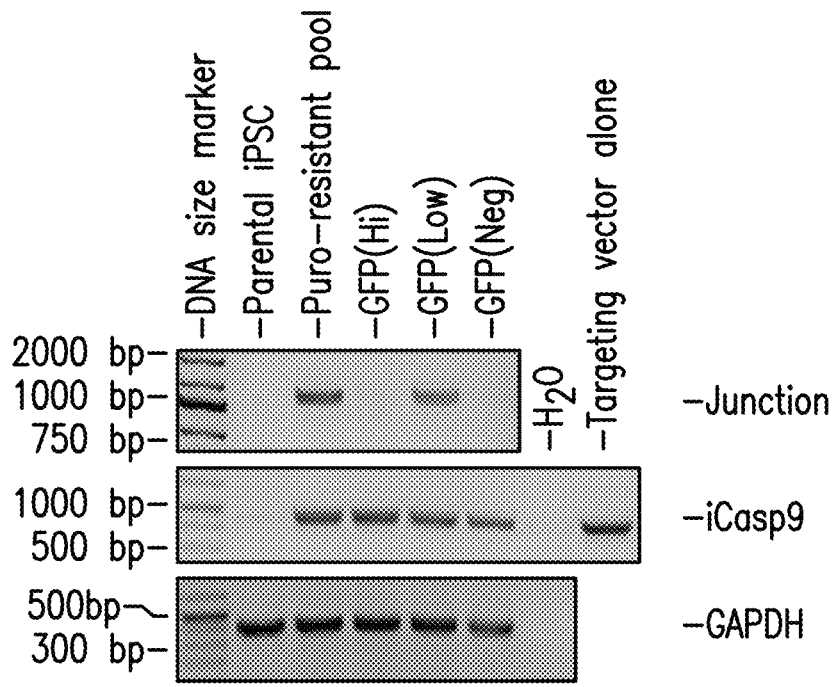

Similar to 293T cells, hiPSCs were transfected with ZFNs specific to AAVS1 locus and a donor construct encompassing CMV-driven iCasp9 (AAVS1-G1.0). The puromycin selection was started 3 days after transfection and continued for 16 days. The puro-resistant cells were analyzed by flow cytometry for GFP expression. Three populations based on the GFP intensity, GFP (neg), GFP (low) and GFP (hi) were sorted by flow cytometry (FIG. 1E). The sorted GFP (neg), GFP (low) and GFP (hi) populations were expanded, and then were subjected to AP1903 treatment (10 nM or 100 nM), or DMSO as control, for 24 hrs. The treated cells were harvested and stained with 7AAD and analyzed by flow cytometry. The 7AAD negative cells (presumably live cells) percentage were plotted for each treatment. However, in contrast to 293T cells with targeted Casp9 insertion at AAVS1 locus, cell death mediated by the AP1903 was not detected in all treatments in iPSCs with targeted Casp9 insertion at AAVS1 locus (FIG. 1F). Junction PCR of genomic DNA from puro-selected and sorted hiPSCs showed the targeted insertion of donor vectors into AAVS1 locus only in GFP (low) population, but not in GFP (neg) or GFP (hi) populations (FIG. 1G). Therefore, the lack of cell death in GFP (hi) population was believed to be associated with incorrect (not targeted) insertion in the genome and presumed absence of iCasp9 expression under the CMV promoter (FIG. 1G, lane 4; lane 1-marker). Whereas, the lack of cell death in GFP (low) was believed to be associated with reduced expression of iCasp9 gene under CMV promoter despite of the correct targeted insertion in iPSCs (FIG. 1G, lane 5). Therefore, AAVS1 safe harbor targeted iCasp9 suicide gene regulated by CMV promoter elicits variable responses, probably depending on the cell type for integration and integration sites in the genome, when activated by AP1903.

Figure 2A:
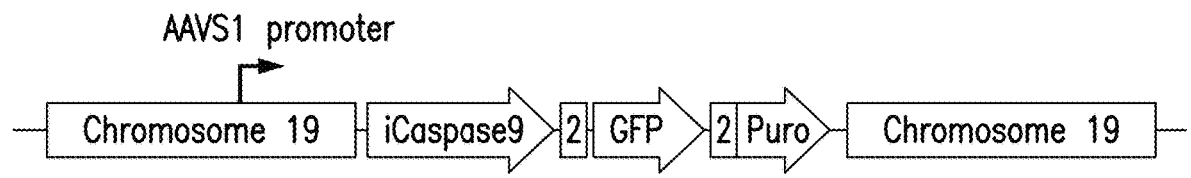
FIGS. 2A-F are a graphic representation of safe harbor loci targeted insertion of iCasp9 under various endogenous and exogenous promoters in hiPSCs. A. Illustration of construct designed to target the AAVs1 locus with AAVS1 promoter driving gene expression. B. hiPSCs were transfected with ZFNs specific to AAVS1 locus and a donor construct encompassing iCasp9 under the control of AAVS1 endogenous promoters; puro-resistant cells were analyzed by flow cytometry for GFP expression. C. Expanded puro-resistant iPSCs were subjected to AP1903 (or DMSO control) treatment for 24 hrs. The treated cells were harvested and stained with 7AAD. The 7AAD negative cell percentage were plotted for each treatment. D. Junction PCR of genomic DNA from puro-resistant pool showed the targeted insertion of donor vectors into AAVS1 locus in this populations. E. Illustration of construct designed to target the AAVs1 locus with various promoters. F. hiPSCs were transfected with ZFNs specific to AAVS1 locus and a donor construct encompassing iCasp9 under the control of various endogenous and exogenous promoters, and the puro-resistant cells were analyzed by flow cytometry for GFP expression.
Figure 2B:
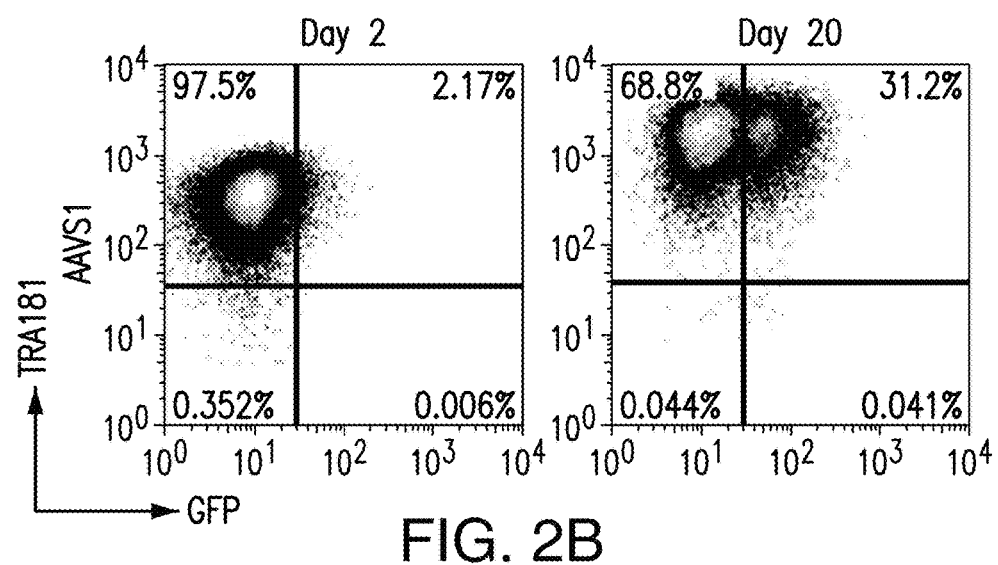
Figure 2C:
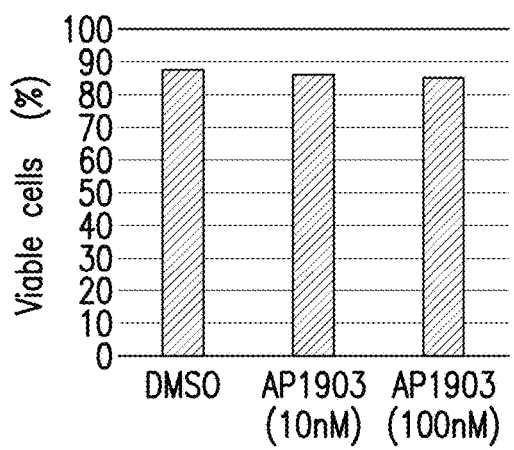
Figure 2D:
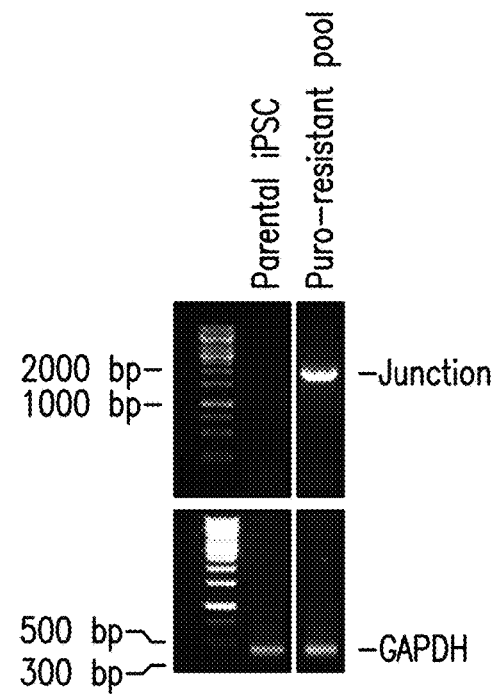

Example 3—Safe Harbor Loci Targeted Insertion of iCasp9 Under Various Endogenous and Exogenous Promoters in hiPSCs Because in the previous study puromycin selection under the AAVS1 promoter was robustly expressed to maintain viability and growth during selection, next a donor construct encompassing iCasp9 was designed to target the AAVS1 locus with endogenous AAVS1 promoter driving iCasp9 gene expression upon insertion (and GFP, and puromycin marker genes) (FIG. 2A). hiPSCs were transfected with ZFNs specific to AAVS1 locus and the donor construct encompassing iCasp9 under the control of AAVS1 endogenous promoter. Puromycin selection was started 3 days after transfection and continued for 20 days before the puro-resistant cells were analyzed by flow cytometry, and were shown to have GFP expression (FIG. 2B). Expanded puro-resistant iPSCs were then subjected to AP1903 (or DMSO control) treatment for 24 hrs. The treated cells were harvested and stained with 7AAD and analyzed by flow cytometry. The 7AAD negative cells, i.e., live cells, percentage were plotted for each treatment. However, cell death mediated by the AP1903 was not detected in all treatments in iPSCs with targeted insertion of Casp9 at AAVS1 locus, and controlled Casp9 expression by endogenous AAVS1 promoter (FIG. 2C). The Junction PCR of genomic DNA from puro-resistant pool showed the targeted insertion of donor vectors into AAVS1 locus in this populations (FIG. 2D). As such, AAVS1 safe harbor targeted iCasp9 suicide gene regulated by endogenous AAVS1 promoter seems to have failed to elicit iCasp9 expression despite the correct insertion at the AAVS1 locus. Based on the GFP expression intensity, again it appears that low level expression is not sufficient for iCasp9 mediated cell death.

Figure 2E:
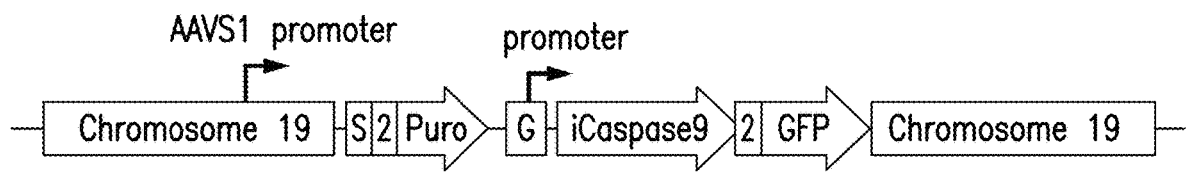
Figure 2F:
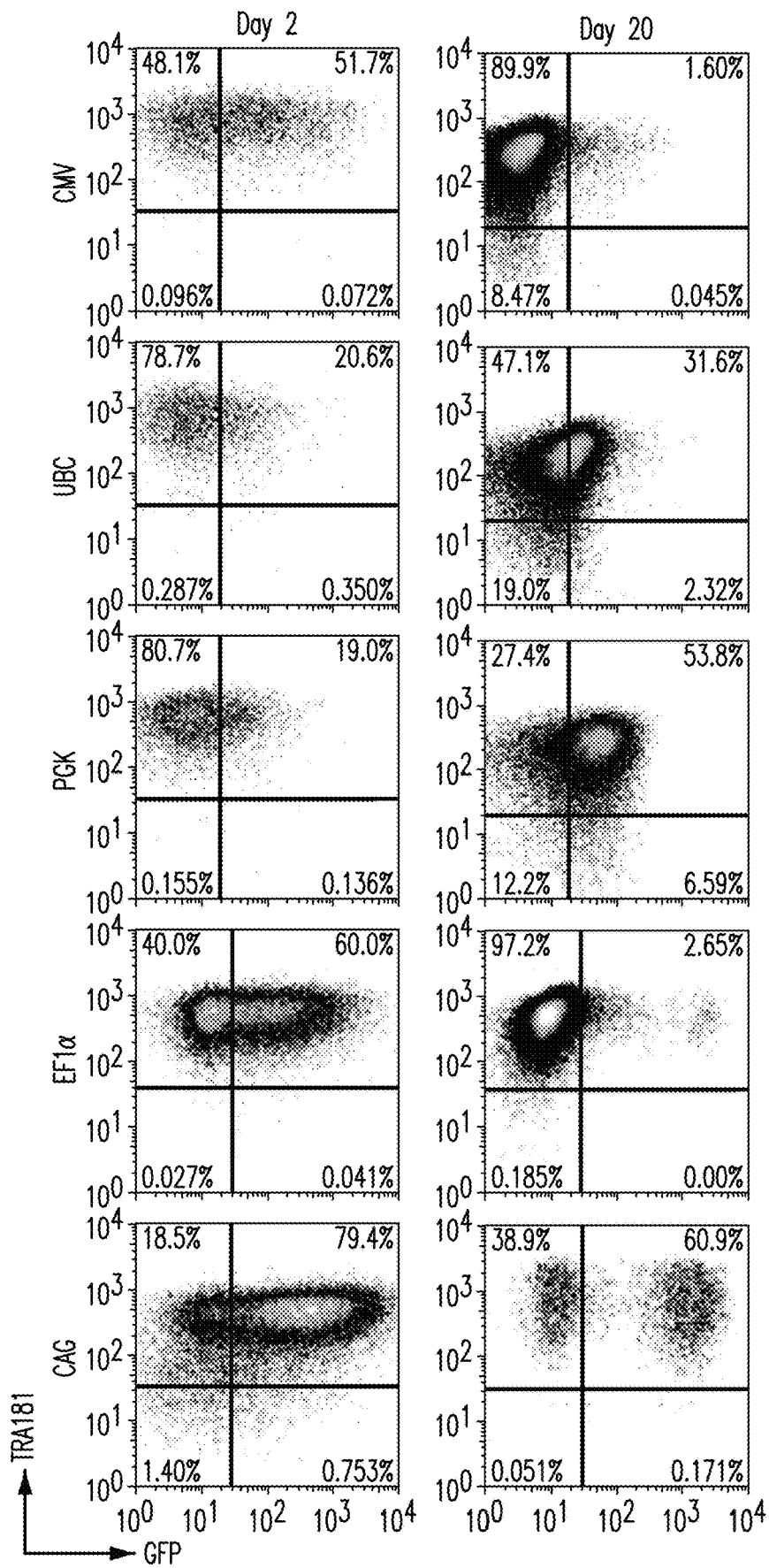

It appears that unlike other gene delivery strategies such as lentiviral mediated transgene integration where multiple copies of the gene are introduced per individual cells, in the method of locus specific targeting, the properties of different promoters will play a significant role in functional output. To survey which promoter maintains robust expression at the desired level, a construct was then designed to target the AAVS1 locus with various exogenous promoters driving iCasp9 expression, and with AAVS1 endogenous promoter driving GFP and puromycin marker genes (FIG. 2E). The tested exogenous promoters included CMV, UBC, PGK, EF1α, and CAG hiPSCs were transfected with ZFNs specific to AAVS1 locus and a donor construct encompassing iCasp9 under the control of one of the selected exogenous promoters. The puromycin selection was started 3 days after transfection and continued for 20 days before the puro-resistant cells were analyzed by flow cytometry for GFP expression. It was observed hiPSCs transfected with constructs encompassing iCasp9 under the control of EF1α, and CAG (see SEQ ID NO: 1) demonstrated high GFP expression upon transfection with CAG alone demonstrating robust expression (FIG. 2F and Table 1). These two strategies were selected for further analysis.

Example 4—Targeted Insertion of EF1α Promoter-Driven iCasp9 into AAVS1 Safe Harbor in iPSC A donor construct encompassing EF1α-driven iCasp9 was designed to target the AAVS1 locus according to FIG.

Figure 3A:
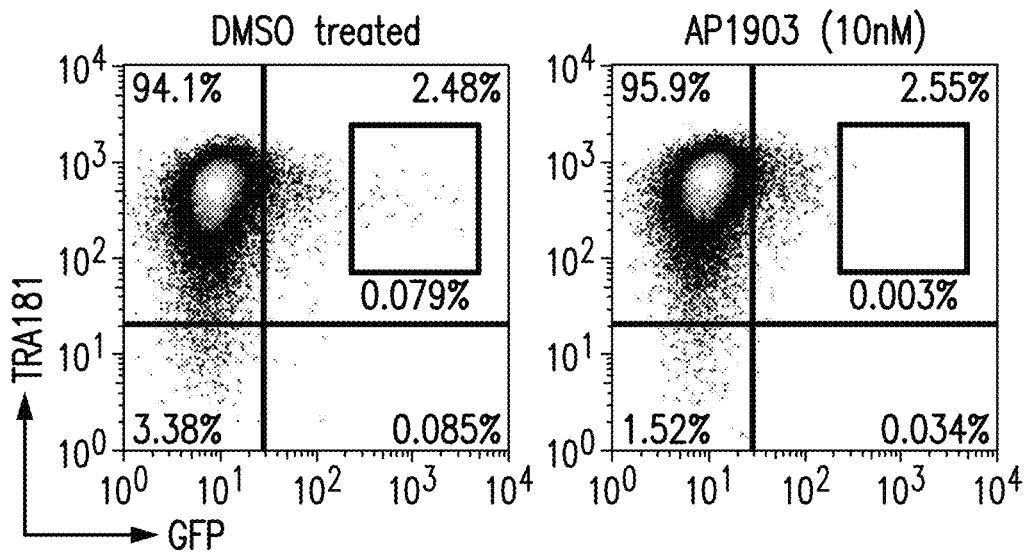
FIGS. 3A-E are a graphic representation of targeted insertion of EF1α promoter-driven iCasp9 into AAVS1 Safe Harbor in iPSC. A. hiPSCs transfected with ZFNs specific to AAVS1 locus and a donor construct encompassing EF1α-driven iCasp9 (see FIG. 2) were puromycin selected followed by AP1903 treatment. The gated area highlights the GFP positive cells responsive to the AP1903 cell death induction. B. TRA181 and GFP positive hiPSCs were sorted in bulk or individually in 96-well plate. C. GFP positive bulk-sorted hiPSCs were maintained in puromycin-free medium overtime to determine population profile over time. D. Bright filed image of a clonal hiPSC derived from single cell sorted TRA181 and GFP cells. E. Clonal hiPSCs were expanded, and the GFP expression lost to various degrees after expansion.
Figure 3B:
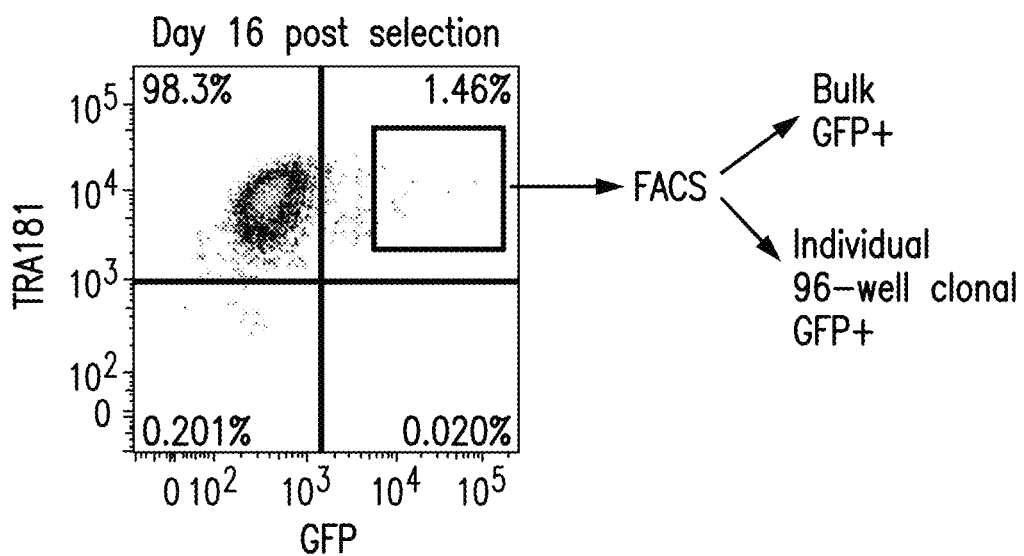
Figure 3C:
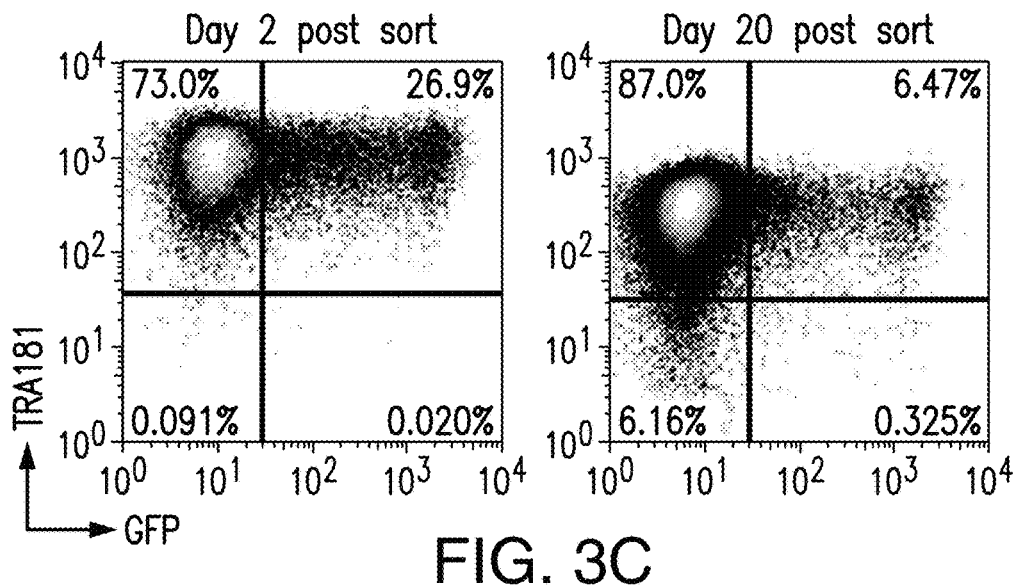
Figure 3D:
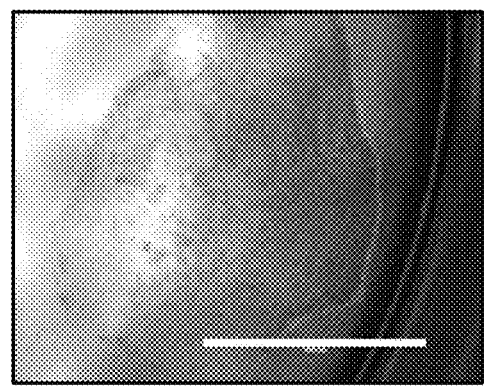
Figure 3E:
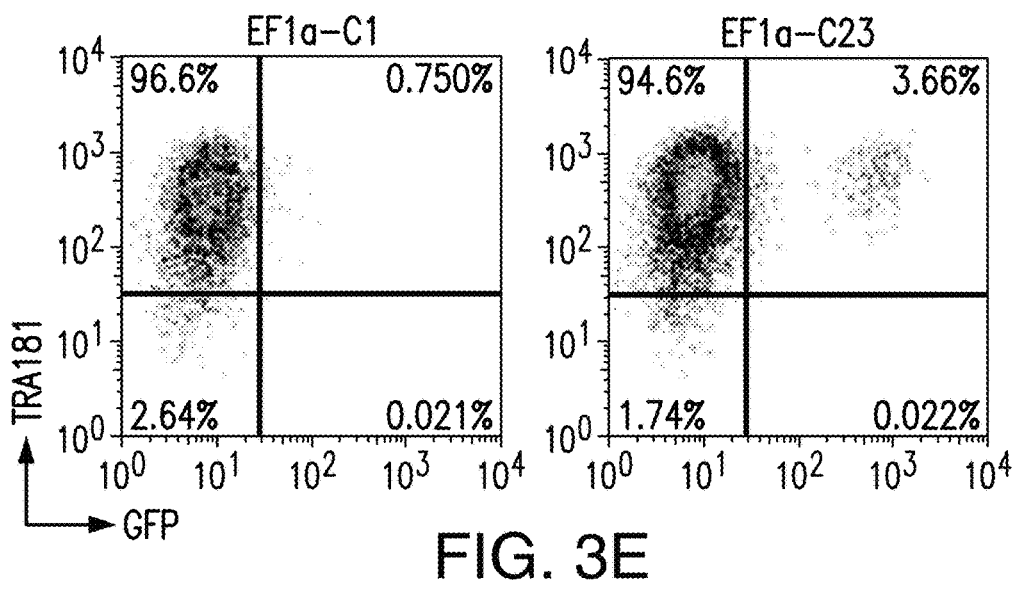

2E. hiPSCs transfected with ZFNs specific to AAVS1 locus and the donor construct encompassing EF1α-driven iCasp9 were puromycin selected for 20 days followed by AP1903 treatment. The gated area in FIG. 3A showing the flow cytometry analysis highlights the GFP positive iPSC cells with targeted insertion, although few, were responsive to the AP1903 cell death induction. To determine whether these GFP positive population can be enriched and maintained, TRA181 (a marker showing pluripotent and undifferentiated state) and GFP positive (indication of iCasp9 expression) hiPSCs were sorted in bulk or individually in 96-well plate around day 16 post selection (FIG. 3B). GFP positive bulk-sorted hiPSCs were maintained in puromycin-free medium overtime to determine population profile over time (FIG. 3C). It was observed the percentage of cells expressing high TRA181 and high GFP reduced over time (for example, from Day 2 post sort to Day 16 post sort). This data suggests that although EF1α displayed high-level expression, it was not capable of maintaining that expression, most likely due to silencing in the pluripotent state. To determine whether individual hiPSCs containing robust EF1α mediated expression could be found, the individual hiPSC sorted cells were screened. The bright filed image of a clonal hiPSC derived from single cell sorted TRA181 and GFP cells demonstrated the morphology of hiPSC colony derived from a single sorted cell (FIG. 3D). Clonal hiPSCs having targeted insertion at AAVS1 locus EF1α-driven iCasp9 were then expanded and assessed for GFP expression. However, all the colonies lost GFP expression to various degrees after expansion, suggestive of EF1α promoter's inability to maintain expression in hiPSCs during expansion after insertion (see FIG. 3E, EF1α clone C1 and C23 for example). Collectively at the bulk and individual sorted level, EF1α was not able to robustly maintain GFP and in turn iCasp9 expression.

Example 5—Targeted Insertion of CAG Promoter-Driven iCasp9 into AAVS1 Safe Harbor in hiPSC Several endogenous promoters were found to drive persistent expression of iCasp9 during clonal expansion of hiPSCs, but the expression level was determined to be too low to effectively respond to AP1903 treatment. Expression of iCasp9 under the control of various exogenous promoters was also shown to be lost during prolonged clonal expansion of hiPSCs, and failed to drive AP1903-induced cell death. hiPSCs transfected with ZFNs specific to AAVS1 locus and a donor construct encompassing CAG-driven iCasp9 were next assessed (FIG. 2E and Table 1).

Figure 4A:
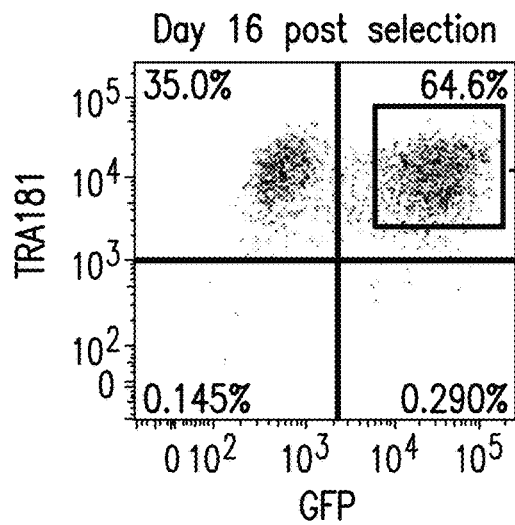
FIGS. 4A-G are a graphic representation of targeted insertion of CAG promoter-driven iCasp9 into AAVS1 Safe Harbor in hiPSC. A. hiPSCs were transfected with ZFNs specific to AAVS1 locus and a donor construct encompassing CAG-driven iCasp9 (see FIG. 2). The puro-resistant cells were sorted in bulk or individually in 96-well plates. B. GFP+ bulk-sorted iPSCs were maintained in puromycin-free medium for 21 days before analyzed by flow cytometry for GFP expression. C. When treated with AP1903, the GFP positive cells become 7AAD-staining positive. D. Bright-filed image of a typical colony post individual sort. E. The colonies originated from a single cell were expanded, and flow cytometry assessment showed high GFP and TRA181 expression. F. Mean fluourescence intensity of selected clones. G. Junction PCR of genomic DNA to detect the homologous recombination of donor construct and AAVS1 locus in both parental hiPSCs and CAG hiPSC population pools.
Figure 4B:
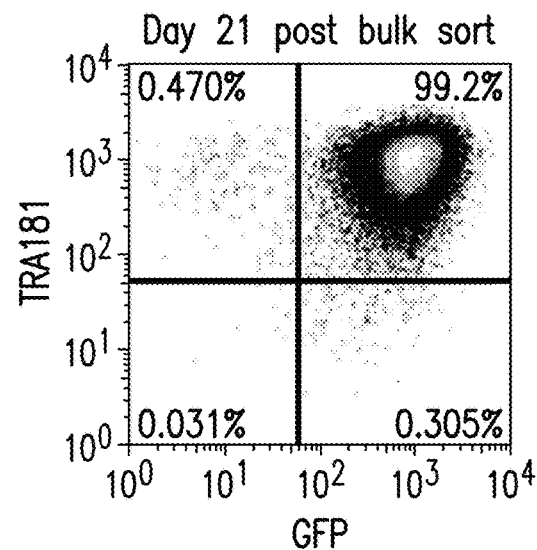
Figure 4C:
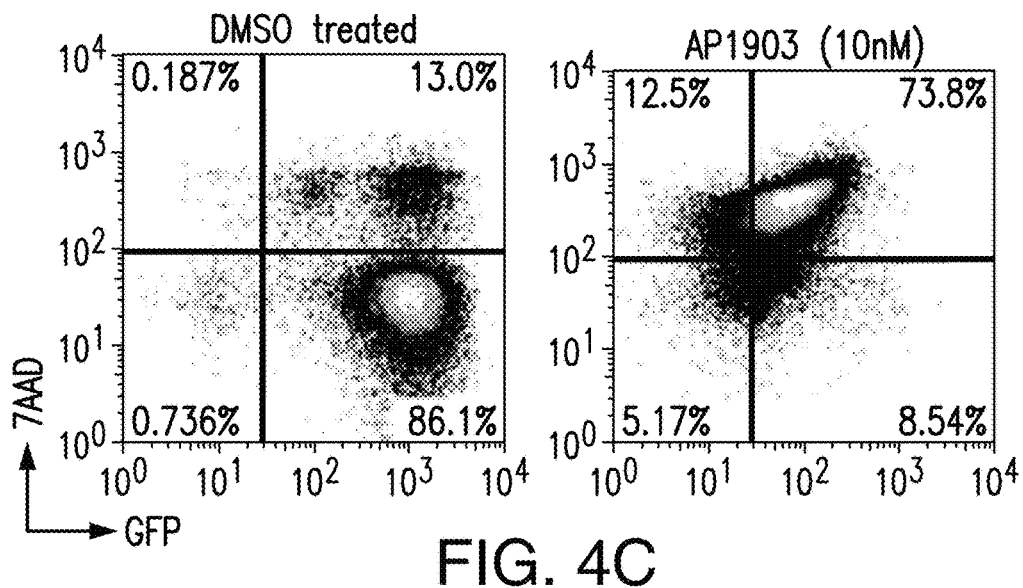
Figure 4D:
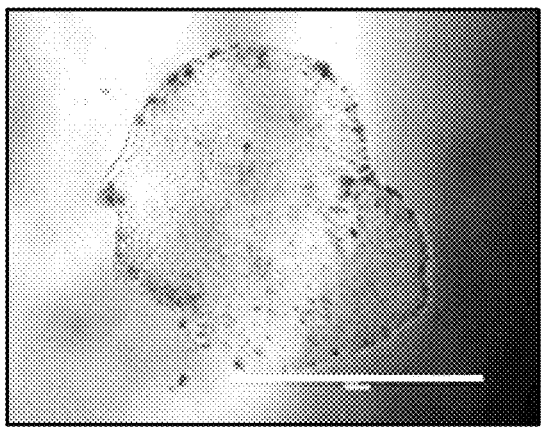
Figure 4E:
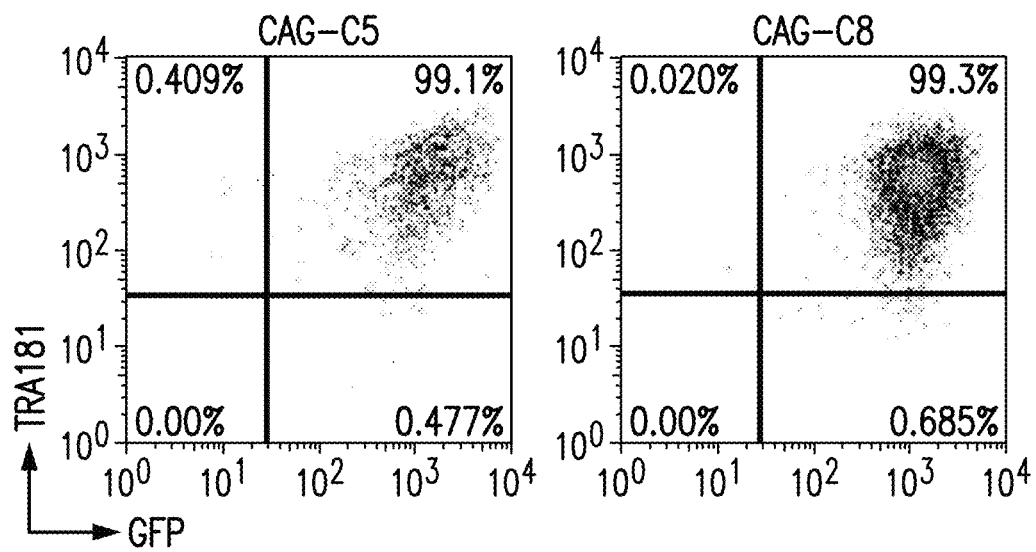
Figure 4E:
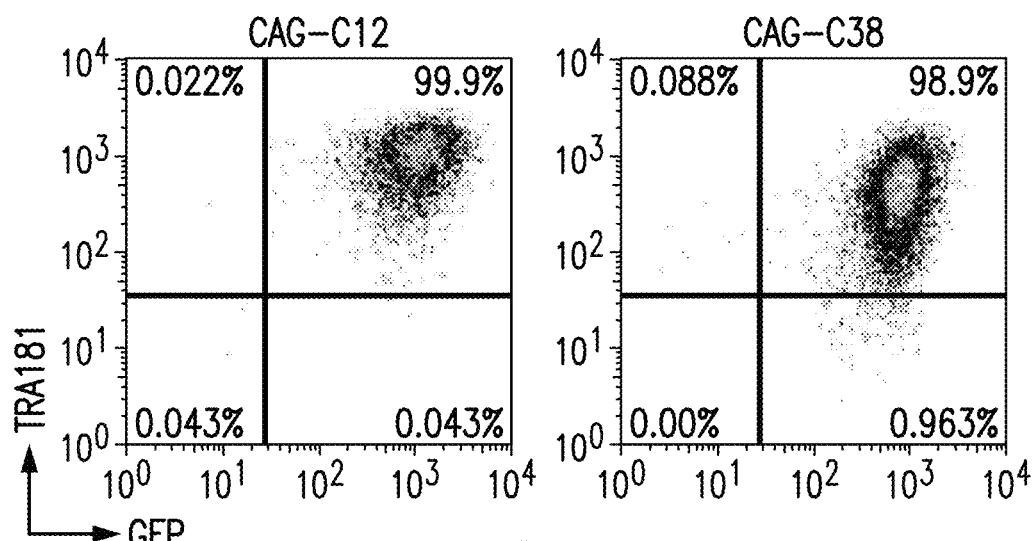
Figures 4F, 4G:
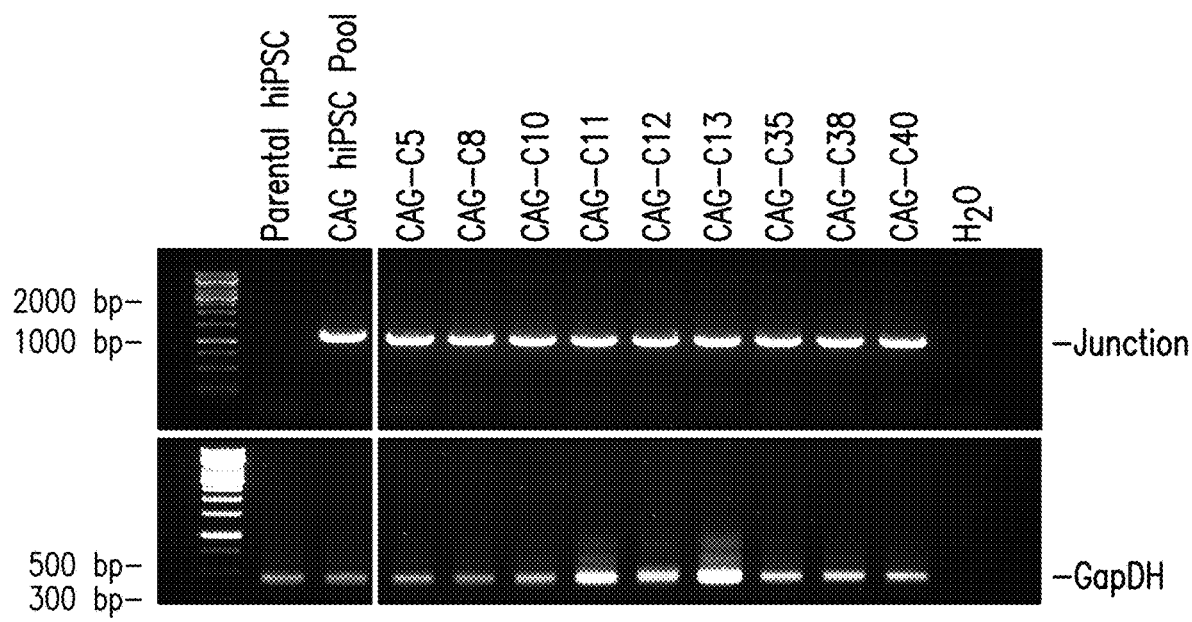

Puromycin selection was started 3 days after transfection and continued for 16 days before the puro-resistant cells were sorted in bulk or individually in 96-well plates for high GFP expression. GFP positive bulk-sorted iPSCs after targeting and puro-selection were maintained in puromycin-free medium for 21 days before analyzed by flow cytometry to demonstrate whether the high GFP expression can be maintained during iPSC expansion. FIG. 4B showed the GFP positive cell percentage were not only maintained during the prolonged expansion, but the percentage of GFP positive cell was higher than 99%. This is a first time observation that a promoter targeted to a specific locus was capable of maintaining a robust expression similar to that of a lentiviral method where multiple copies are inserted into the genome. Next, the iCasp9 gene response of the bulk sort maintaining 99% GFP expression was tested. FIG. 4C showed that when treated with AP1903, the GFP positive cells undergo induced cell death, and become 7AAD-staining positive after treatment. With the CAG bulk population demonstrating robust expression that translates to an effective iCasp9 mediated cell death, we next assessed the individual clones. Next, the puro-resistant iPSCs sorted clonally into matrigel-coated 96-well plate were assessed. The bright-filed image of a typical colony post individual sort shows high quality pluripotent morphology (FIG. 4D). The colonies originated from a single cell were individually expanded and assessed for GFP and TRA181 expression by flow cytometry. All selected colonies (for example, CAG-C5, -C8, -C12, -C38) were shown to have maintained high-percentage of GFP and TRA181 expression during expansion (FIG. 4E). The mean fluorescence intensity (MFI) of selected clones are depicted in FIG. 4F, with CAG-C5 having the highest MFI, 1500, and CAG-C38 has relatively the lowest MFI among the four clones, which is 858. The Junction PCR of genomic DNA was performed with all selected GFP+ clones to detect the homologous recombination of donor construct and AAVS1 locus. Parental hiPSCs represents original hiPSC line before transfection.

CAG hiPSC population pool represents population after targeting transfection and 16 days of puromycin selection. GAPDH genomic sequence were amplified to ensure the quality of genomic DNA. All selected GFP positive clones demonstrated correct insertion at AAVS1 locus (FIG. 4G). Therefore, the above data suggested that CAG is the only promoter has the ability to robustly maintain a high-level expression of the gene under its control during iPSC expansion after targeted into the AAVS1 locus in hiPSC cells.

The performance of additional promoters at time of transfection (Day 2-3 post transfection), maintenance post puromycin selection (Day 20 post puro-selection), and functional response after AP1903 treatment were similarly evaluated. Table 1 below outlines the performance of exogenous promoters CMV, UBC, EF1α, CAG, and PGK, and endogenous promoter AAVS1. In Table 1, the suicide gene response is quantified based on the number of GFP positive cells responding to AP1903 treatment.

TABLE 1

AAVS1 targeted promoter mediated gene expression maintenance, intensity and functional response.

| Safe-harbor locus | Promoter | % GFP (Day 2-3, post transfection) | MFI (Day 2-3, post transfection) | % GFP (Day 20, post selection) | MFI (Day 20, post selection) | Suicide gene response |
|---|---|---|---|---|---|---|
| AAVS1 | CMV | 51.7 | 113 | 1.6 | 4.4 | − |
| AAVS1 | UBC | 20.6 | 20.3 | 31.6 | 16.5 | − |
| AAVS1 | EF1a | 60 | 163 | 2.65 | 16.5 | +/− |
| AAVS1 | CAG | 79.4 | 531 | 60.9 | 828 | +++ |

TABLE 1-continued

AAVS1 targeted promoter mediated gene expression maintenance, intensity and functional response.

| Safe-harbor locus | Promoter | % GFP (Day 2-3, post transfection) | MFI (Day 2-3, post transfection) | % GFP (Day 20, post selection) | MFI (Day 20, post selection) | Suicide gene response |
|---|---|---|---|---|---|---|
| AAVS1 | PGK | 19.0 | 15.8 | 53.8 | 38.9 | – |
| AAVS1 | AAVS1 | 2 | 11.1 | 32.1 | 31.0 | – |

As such, CAG among all tested promoters, demonstrates the best performance on all counts, and the CAG-iPSC clones were further characterized below.

Example 6—Pluripotency Characterization of CAG-hiPSC Clones

Figure 5A:
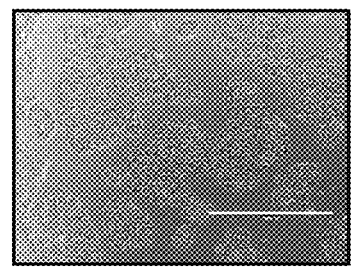
FIGS. 5A-E are a graphic representation of pluripotency characterization of CAG-hiPSC clones. A. Representative image of CAG clone C38 maintained on feeder free culture. B. Immunofluorescence staining of pluripotency markers NANOG and OCT4. C. Quantitative RT-PCR for expression of various endogenous pluripotency marker. D. Selected CAG clones were directed to lineage specific differentiation and assessed for lineage markers. Nestin, ectoderm; αSMA, mesoderm, SOX17, endoderm. E. CAG-C38 was assessed for its potential to give rise to a teratoma consisting of various lineages. Teratoma was harvested 6 weeks post injection.
Figure 5B:
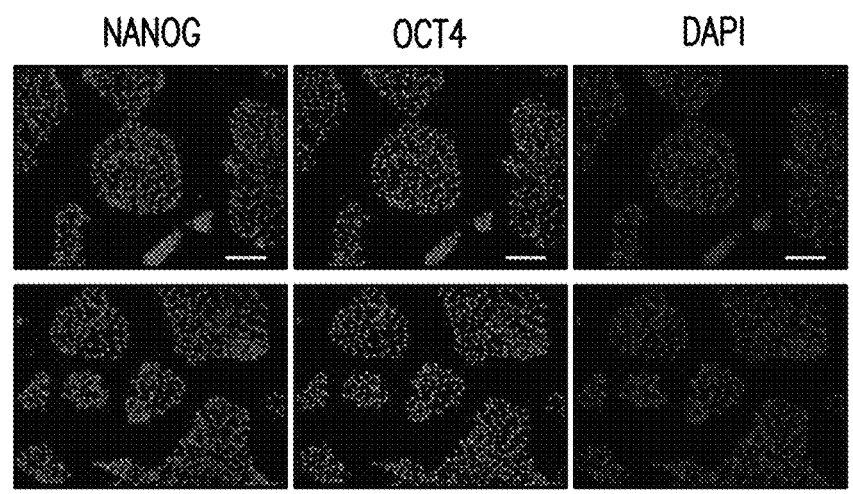
Figure 5C:
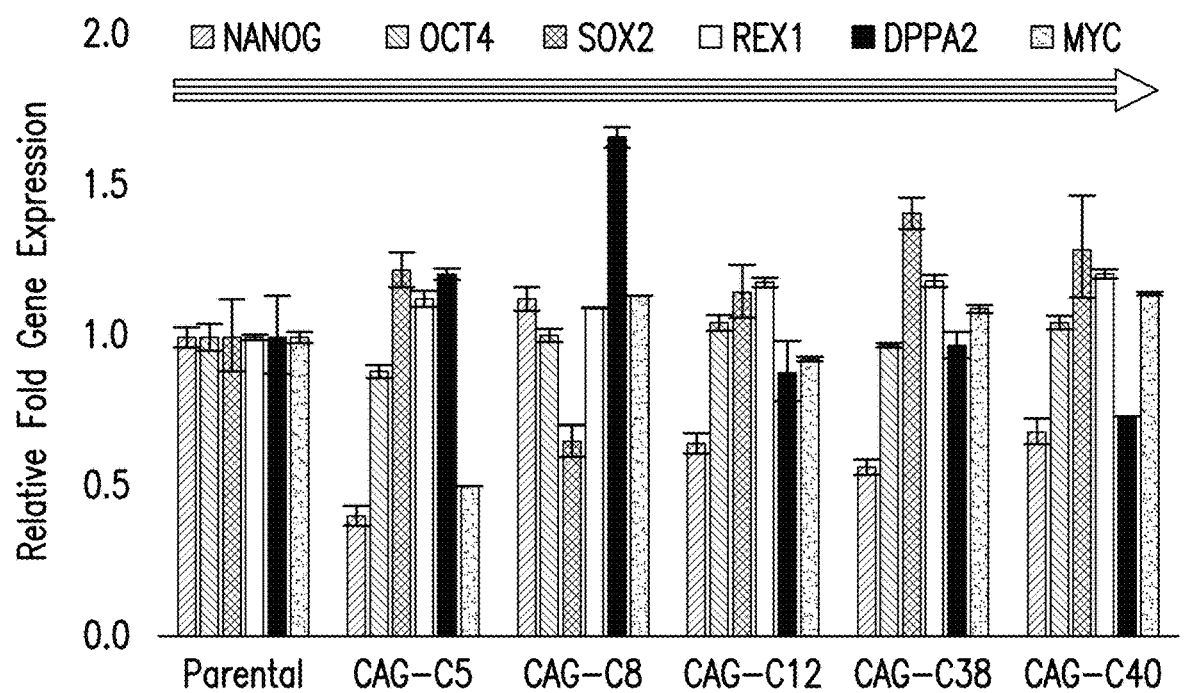
Figure 5D:
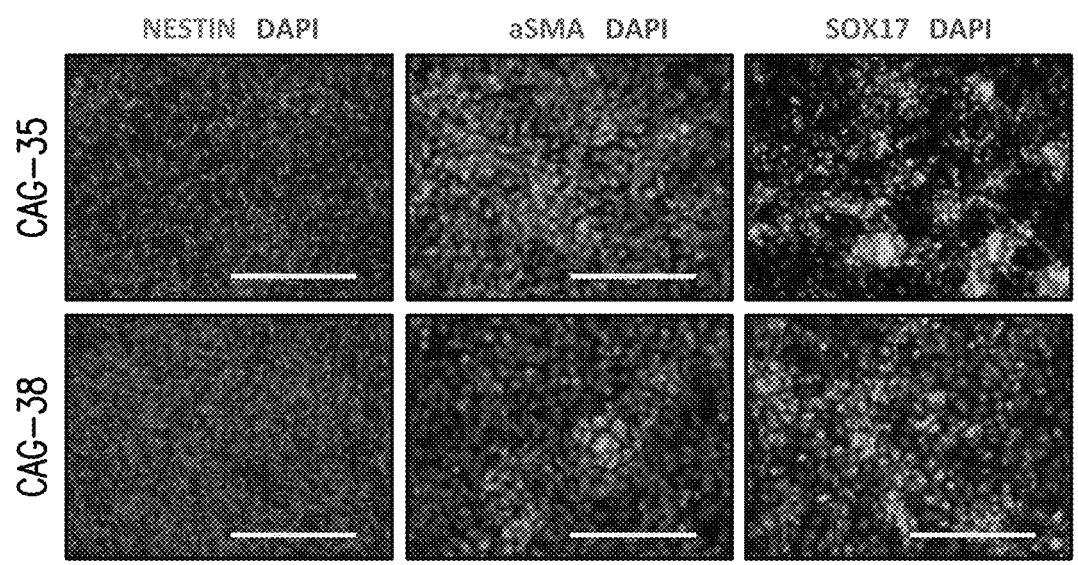
Figure 5E:
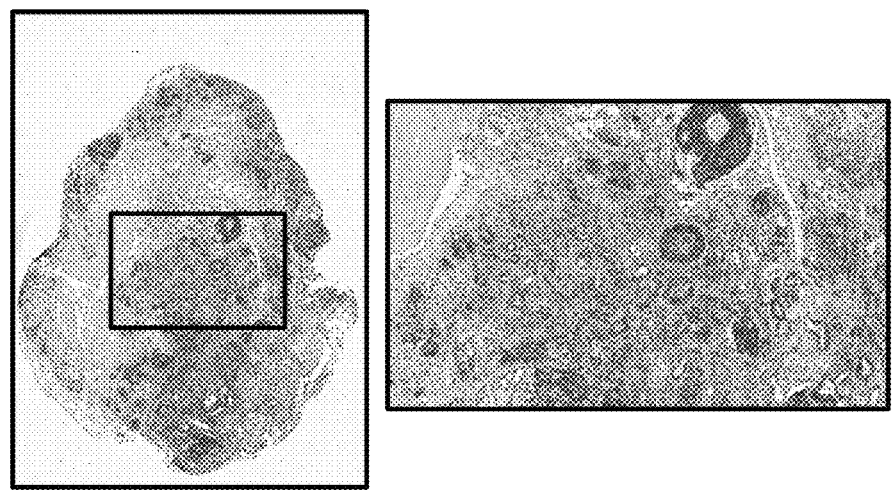

All selected CAG-hiPSC clones were analyzed for pluripotency characterization. FIG. 5A is the representative image of CAG clone C38 maintained on feeder free culture, which shows a homogeneous culture of hiPSCs with individual cells consisting of a high nuclei to cytoplasm ratio. The immunofluorescence staining of pluripotency markers NANOG and OCT4 in FIG. 5B shows that the CAG-hiPSC clones are pluripotent, and without differentiation. Quantitative RT-PCR for expression of various endogenous pluripotency marker including NANOG OCT4, SOX2, REX1, DPPA2, and MYC, were also conducted to depict the pluripotency state of the selected CAG-hiPSC clones (CAG-C5, -C8, -C12, -C38, and -C40). It is shown that NANOG expression is lower than the parental iPSC in all CAG-hiPSC clones. Flow cytometry analysis was also conducted for TRA181, SSEA3 and CD30 marker expression. Next, selected CAG clones were directed to lineage specific differentiation and assessed for lineage markers. FIG. 5D shows the expression of NESTIN, a marker for ectoderm; αSMA, a marker for mesoderm; and SOX17, a marker for endoderm, after the selected CAG clones were directed to differentiation. One of the CAG-iPSC clone, CAG-C38, was further assessed for its potential to give rise to a teratoma consisting of various lineages. In FIG. 5E, the teratoma was harvested 6 weeks post injection and demonstrates three germ layers (endoderm, mesoderm or ectoderm). These data demonstrate that the CAG-iPSC clones retained the pluripotency and the capacity to differentiate into non-pluripotent cells of all lineages.

Figure 6A:
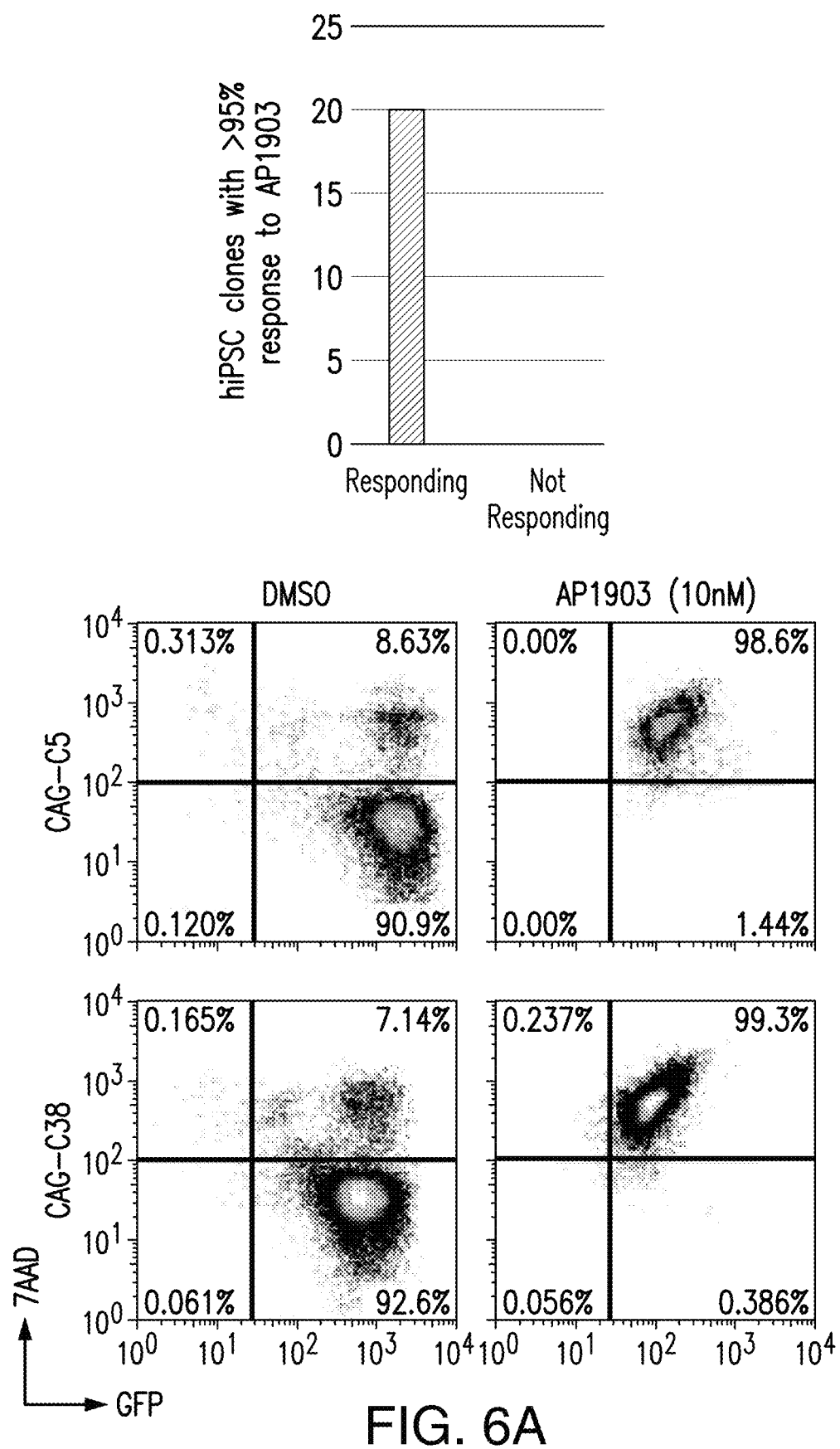
Figure 6B:
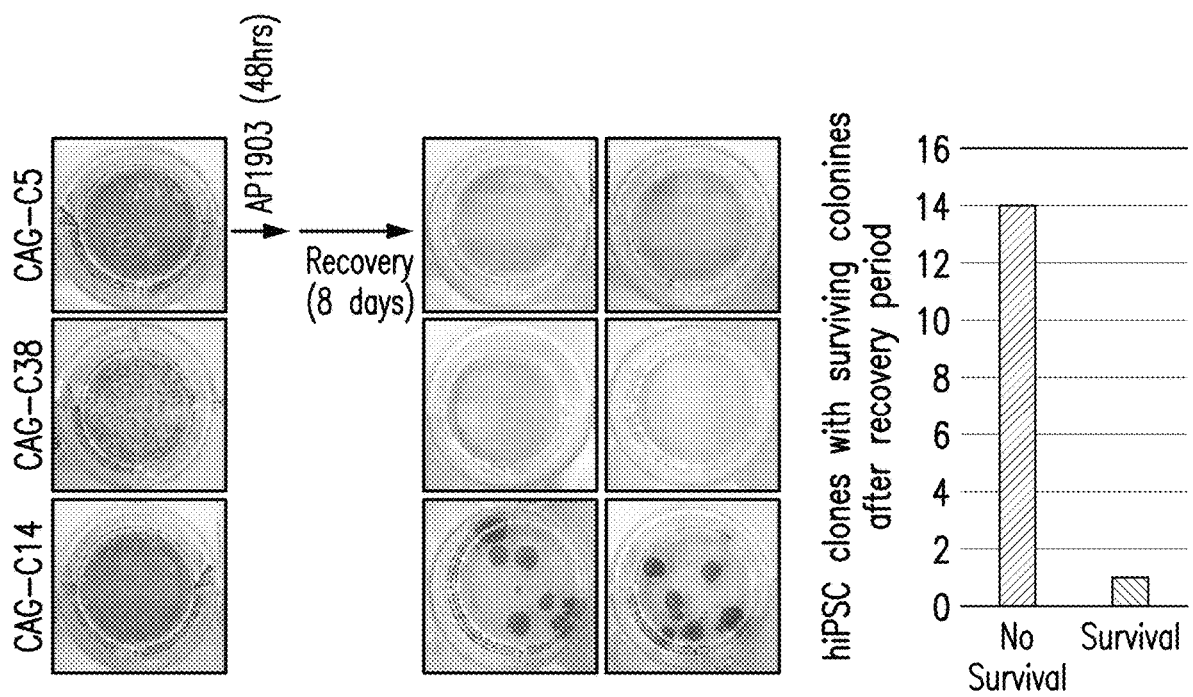
Figure 6C:
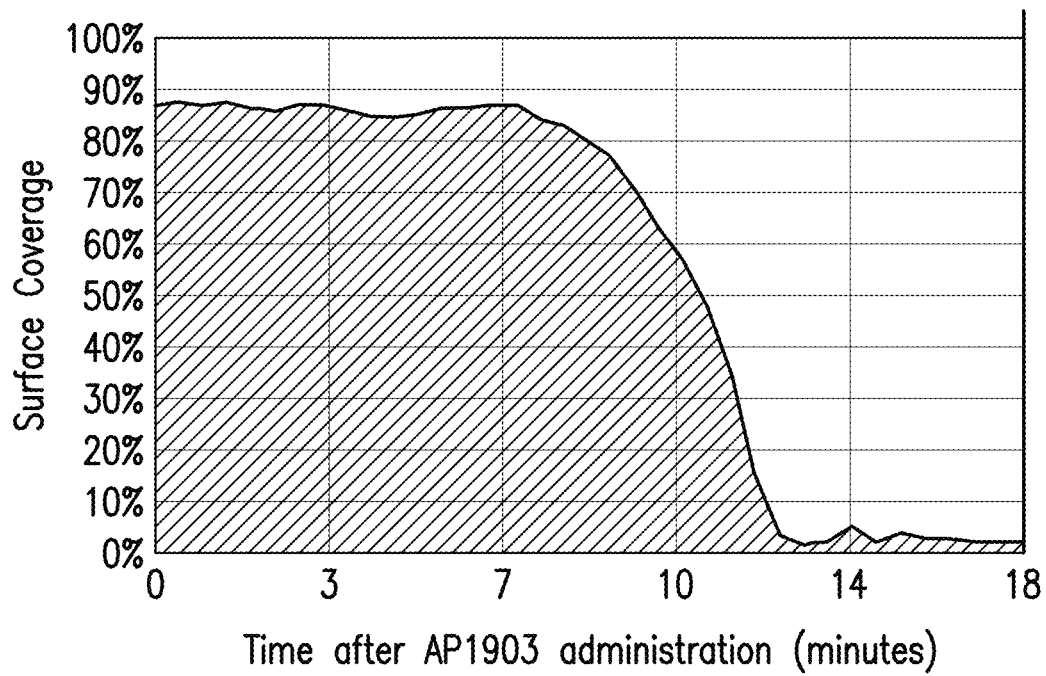
Figure 6D:
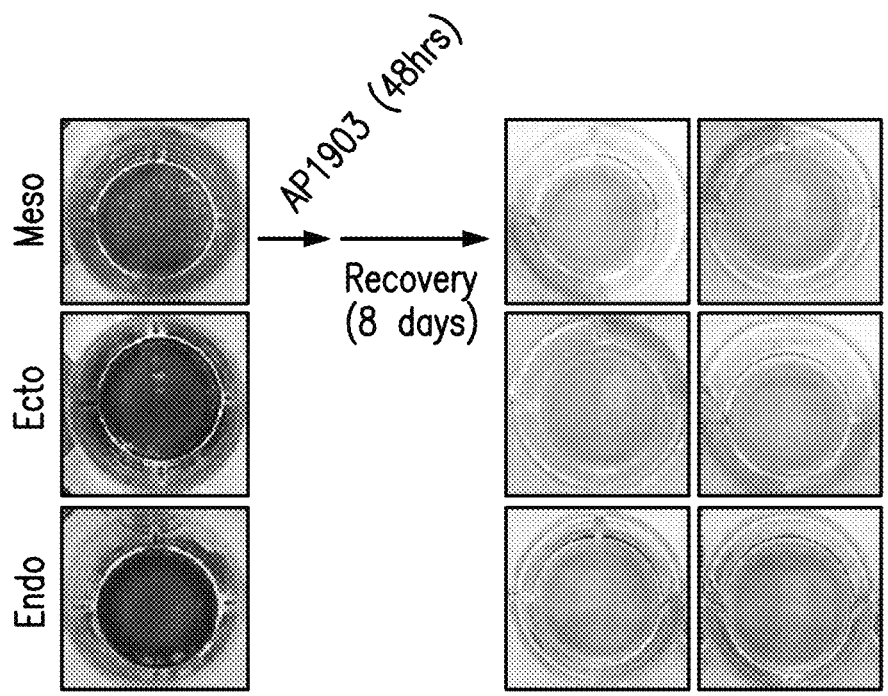

Example 7—Induced Suicide Gene Mediated Killing of hiPSC Clones at Both Pluripotent and Differentiated States with CAG-Driven iCasp9 Targeted into AAVS1 Locus Twenty CAG-iCasp9 targeted hiPSC clones were treated with AP1903 (or DMSO control) for 24 hours before stained with 7AAD and analyzed for GFP and 7AAD staining by flow cytometry. All clones have shown more than 95% 7AAD-staining positive after AP1903 treatment (FIG. 6A). Flow cytometry plots from two representative clones (CAG-C5 and -C38) were also shown to depict the Casp9 gene response in pluripotent state of the CAG-iPSC clones (FIG. 6A). Fifteen CAG-iCasp9 targeted iPSC clones were cultured in triplicate wells in 12-well plate. Upon confluence, one well was stained for alkaline phosphatase and picture was taken, another two wells were treated with AP1903 (10 nM) for 48 hours. The treated wells were washed with PBS and added fresh medium for any residual live cells to recover. Eight days of recovered wells were stained for alkaline phosphatase and pictures taken to record any survival of iPSC clones. Of the fifteen clones, only clone CAG-C14 contained surviving clones, i.e. has escaped the induced death (FIG. 6B). The other fourteen clones did not show any staining which indicated that no cells survived upon the induced expression of Casp9. FIG. 6C demonstrated the live cell coverage kinetics of clone CAG-C5 on a 10 cm dish after AP1903 (10 nM) treatment. Live cells started dying around 8 minute post treatment, and nearly all live cells were killed 12 minutes after AP1903 treatment. Next, the CAG-iCasp9 targeted hiPSC clones were induced to differentiate into cells from three germ layers, endoderm, mesoderm or ectoderm, and was each treated with AP1903 for 48 hours and allowed to recover in differentiation medium for 5 days. The replicate wells before treatment and after recovery were stained with crystal violet and imaged as shown in FIG. 6D. Images from CAG-C5 clone were shown as a representation, demonstrating that cells of all lineages were killed after AP1903 treatment. Lastly, the CAG-iCasp9 targeted hiPSC clones were induced to differentiate into CD34+ cells, and treated with AP1903 for 48 hours and flow cytometry analyzed for cell death. The elevated 7AAD staining shown in FIG. 6E indicated CD34+ cell death upon AP1903 treatment. The data shows that regardless of the epigenetic state of the cell, i.e. pluripotent state, versus ectoderm, endoderm or mesoderm, or cell type specific state such as CD34 positive cell, CAG targeted to AAVS1 locus robustly maintains expression of iCasp9.

Figure 7C:
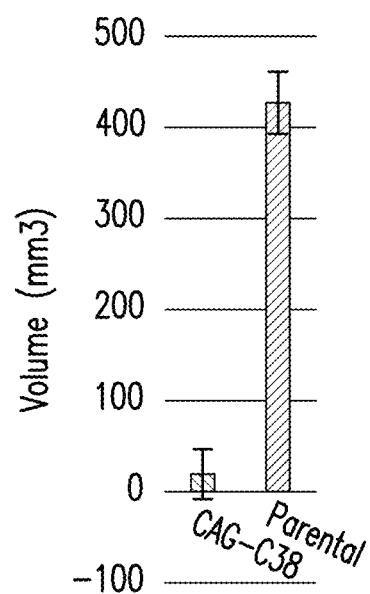
Figure 7D:
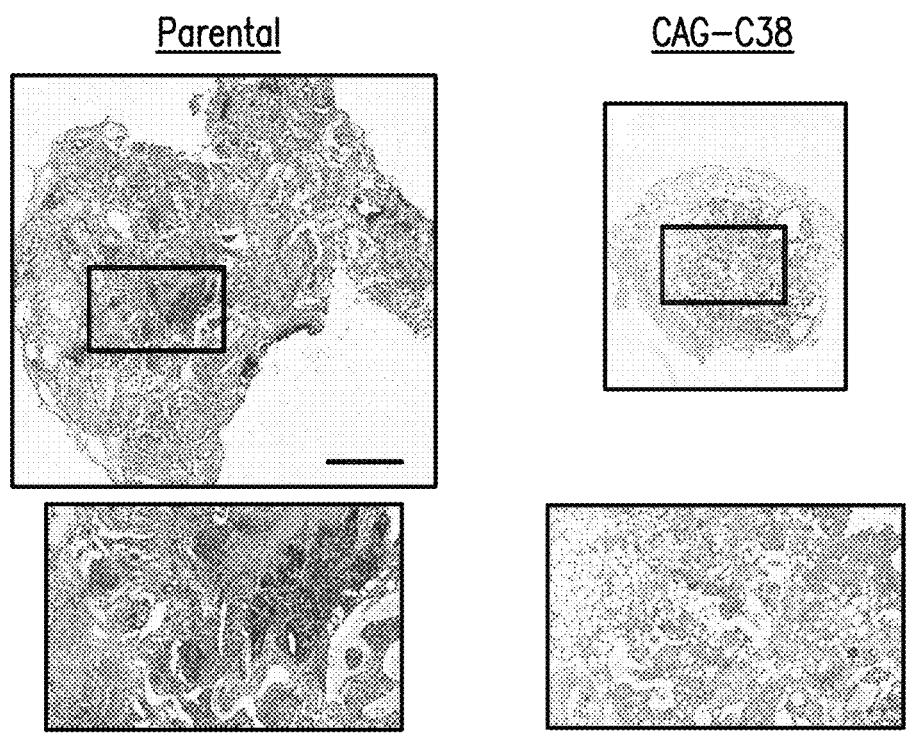
Figure 7E:
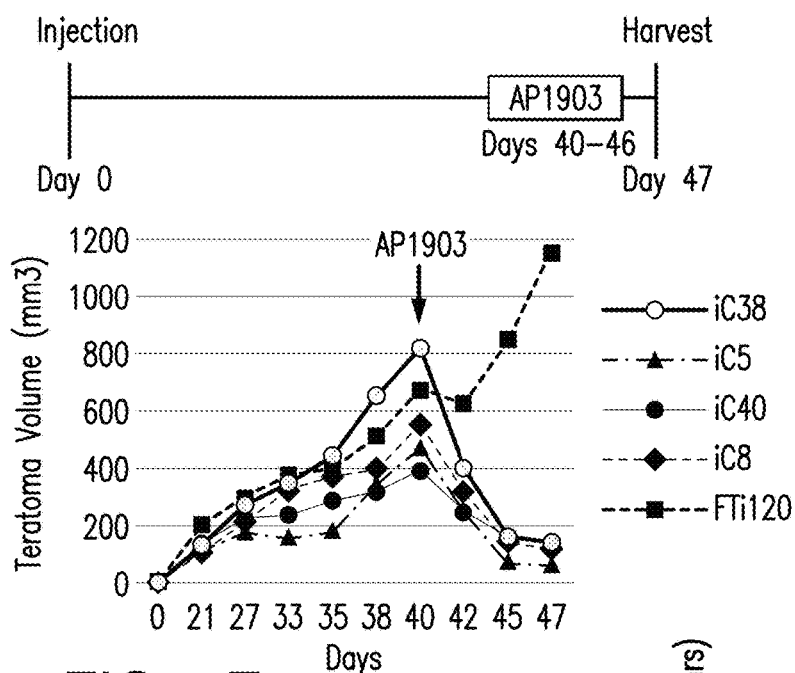

Example 8—In Vivo Demonstration of AP1903-Induced Regression of Teratomas Derived from iCasp9-iPSC Clones The subcutaneous injection positioning in the NSG mice studies was shown in FIG. 7A to demonstrate in vivo cell death mediated through iCasp9 expression and induction. Parental hiPSC line and CAG-C38 clone were injected at 4E6 cells (Day 0) and treated with AP1903 (i.p. 200 tag total) on days 7-11. At day 34 the teratomas were harvested and imaged to show size (FIG. 7B). Of the CAG-C38 harvest, one site of injection did not contain any tumors while the other consisted of mostly fat like cells. The harvested teratomas were also measured for volume (FIG. 7C). Of the harvested tumors, the CAG-38 hiPSC sourced teratomas were either not detected or seen to be significantly smaller than their parental control. The harvested teratomas were Hematoxylin and Eosin stained, and the staining results show the difference in histology between the parental iPSC and CAG-hiPSC clones (FIG. 7D). While parental hiPSC line displays majority of trilineage differentiated cell types, CAG-C38 appears to consist of mostly highly organized fat-like cells presumably contributed from the mouse.

Next, the parental hiPSC line and CAG clones were injected at 4E6 cells and treated with AP1903 (i.p. 200 µg total) on days 40-46. All tumors were routinely measured for volume, and the CAG-iPSC were still responsive to the Casp9 gene expression and causing decreased volume of tumors in mice injected with any of the selected CAG-iPSC clones. Collectively, the data demonstrates robust expression of the CAG promoter targeted to the AAVS1 locus in vitro and in vivo.

Example 9—Genome Editing of Human ROSA26 Locus Using CRISPR/Cas9 for Targeted or Nuclease-Independent Insertion of iCasp9

Figure 9A:
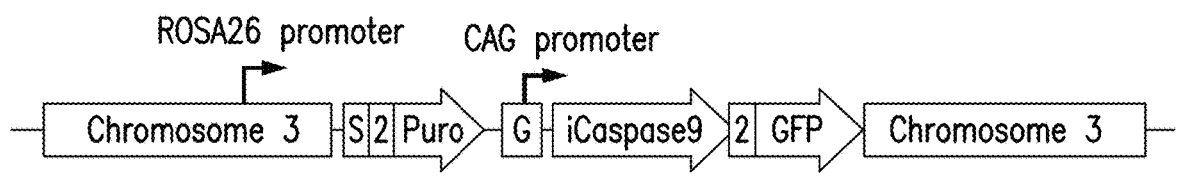
FIGS. 9A-E are a graphic representation of genome editing of human ROSA26 locus using CRISPR/Cas9 for targeted or nuclease-independent insertion of iCasp9. A. Illustration of construct design to target ROSA26 locus with CRISPR/Cas9. B. hiPSCs were transfected with gRNA/Cas9-RFP plasmid specific to ROSA26 locus and a donor construct encompassing CAG-driven iCasp9 as shown in A. Two days after the transfection, the cell population were analyzed by flow cytometry for GFP expression to determine the transfection efficiency (~89%). Puro-resistant cells were analyzed by flow cytometry for GFP expression 20 days post transfection. C. AP1903 induced cell death analysis in 293 T cells transfected with construct. D. Targeted insertion of construct in 293 T cells. E. hiPSCs transfected with construct and puromycin selected to enrich for targeted cells.
Figure 9B:
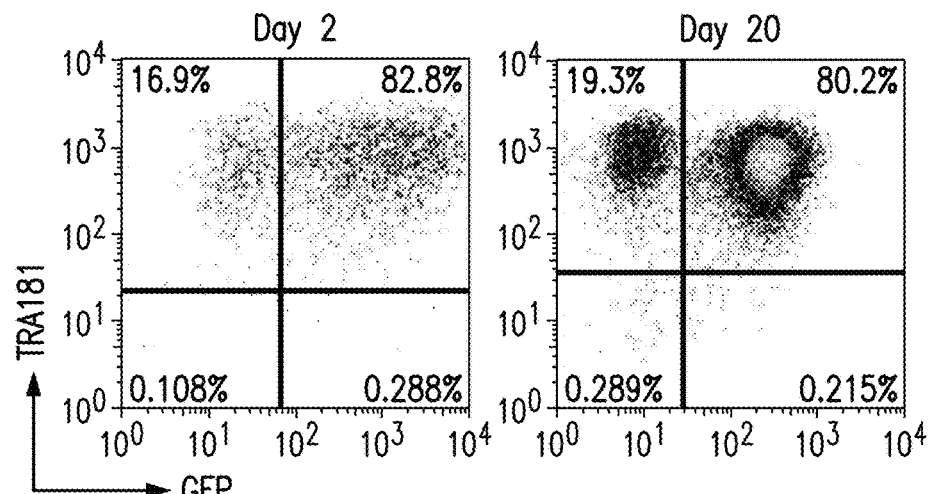

To test the synergy of other targeting strategies and safe harbor loci, in this experiment, a different endogenous locus of the iPSC genome was tested for its potential for nuclease-independent targeted insertion of an exogenous gene driven by CAG promoter. A construct was designed to target ROSA26 locus with CRISPR/Cas9, as shown in FIG. 9A. hiPSCs were transfected with gRNA/Cas9-RFP plasmid specific to ROSA26 locus and a donor construct encompassing CAG-driven iCasp9. Two days after the transfection, the cell population was analyzed by flow cytometry for GFP expression in the cells to determine the transfection efficiency, which is shown to be between about 80% to about 85% (FIG. 9B). Puromycin selection was started 3 days after transfection and continued for 20 days before the puro-resistant cells were analyzed by flow cytometry for GFP expression. GFP expression sustained during iPSC expansion (FIG. 9B). Table 2 below summarizes expression levels and functional response of iPSC with construct shown in FIG. 9A.

TABLE 2

ROSA26 targeted CAG promoter mediated gene expression maintenance, intensity and functional response:

| Safe-harbor locus | Promoter | % GFP (Day 2-3) | MFI (Day 2-3) | % GFP (Day 20, post selection) | MFI (Day 20, post selection) | Suicide gene response |
|---|---|---|---|---|---|---|
| ROSA26 | CAG | 89.1 | 1434 | 85.2 | 301 | +++ |

Figure 9C:
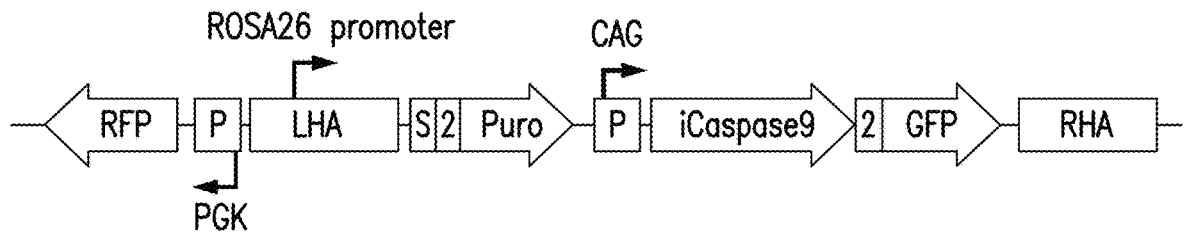
Figure 9D:
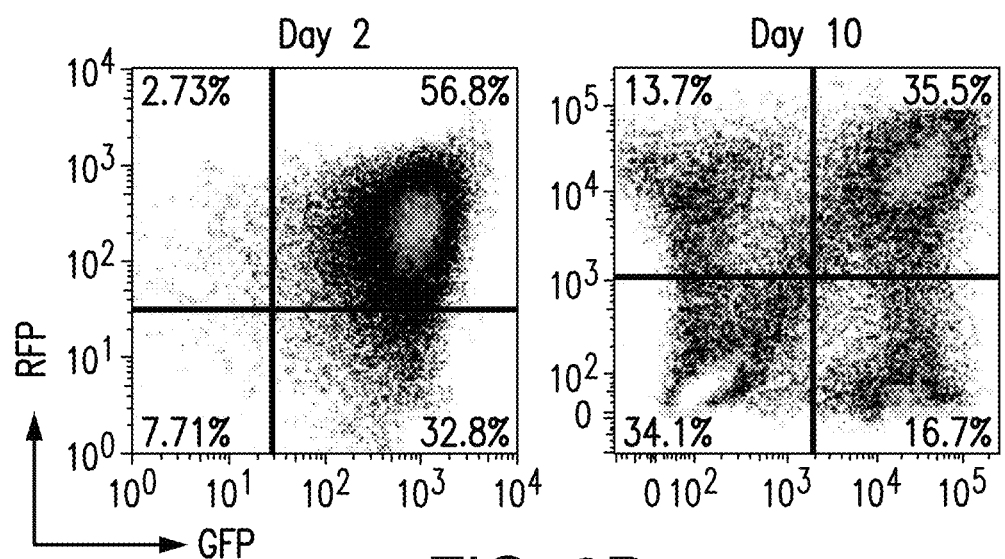
Figure 9E:
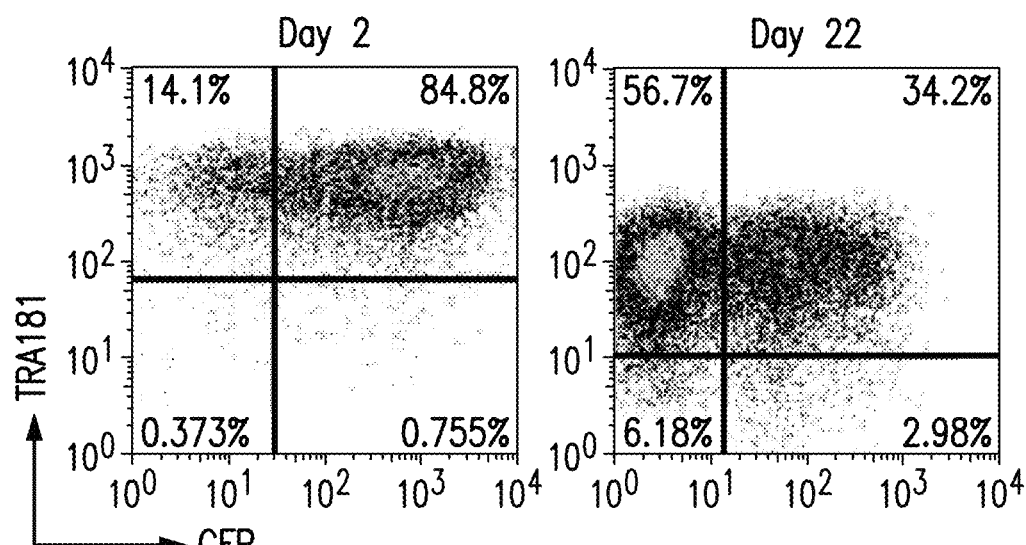

Table 2 demonstrates that CAG driven targeted exogenous gene insertion is suitable for not only AAVS1 locus, but also ROSA26 locus and can be mediated by both ZFN and CRISPR strategies. An additional construct design to target ROSA26 locus with nuclease independent strategy, by utilizing homologous arms, was also employed to test the strategy feasibility. The construct for nuclease independent ROSA26 locus consists of CAG promoter driving GFP and iCasp9 while RFP will indicate off-target integration (FIG. 9C). 293 T cells and hiPSCs transfected with the construct in FIG. 9C and puromycin selected were each enriched for targeted cells (FIG. 9D and FIG. 9E). The data demonstrates that nuclease independent strategy can also be applied to the current platform to efficiently generate targeted hiPSCs.

In summary, CAG promoter maintained high levels of iCasp9 expression during the long-term clonal expansion of hiPSCs, regardless of the targeting strategy, loci, or different states of differentiation. Furthermore, these iCasp9-integrated clonal lines underwent rapid cell death in the presence of AP1903, and no residual cell survival was observed when cultures were allowed to recover in the absence of the dimerizing molecule. Further, hiPSC clones were differentiated into three somatic lineages in vitro and were found to be completely subject to AP1903-induced cell death. Clones were also specifically differentiated towards hematopoietic cells to demonstrate complete induction of cell death by AP1903 treatment. When injected into NSG mice to form teratomas, similar cell death-mediated response was observed in vivo. Similar results were seen with nuclease free CAG-driven targeted integration in iPSC. Therefore, aside from being efficient, precise, and sustainable, CAG driven targeted integration system as provided herein is also reliable, because it does not seem to cause epigenetic landscape alterations that often are seen with other promoters and/or constructs, which alterations would abrogate suicide gene-mediated response in iPSC, expanded iPSC, or iPSC-derived differentiated cells both in vitro and in vivo. Other exogenous gene, and/or at different selected loci can also be applied to this platform. For example, in addition to creating constructs that contain GFP and iCasp9, genes of different functionality can be incorporated to the construct. Targeting modalities such as chimeric antigen receptors or engineered T cell receptors can also be introduced into a specific locus. In another example, the targeting of various genes to specific loci can be conducted at the time or reprogramming. As discussed earlier, the hiPSC platform can select individual cells with variety of attributes, these attributes can include a successfully reprogrammed hiPSC contacting the desired genes introduced into specific loci.

Notably, one hiPSC clone contained certain rare cells and did escape induced cell death, and this clone and these rare cells were characterized to assess the molecular mechanisms of escape.

Figure 8A:
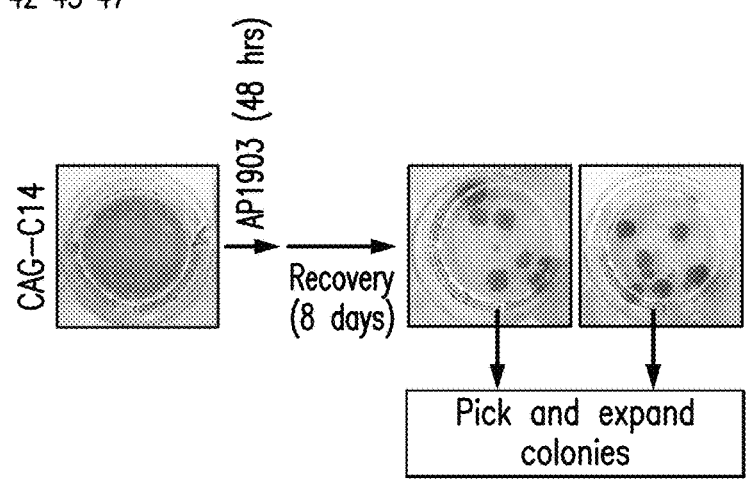
FIGS. 8A-F are a graphic representation of characterization of escaped clones. A. Illustration of method to select clones surviving AP1903 treatment. B. PCR amplification of the iCasp9 transgene, followed by purification and genomic sequencing to determine if there is any sequence alterations. C. The flow cytometry assessment of the escaped clone showed high GFP and TRA181 expression. D. Identification of a single point mutation K189E in all clones sequenced. E. To identify if K189E is the direct reason for the refractory clones, iCasp9 mutant form was created and tested. F. iCasp9 mutant transgene was confirmed as the reason for surviving AP1903 treatment.
Figure 8B:
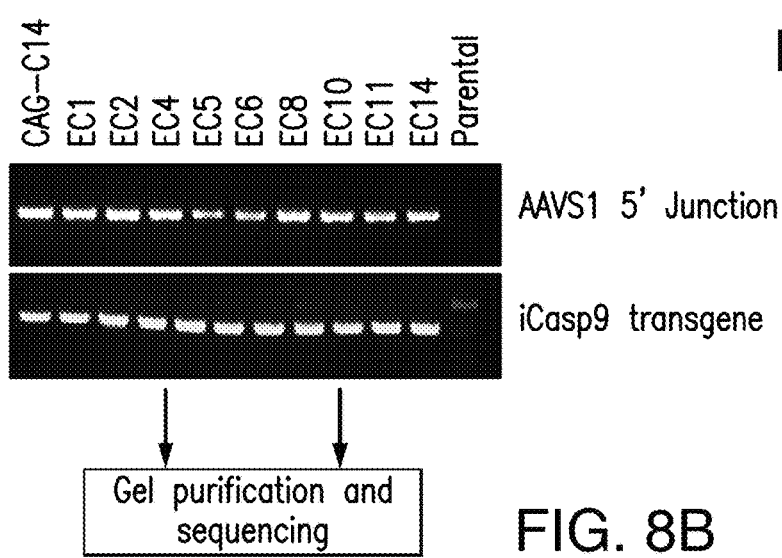
Figure 8C:
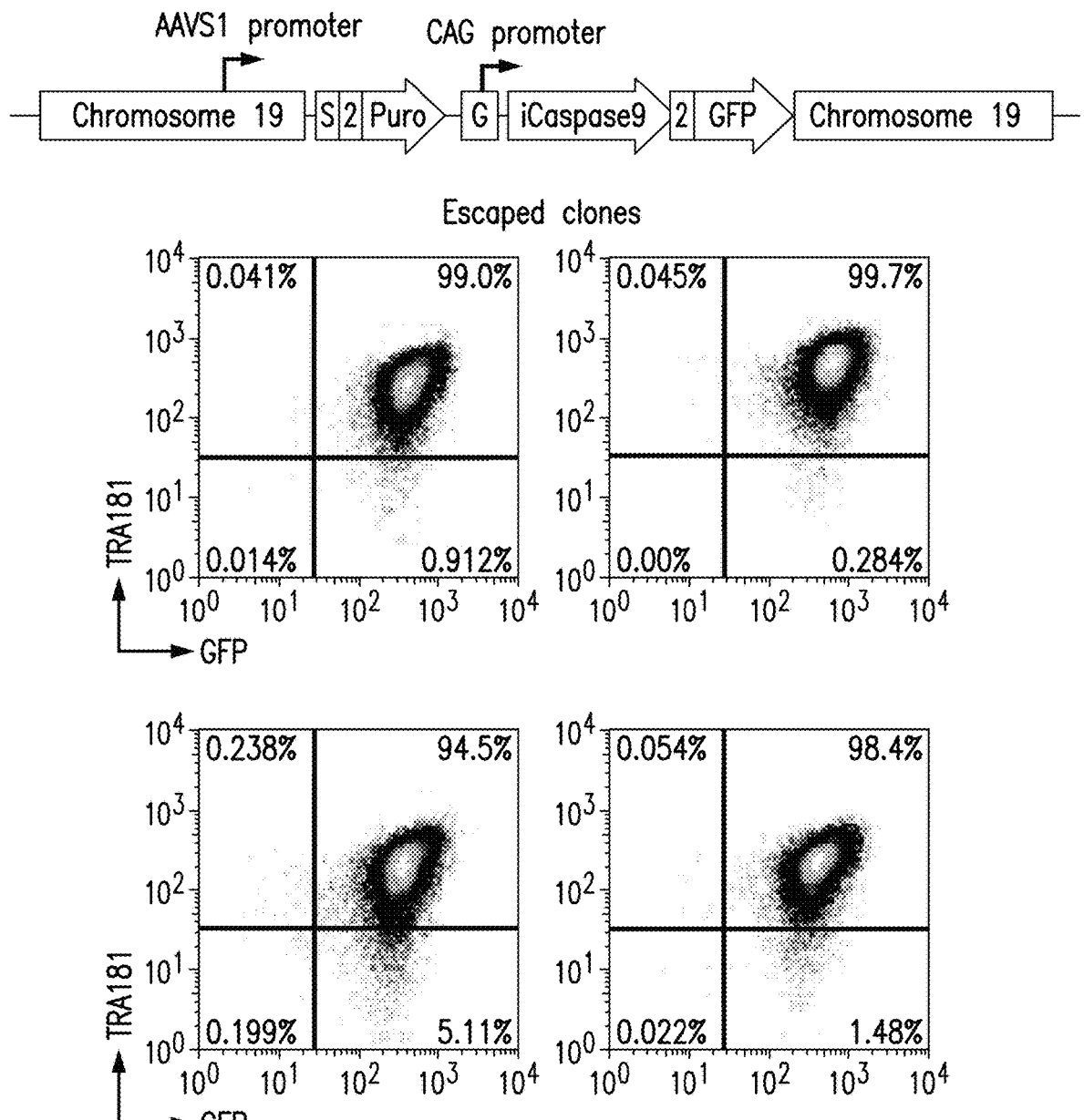
Figure 8D:
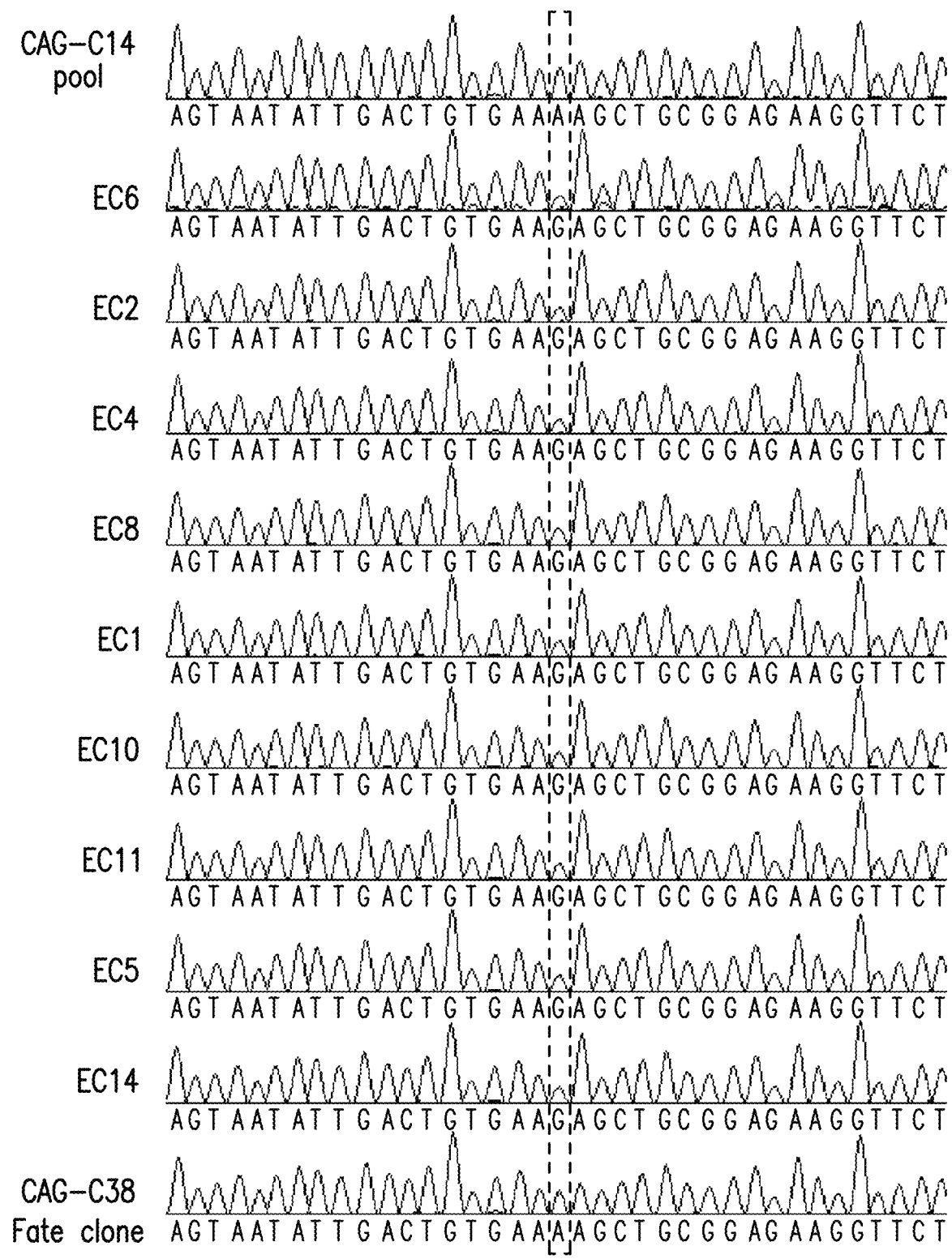
Figure 8E:
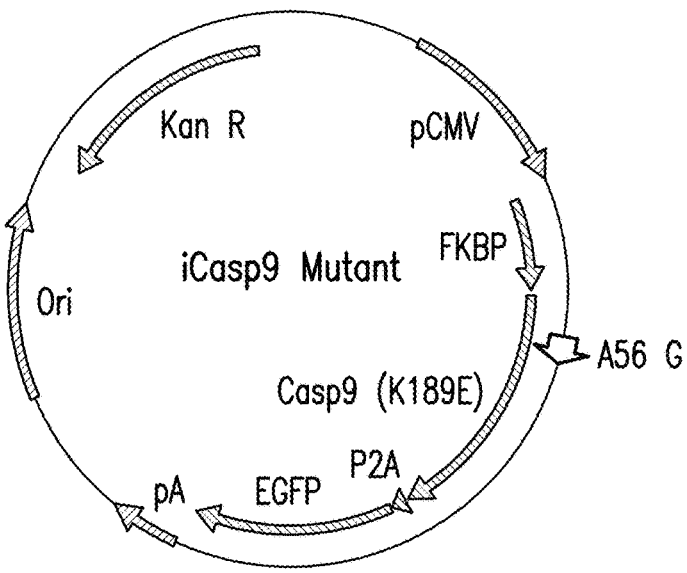
Figure 8F:
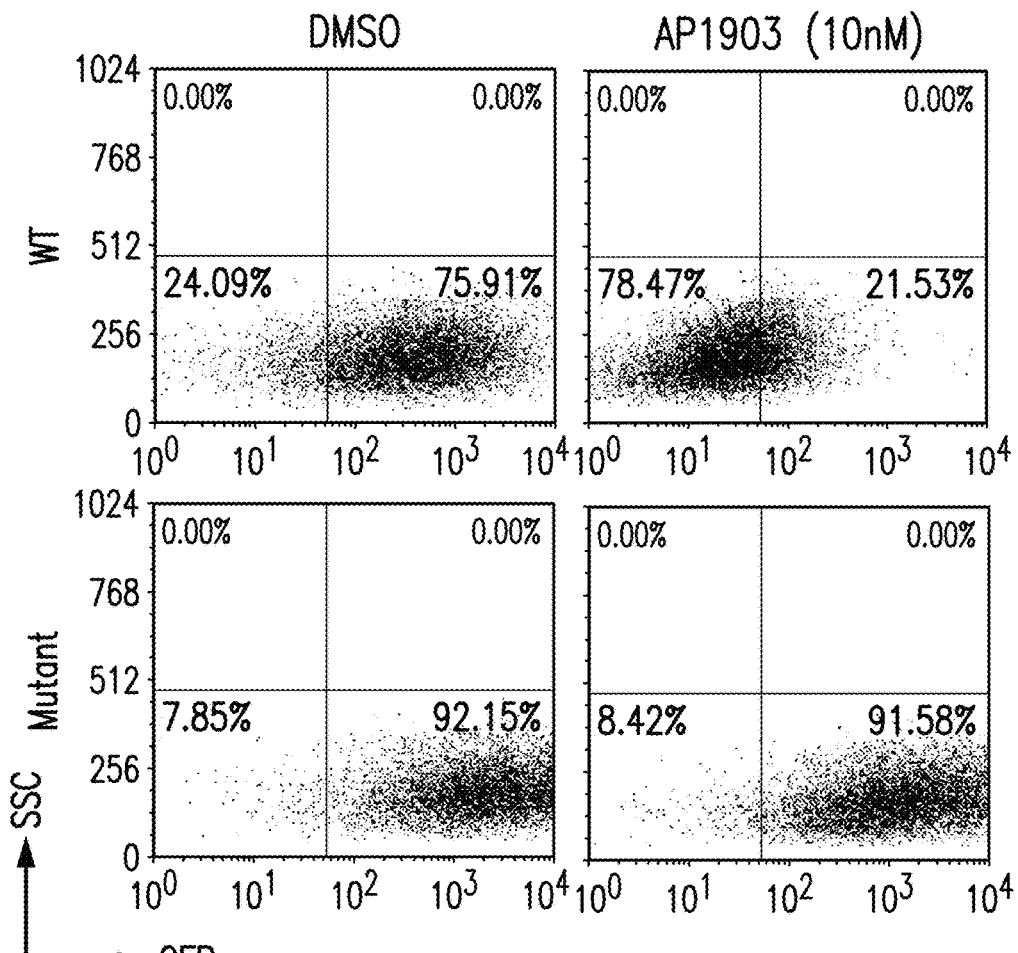

Example 10—Characterization of Escaped Clones Reveals a Single Point Mutation in all Expanded Clones The procedure used to discover surviving clones upon AP1903 treatment was furthered by picking and expanding the clones surviving AP1903 treatment (FIG. 8A). As demonstrated, all escaped clones have correct targeted insertion shown by the Junction PCR. To determine if sequence alterations are seen in the escaped clones, PCR amplification of the iCasp9 transgene was conducted followed by purification and genomic sequencing (FIG. 8B). The sequences of the iCasp9 transgene of those escaped clones presented a single point mutation K189E in all clones sequenced (FIG. 8C). To confirm if K189E is the direct reason for the refractory clones, iCasp9 mutant form was created according to FIG. 2E, and was used for transfection and the resultant targeted iPSC cells were tested. FIG. 8E depicts that GFP expressing CAS-iCasp9m iPSC cells are not responsive to AP1903 treatment, and all cells survived upon treatment with the same high level of GFP expression, in comparison to CAS-iCasp9 wt iPSC cells.

Example 11—Approaches to Rescue Escaped Clones Comprising the Consensus Single Point Mutation The above example showed that the in vitro treatment-resistant clones derived from a single refractory line comprise a consensus inactivating point mutation in iCasp9 for all tested clones. However, killing kinetics were improved and rate of resistance was lessened in vitro and in vivo by selecting hiPSC clones with biallelic iCasp9 insertions. Therefore, to guard against the potential to develop resistance to a single inducible safety system, the generation and selection of hiPSC clones containing multiple conditional suicide genes were explored, including iCasp9 and herpes simplex virus thymidine kinase, each incorporated into a unique safe harbor locus. The dual safe guard system was compared in vitro and in vivo to the single iCasp9 safety switch to evaluate safety and efficient elimination of engrafted cells.

Figure 10A:
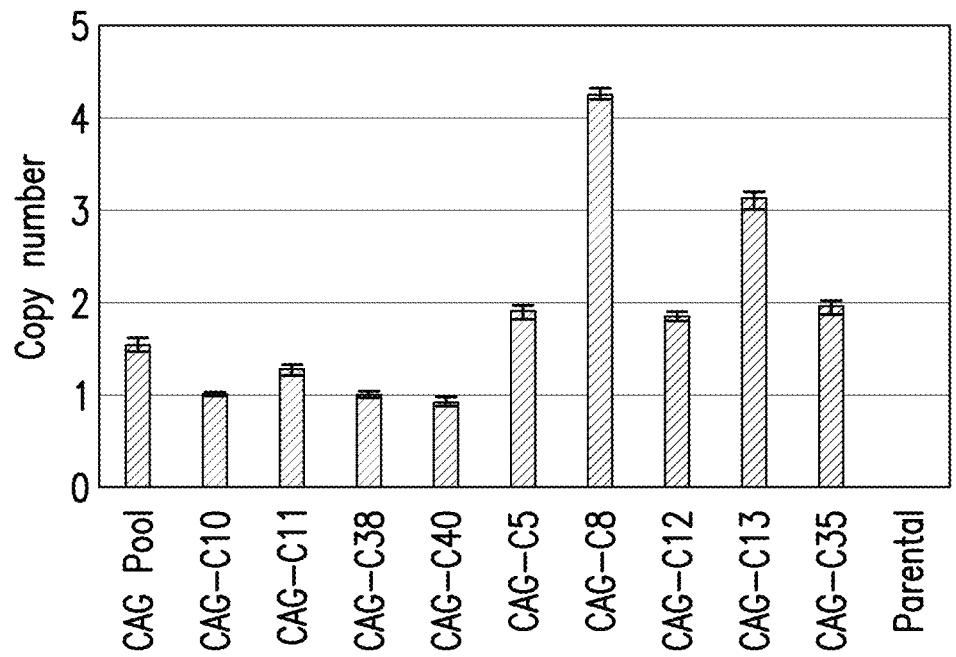
FIGS. 10A-E are a graphic representation of generation of iPSC clones with mono-allelic and bi-allelic iCasp9 targeted integration. A. Quantitative PCR-based assessment of transgene (iCasp9-GFP) copy number in indicated CAG promoter-driven iCasp9 clones. B. Mean fluorescence intensity (MFI) of iCasp9-GFP in sorted pooled culture (black) or in clones with monoallelic (light gray) or biallelic (dark gray) iCasp9 targeted insertions as determined by flow cytometry. C. PCR analysis of transgene integration using primers overlapping the AAVS1-transgene junction in targeted pooled cells and clones. D. Evaluation of number of targeted integrations into AAVS1 alleles using a PCR-based method and primers specific for the AAVS1 integration site. E. Assessment of plate surface coverage by unsorted targeted pool cells, targeted pool cells sorted for iCasp9-GFP and clonal CAG-C38 and CAG-C5 cell lines immediately after addition of 10 nM AP1903 using live cell imaging.
Figure 10B:
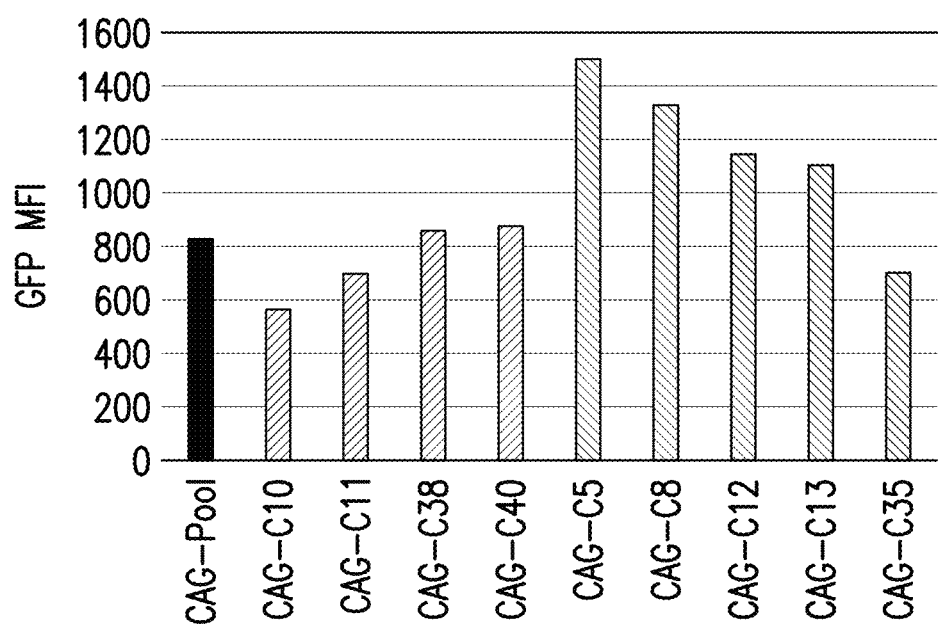
Figure 10C:
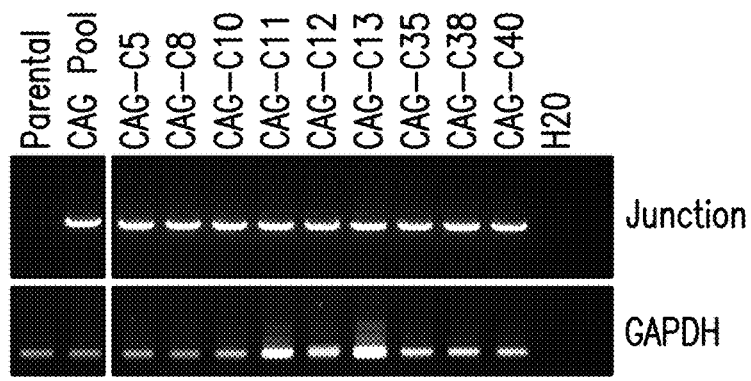
Figure 10D:
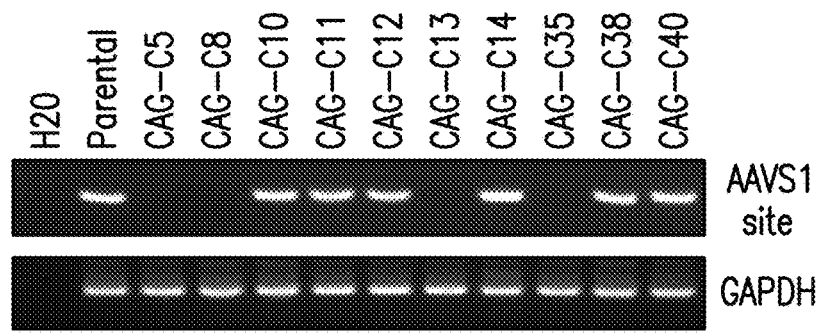
Figure 10E:
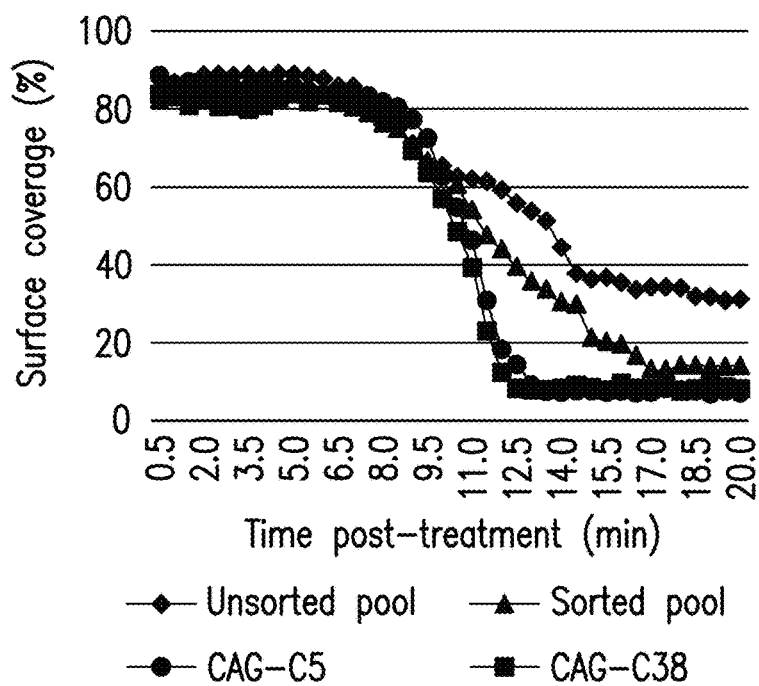

Example 12—Copy Number of Targeted Insertion of CAG Promoter-Driven iCasp9 at AAVS1 Safe Harbor in hiPSC Quantitative PCR-based assessment of transgene (iCasp9-GFP) copy number in CAG promoter-driven iCasp9 clones revealed that a small number of clones have more than one copy of the transgene. As shown in FIG. 10A, a copy number of 1 suggests a mono-allelic iCasp9 integration, a copy number of 2 suggests a bi-allelic iCasp9 integration whereas higher than 2 suggests a potential random integration. The mean fluorescence intensity (MFI) of iCasp9-GFP, as shown in FIG. 10B, in sorted pooled culture or in clones with monoallelic or biallelic iCasp9 targeted insertions demonstrated that the transgene expression level corresponds to the copy number, the higher the copy number, the higher the MFI readout. PCR analysis of transgene integration using primers overlapping the AAVS1-transgene junction in targeted pooled cells and clones confirmed the specific integration of iCasp9-GFP transgene into the AAVS1 locus (FIG. 10C). Primers specific for the AAVS1 integration site was used to evaluate the number of alleles having targeted integrations. Lack of a band suggests that the integration site at both AAVS1 alleles were disrupted, i.e. biallelic insertion, whereas the presence of a band suggests that one or both alleles are undisturbed (FIG. 10D). As shown by FIGS. 10C and 10D, CAG-C5 and CAG-C35 clones have biallelic insertion of two copies of transgene, whereas CAG-C38 clone has one copy inserted into the targeted location in one allele. Plate surface coverage was assessed immediately after addition of 10 nM AP1903 using live cell imaging. As shown in FIG. 10E, unsorted targeted pool cells (integrated and non-integrated) have the least induced killing ability, whereas targeted pool cells sorted for iCasp9-GFP (targeted and random integration, with variable copy numbers) showed a slightly better induced killing ability. Clonal CAG-C38 (mono-allelic targeted insertion) and CAG-C5 (biallelic targeted insertion) cell lines have much higher killing rate and efficiency when compared to pooled cells.

Figure 11A:
FIGS. 11A-G are a graphic representation showing that exogenous CAG promoter enabled iCasp9-mediated elimination of established iPSC-derived teratomas. A. Schematic description of study design. B. Bioluminescence imaging of indicated 3 groups of NSG mice (n=2) before (top panels) and 3 days after the end of the AP1903 administration (125 μg i.p. from day 19-25, lower panels). C. Total flux (photons/s) for teratomas from indicated cell types shown as average and SD. D. Ratio of total flux after treatment to that before (average−/+SD) for indicated cell types. E. Results for mice injected with both clonal CAG-C38 and CAG pooled cells. F. Terminal volume measurements of teratomas derived from indicated cell types (day 28). G. Image of teratomas on day 28. No teratomas were detected from sides injected with CAG-C38 clone or CAG-iCasp9 pooled cells. *p value<0.05 measured by unpaired T-test. ns; not significant.
Figure 11B:
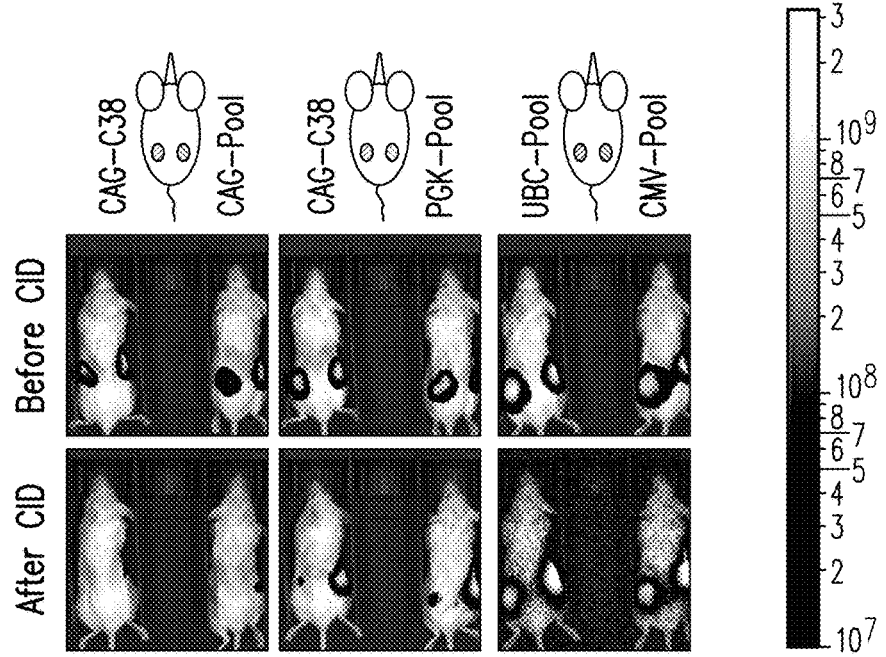
Figure 11C:
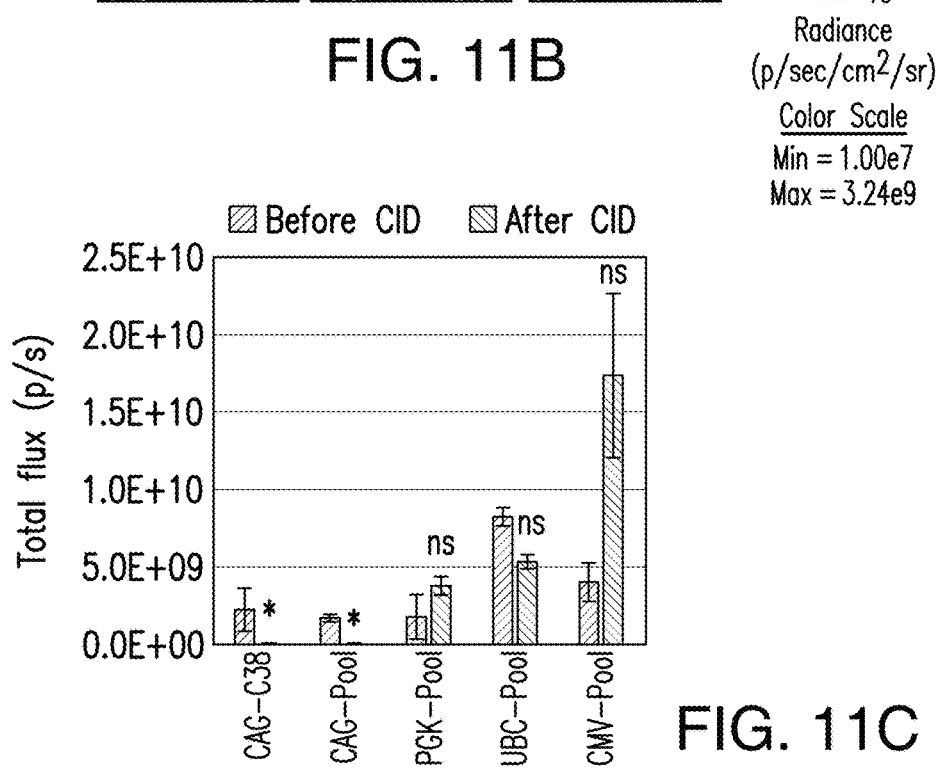
Figure 11D:
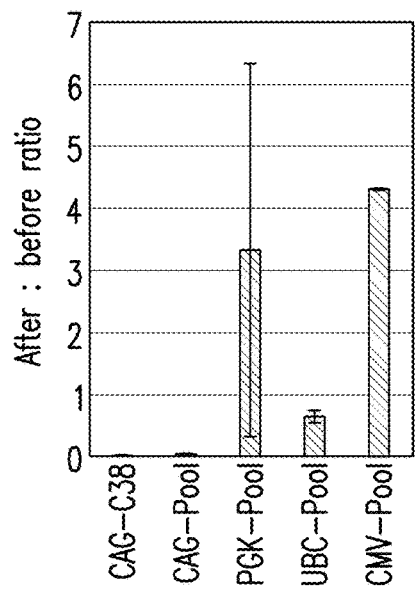
Figure 11E:
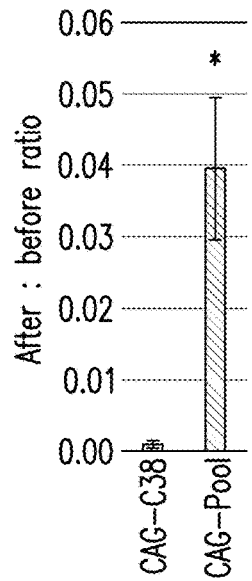
Figure 11F:
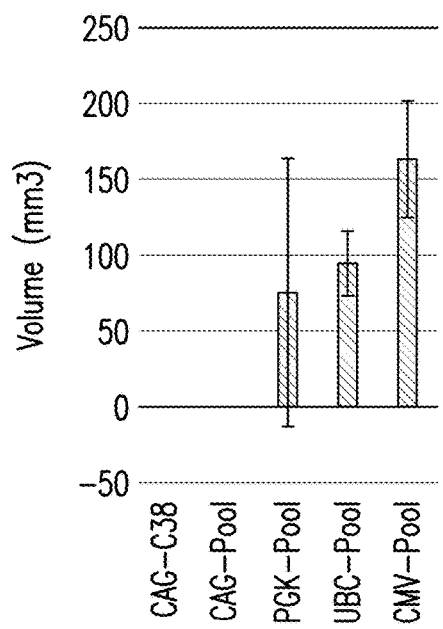
Figure 11G:
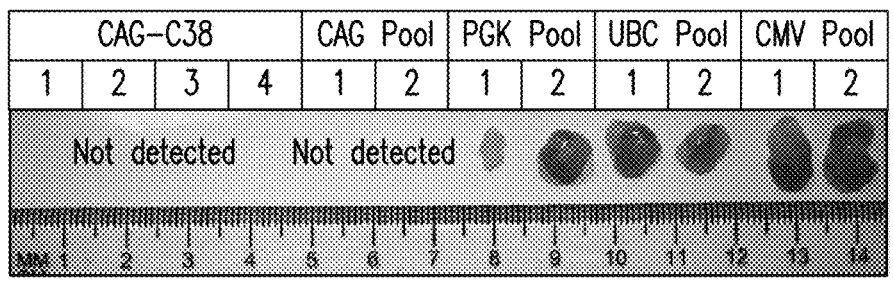

Example 13—Comparing Transplanted Biallelic and Mono-Allelic iCasp9 Clones in Inducible Killing and Regression of Teratomas In Vivo The NSG mice studies with subcutaneous positioning injection was shown in FIG. 11A to demonstrate in vivo cell death mediated through iCasp9 expression and induction in CAG-C38 clone, CAG-pool, PGK-pool (PGK-iCasp9 transgene), UBC-pool (UBC-iCasp9 transgene) and CMV-pool (CMV-iCasp9 transgene). CAG-C38 clone and pools were injected in three groups of NSG mice (n=2) at 4E6 cell on Day 0, and the mice were treated with AP1903 (i.p. 125 µg) on days 19-25. At day 28 the teratomas were harvested and imaged to show size. Bioluminescence imaging of the 3 groups of NSG mice before (FIG. 11B, top panels) and 3 days after the end of the AP1903 administration (FIG. 11B, lower panels) showed that only exogenous CAG promoter enabled iCasp9-mediated elimination of established iPSC-derived teratomas. This observation was further depicted in FIG. 11C-11G Total flux (photons/s) indicative of the quantity of tumor cells in teratomas from indicated cell types shown as average and SD in FIG. 11C corroborated with the findings of teratomas size in FIG. 11B. The ratio of total flux after treatment to that before (average±SD) for indicated cell types was shown in FIG. 11D. Results for mice injected with both clonal CAG-C38 and CAG pooled cells were plotted separately in FIG. 11E with a higher definition. Terminal volume measurements of teratomas derived from indicated cell types on Day 28 were demonstrated in FIG. 11F. FIG. 11G shows the image of teratomas derived from indicated cell types on day 28. No teratomas were detected from sides injected with CAG-C38 clone or CAG-iCasp9 pooled cells. Collectively, these data confirmed in vitro studies of the different promoters driving the expression of iCasp9-GFP transgene and showed that the CAG promoter is the most effective among the tested in vitro and in vivo. The data also indicates that CAG-C38 clone, despite a mono-allelic for iCasp9-GFP, is more effective than CAG pooled cells in teratomas elimination upon suicide gene induction.

Figure 12A:
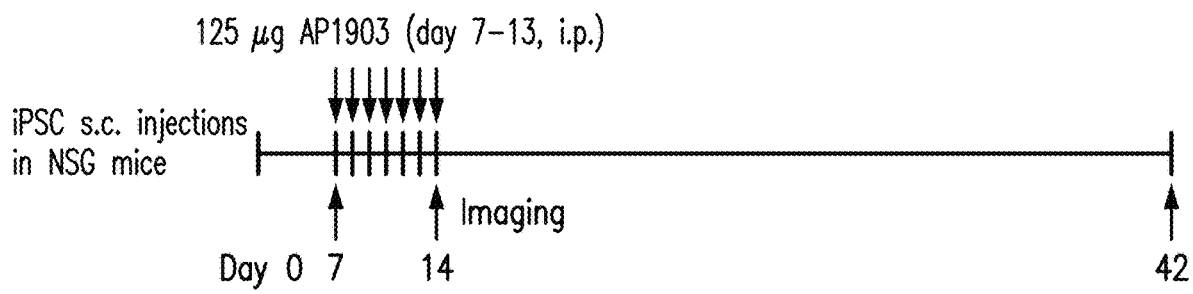
FIGS. 12A-D are a graphic representation showing that more effective inducible killing of transplanted biallelic iCasp9 clone than that of mono-allelic iCasp9 clone. A. Schematic description of study design. B. Bioluminescence imaging of NSG mice transplanted with indicated cell types (bi-allelic CAG-C5 clone, mono-allelic CAG-C38 clone and parental iPSCs) on day 7, 14 and 42 after iPSC transplantation. Imaging on day 7 was performed immediately before AP1903 administration (125 µg i.p.; day 7-13). C. Lower panels show images of collected teratomas, if found, on day 42. D. Total flux (photons/s) for teratomas from indicated groups shown as average and SD. *p value<0.05; p value<0.01; * **p value<0.001 as measured by unpaired T-test. ns; not significant.

Moreover, inducible killing of transplanted biallelic iCasp9 clone was tested and compared to that of monoallelic iCasp9 clone. The NSG mice studies with subcutaneous positioning injection was shown in FIG. 12A to demonstrate in vivo cell death mediated through iCasp9 expression and induction in parental cell, CAG-C5 clone, and CAG-C38 clone. The respective cell types were injected in 4 groups of NSG mice (n=2) on Day 0, and the mice were treated with AP1903 (i.p. 125 µg) on days 7-13. On day 7, 14, and 42 the teratomas were imaged. On Day 42, the teratomas were harvested and imaged to show size.

Figure 12B:
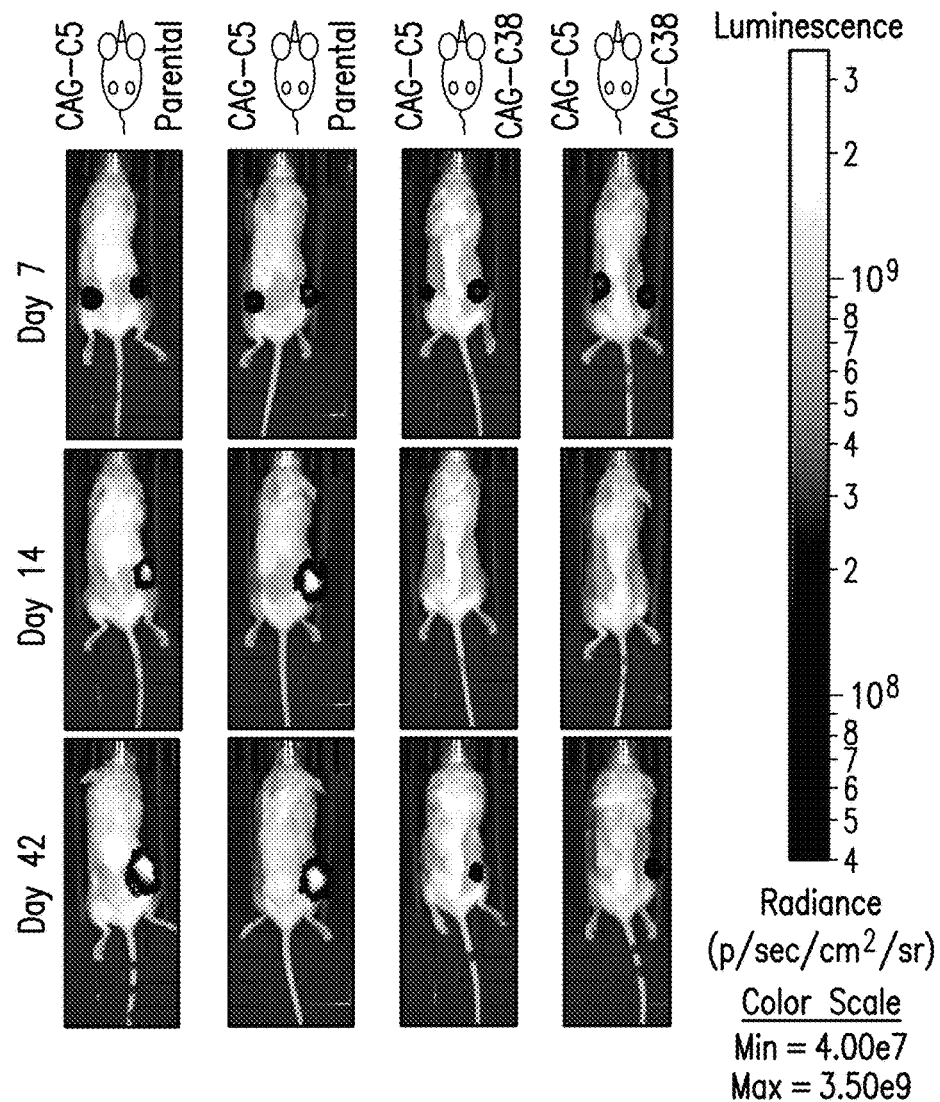
Figure 12C:
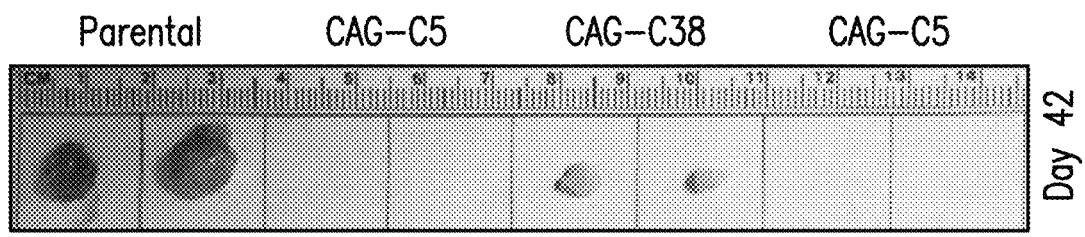
Figure 12D:
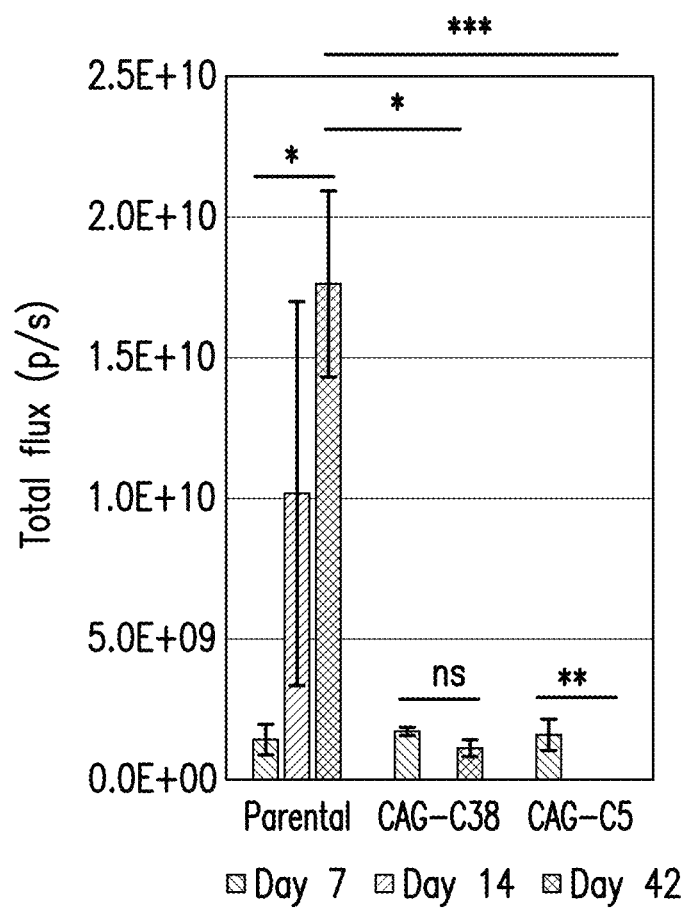

Bioluminescence imaging of NSG mice transplanted with indicated cell types (bi-allelic CAG-C5 clone, mono-allelic CAG-C38 clone and parental iPSCs) on day 7, 14 and 42 after iPSC transplantation (FIG. 12B). Imaging on day 7 was performed immediately before AP1903 administration (125 µg i.p.; day 7-13). Middle panels show images of collected teratomas, if found, on Day 14, and lower panels show images of collected teratomas, if found, on day 42. As shown, both CAG-C5 and CAG-C38 are able to eliminate teratomas on Day 14 in all tested mice. However, teratomas regressed in mice transplanted with CAG-C38 no later than Day 42, whereas the eliminated teratomas in mice transplanted with CAG-C5 did not grow back. FIG. 12C shows the image of teratomas derived from indicated cell types on day 42. The total flux (photons/s) for teratomas from indicated groups shown as average and SD in FIG. 12D corroborated with the imaging data in FIGS. 12B and 12C. Collectively, these data demonstrated more effective inducible killing of transplanted biallelic iCasp9 clone than that of mono-allelic iCasp9 clone.

Figure 13:
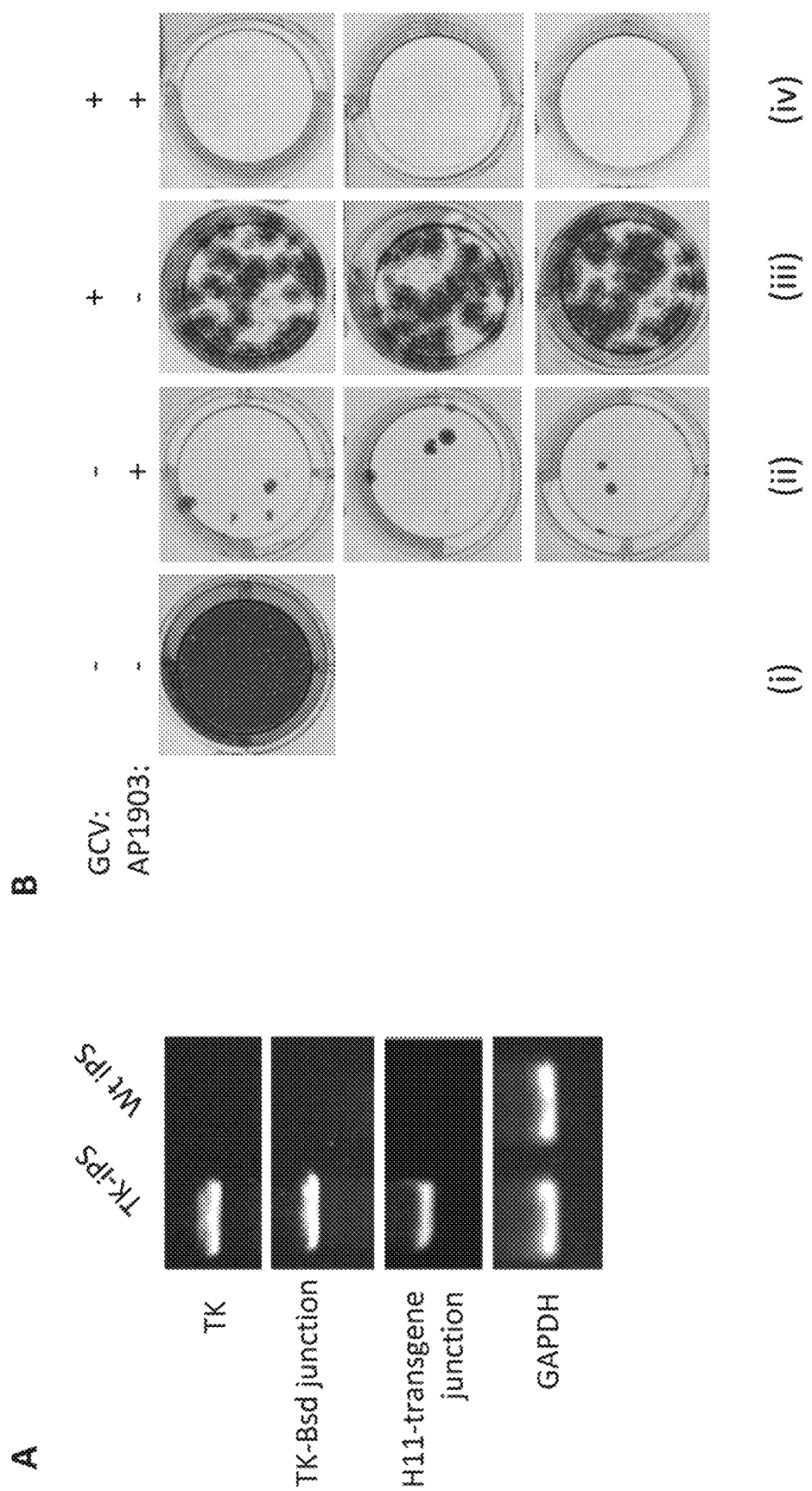
FIGS. 13A-B is a graphic representation showing generation of safe guard system with dual suicide genes targeted into separate safe harbor loci. A. PCR analysis of specific genomic integration of sr39TK into H11 safe harbor locus using primers specific to sr39TK, sr39TK-blasticidin (Bsd) junction or endogenous H11 sequence-transgene junction. GAPDH is used as a loading control. B. CAG-C38 iCasp9 iPSC clone with targeted insertion of sr39TK into H11 locus (i) growing without either GCV or AP1903 treatment; (ii) treated with AP1903 only for 2 days; (iii) treated with GCV only for 9 days; and (iv) concurrent treatment with both AP1903 and GCV for 2 days, then AP1903 was washed off, continuing treatment with GCF for 7 more days.

Example 14—Generation of Safe Guard System with a Dual Suicide Genes Targeted into Separate Safe Harbor Loci To demonstrate the ability and efficacy of high-resolution precision engineering at the single cell level, clonal iPSCs having a safe guard system with dual suicide genes targeted into separate safe harbor loci were generated. In addition to CAG-iCasp9 integrated into AAVS1 locus, CAG-sr39TK was integrated into H11 safe harbor in CAG-C38 clonal iPSC using targeted insertion method described herein. As shown in FIG. 13A, PCR analysis confirmed the specific genomic integration of sr39TK into H11 safe harbor locus using primers specific to sr39TK, sr39TK-blasticidin (Bsd) junction or endogenous H11 sequence-transgene junction, with GAPDH being used as a loading control. iCasp9 iPSC clone with targeted insertion of sr39TK into H11 locus (non-clonal for sr39TK) was treated with 25 µg/mL Ganciclovir (GCV) for nine days with or without treatment in the first two days with 10 nM AP1903. Treatment of CAG-C38 iCasp9 clone (mono-allelic for iCasp9) with AP1903 alone for two days led to inducible killing of most cells but rare cells remained (FIG. 13B(ii)). Treatment of CAG-C38 iCasp9 clone with GCV treatment alone for nine days leaded to expanded GCV-refractory cells (FIG. 13B(iii)). However, the concurrent treatment with both AP1903 and GCV, all refractory cells were effectively eliminated indicating that use of dual suicide safe guard system is more effective than the use of iCasp9 suicide gene alone by killing residual cells that escaped under either inducible suicide gene.

Figure 33:
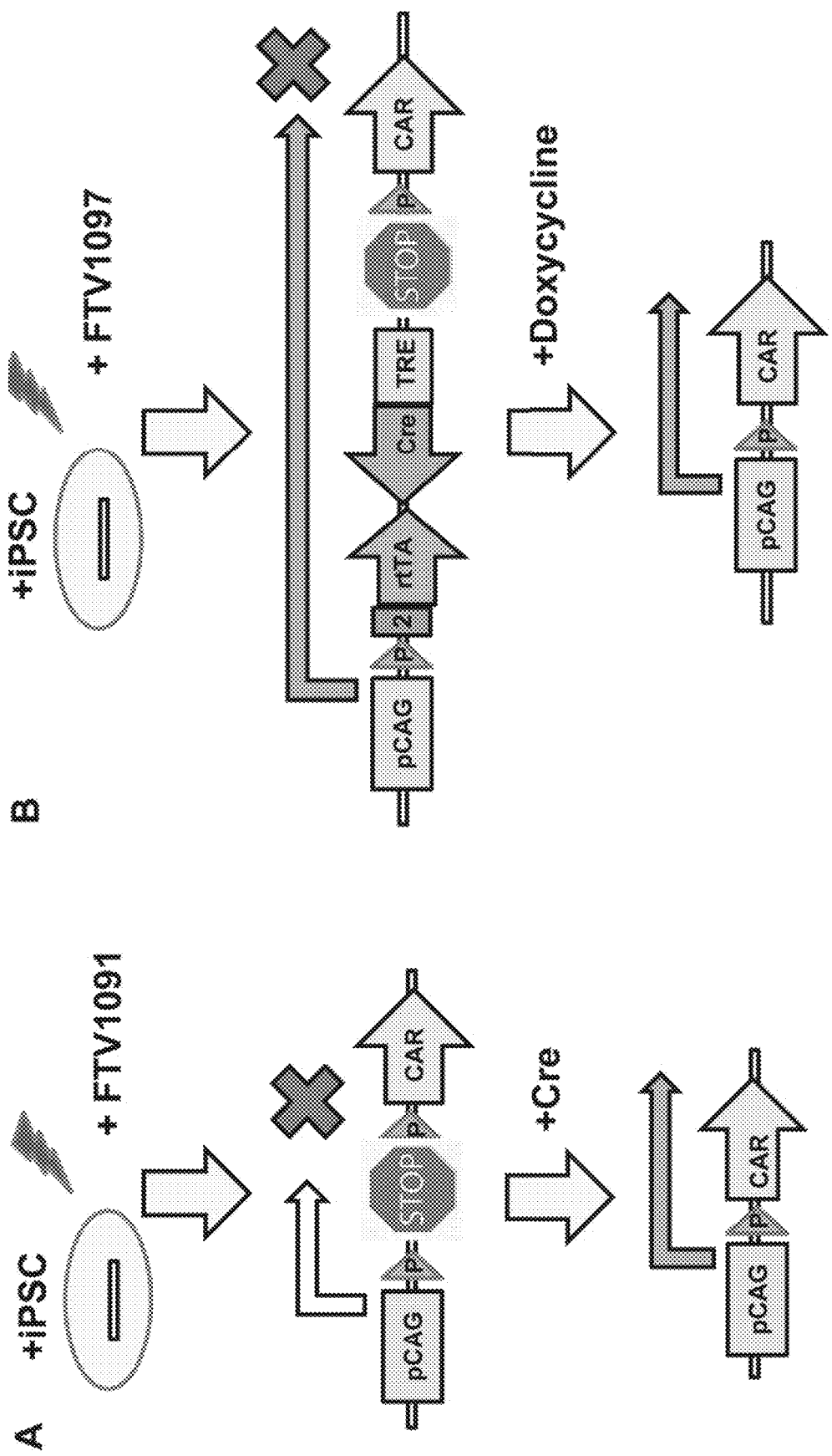
FIGS. 33A-B illustrates Cre or Doxycycline inducible expression in iPSC: A. the stop codons are removed and CAR expression is activated upon A. a one-time Cre Recombinase induction; B. doxycycline induction.

Also provided herein is the design of iPSCs comprising an inducible cassette at a safe-harbor locus, for controllable expression of a gene of interest. The locus specific insertion of inducible cassette takes place at the iPSC level. The expression of gene of interest, a CAR here, depicted as an example, is inactivated by translation stop codons flanked by two loxP sites. Upon a one-time induction by Cre Recombinase (FIG. 33A) or Doxycycline (FIG. 33B), the stop codons are removed as a result and CAR expression is activated. The inducer can be administrated at any chosen stage during ex vivo iPSC differentiation, facilitating the optimization of differentiation procedure. The CAR is driven by a strong constitutive promoter for high level and lasting expression in the final product, such as iT or iNK.

Figure 34A:
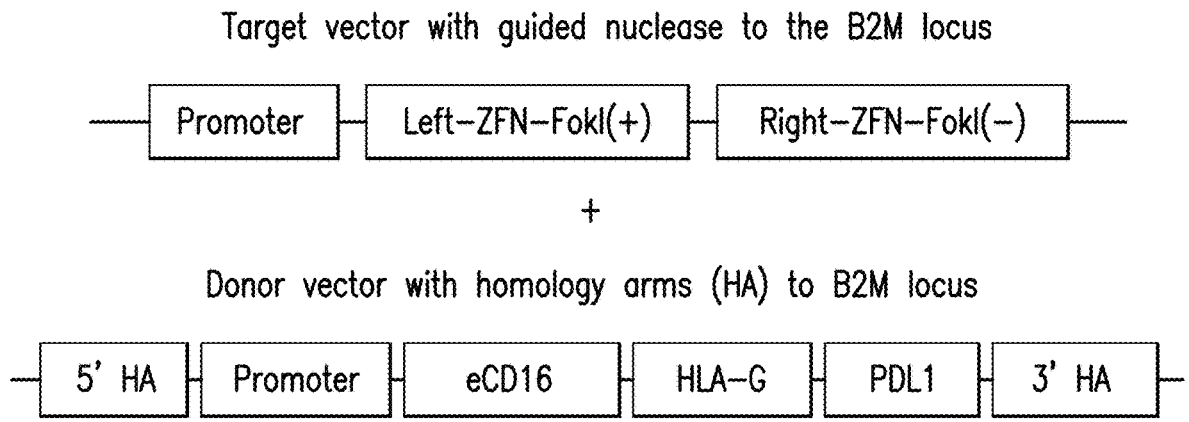
FIGS. 34A-B illustrate insertion of gene of interest at a gene locus chosen for disruption, and hiPSC clonal selection after the genetic editing: A. a construct design for the target vector and donor vector for inserting genes of interest at B2M locus; B. hiPSC selection after genetic editing for a clonal population containing genes of choice at the chosen locus for insertion.
Figure 34B:
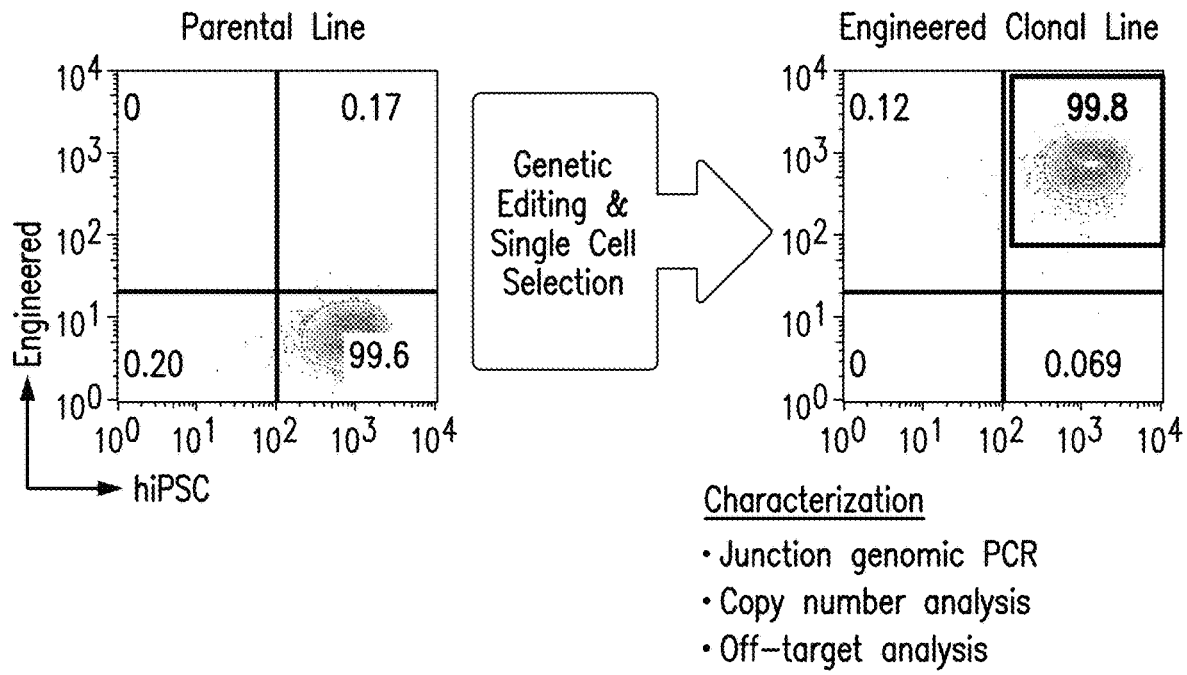

A novel strategy was also developed to uniquely target a locus of choice for gene specific disruption while at the same time inserting new genes of interest in hiPSC population, which is subsequently single cell sorted in a high-throughput manner to select hiPSC clones containing all the required criteria including unique copy number of the inserted genes, functional disruption of the targeted gene and absence of off-target effect. FIG. 34A demonstrates a construct design for the target vector containing negative and positive strand directed nuclease binding and donor vector containing homology arms for B2M, an exemplified gene for disruption, and genes of interest (for example, CD16, HLA-G and PDL1) for insertion at the disrupted locus. FIG. 34B depicts an illustration of hiPSC selection after genetic editing for a clonal population containing genes of choice in the locus of choice.

Figure 14:
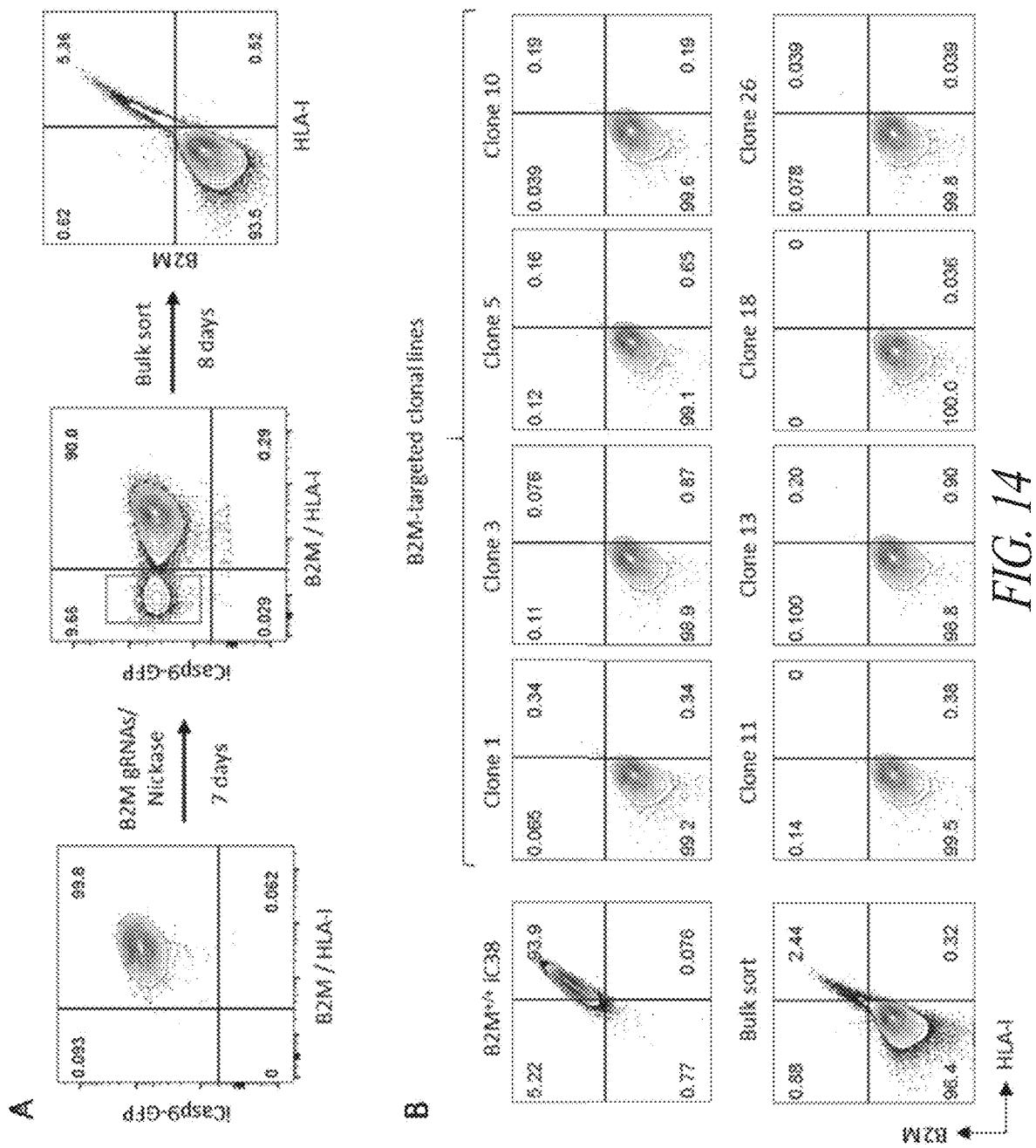
FIGS. 14A-B is a graphic representation of the generation of B2M−/−, HLA I-deficient iPSCs. A. Flow cytometry analysis of GFP and B2M and HLA-I expression before (left panel) and after transfection (middle panel). Cells negative for both B2M and HLA-I were sorted in bulk (right panel). B. Flow cytometry analysis of B2M and HLA-I negative cells sorted clonally into 96-well plates.

Example 15—Generation of B2M$^{null}$ (B2M−/−), HLA I-Deficient iPSCs and the Modifications Thereof To demonstrate the capability to perform single cell genetic editing to achieve HLA complex modifications, an iPSC line was transfected with B2M-targeting gRNA pair in a plasmid expressing Cas9 nickase, which is engineered to provide less off-target effects compared to wild type Cas9. FIG. 14A showed the flow cytometry analysis of GFP and B2M/HLA-I expression before (left panel) and after transfection (middle panel). B2M and HLA-I were detected simultaneously using B2M- and HLA-I-specific antibodies conjugated to the same dye. Cells negative for both B2M and HLA-I (enclosed population) were sorted in bulk (FIG. 14A) or clonally into 96-well plates to generate clonal lines (FIG. 14B). The B2M−/− and HLA I-deficient clones using targeted editing were further analyzed by clonal genomic DNA sequencing and were confirmed to have small deletions or insertions leading to B2M knockout phenotype.

Figure 16A:
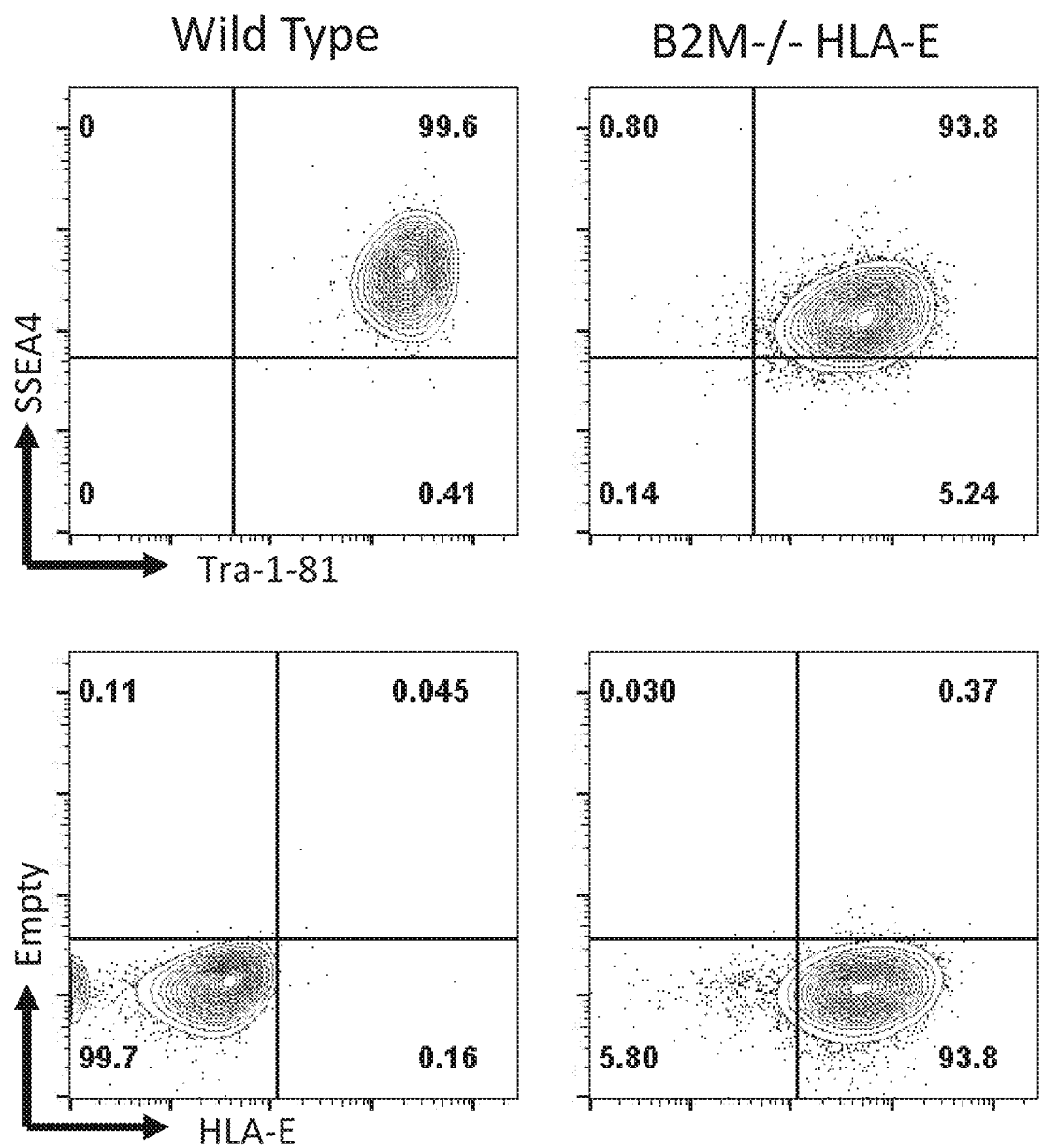
FIGS. 16A-B show Modulation of HLA class I on iPSC increases persistence of iPSC in immune-competent recipients. A. the genetically engineered HLA-modified iPSCs express HLA-E on the cell surface and maintain a pluripotent phenotype. B. In vivo luciferin imaging of teratomas at 72-hour post injection with the B2M−/−HLAE iPSC showing increased persistence compared to wildtype iPSC.

The HLA class I deficient iPSCs (B2M−/− iPSCs, also called HLA I null iPSCs) were then genetically engineered, for example, using lentivirus to introduce a HLA-E/B2M fusion protein for the purpose of further modifying the HLA I deficient cells. The quality (i.e., the pluripotency state) of the modified HLA I-deficient iPSCs (B2M−/− HLA-E iPSCs) was assess by flow cytometry for the pluripotency markers TRA-181 and SSEA4 as well as the expression of HLA-E. FIG. 16A shows that the modified HLA I-deficient iPSCs express HLA-E on the cell surface and maintain a pluripotent phenotype. Similar results were seen when the HLA-E/B2M fusion protein expressing nucleotides are integrated in the HLA I deficient iPSCs in comparison to the results from lentivirus transduction.

Figure 21:
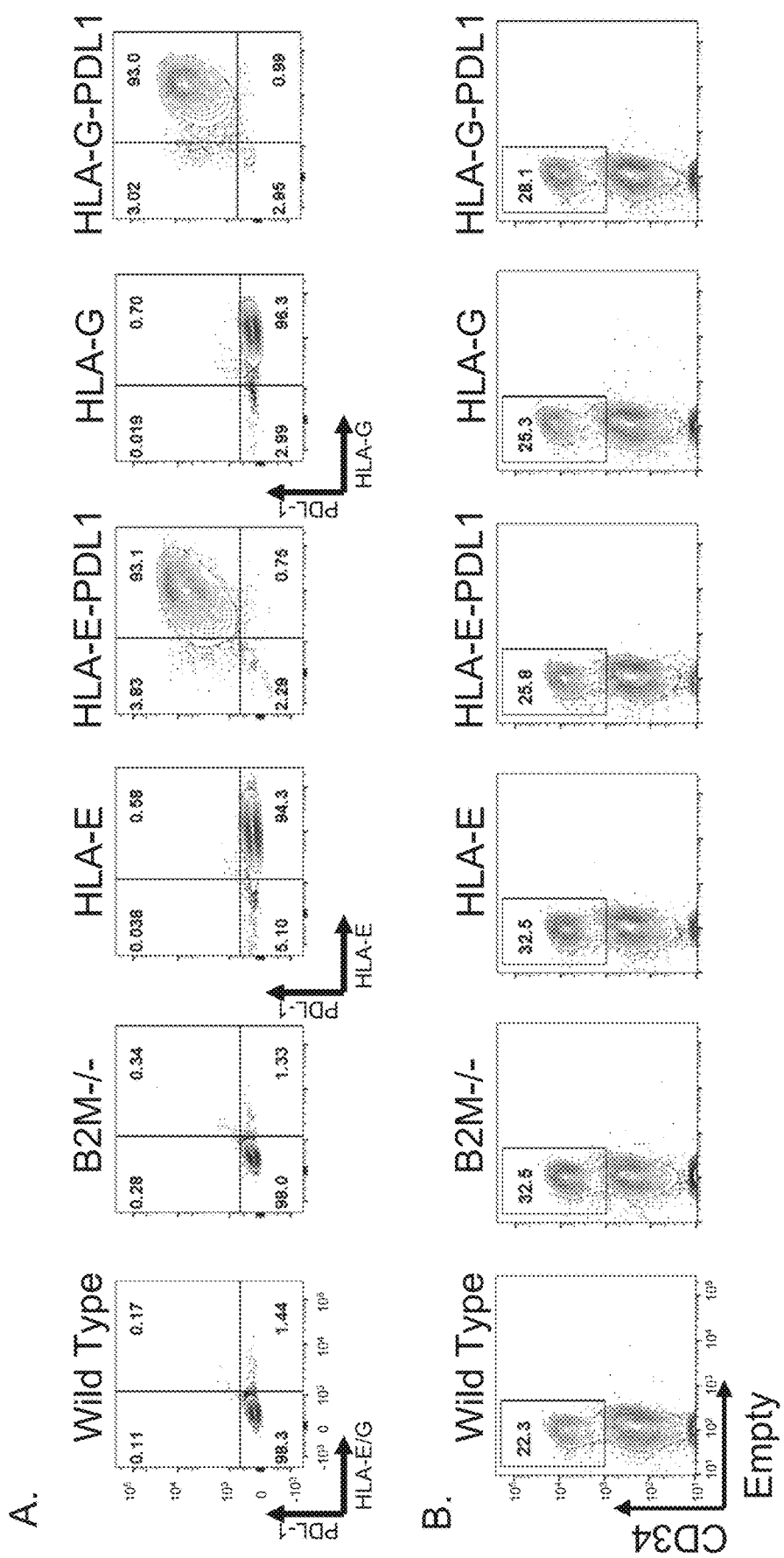
FIGS. 21A-B shows that hiPSC engineered to express immunosuppressive proteins can generate CD34 cells: A. the expression of HLAE, HLAG and PDL1 on the cell surface of the modified HLA I-deficient iPSCs; B. all modified HLA I-deficient iPSCs differentiate to CD34+HE after 10 days of differentiation culturing.

The B2M−/− HLA-E iPSCs were subsequently genetically engineered to contain PDL1 protein, generating a modified HLA I deficient iPSC: B2M−/− HLA-E PDL1 iPSCs. Additionally, the B2M−/− iPSC were genetically engineered to contain the HLA-G/B2M fusion protein and then subsequently genetically engineered to contain the PDL1 protein, generating another HLA I modified B2M null iPSC: B2M−/− HLA-G PDL1 iPSCs. FIG. 21A shows the expression of HLA-E, HLA-G and PDL1 on the cell surface of the modified HLA I-deficient iPSCs. Similar results were seen when the HLA-G/B2M fusion protein expressing nucleotides are integrated in the HLA I deficient iPSCs.

Figure 22A:
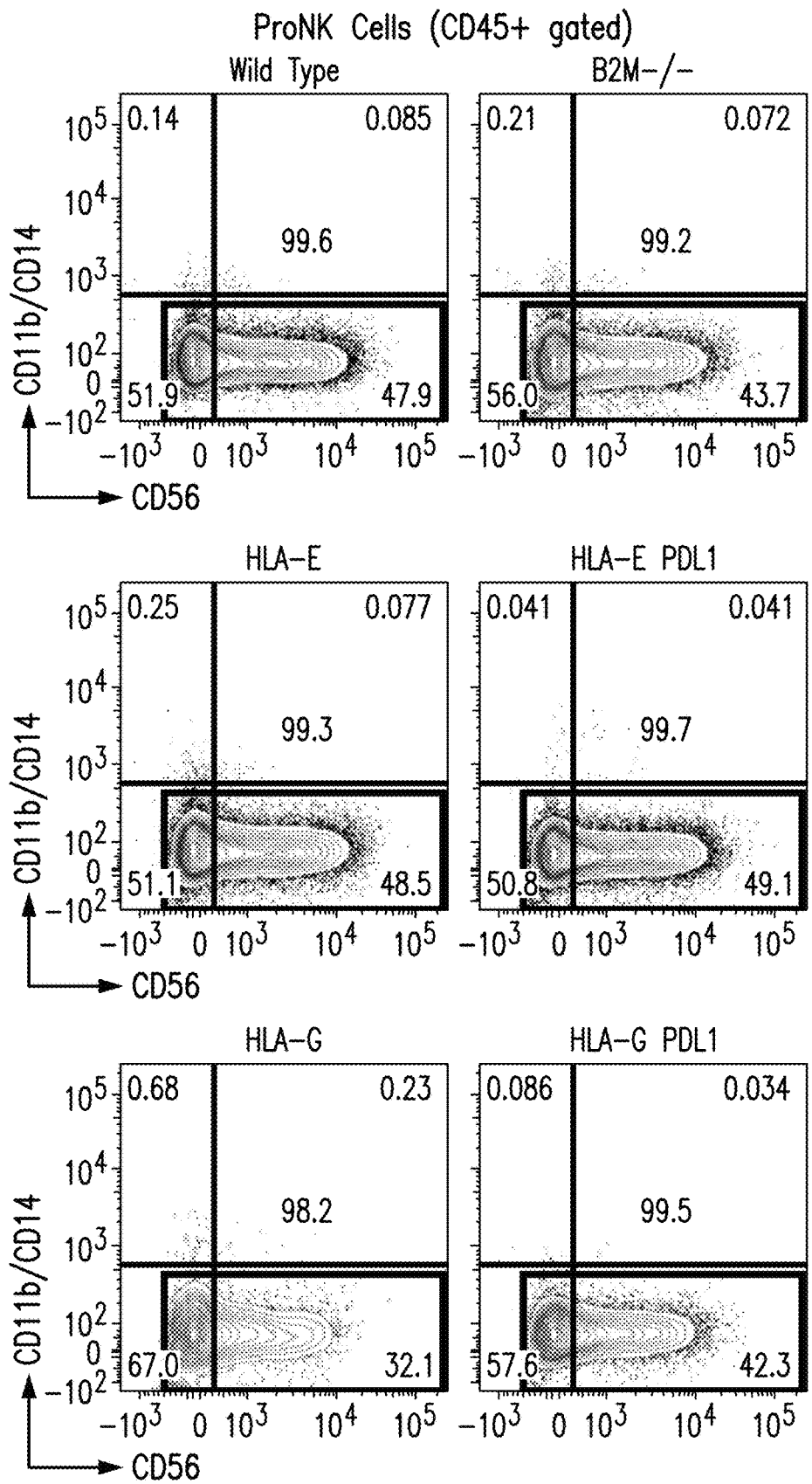
FIGS. 22A-B show that hiPSC engineered to express immunosuppressive proteins can generate hematopoietic lineage cells including, for example: A. ProNK cells and B. ProT cells.
Figure 22B:
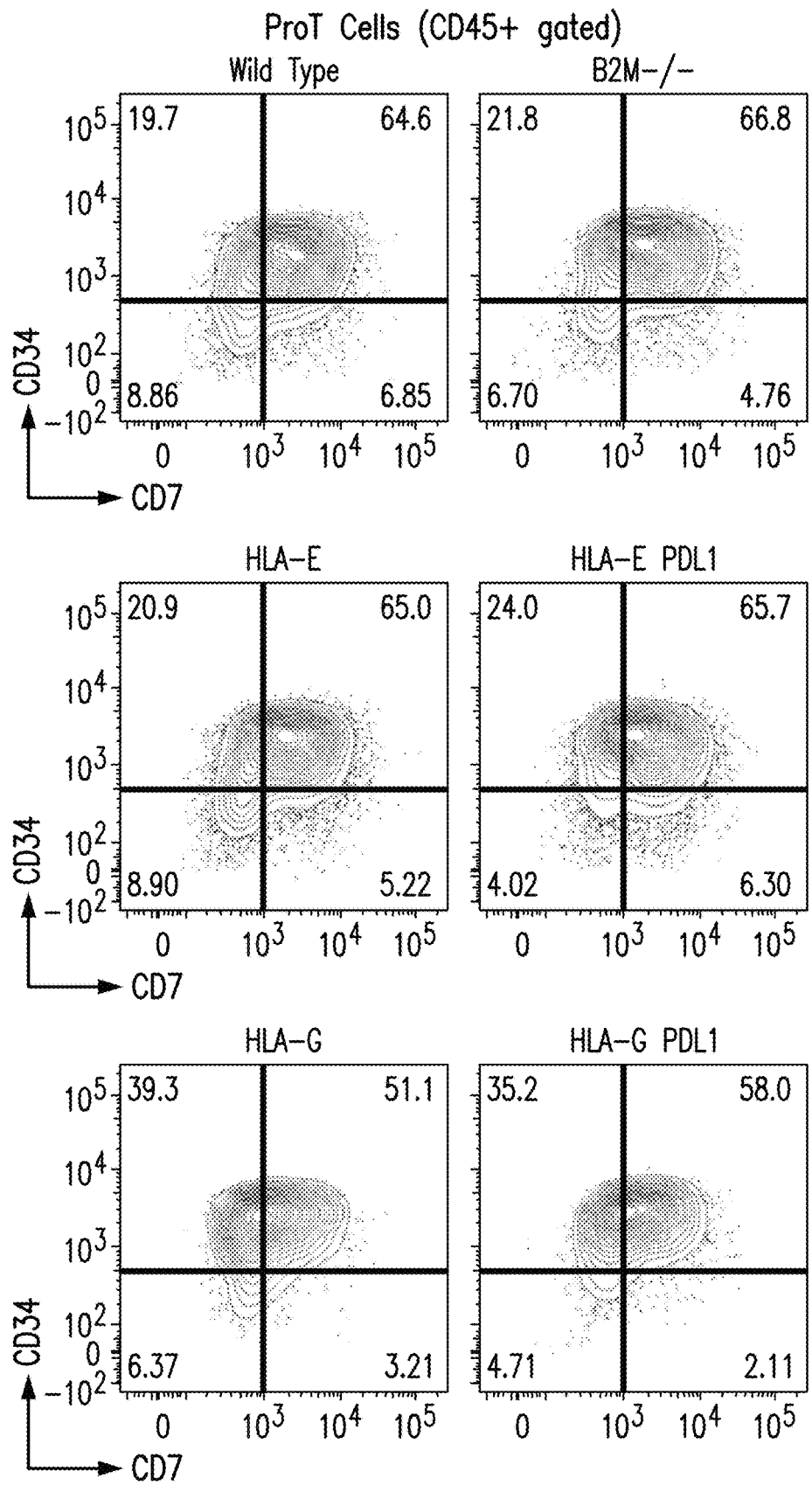

To determine if the modified HLA-I deficient iPSCs maintained their hematopoietic differentiation capability, various modified HLA-I deficient iPSCs (B2M−/−, B2M−/− HLA-E, B2M−/−HLA-E/PDL1, B2M−/−HLA-G and B2M−/−HLA-G/PDL1) were differentiated respectively to CD34+HE using the iCD34 differentiation protocol used herein. FIG. 21B demonstrates that all modified HLA I deficient iPSCs can differentiate to CD34+HE as seen by flow cytometry after 10 days of differentiation. The CD34+ cells were isolated and placed in iNK or iT lymphoid differentiation cultures. FIG. 22 demonstrates that the modulation of HLA I deficient iPSCs via genetically engineered immune-resistant modalities, for example, HLA-E, HLA-G or PDL1, does not perturb the ability of iCD34 cells to generate ProNK (NK progenitor; CD45+CD56) and ProT (T cell progenitor; CD45+CD34+CD7+) cells following an additional 10 days of differentiation as seen by flow cytometry. Similar results were seen when the PDL1 protein expressing nucleotides are integrated in the HLA I deficient iPSCs.

Figure 23A:
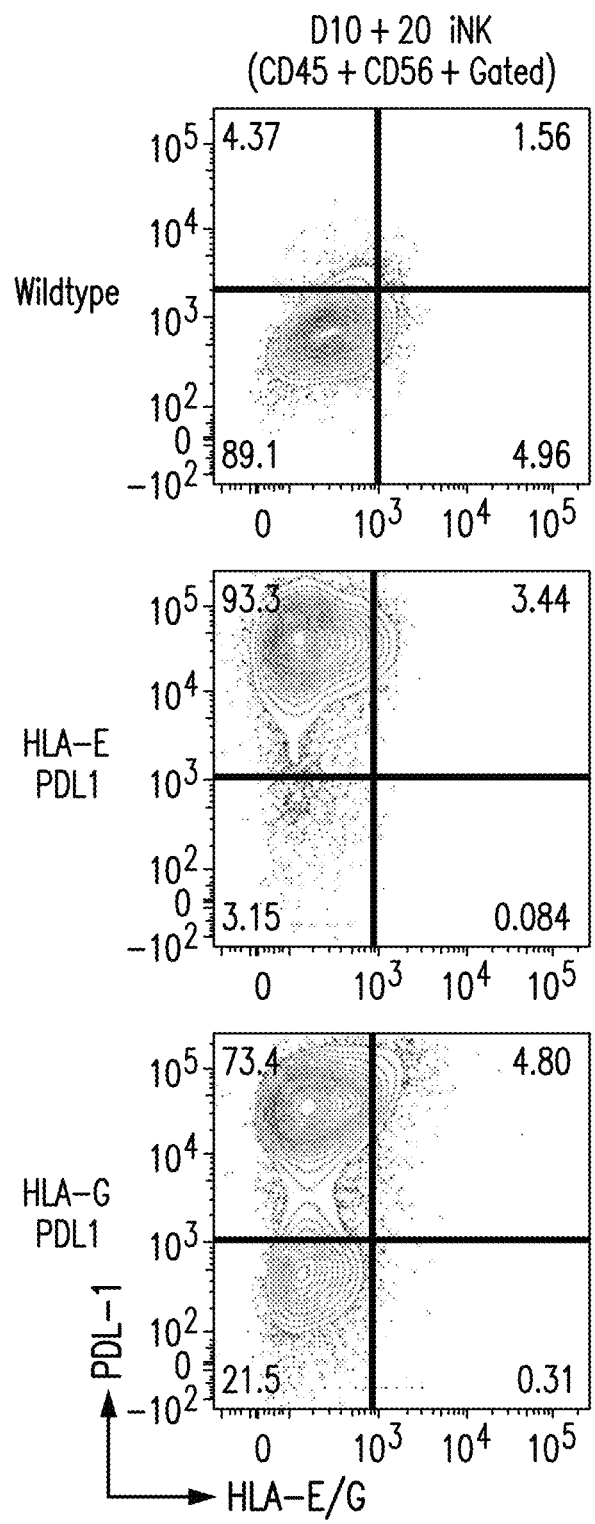
FIGS. 23A-B show that the expression of engineered non-classical HLA immunosuppressive proteins is down-regulated during hematopoietic differentiation of hiPSCs: A. HLA-E and HLA-G proteins are absent while PDL1 expression is maintained; B. HLA-E and HLA-G proteins in the supernatant fractions indicating protein shedding.
Figure 23B:
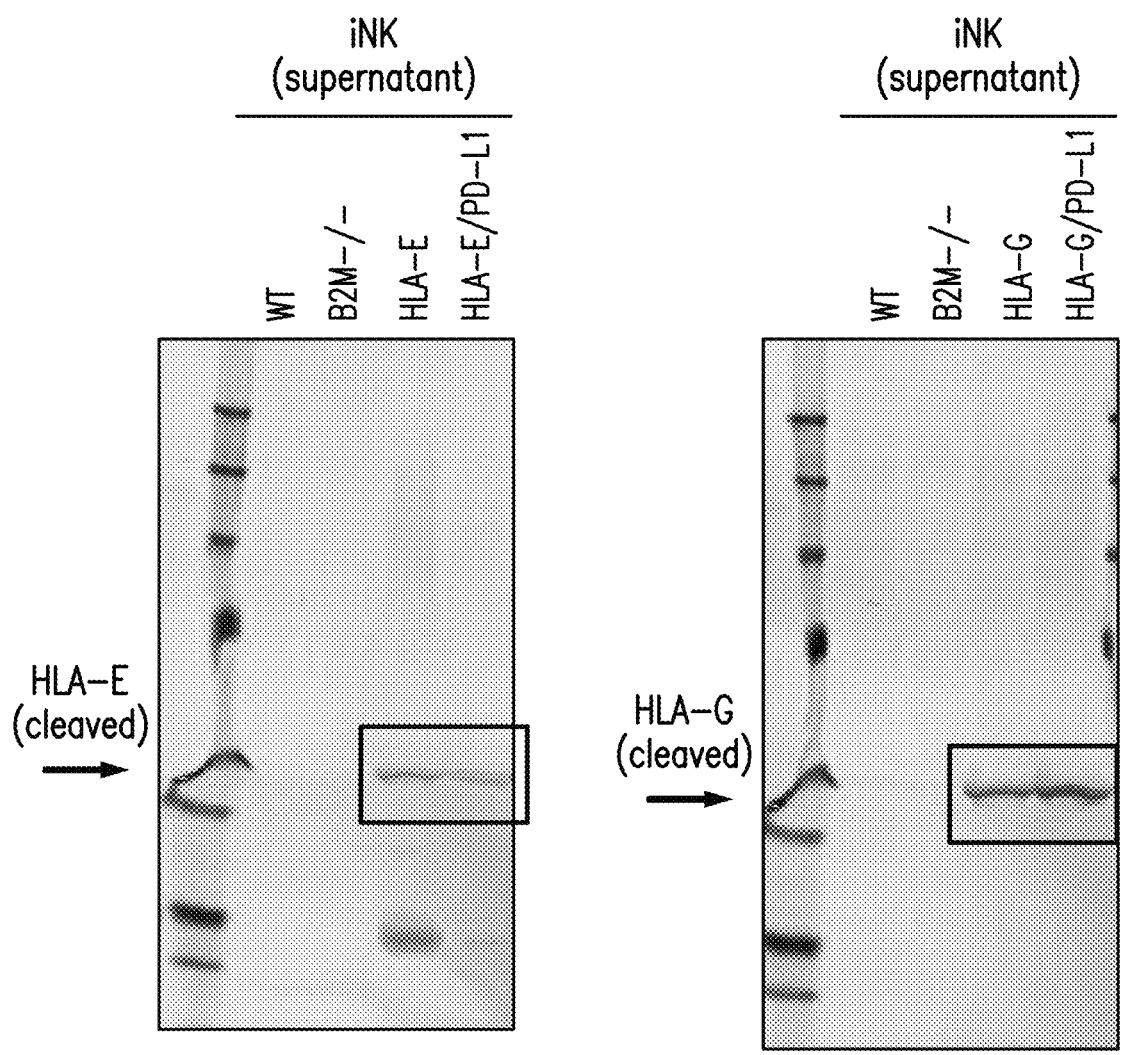

To determine if the expression of genetically engineered immune-resistant proteins is maintained during hematopoietic differentiation, iNK cells that were differentiated for 20 days from modified HLA-I deficient CD34+ cells were assessed for the expression of HLA-E, HLA-G and PDL1 on the cell surface by flow cytometry. FIG. 23A demonstrates that the HLA-E and HLA-G proteins are absent while PDL1 expression is maintained. To determine if the HLA-E and HLA-G proteins were being cleaved from the cell surface during hematopoietic differentiation protein lysates from 20 day iNK cells and 20 day culture media supernatants were examined for the expression of HLA-E and HLA-G protein by western blot analysis. FIG. 23B demonstrates that HLA-E and HLA-G proteins are found in the supernatant fractions and therefore concludes that HLA-E and HLA-G proteins are being shed from the cell surface of iPSC-derived NK cells.

Figure 24:
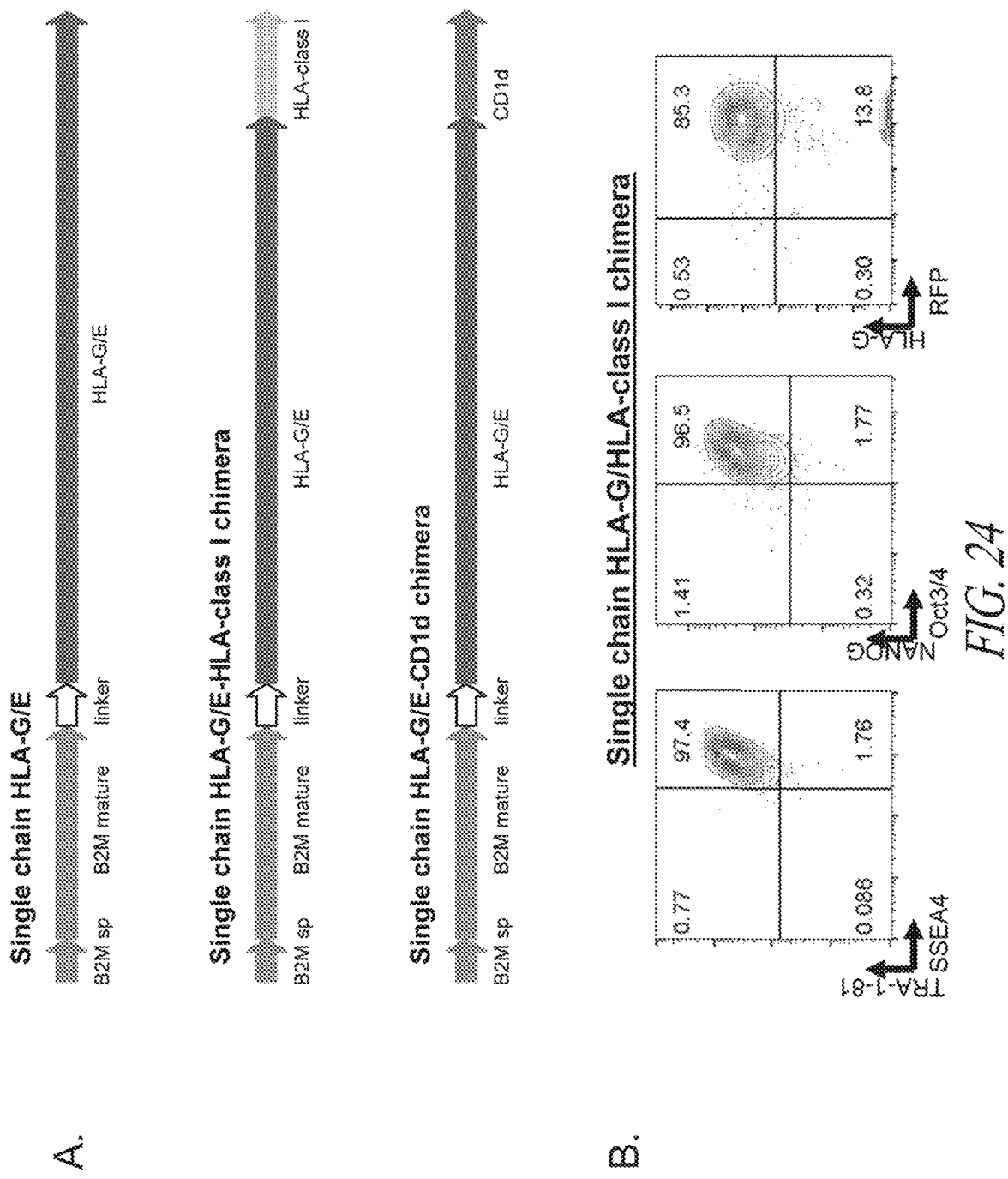
FIGS. 24A-B shows the design and expression of non-cleavable HLAG fusion proteins in hiPSC. A. the design of cleavage-resistant forms of HLA-E/B2M and HLA-G/B2M fusion proteins; B. the HLA-G/HLA-A3 non-cleavable protein is expressed on the cell surface without affecting the quality of the iPSC.

To maintain enhanced persistence of modified HLA I-deficient iPSC-derived lymphoid effector cells cleavage-resistant forms of HLA-E/B2M and HLA-G/B2M fusion proteins were designed (FIG. 24A) and B2M−/− iPSCs were genetically engineered to contain the non-cleavable HLA-G/HLA-A3 fusion protein. FIG. 24B demonstrates that the HLA-G/HLA-A3 non-cleavable protein is expressed on the cell surface by flow cytometry for the expression of HLA-G and does not affect the quality of the iPSC as seen by expression of pluripotent proteins (TRA-181, SSEA4, NANOG and OCT3/4).

Figure 25:
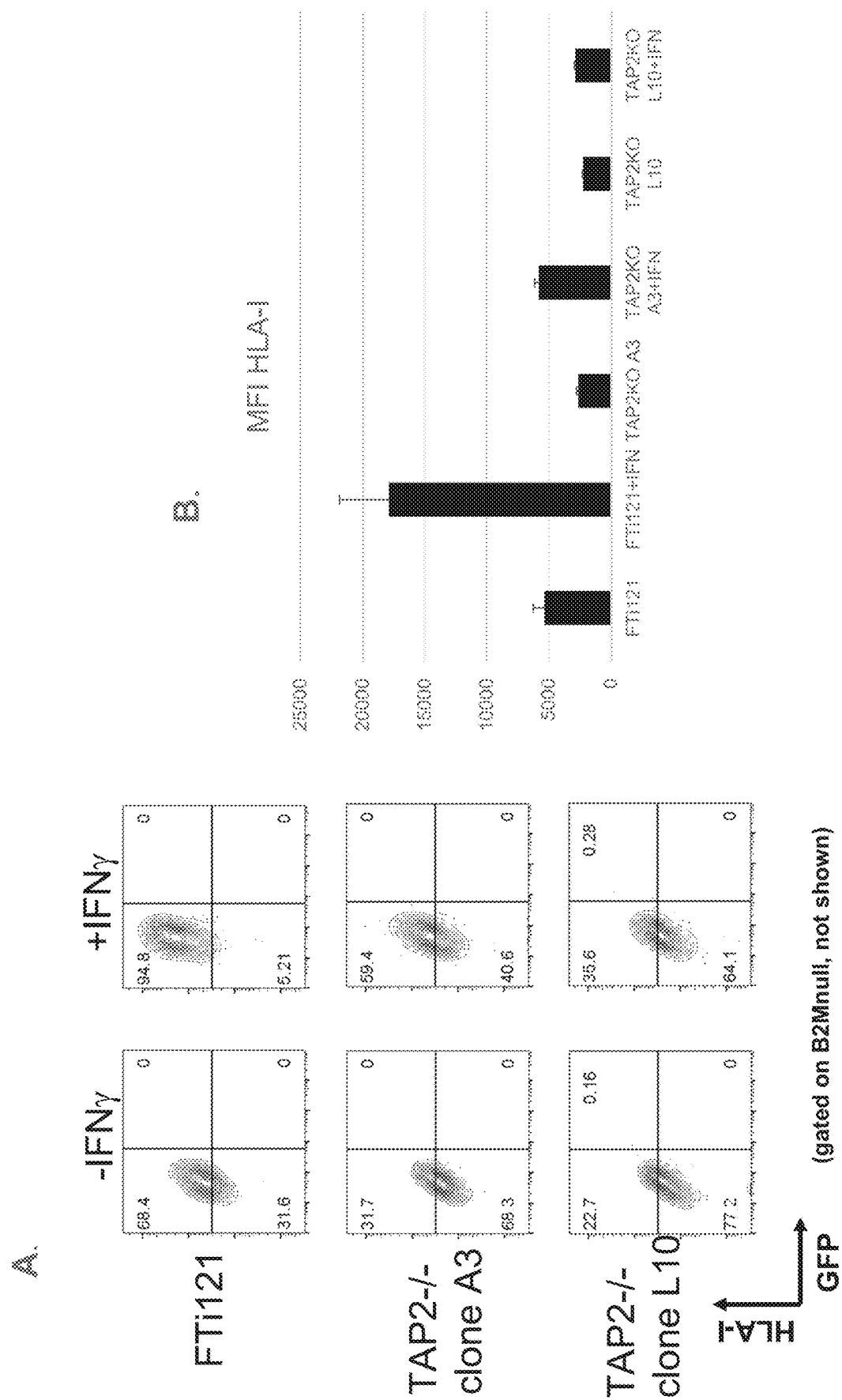
FIGS. 25A-B shows the generation of TAP2−/− iPSC exhibiting decreased expression of HLA class I: A. flow cytometry analysis of 2 selected clones that exhibit a significant decrease in HLA class I expression compared to parental FTi121; B. following the treatment with IFNγ the TAP2−/− clones exhibit decreased expression of HLA class I compared to wildtype FTi121.

An alternative method to create HLA class I deficient iPSCs is to disrupt the peptide loading complex (PLC) which is responsible for loading peptides onto HLA class I molecules. Transporter associated with antigen processing (TAP) is an integral member of the PLC and disruption of the gene results in a significant decrease of stable HLA class I molecules on the cell surface. It is unknown, however, whether TAP2$^{null}$ (TAP2-/-), HLA I deficient iPSCs has any effect on differentiation potential or persistence of the iPSCs. To generate TAP2$^{null}$ iPSC lines FTi121 iPSCs were transfected with TAP2 gRNA pair in a plasmid expressing Cas9 nickase. Cells negative/low for HLA-I were sorted clonally into 96 well plates to generate clonal lines. FIG. 25A shows the flow cytometry analysis of 2 selected clones that exhibit a significant decrease in HLA class I expression compared to parental FTi121. The treatment of iPSC with IFNγ induces the upregulation of HLA class I molecules on the surface. FIG. 25B demonstrates that following the treatment with IFNγ the TAP2-/- clones exhibit decreased expression of HLA class I compared to wildtype FTi121 suggestive of a unique strategy to identify an optimal level of HLA complex expression to evade both T cell and NK cell detection.

Example 16—B2M-/- and HLA I-Deficient iPSCs have Improved Persistence

Figure 15A:
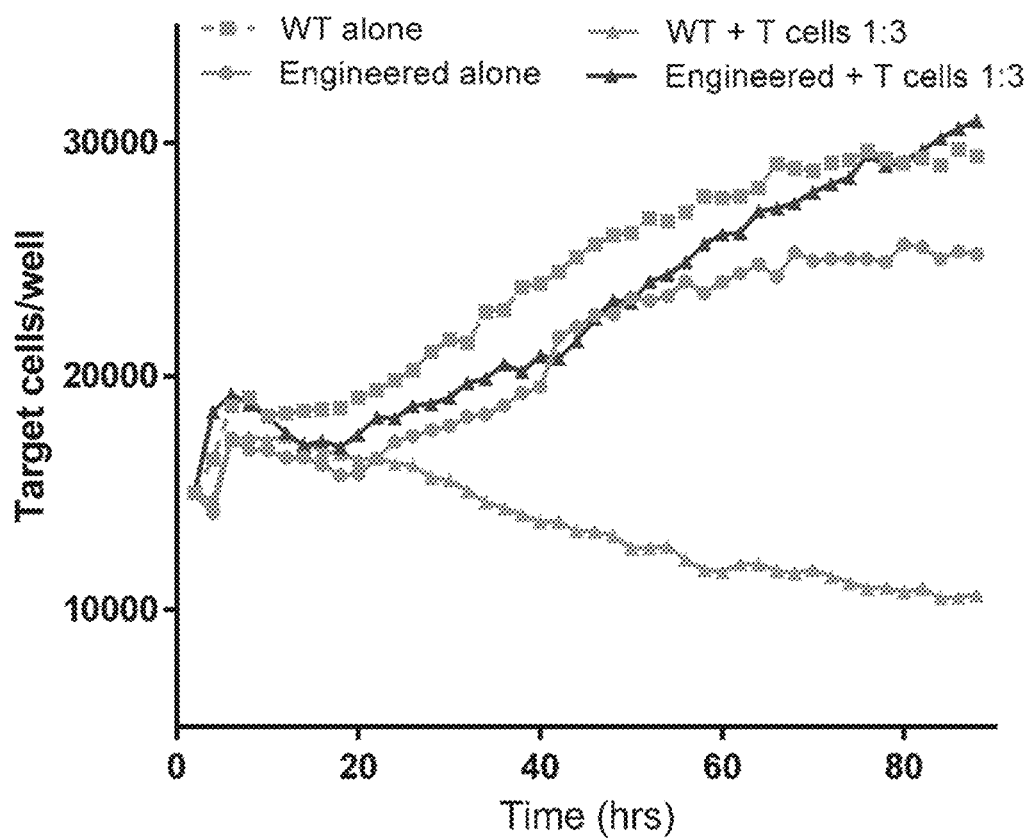
FIGS. 15A-D are a graphic representation of the improved persistence of B2M−/−, HLA I-deficient iPSCs. A. B2M−/− hiPSCs not killed by primed T cells. B. B2M−/− hiPSCs not recognized in co-culture by NK cells in a single well. C. B2M−/− hiPSCs not recognized in co-culture by NK cells in separate wells. D. B2M−/− hiPSCs have gained persistence in immunocompetent mice.

To determine if the absence of HLA-I enables the B2M-/- hiPSCs to evade T lymphoid response, peripheral blood T cells were primed by co-culturing with hiPSCs for 10 days. After 10 days the expanded and primed T cells were harvested and used as cytotoxic effector cells. Wildtype hiPSC (WT) or B2M-/- (engineered) hiPSC target cells were plated either alone or in co-culture with primed T cells at a ratio of 1:3. The number of target cells per well was measured over 5 days using the Incucyte Zoom. As shown in FIG. 15A, the WT hiPSC target cells were recognized and killed by primed T cells while the engineered hiPSC were not affected.

Figure 15C:
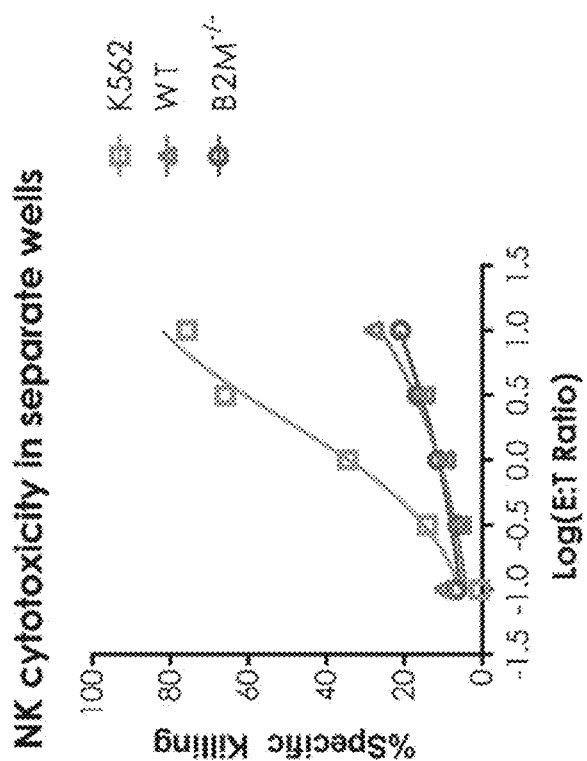
Figure 15B:
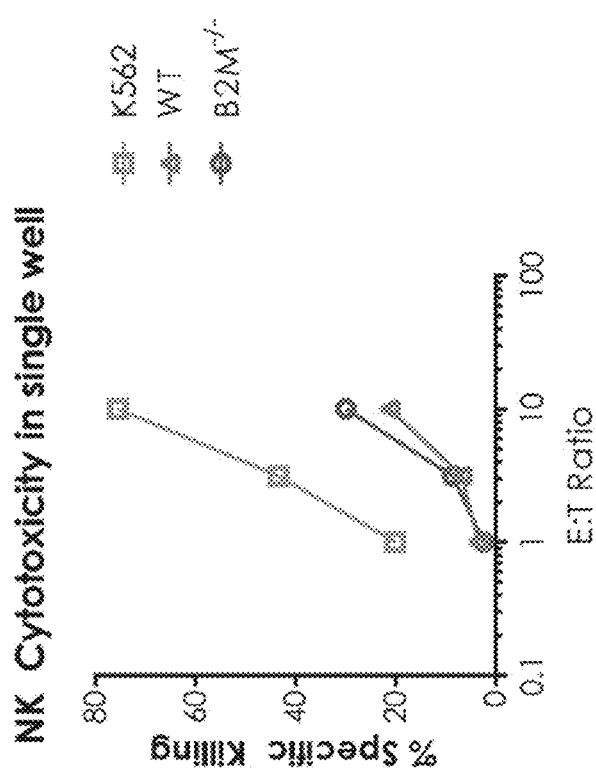

While the B2M-/- hiPSCs were shown to be able to evade recognition and killing by T cells, there was a concern that these cells may be killed more efficiently by NK cells because NK cells are known to activated by cells lacking MHC class I, which is the case for cells lacking B2M; and if so, that could contribute to rejection in vivo. To test whether B2m-/- hiPSCs have increased NK cell recognition, K562 cells, CD45+ cells differentiated from wild-type iPSC (WT), or CD45+ cells differentiated from B2M-/- iPSC (B2M$^{-/-}$) were separately labelled with CFSE, e670 proliferation dye (eBioscience), or e450 proliferation dye (eBioscience), respectively. All three labelled target cells were mixed in equal ratios and added to NK cell effectors in a single well at the indicated ratios (FIG. 15B), or the three labelled target cells were each added to NK cell effectors in respective separate wells (FIG. 15C). Cells were incubated for 4 hours prior to flow cytometry based quantitation of cellular cytotoxicity. As shown in FIGS. 15B and 15C, there appeared to have no increased NK cell recognition in vitro, where both the B2M-/- and WT hiPSC CD45+ cells were killed at the same rate, and both at relatively low levels, in comparison to the killing of K562 cells, a known NK cell target included as a positive control. Therefore, the data suggested that this B2M-/- iPSC line is able to avoid T cell mediated killing while not inducing NK cell recognition, indicating a universally donor/recipient compatible hiPSC clonal line with improved persistence.

Figure 15D:
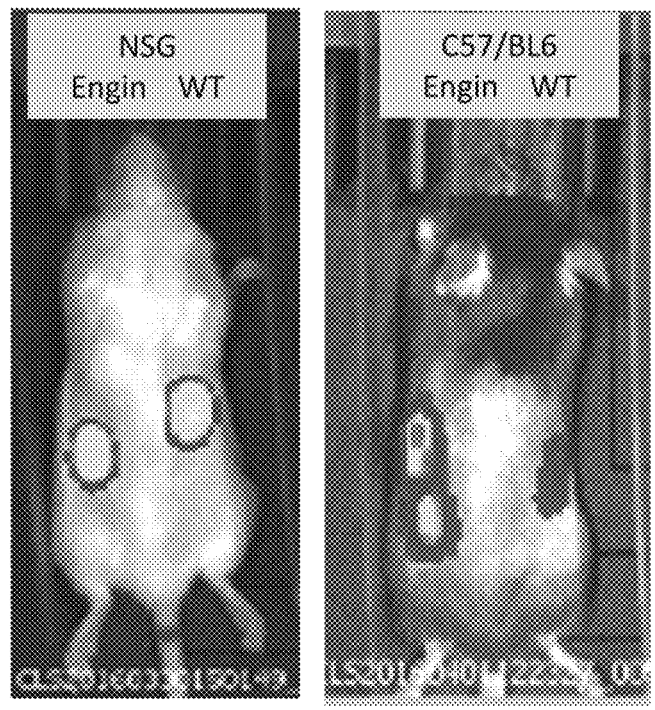

The improved persistence of the universal B2M-/- hiPSC clonal line was further assessed in vivo. To determine if the absence of HLA-A allows an increase in persistence in the presence of a competent immune system in vivo, luciferized WT hiPSC (WT) and B2M-/- hiPSCs (engineered) were injected subcutaneously and bilaterally into either immunocompromised NSG (FIG. 15D left) or immunocompetent WT C57BL/6 (FIG. 15D right) recipient mice to form teratomas. After 96 hours the mice were subjected bioluminescent IVIS imaging to detect the teratoma. In the NSG recipient both the WT and engineered teratomas were detected with equal intensity, whereas in the WT C57BL/6 mice the engineered B2M-/- hiPSCs exhibited increased persistence compared to the WT hiPSC.

Figure 16B:
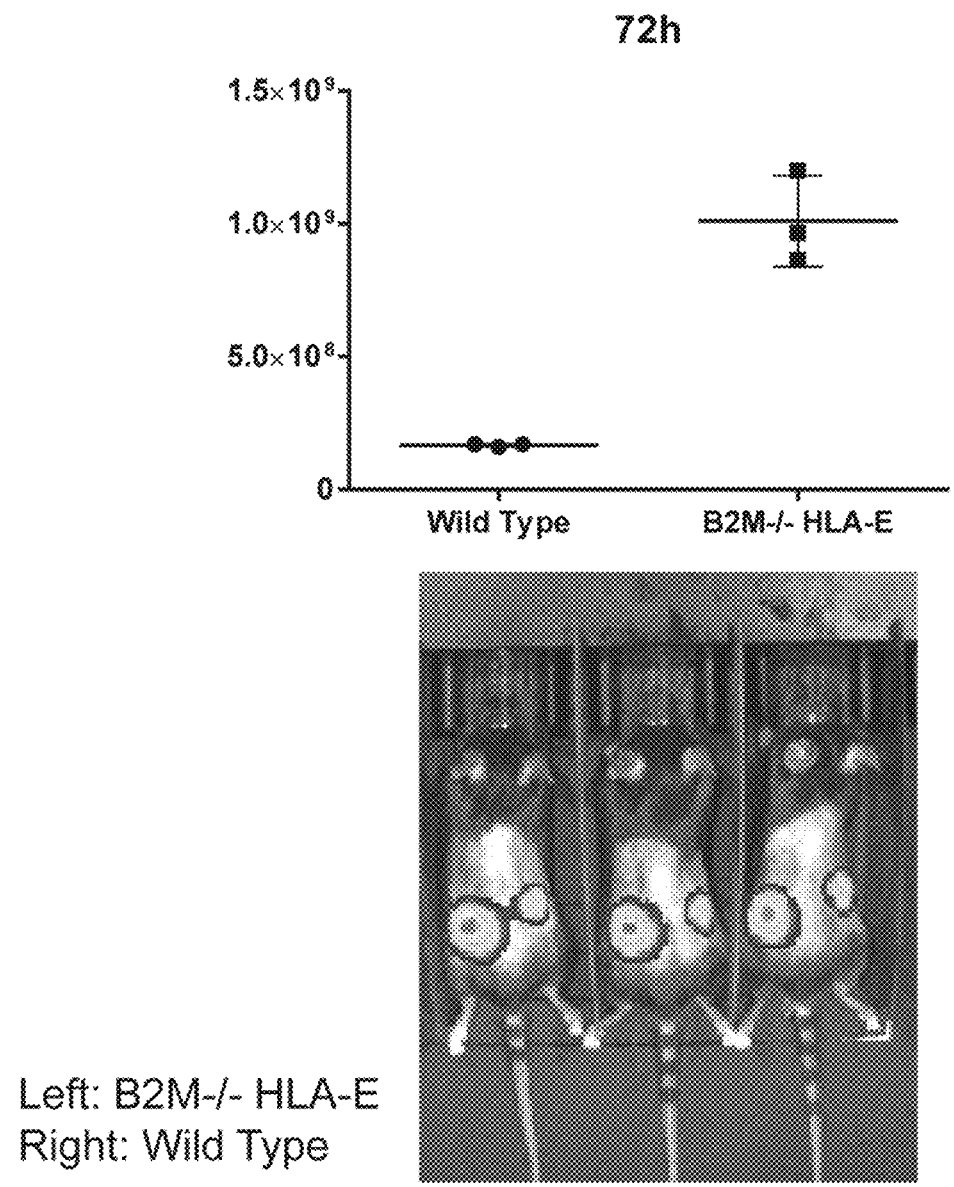

Example 17—Modulation of HLA Class I on iPSC Increases Persistence of iPSC In Vivo To determine if the modified HLA I-deficient iPSC have increased persistence in vivo, luciferized wildtype and the B2M-/- HLA-E iPSCs were injected subcutaneously on opposing flanks of fully immune-competent C57BL/6 recipients in a teratoma assay. Mice were analyzed daily by IVIS imaging in conjunction with luciferin injection to visualize the developing teratoma. FIG. 16B demonstrates that at 72-144 hour post injection the B2M-/- HLA-E iPSCs show increased quantitative persistence of about 6 fold compared to wildtype iPSC. Three representative mice depicting increased luciferin imaging with the B2M-/- HLA-E iPSC teratomas were also presented in FIG. 16B. A similar improvement in persistence was observed when HLA-G was used instead of HLA-E. Additionally, as described above, a modified version of HLA-E or HLA-G to avoid cleavage is applied to further enhance in vivo persistence of HLA class I modified iPSCs. Interestingly, we recognized that in some scenarios where the NK cell obtained from CMV+ donors exhibit NKG2C expression and thus are activated, the HLA-E surface expression instead activates NKG2C and thus leads to adverse effects including NK cell recognition and the resultant killing of the HLA-E expressing cells. In contrast to where the NK cell expresses NKG2A, the NK cells can be inactivated by HLA-E surface expressing iPSCs and differentiated progeny, thereby augmenting persistence of these HLA-E surface expressing cells.

Figure 26A:
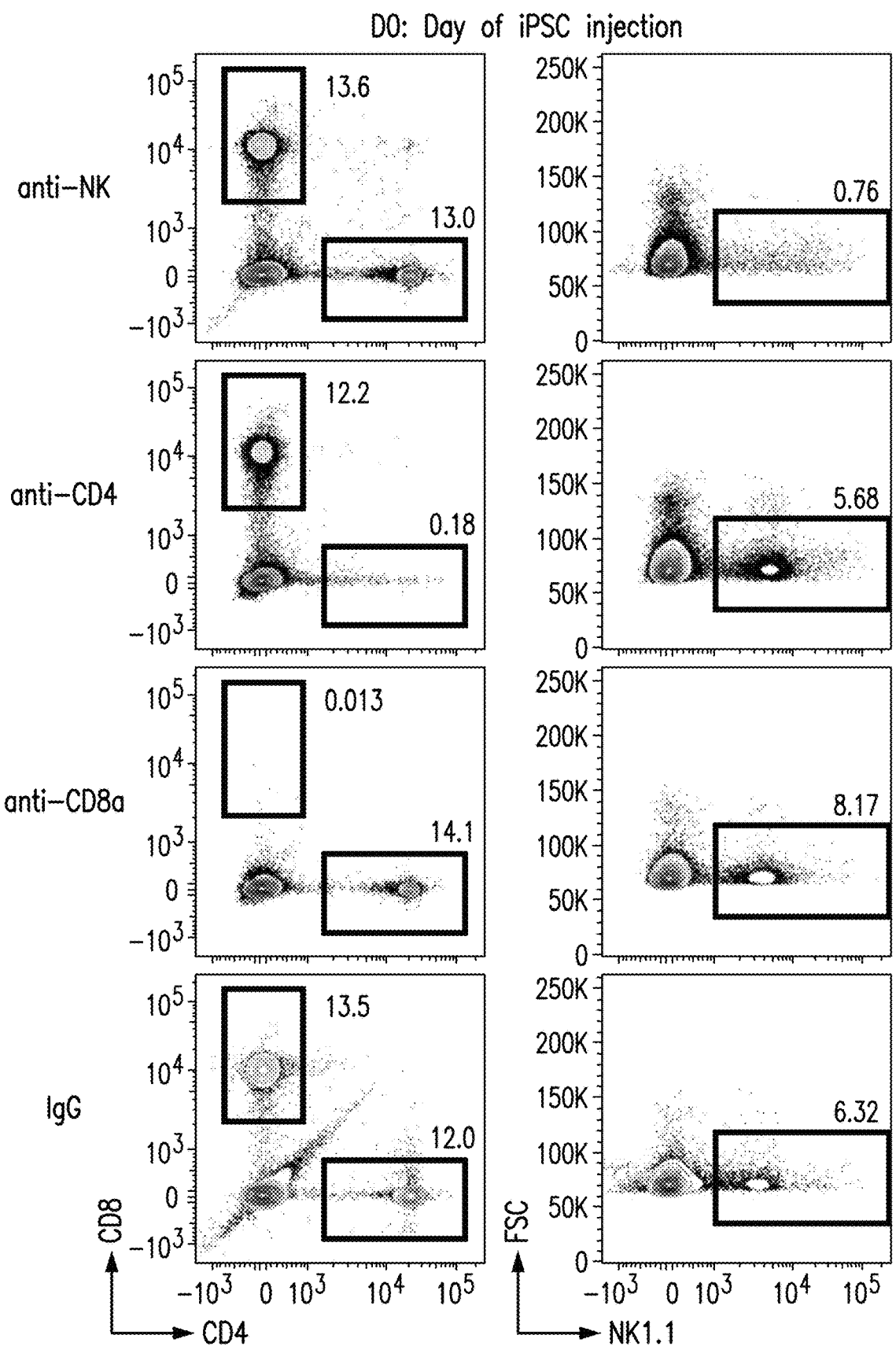
FIGS. 26A-B show that host NK cells contribute to hiPSC teratoma rejection in immune-competent recipients: A. the absence of the CD4+ T cells, CD8+ T cells and NK cells 3 days post antibody injection; B. NK depleted mice at 120 hrs post iPSC injection exhibited the highest resistance to tumor rejection compared to IgG control treated animals.
Figure 26B:
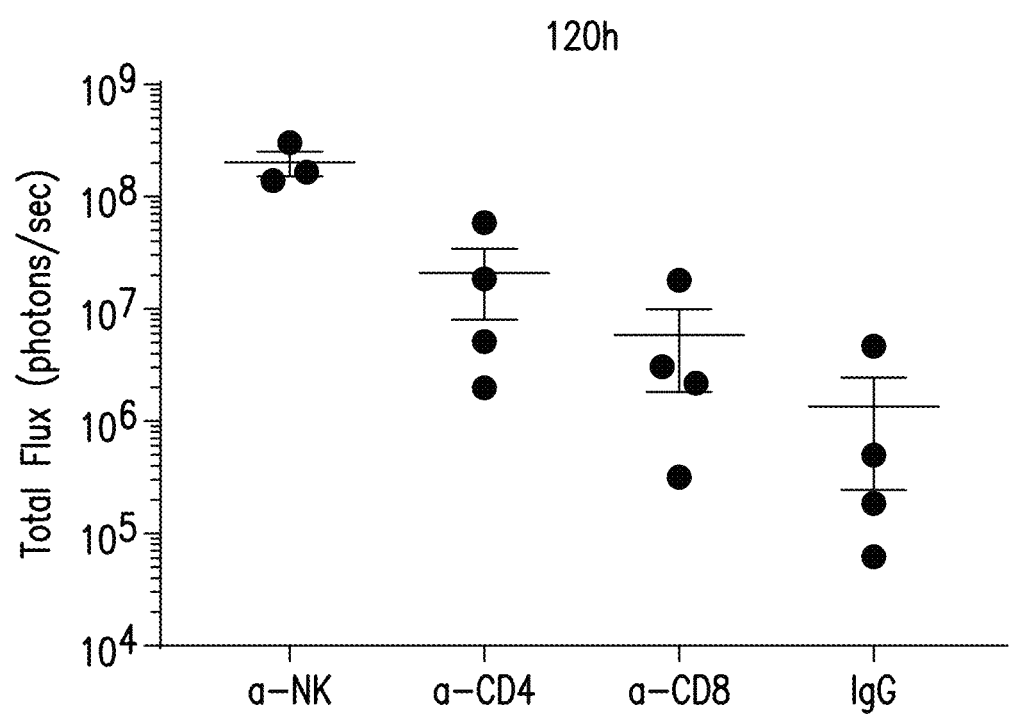

To determine what component of the host immune response is involved in the rejection of enhanced modified HLA I-deficient iPSCs in wildtype recipient mice, CD4+ T cells, CD8+ T cells and NK cells were individually depleted through injection of anti-CD4, anti-CD8a and anti-NK1.1 antibodies respectively. FIG. 26A demonstrates the absence of the CD4+ T cells, CD8+ T cells and NK cells three days post antibody injection. Three days after antibody-mediated depletion luciferized B2M-/- HLA I-modified iPSCs were injected subcutaneously on the flank of immune-competent C57BL/6 mice to form a teratoma. Mice were analyzed daily by IVIS imaging in conjunction with luciferin injection to visualize the developing teratoma. FIG. 26B demonstrates that at 120 hrs post iPSC injection mice in which NK cells were depleted exhibited the highest resistance to tumor rejection compared to IgG control treated animals.

Figure 27A:
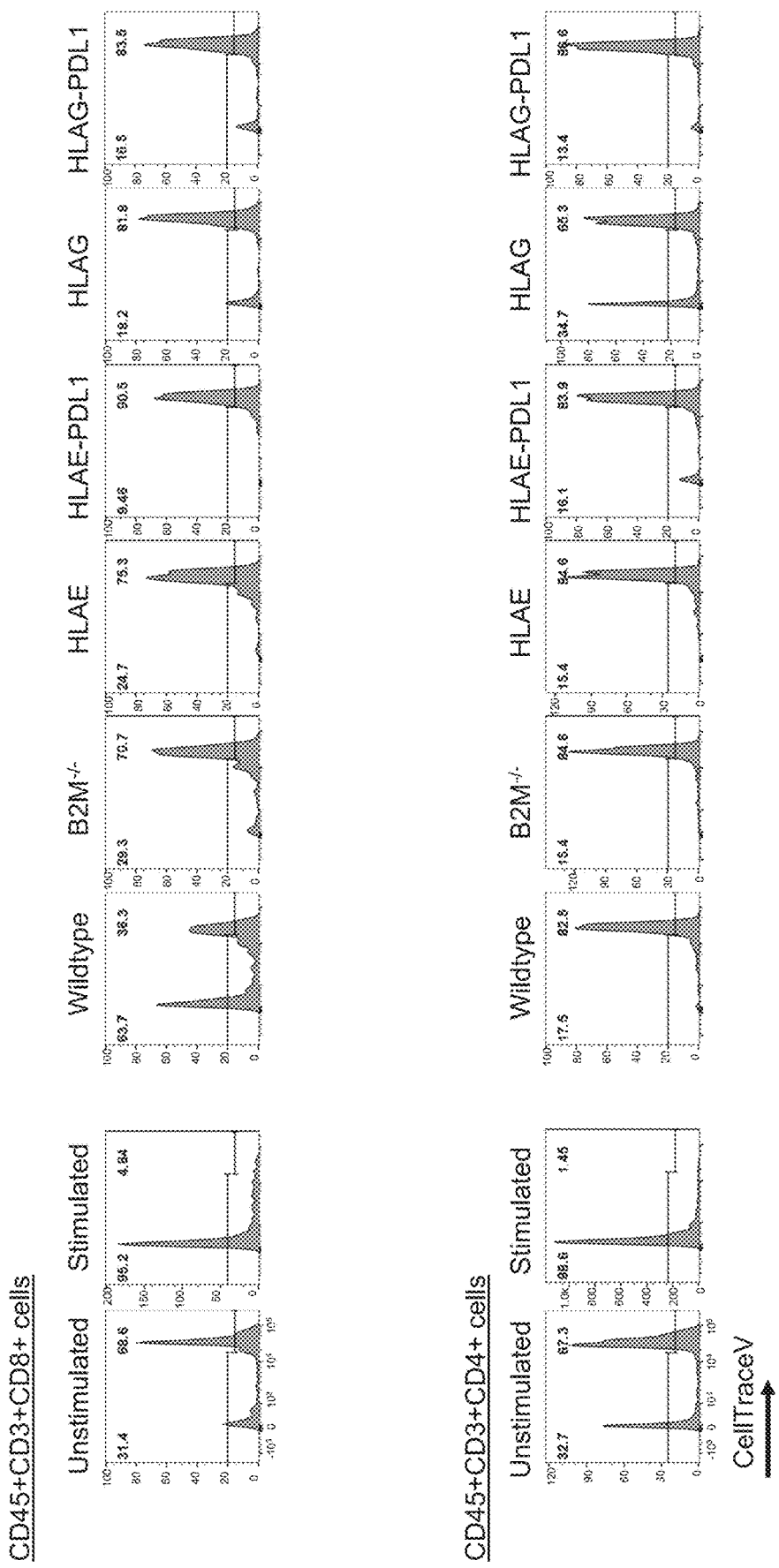
FIGS. 27A-C show modified HLA I-deficient iPSCs have increased persistence and resistance in vitro. Expression of immunosuppressive proteins on hiPSC-derived cells prevents recognition and proliferation of: A. purified allogenic human T cells; B. PBMC allogenic human T cells; C. PBMC allogenic human NK cells.
Figure 27B:
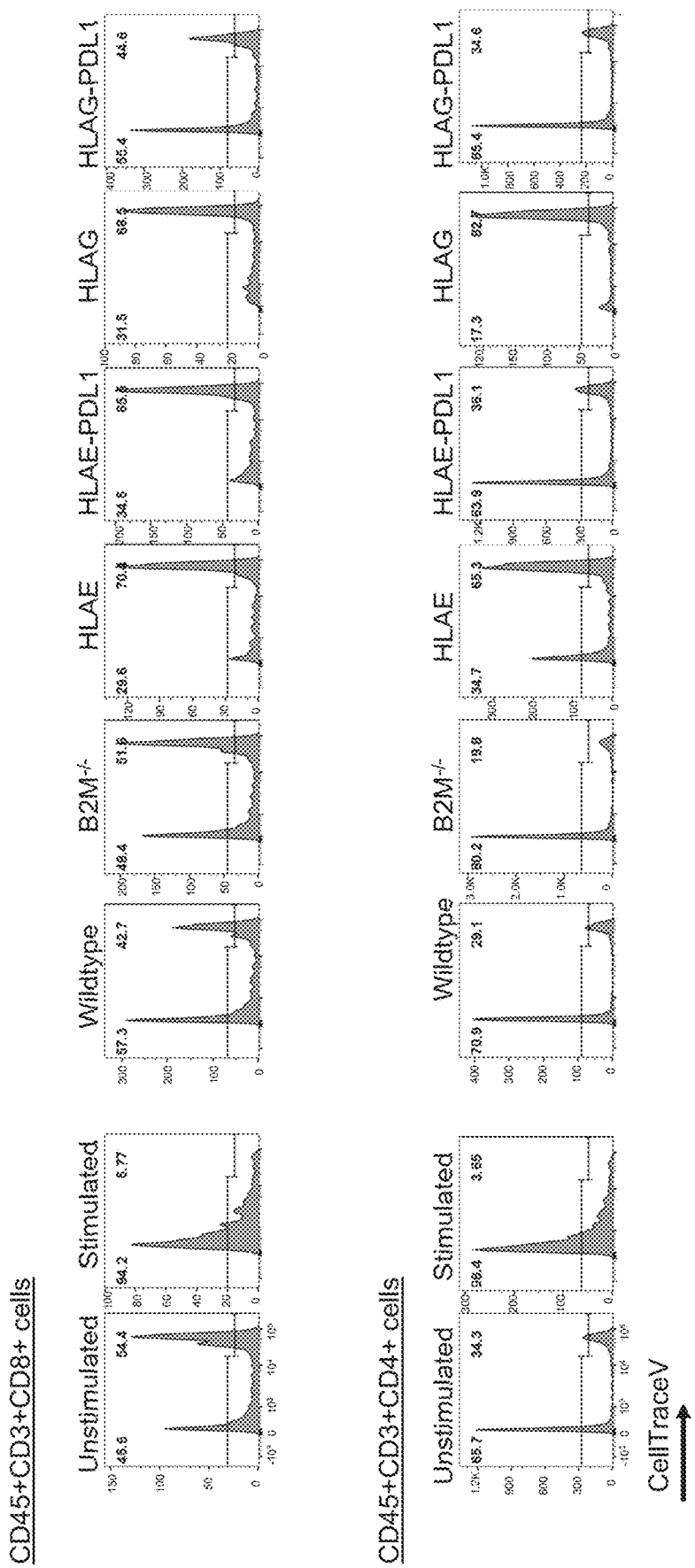
Figure 27C:
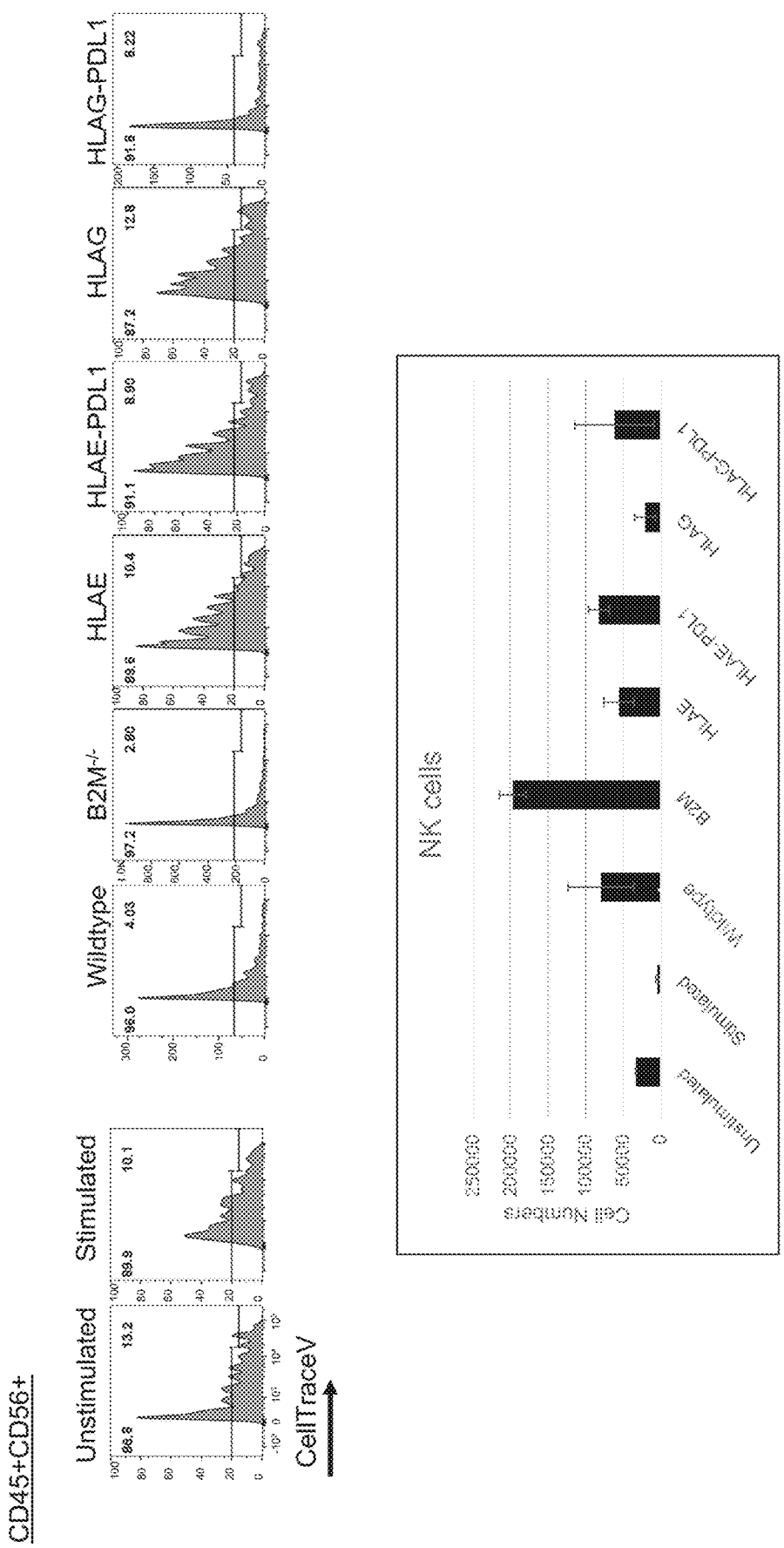

To determine if the genetically engineered HLA I-modified iPSC have increased persistence and resistance in vitro B2M−/− PDL1 HLA-I modified iPSCs were cultured in suspension for 3 days and then treated with IFNγ for 24 hours to induce expression of HLA class I. The treated iPSCs were then placed in co-culture with allogenic purified T cells (FIG. 27A), allogenic T cells and NK cells contained in whole peripheral blood mononuclear cells (PBMCs, FIGS. 27B and 27C) that were previously labeled with Cell Trace Violet (CTV) to monitor cellular proliferation. T cells/PBMCs alone (unstimulated) and T cells/PBMCs stimulated with anti-CD3/CD28 beads (stimulated) to induce activation and proliferation were used as controls. 12 days after initiation of co-culture the cells were assessed by flow cytometry to determine the amount of proliferation of the CD4+ T cells, CD8+ T cells and CD56+NK cells as a measure of their ability to recognize and respond to HLA I-modified iPSC-derived cells. FIGS. 27A and 27B demonstrates that compared to T cells co-cultured with wildtype iPSC-derived cells, T cells co-cultured with B2M−/− and furthermore B2M−/−HLA I-modified iPSC-derived cells exhibited less proliferation as seen by dilution of the CTV proliferation dye. FIG. 27C demonstrates a similar effect on NK cell proliferation collectively signifying the ability of the HLA class I modifications to enhance immune resistance to T and NK cells.

Example 18—Generation of iPSCs with Enhanced Properties Through Additional Editing Molecules that are modified or modulated at iPSC level may be used to enhance properties desirable in immune therapies using the derivative lymphocytes obtained through the present differentiation platform. These molecules may include safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In addition to B2M/HLA-I and HLA-E/G the targeted molecules contributing to desirable properties further include, but are not limited to, CD16 receptor and 41BBL costimulatory molecule, CD3, CD4, CD8, CD47, CD113, CD131, CD137, CD80, PDL1, A2AR, CAR (chimeric antigen receptor), TCR (T cell receptor), TAP1, TAP2, Tapasin, NLRC5, PD1, LAG3, TIM3, RFXANK, CIITA, RFX5, RFXAP, any gene in the chromosome 6p21 region, an engager, and a surface triggering receptor for coupling bi- or multi-specific or universal engagers. More specifically, the genetic modification of the targeted molecules in iPSC include one or more of: deletion or reduced expression of B2M, TAP1, TAP2, Tapasin, NLRC5, PD1, LAG3, TIM3, RFXANK, CIITA, RFX5, RFXAP, and any gene in the chromosome 6p21 region; introduced or increased expression of HLA-E, HLA-G HACD16, 41BBL, CD3, CD4, CD8, CD47, CD113, CD131, CD137, CD80, PDL1, A2AR, CAR, TCR, Fc receptor, an engager, or surface triggering receptors for coupling with bi- or multi-specific or universal engagers. The increased or reduced expression of the targeted molecules can be permanent, transient, temporal or inducible, and can be controlled by endogenous or exogenous promoters.

Figure 17A:
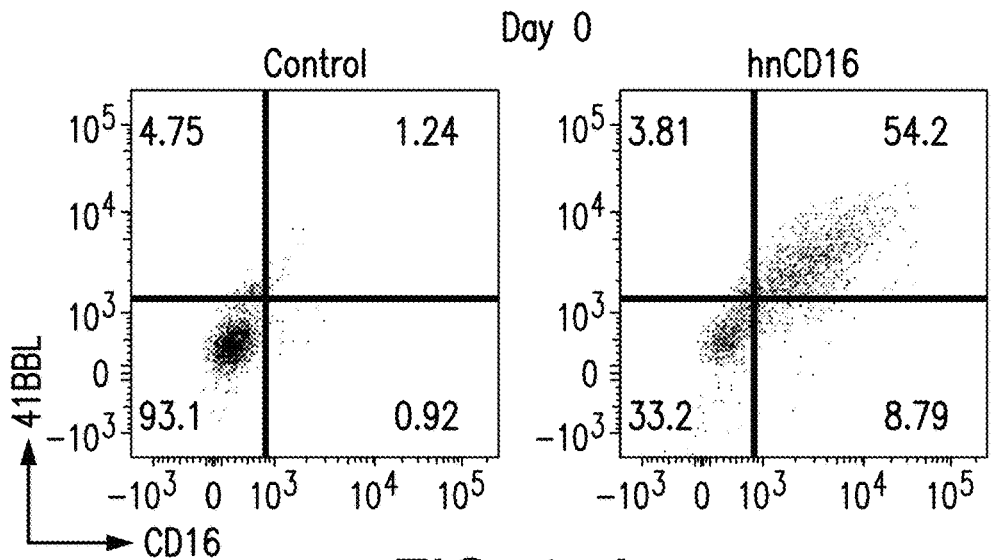
FIGS. 17A-B show that iPSC genetically engineered to express the high-affinity non-cleavable CD16 receptor and 41BBL co-stimulatory molecule retain expression throughout differentiation to iCD34 cells. A. Day 0 undifferentiated cells. B. Day 10 differentiated cells.
Figure 17B:
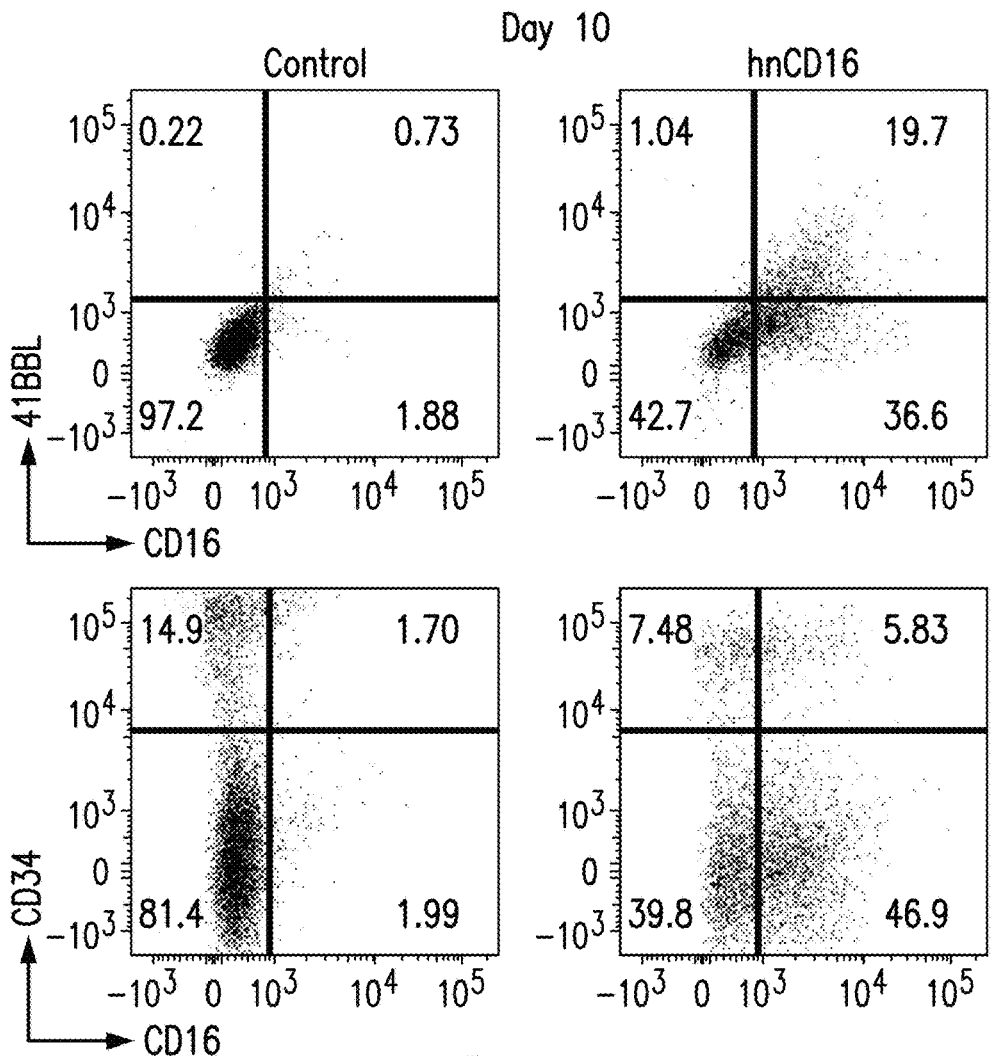

These desired modality may be introduced into iPSC using various delivery methods known in the art. In this exemplary illustration, iPSCs were genetically engineered to contain the high-affinity non-cleavable CD16 receptor (hnCD16) and 41BBL co-stimulatory molecules to generate iPSC having enhanced cytotoxicity. FIG. 17A demonstrates the efficient expression of hnCD16 and 41BBL on the surface of iPSC following lenti-viral transduction by flow cytometric analysis. FIG. 17B demonstrates that the expression of hnCD16 and 41BBL expression is maintained and does not perturb the ability of iPSC to generate CD34+HE cells following 10 days of differentiation.

Figure 28A:
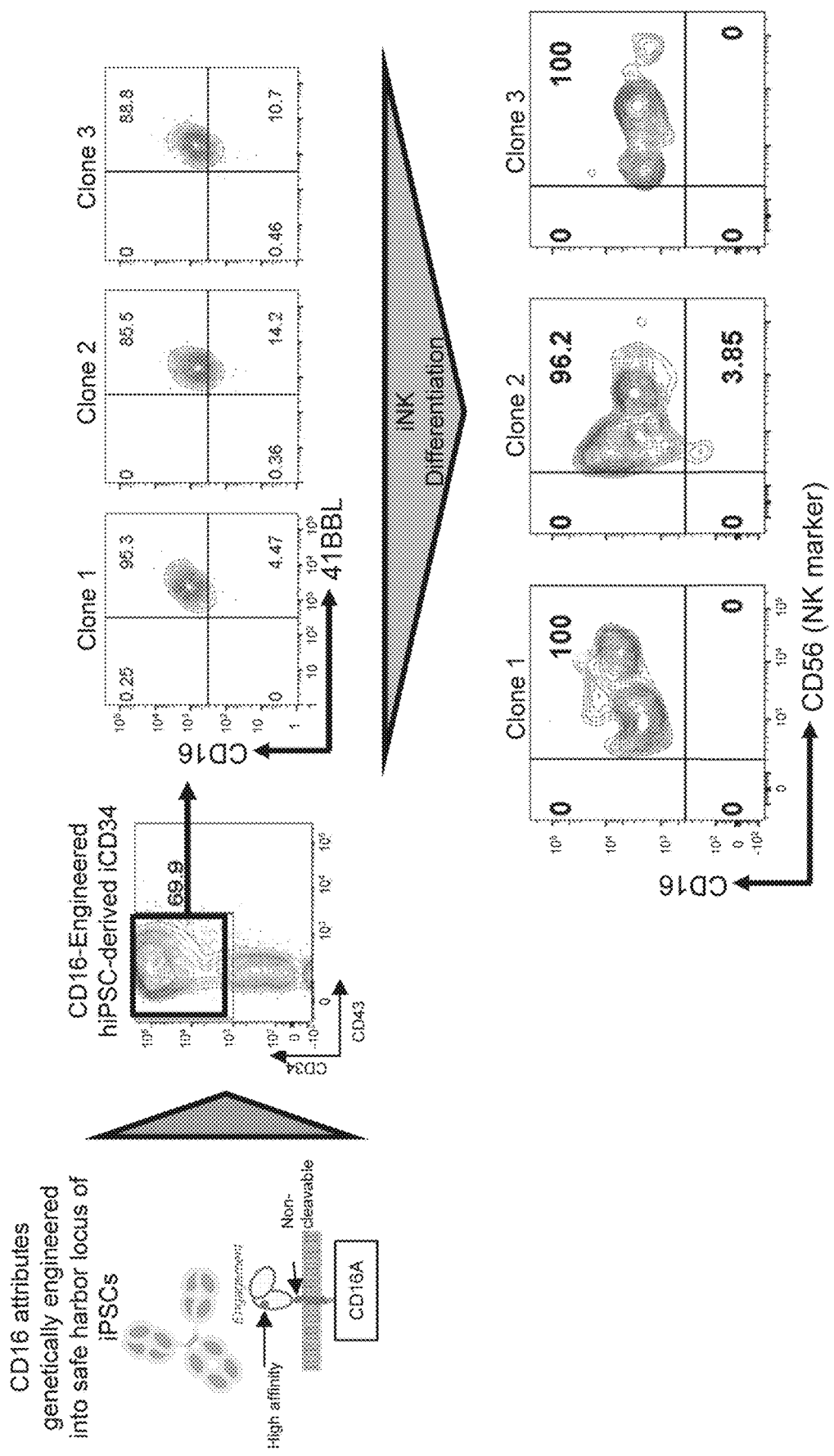
FIGS. 28A-B show the expression of the hnCD16 protein does not affect the hematopoietic differentiation potential of the engineered iPSCs. A. Engineered iNK Cells with hnCD16 surface expression; B. hnCD16 is constitutively expressed and continuously maintained on iNKs derived from the genetically engineered iPSCs.

To assess if the expression of the hnCD16 (high-affinity non-cleavable CD16 receptor) protein affects the hematopoietic differentiation of engineered iPSCs the pool of hnCD16/41BBL genetically engineered iPSCs were sorted clonally into 96 well plates. Three positive clones were selected and differentiated for 10 days to generate iCD34+ cells. FIG. 28A demonstrates the homogenous expression of hnCD16 and 41BBL on CD34+HE as seen by flow cytometry. The CD34+ cells were isolated and further differentiated for 10 days under NK promoting conditions to generate proNK cells. FIG. 28A shows that the CD56+NK progenitors maintain high levels of expression of the hnCD16 protein and demonstrates that the expression of hnCD16 and 41BBL does not perturb the hematopoietic differentiation capacity of the engineered iPSCs.

Figure 28B:
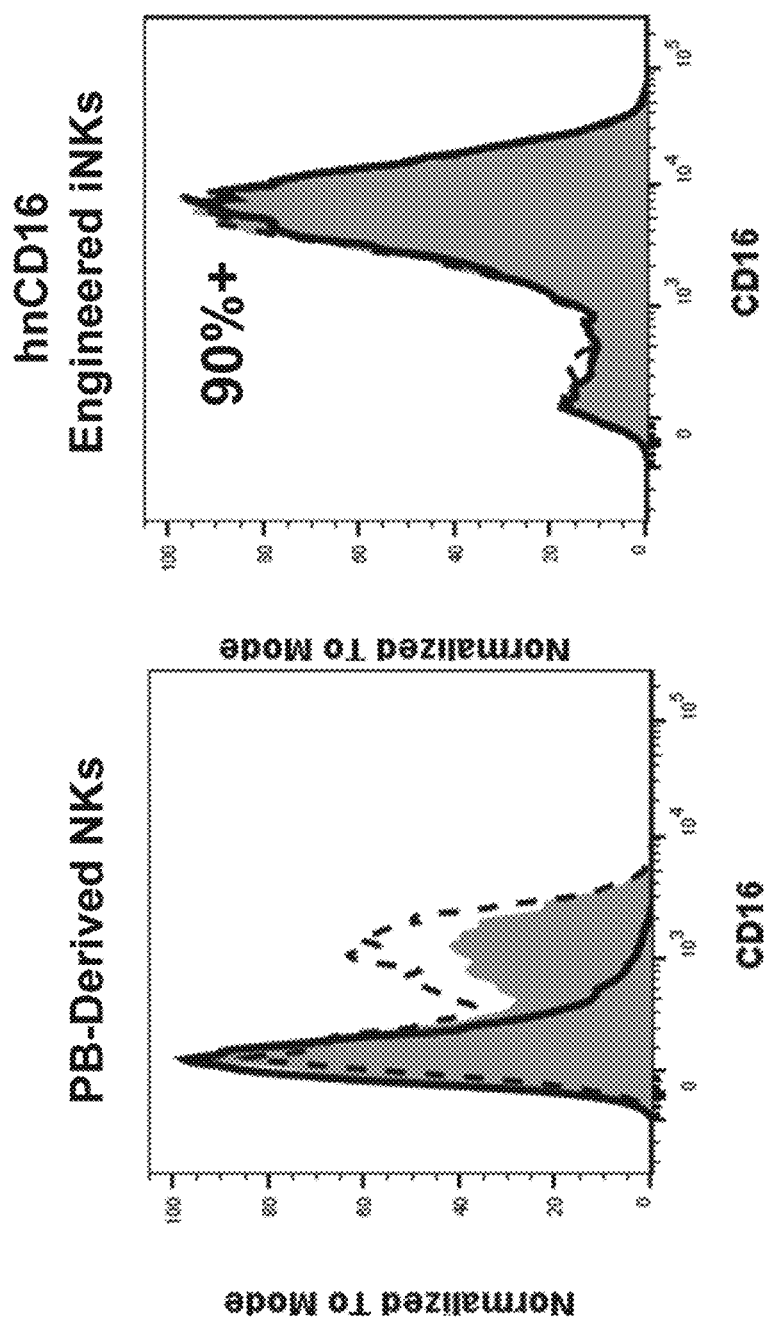

The endogenous CD16 receptor expressed by NK cells gets cleaved from the cellular surface following NK cell activation. To confirm that the hnCD16 engineered protein does not become cleaved, hnCD16 expressing iNK cells and peripheral blood (PB)-derived NK cells were cultured in 1) homeostatic culture, 2) homeostatic culture in the presence or absence of a TACE/ADAM inhibitor that suppresses CD16 cleavage or 3) stimulated with K562 target cells to promote NK cell activation and subsequent CD16 shedding. PB-derived NK cells and iNK cells without stimulation represent homeostatic control. FIG. 28B demonstrates that PB-derived NK cells' loss of CD16 expression during homeostatic culture is reduced or inhibited by the TACE/ADAM inhibitor and upon co-culturing with K562 targets cells the loss of CD16 expression is augmented. In contrast, the expression of CD16 on the hnCD16 engineered iNK remains constant upon iNK cell activation by K562 target cells thus confirming the integrity of the non-cleavable high affinity CD16 receptor.

Figure 29A:
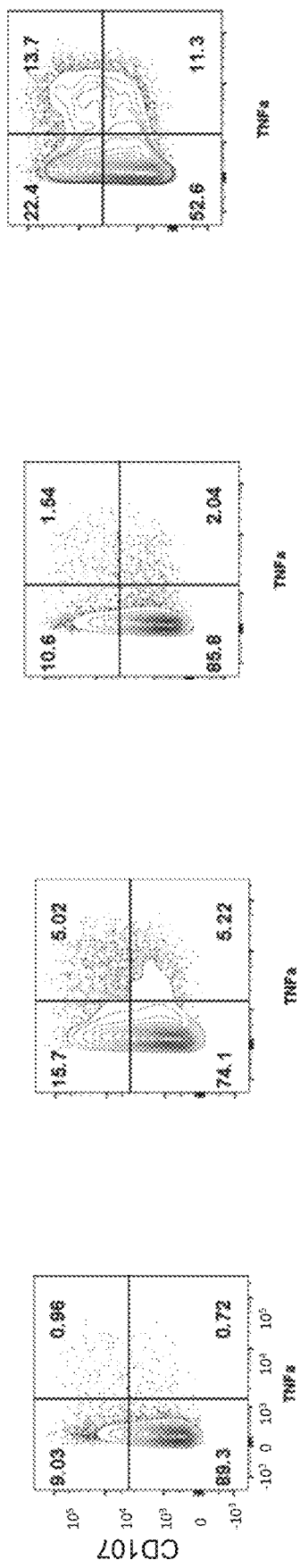
FIGS. 29A-B show the enhanced functionality of the hnCD16-expressing iNK cells: A. enhanced cytokine production induced by CD16 stimulation in hnCD16-expressing iNK cells; B. hnCD16 enhances Antibody-dependent cell-mediated cytotoxicity (ADCC) of hnCD16-expressing iNK cells.

To assess the enhanced functionality of the hnCD16 receptor hnCD16-expressing iNK cells were left unstimulated or stimulated with 5 ug/ml anti-CD16, or with a 1:1 ratio of P815 cells either alone or in combination with 5 ug/ml anti-CD16. iNK cells were assessed by flow cytometry for proinflammatory cytokine release and degranulation which are hallmarks of NK cell activation. FIG. 29A depicts iNK cells gated on the CD45+CD56+CD3− fraction and show IFN☐, TNF☐, and CD107a surface expression. hnCD16 expressing iNK cells have increased expression of TNFα and CD107a in response to anti-CD16 antibody, which can be further enhanced by co-culturing with P815 cells and anti-CD16. These data demonstrated that the hnCD16 receptor is functional on iPSC-derived iNK cells.

Figure 29B:
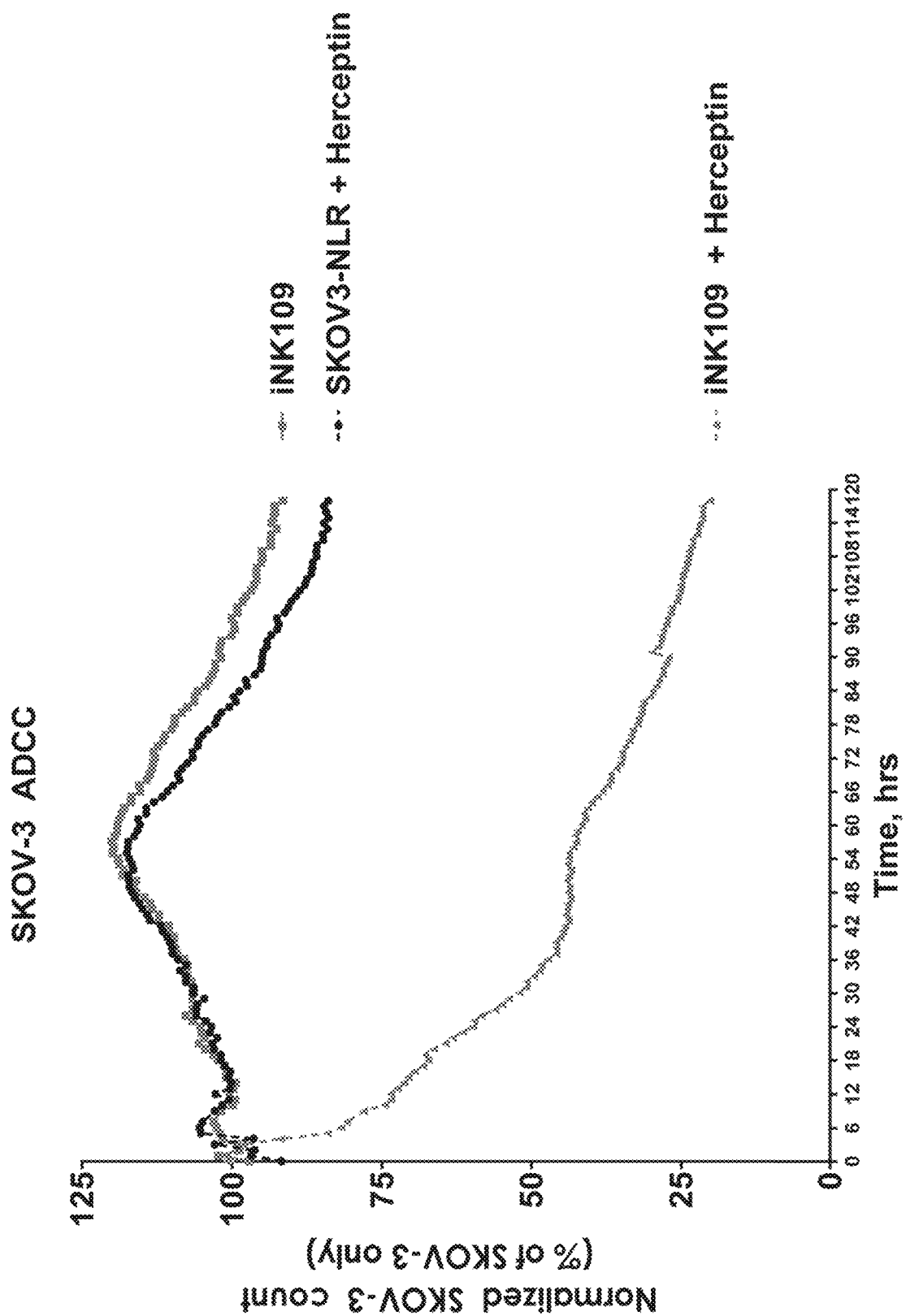

Antibody-dependent cell-mediated cytotoxicity (ADCC) is a mechanism of NK cell mediated lysis through the binding of CD16 to antibody-coated target cells. To assess ADCC function, hnCD16-expressing iNK cells were co-cultured with nuclear red-labeled SKOV target cells with or without Herceptin antibody for 120 hours. Quantification of target cells was analyzed every 2 hours with the Incucyte ZOOM cell analysis system (Essen BioScience, Ann Arbor, Mich.). FIG. 29B demonstrates that hnCD16 expressing iNK cells have potent ADCC in the presence of Herceptin antibody providing further evidence for the enhanced functionality of the engineered iNK cells.

Figure 30:
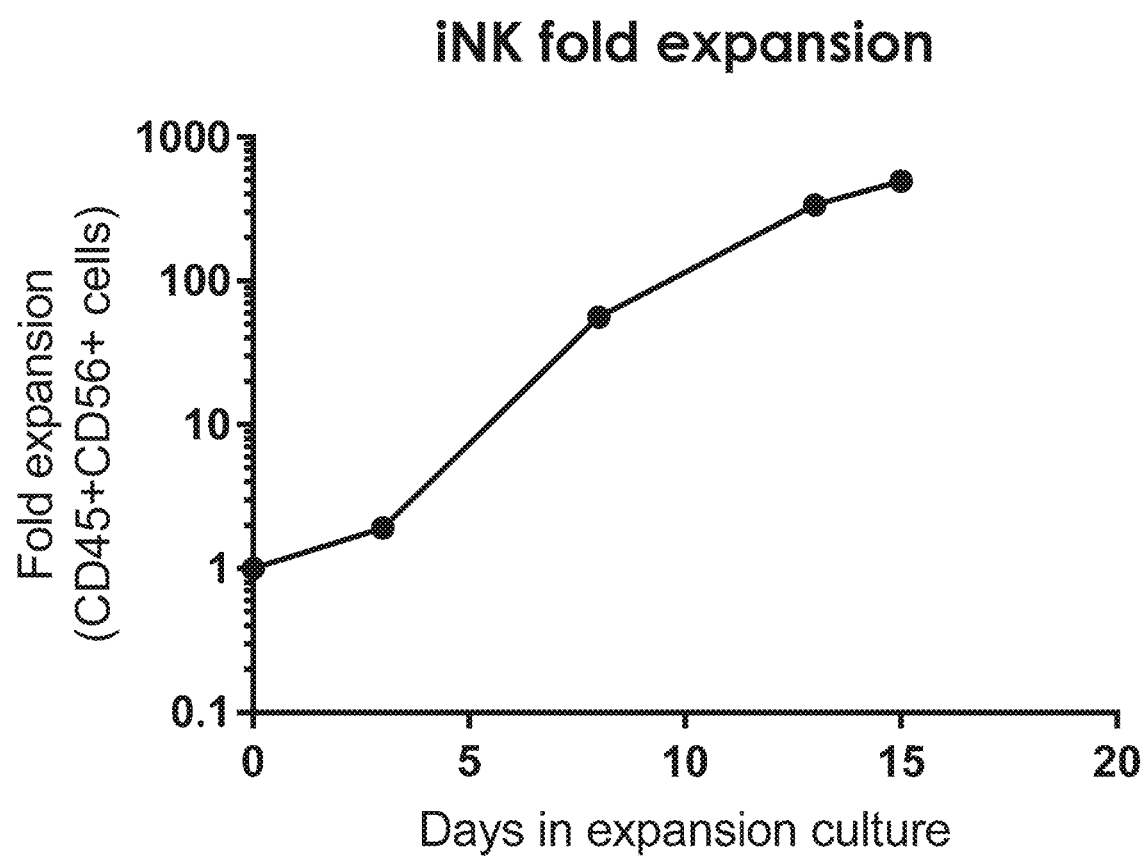
FIG. 30 shows the quality of the iPSC-derived iNK cells by way of iNK cell expansion.

To further evaluate the quality of the iPSC-derived iNK cells, cultures were placed in expansion-promoting conditions as follows. CD45+CD3−CD56+(~66%) were obtained on day 18 of iNK differentiation from CD34+ cells. Cells (2.5×10^5/mL) were cultured weekly with equal numbers of irradiated K562/mbIL-21/41BBL feeders plus 250 U/mL rhIL-2. After each round of feeder addition, fresh medium (BO) plus IL-2 was added on day 3. Cells were diluted to 2.5×10^5/mL on day 5 and fed with fresh medium plus IL-2 (250 U/mL). Cell counts and flow cytometry were used to determine the fold expansion of NK cells. FIG. 30 demonstrates that iNK cells undergo a 495 fold expansion during 15 days of culture.

Accordingly, iPSCs are generated to comprise one or more of B2M null or low, HLA-E/G, PDL1, $A_{2A}R$, CD47, LAG3 null or low, TIM3 null or low, TAP1 null or low, TAP2 null or low, Tapasin null or low, NLRC5 null or low, PD1 null or low, RFKANK null or low, CIITA null or low, RFX5 null or low and RFXAP null or low. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen.

Also generated are iPSCs comprise one or more of HLA-E, HLA-G, CD16, 41BBL, CD3, CD4, CD8, CD47, CD113, CD131, CD137, CD80, PDL1, A2AR, CAR, and TCR, providing improved immune effector ability.

Example 19—CAR-T Derived iPSCs Retain CAR

Chimeric antigen receptors (CARs) are engineered transmembrane receptors that serve to apply specificity onto an immune effector cell such as a T or NK cell. CARs are fusion proteins typically consisting of a single-chain variable fragment (scFV) derived from monoclonal antibodies to provide antigen recognition and a combination of intracellular signaling domains to provide activation signals to the immune effector cell. CARs hold great potential as a potent universal cancer immunotherapy as CAR-immune effector cells can be engineered to recognize any tumor associated antigen and thus target the engineered immune effector cells only to the tumor cells without the requirement for HLA matching.

Figure 18:
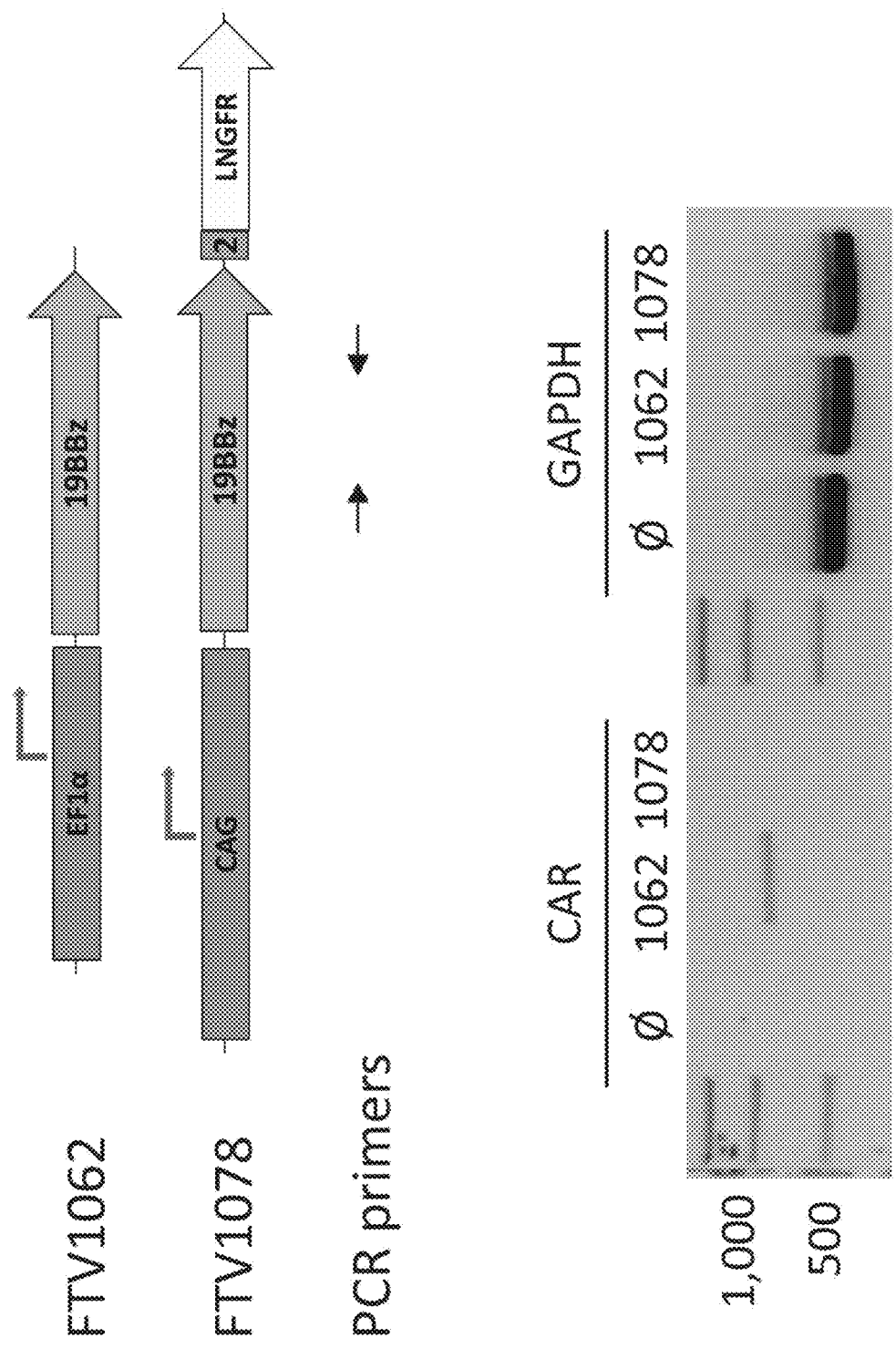
FIG. 18 shows reprogramming of a CAR-T cell to iPSCs (TiPSCs) which retain the same genetic imprint of the source T cell by PCR analysis of CAR (FTV106) integration in iPSCs derived from T cells genetically engineered with FTV106.
Figure 19A:
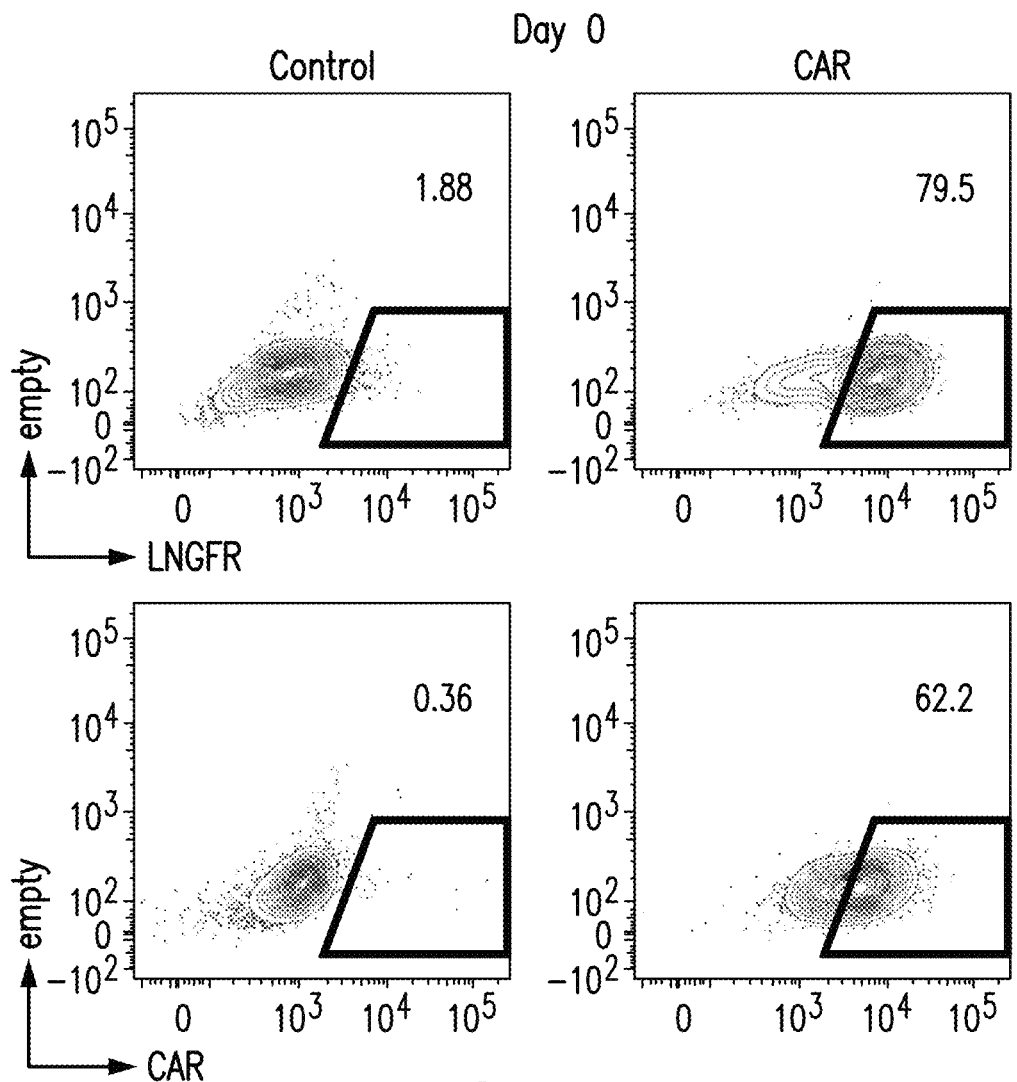
FIGS. 19A-B show that iPSC genetically engineered to express the CD19 chimeric antigen receptor (CAR) and truncated LNGFR cell surface marker as an co-identifier for the CAR retain expression through differentiation to iCD34 cells. A. Day 0 undifferentiated cells. B. Day 10 differentiated cells.
Figure 19B:
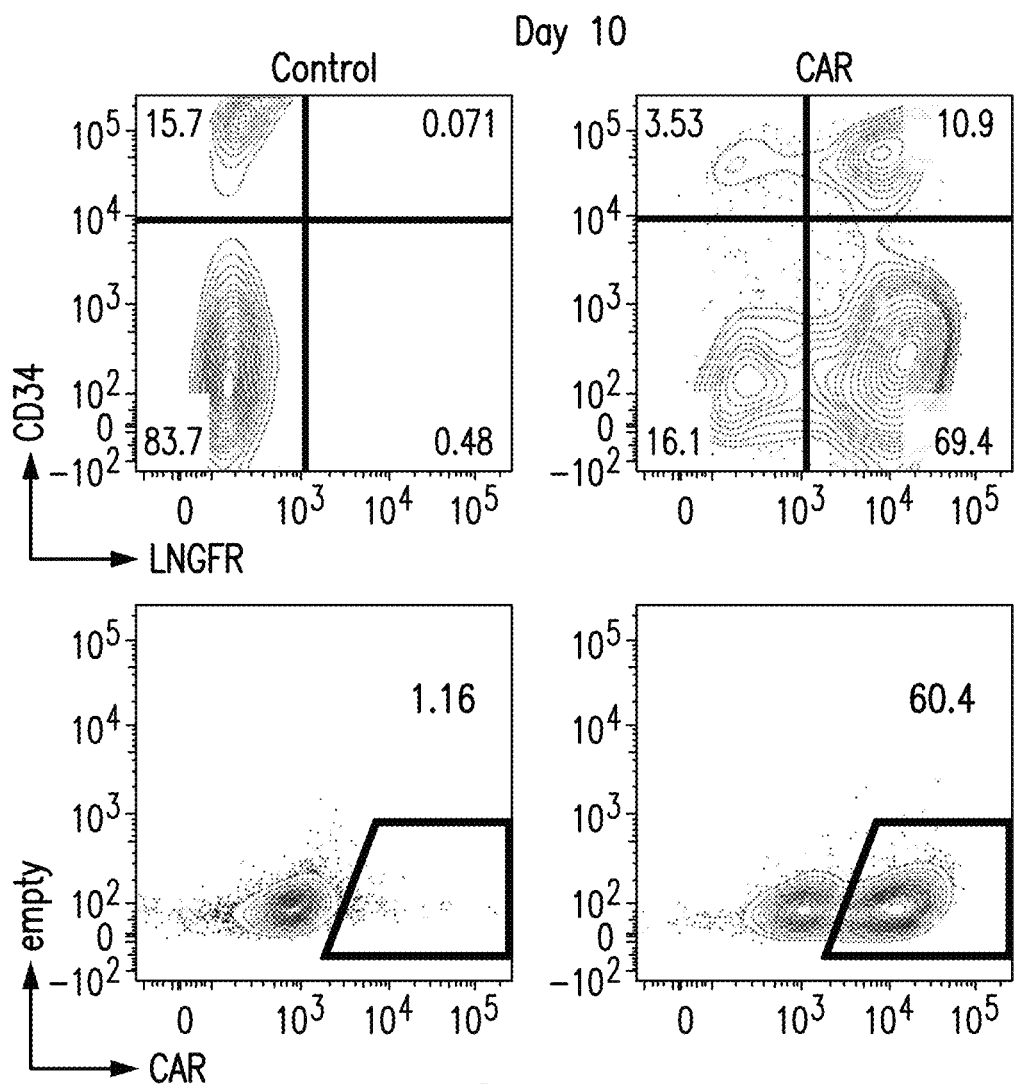

We have shown the reprogramming of a CAR-T cell to iPSCs which retain the same genetic imprint of the source cell, i.e., the same chimeric antigen receptor (FIG. 18). The iPSCs genetically engineered to express the CD19 chimeric antigen receptor (CAR) and truncated LNGFR cell surface marker as an co-identifier for the CAR retain expression through differentiation to iCD34 cells (FIG. 18).

Figure 20:
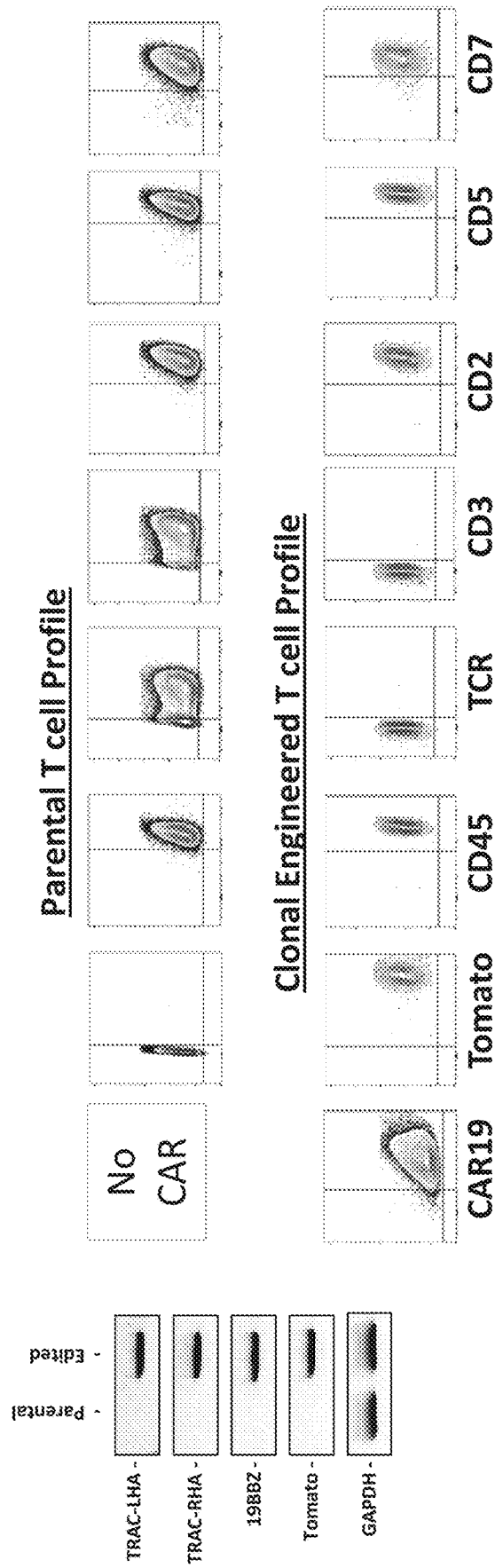
FIG. 20 shows the cell type specific expression of CAR driven by the endogenous TCR promoter, and the expression and function knock-out of TCR due to the locus specific insertion of CAR.

Also provided herein are iPSCs comprising a CAR at an endogenous TCR locus. The locus specific insertion of CAR was achieved at the level of T cell, which is subsequently reprogrammed into iPSC comprising the targeted insertion of CAR. Alternatively, the locus specific insertion of CAR can take place at the iPSC level. Because there is only one expressive TCR locus, the copy number of CAR insertion that is expressive is under control through the locus specific insertion. Further, the CAR is inserted in the constant region of TCR. The truncation of TCR constant region leads to TCR knock-out, which eliminates the HLA matching requirement in cell therapies. Moreover, the CAR expression is controlled by the TCR endogenous promoter, and thus is at the same level and in the same developmental stage as TCR. The controlled CAR expression mimicking the endogenous TCR avoids potential impact to differentiation potency during the course of iPSC differentiation. FIG. 20 shows the expression of CAR at a comparable level compared to TCR expression in the parental line, and the elimination of both expression and function of TCR in the engineered cell lines. The engineered T cell is then reprogrammed to iPSC comprising a CAR at the endogenous TCR locus.

Figure 32A:
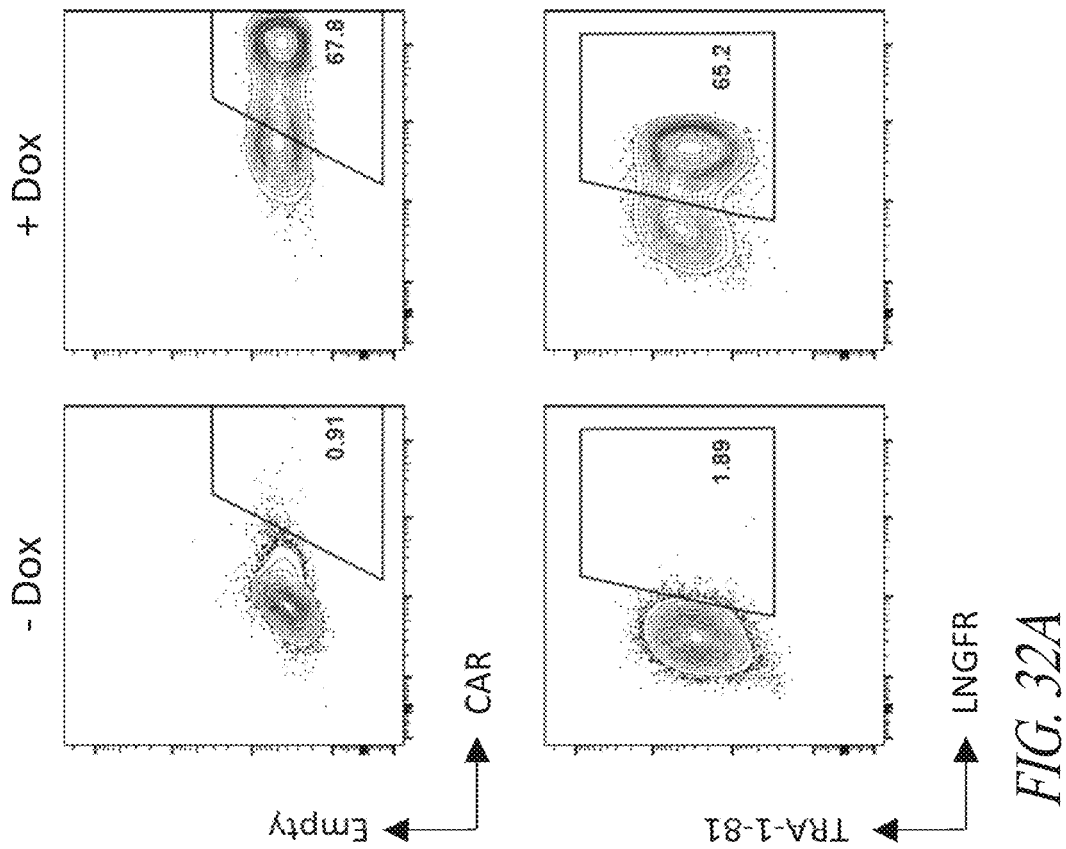
FIGS. 32A-B show Tet-inducible CAR-2A-LNGFR expression in an iPSC line that was genetically engineered with doxycycline-inducible CAR: A. inducible CD19CAR expression in TetCAR iPSC; B. iNK-mediated cytotoxicity was assessed by flow cytometry for expression of Caspase-3 on the target cells, and iNK cytotoxicity is enhanced by inducible CD19CAR expression.

Additionally we have generated an iPSC line that has doxycycline-inducible CAR expression. iPSCs were genetically engineered by transducing lentivirus containing the tetracycline response element (TRE), CD19 CAR and truncated LNGFR surface marker as a co-identifier. A separate lentivirus containing the Tet-On advanced transactivator (rtTA) was also genetically engineered into the iPSC to generate TetCAR iPSC. To determine the efficiency of the doxycycline inducible system TetCAR, iPSC were cultured with or without doxycycline and the expression of the CAR and the LNGFR marker were assessed by flow cytometry. Additionally the iPSCs were stained for Tra-181 to assess the pluripotent quality of the iPSC. FIG. 32A demonstrates that following doxycycline treatment ~65% of the iPSC are positive for expression of the CAR and LNGFR while maintaining Tra-181 expression.

Figure 32B:
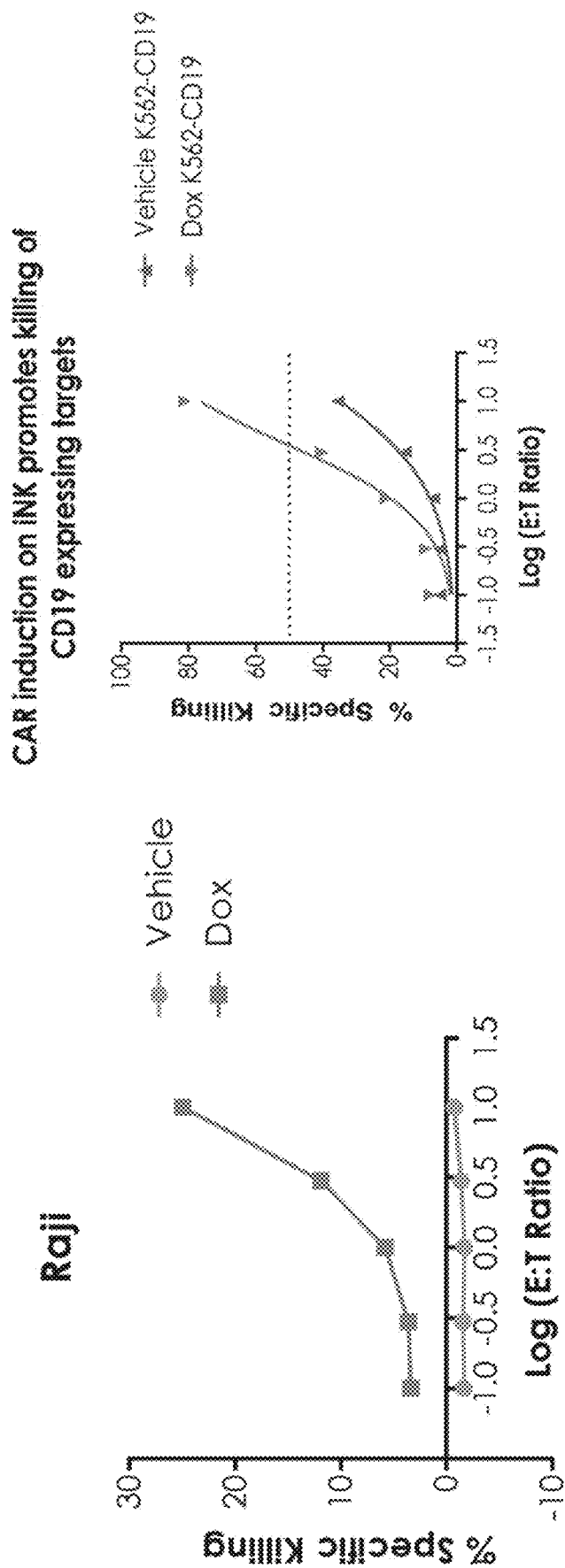

To determine if the TetCAR iPSC have enhanced functionality, the TetCAR iPSC were differentiated for 10 days to generate CD34+HE. The CD34+HE was isolated and the cells were differentiated for an additional 30 days to generate iNK cells. iNK cells were treated with doxycycline for 24 hours to induce CAR expression. Then iNK cytotoxicity was assessed by co-culture for 24 hrs with the CD19-expressing Raji B cell lymphoma line, K562 cells without expression of CD19, or K562 cells engineered to expression human CD19. iNK-mediated cytotoxicity was assessed by flow cytometry for expression of Caspase-3 on the target cells. FIG. 32B demonstrates that the TetCAR iNK cells that were treated with doxycycline exhibited increased cytotoxicity compared to non-treated controls confirming that the CAR confers enhanced function to iPSC-derived lymphoid effector cells.

Example 20—Generating iPSC Comprising a Universal Engager for Improved Targeting Specificity The cellular cytotoxicity of iPSC and derived lymphoid effector cells, including T, NK, NKT cells, macrophages, and neutrophils, can be further enhanced by coupling bi- or multi-specific engagers that are capable of redirecting the effector cells to targeted tumor cells. In general, the concept of the bi- or multi-specific engagement focus on retargeting of effector cells to specific tumor cells using bi- or multi-specific antibodies that simultaneously target a tumor-associated antigen and an activating receptor at the surface of effector cells. This bispecific binding also stimulates effector cell function, leading to effective effector cell activation and ultimately to tumor cell destruction. Because effector cell activation and tumor cell killing occur only when effector and target cells are crosslinked by the bispecific engager, it provides a safety control mechanism. Furthermore, through this retargeting engager, major histocompatibility complex (MHC)-restricted activation is bypassed.

On the side of the tumor cell, established tumor-associated antigens that can be used for bispecific engager coupling include, but not limited to, CD19, CD20 or CD30 of hematologic malignancies; EGFR (epidermal growth factor receptor), HER2/ERBB2/neu (human epidermal growth factor receptor 2), EPCAM (epithelial cell adhesion molecule), EphA2 (erythropoietin-producing hepatocellular carcinoma A2) and CEA (carcinoembrantigen) for solid tumors. Additionally, the surface bispecific antibodies/engagers may further comprise additional features, such as biotinylated protein(s) to enhance bispecific engagement and binding, surface membrane anchor domain(s) for long-term surface presentation, costimulatory domain(s) to enhance signaling upon bispecific interaction, and on and off-switch mechanism for inducible or temporal expression control of the engager.

Bispecific engager mediated effector cell retargeting involves coupling of the surface receptors on the side of effector cells. Naturally existing surface receptors include, but not limited to, CD3, FcgRIII (CD16), FcgRI (CD64), and FcaR (CD89), expressed on T cells, NKT cells, NK cells, macrophages, and neutrophils, respectively. Additionally, engineered surface triggering receptors can be introduced to express on effector cell surface for the purpose of retargeting engager coupling. The genetically engineered surface triggering receptor facilitates bi- or multi-specific antibody engagement between the effector cells and specific target cell independent of their natural receptors and cell types. Using this approach, it is feasible to generate iPSCs comprising a universal surface triggering receptor using the methods disclosed herein, and then differentiate such iPSCs into populations of various effector cell types that express the universal surface triggering receptor. Generally, an engineered universal surface triggering receptor contains an anti-epitope, and a co-stimulatory domain. The anti-epitope of the surface triggering receptor directs the coupling of any effector cell expressing the receptor with a bi- or multi-specific engager having matching epitope on one end. The targeting specificity of the engager on the other end directs the coupled effector cell to tumor cells having specific antigens for killings. For a universal surface triggering receptor, in one example, the co-stimulatory domain may comprise IL2 protein or part thereof to achieve canonical or noncanonical cellular activation and/or enhance effector cell function irrespective of the effector cell type.

Figure 31:
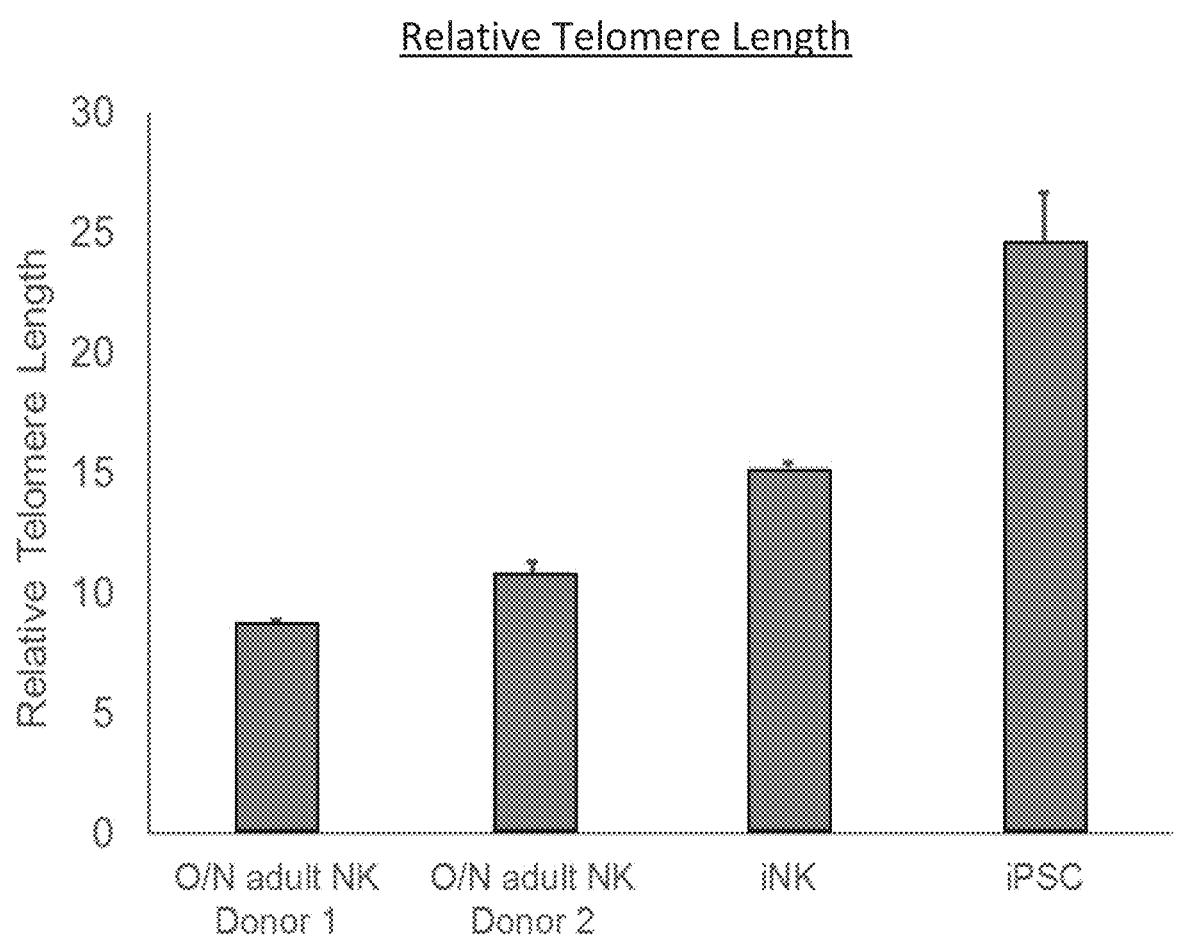
FIG. 31 shows that iNK cells have longer telomeres relative to adult NK cells

Example 21—iPSC-Derived Cellular Products have Longer Telomere Length Representative of Greater Proliferative, Survival and Persistence Potential Telomere shortening occurs with cellular aging and is associated with stem cell dysfunction and cellular senescence. An important incentive of iPSC-derived cellular therapy is that iPSC-derived cellular products would have longer telomere length representative of greater proliferative potential. To assess telomere integrity of iPSC-derived iNK cells, CD56+ cells were isolated from 27 day iNK cell cultures and adult PB-derived NK cells. After purification, each sample was combined with an equal number of reference cells, a human T cell leukemia cell line (1301 cell line) with telomeres greater than 30 kb. For each sample/reference cell mixture, DNA was denatured in the presence of hybridization solution without probe or in hybridization solution containing fluorescein-conjugated peptide nucleic acid (PNA) telomere probes (Telomere PNA kit, Dako Inc). Sample/reference cell mixtures were incubated in the dark at room temperature (RT) overnight, then washed to remove unbound probe. A DNA staining solution was added to all samples, then acquired on a BD Fortessa X-20 (BD Biosciences). Relative telomere length, compared to the 1301 cell line, was calculated as the ratio between the telomere signal of each sample and the reference cells (1301 cell line) with correction for the DNA index of G0/1 cells. FIG. 31 demonstrates that the iNK cells have increased telomere length compared to two separate adult NK cell donors but shorter telomere length compared to iPSC controls, representing greater proliferation, survival and persistence potential in the iPSC derived NK cells in comparison to donor NK cells.

Figure 35:
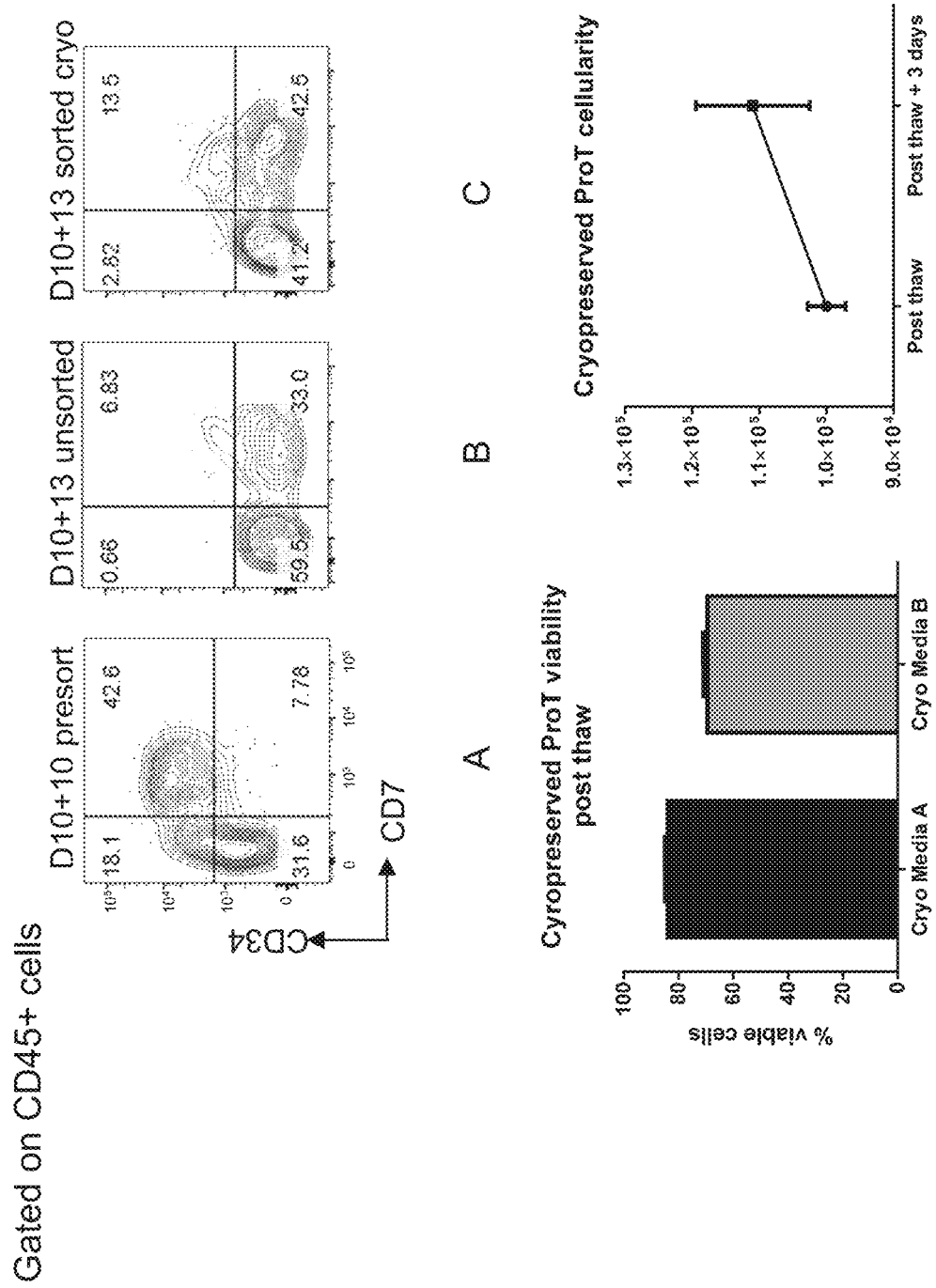
FIGS. 35A-E shows iProT conversion, cryopreservation, and the expression of CD34 and CD7 by flow cytometry in proT cells: A. prior to proT cell isolation; B. 3 days post thaw; C. day 10+13 cryopreserved; D. that were not cryopreserved; E. proT cells are viable post thaw and demonstrate increased cell proliferation when cultured in T cell differentiation media.

Example 22—Cryopreserved iPSC-Derived Cellular Products Maintain their Differentiation Potential and Genetic Imprints as Functional Cells Using iPSC-derived ProT (T progenitors) as an example, the iPSC-derived cellular products were assessed for their ability to be cryopreserved; and as to iPSC-derived progenitor cell products, their ability to maintain the potential for further differentiation into fully differentiated cells. Sorted CD34+ cells derived from iPSCs were differentiated for an additional 10 days in T cell differentiation cultures. At day 10+10 the CD45+CD34+CD7+ ProT cells were isolated by FACS and cryopreserved in two separate cryopreservation media. The ProT cells were cryopreserved and then thawed and placed back into T cell differentiation cultures. FIG. 35 depicts the expression of CD34 and CD7 by flow cytometry prior to proT cell isolation (A), and then 3 days post thaw (B and C). Day 10+13 cryopreserved ProT cells undergo further differentiation to CD34-CD45+CD7+ cells (C) in a similar manner in comparison to ProT cells that were not cryopreserved (B). FIG. 35 further demonstrates that the ProT cells are viable post thaw (D), and demonstrate increased cell proliferation when cultured in T cell differentiation media (E).

Figure 36:
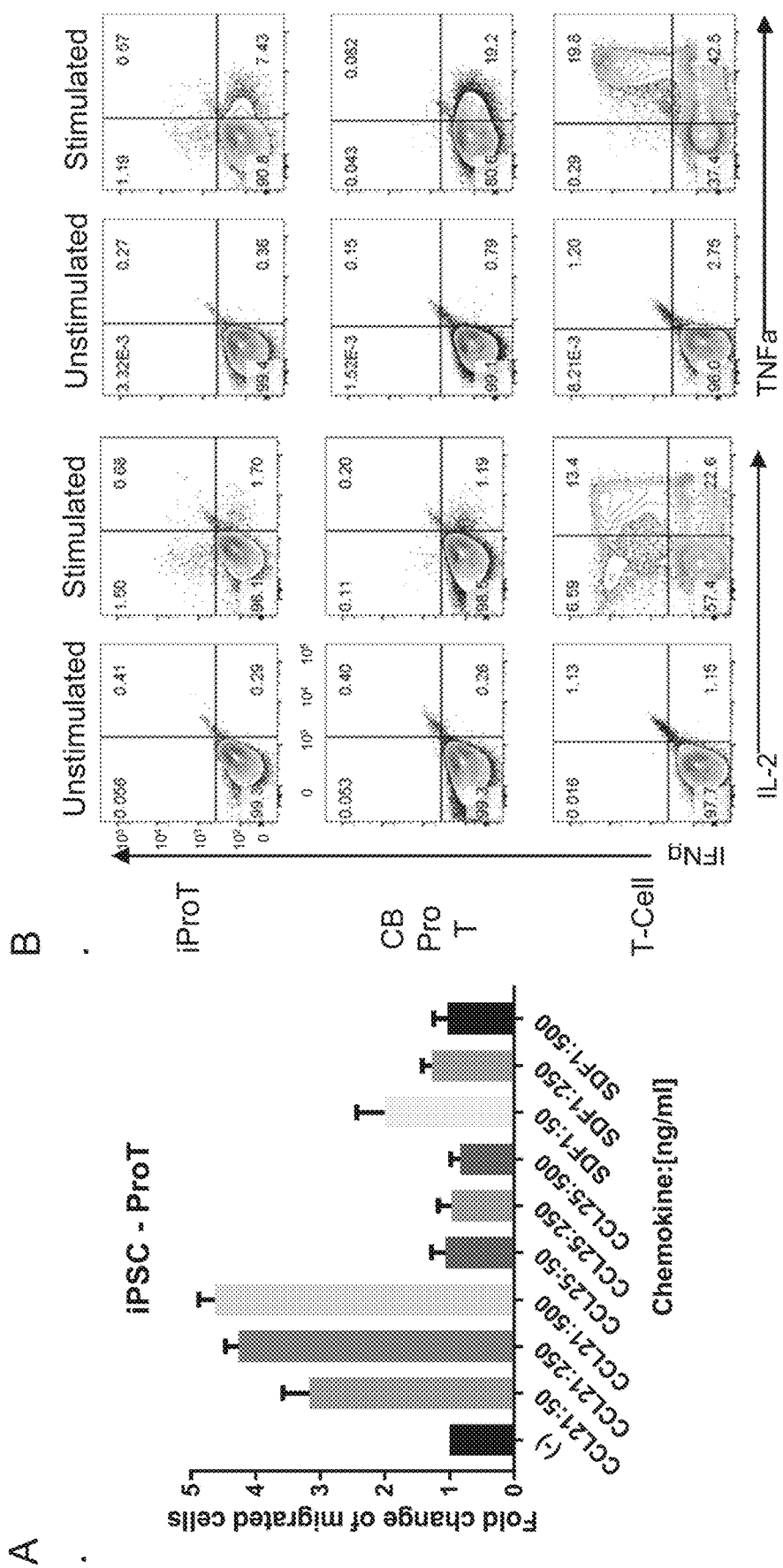
FIGS. 36A-B shows functional characterization of iPSC- and CB-derived ProT cells: cytokine release and chemotaxis: A. the iPSC-derived ProT cells can successfully migrate towards CCL21 and SDF; B. iPSC-derived proT cells can respond to produce and secrete the IFNγ and TNFα cytokines.

During T cell development, hematopoietic progenitor cells migrate from the bone marrow to the thymus to differentiate into ProT cells. To further characterize the iPSC-derived proT cells, we assessed their ability to migrate towards chemokines that are known to be expressed in the thymus to recruit developing T cells. Day 10+10 iPSC-derived ProT cells were isolated by FACS for the markers CD45+CD7+ and the cells were plated in transwell migration assays with the chemokines CCL21, CCL25 and SDF. After 4 hours the number of viable ProT cells that migrated towards the chemokines were quantified by flow cytometry with Accucount quantification particles (Spherotech, Lake Forest, Ill.). FIG. 36A demonstrates that the iPSC-derived ProT cells can successfully migrate towards CCL21 and SDF, providing further evidence for the T cell lineage commitment. Upon entry to the thymus ProT cells respond to the thymic environment to secrete the cytokines IFNγ, TNFα and IL2. To assess iPSC-derived proT cells' ability to respond to the thymic environment, iPSC-derived proT cells, CB-derived proT cells and peripheral blood T cells were either unstimulated or stimulated with PMA+ionomycin for 4 hours. After 4 hours the cells were collected and stained for IFNγ, TNFα and IL2. FIG. 36B demonstrates that iPSC-derived proT cells can respond to produce and secrete the IFNγ and TNFα cytokines.

An additional characteristic of functional proT cells is the initiation of VDJ recombination of the TCR gamma locus to generate a function T cell receptor. To determine if iPSC-derived ProT cells have initiated VDJ recombination, genomic DNA was isolated. Genomic regions (V-Jγ and V-DJβ) that are lost after TCR gene recombination were amplified by qPCR as a control for germline DNA. Another region (C32) that remains unchanged was also amplified as a control for germline DNA. Genomic DNA obtained from a fibroblast line was used to construct a standard curve. Percent of TCRγ locus or TCRβ locus remaining in germline configuration was calculated by comparing copy number of the V-Jγ or V-DJβ to copy number of Cβ2, respectively.

Figure 37:
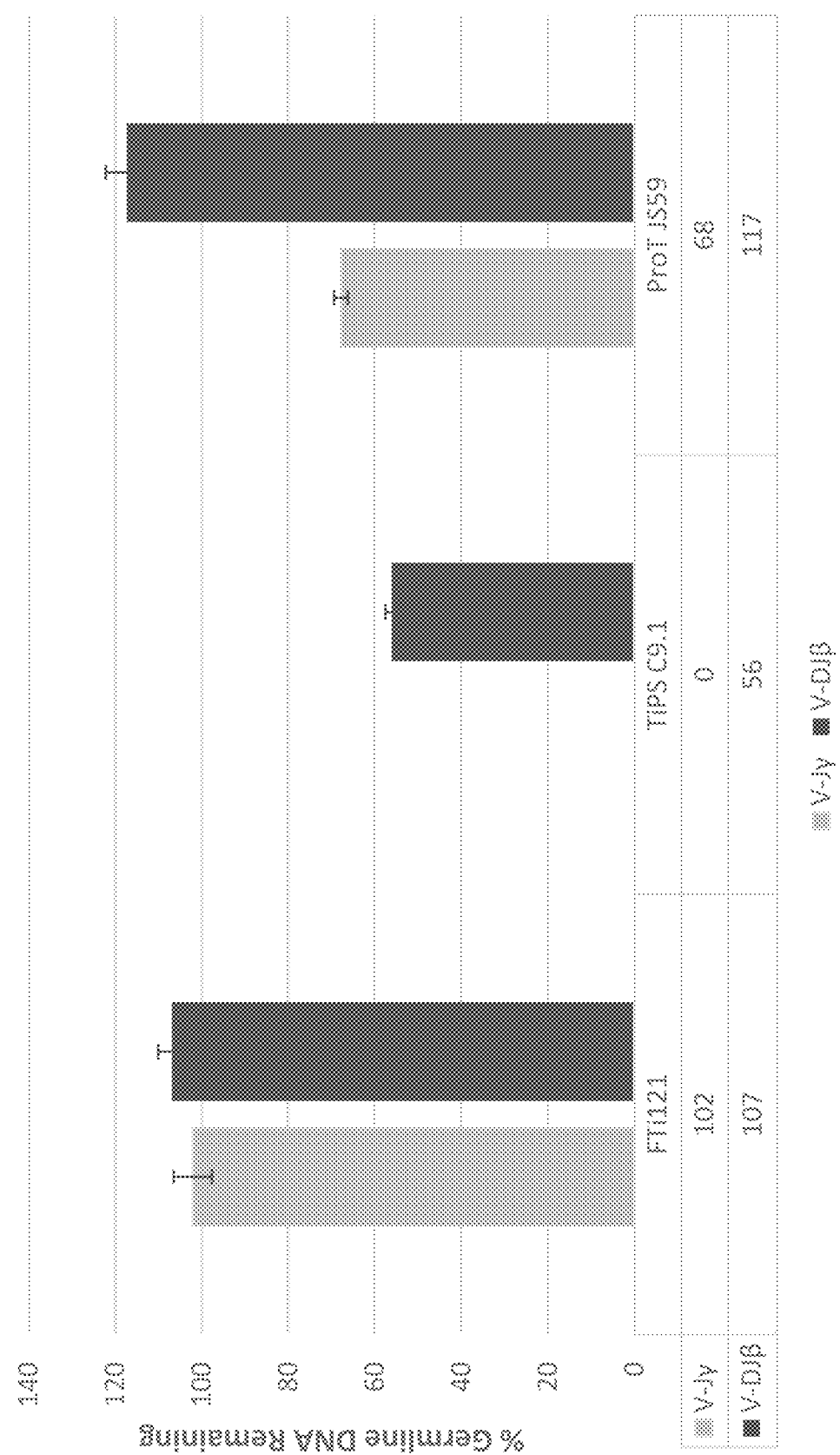
FIG. 37 shows iPSC-derived ProT cells have a decreased percentage of germline remaining from the TCR gamma locus, initiating VDJ recombination of the TCR locus.

FTi121 iPSCs and iPSC reprogrammed from T cells (TiPS C9.1) serve as negative and positive controls respectively. FIG. 37 demonstrates that FTi121 iPSC-derived ProT cells have a decreased percentage of germline remaining from the TCR gamma locus when compared to FTi1121 and TiPS C9.1 indicating that they have begun rearrangement of the TCR locus and are committed to the T cell lineage.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An induced pluripotent cell (iPSC) derived cell or a population thereof, wherein (i) the iPSC-derived cell is a hematopoietic lineage cell differentiated from an iPSC; (ii) the iPSC-derived cell comprises a polynucleotide encoding at least one chimeric antigen receptor (CAR) introduced into a constant region of a T cell receptor (TCR) locus, wherein the at least one CAR is expressed in the iPSC-derived cell; (iii) an endogenous TCR gene of the iPSC-derived cell is knocked out; (iv) the iPSC-derived cell comprises introduced or increased expression of CD16; and (v) the iPSC-derived cell further comprises:
(a) a deletion or reduced expression of at least one of B2M and/or CIITA genes; or
(b) introduced or increased expression of CD3.

2. The iPSC-derived cell or population thereof of claim 1, wherein the polynucleotide encoding the at least one CAR is under control of an endogenous TCR promoter of the TCR locus.

3. The iPSC-derived cell or population thereof of claim 1, wherein the given iPSC is obtained by:
(A) reprogramming a T cell into an iPSC into an iPSC and inserting one or more exogenous polynucleotides encoding the at least one CAR into the constant region of the TCR locus of the iPSC; or
(B) reprogramming a T cell comprising one or more exogenous polynucleotides encoding the at least one CAR introduced into a constant region of the TCR locus of the T cell into an iPSC.

4. The iPSC-derived cell or population thereof of claim 1, wherein the given iPSC is obtained by:
(A) reprogramming a T cell into an iPSC and inserting one or more exogenous polynucleotides encoding the at least one CAR into the constant region of the TCR locus of the iPSC; or
(B) reprogramming a T cell comprising one or more exogenous polynucleotides encoding the at least one CAR introduced into a constant region of the TCR locus of the T cell into an iPSC.

5. The iPSC-derived cell or population thereof of claim 4, wherein the one or more exogenous polynucleotides present in the nucleic acid encoding the constant region of the TCR locus is introduced into the iPSC of (A), or said T cell of (B), using a CRISPR endonuclease.

6. The iPSC-derived cell or population thereof of claim 1, wherein the iPSC-derived cell comprises (i) a deletion or reduced expression of at least one of TAP1, TAP2, Tapasin, NLRC5, PD1, LAG3, TIM3, RFXANK, RFX5, and/or RFXAP; and/or (ii) introduced or increased expression of at least one of HLA-E, HLA-G, 41BBL, CD4, CD8, CD47, CD113, CD131, CD137, CD80, PDL1, $A_{2A}R$, Fc receptor, an engager, and a surface triggering receptor for coupling with bi-, multi-specific, or universal engagers, as compared to a corresponding unmodified iPSC-derived cell.

7. The iPSC-derived cell or population thereof of claim 1, wherein the CD16 is a high affinity non-cleavable CD16 (hnCD16).

8. The iPSC-derived cell or population thereof of claim 1, wherein the iPSC-derived cell comprises (i) a deletion or reduced expression of at least one of B2M and CIITA; and (ii) optionally comprises introduced or increased expression of HLA-G, as compared to a corresponding unmodified iPSC-derived cell.

9. The iPSC-derived cell or population thereof of claim 1, wherein the iPSC-derived cell comprises introduced or increased expression of CD3.

10. The iPSC-derived cell or population thereof of claim 9, wherein the polynucleotide encoding the at least one CAR is under control of an endogenous TCR promoter of the TCR locus.

11. The iPSC-derived cell or population thereof of claim 1, wherein the hematopoietic lineage cell differentiated from the given iPSC comprises a T cell or a T cell progenitor, and wherein the T cell or T cell progenitor has at least one of the following characteristics:
(i) does not require HLA matching in cell therapies;
(ii) comprises a longer telomere length than a cell of the same type that is not derived from an iPSC;
(iii) exhibits a greater proliferative, survival and/or persistence potential, in comparison to a cell of the same type that is not derived from an iPSC.

12. A therapeutic composition comprising the iPSC derived cell or population thereof of claim 1.

13. The therapeutic composition of claim 12, wherein the iPSC derived hematopoietic lineage cell comprises a T cell comprising the at least one CAR at a T cell receptor alpha constant region (TRAC) locus, a TCR knockout, and a hnCD16.

14. A method of obtaining the iPSC-derived cell or a population thereof of claim 1, comprising steps of (I) or (II):
(I):
(i) reprogramming a T cell to an induced pluripotent stem cell (iPSC); and
(ii) genomically editing the iPSC to simultaneously, or sequentially,
(a) knock out a T cell receptor (TCR) by disrupting a polynucleic acid encoding a constant region of a TCR locus; and
(b) knock in a polynucleotide encoding at least one chimeric antigen receptor (CAR) at the polynucleic acid encoding the constant region of the TCR locus; and the polynucleotide encoding at least one CAR is expressed under control of an endogenous TCR promoter of the TCR locus,
thereby obtaining a genomically edited iPSC; and
(iii) directing differentiation of the genomically edited iPSC of step (I)(ii) to obtain the iPSC-derived cell or a population of claim 1;

or, (II):
  (i) genomically editing a T cell, to simultaneously, or sequentially,
    (a) knock out a T cell receptor (TCR) by disrupting a polynucleic acid encoding a constant region of a TCR locus; and
    (b) knock in a polynucleotide encoding at least one chimeric antigen receptor (CAR) at the polynucleic acid encoding the constant region of the TCR locus; and the polynucleotide encoding at least one CAR is expressed under control of an endogenous TCR promoter of the TCR locus, thereby obtaining a genomically edited T cell;
  (ii) reprogramming the genomically edited T cell of step (II)(i) to an induced pluripotent stem cell (iPSC), wherein the iPSC comprises the same genomic edit as the T cell of step (II)(i); and
  (iii) directing differentiation of the genomically edited iPSC of step (II)(ii) to obtain the iPSC-derived cell or a population of claim 1.

15. The method of claim 13, wherein the genomically editing of (I)(ii) or (II)(i) further comprises deletion or reduced expression of at least one of B2M, TAP1, TAP2, Tapasin, NLRC5, PD1, LAG3, TIM3, RFXANK, CIITA, RFX5, and/or RFXAP as compared to a corresponding unmodified iPSC-derived cell; and/or (ii) introduced or increased expression of at least one of HLA-E, HLA-G, 41 BBL, CD4, CD8, CD47, CD113, CD131, CD137, CD80, PDL1, $A_{2A}R$, Fc receptor, an engager, and a surface triggering receptor for coupling with bi-, multi-specific, or universal engagers as compared to a corresponding unmodified iPSC-derived cell.

16. The method of claim 14, wherein the genomically editing of (I)(ii) or (II)(i) further comprises deletion or reduced expression of at least one of B2M, TAP1, TAP2, Tapasin, NLRC5, PD1, LAG3, TIM3, RFXANK, CIITA, RFX5, and/or RFXAP as compared to a corresponding unmodified iPSC-derived cell; and/or (ii) introduced or increased expression of at least one of HLA-E, HLA-G, 41BBL, CD4, CD8, CD47, CD113, CD131, CD137, CD80, PDL1, $A_{2A}R$, Fc receptor, an engager, and a surface triggering receptor for coupling with bi, multi- specific or universal engagers, as compared to a corresponding unmodified iPSC-derived cell.

17. The method of claim 14, wherein the genomically editing of (I)(ii) or (II)(i) further comprises introducing expression of CD16, wherein the CD16 is a high affinity non-cleavable CD16 (hnCD16).

18. The method of claim 14, wherein the genomically editing of (I)(ii) or (II)(i) further comprises introducing or increasing expression of CD3.

* * * * *

UNITED STATES PATENT AND TRADEMARK OFFICE
CERTIFICATE OF CORRECTION

PATENT NO. : 11,072,781 B2  
APPLICATION NO. : 16/379668  
DATED : July 27, 2021  
INVENTOR(S) : Bahram Valamehr et al.

Page 1 of 1

It is certified that error appears in the above-identified patent and that said Letters Patent is hereby corrected as shown below:

In the Claims

Column 99, Line 32, in the first line of Claim 3, delete text beginning "3. The iPSC-derived cell" to and ending "into an iPSC." in the last line of Claim 3 in Column 99, Line 41, and insert the following claim:
--3. The iPSC-derived cell or population thereof of claim 1, wherein the at least one CAR comprises a CD19 CAR.--

Column 100, Line 25, in the first line of Claim 10, delete text beginning "10. The iPSC-derived cell" to and ending "the TCR locus." in the last line of Claim 10 in Column 10, Line 28, and insert the following claim:
--10. The iPSC-derived cell or population thereof of claim 1, wherein the hematopoietic lineage cell differentiated from the given iPSC comprises a definitive hemogenic endothelium cell, a T cell progenitor, a T cell, an NK cell progenitor, an NK cell, or a B cell, wherein the hematopoietic lineage cell differentiated from the given iPSC comprises a longer telomere length than a cell of the same type that is not derived from an iPSC.--

Column 101, Line 21, in the first line of Claim 15, delete text beginning "15. The method of claim 13" to and ending "iPSC-derived cell." in the last line of Claim 15 in Column 102, Line 6, and insert the following claim:
--15. The method of claim 14, wherein the at least one CAR comprises a CD19 CAR.--

Column 101, Line 16, in Claim 16, delete "coupling with bi," and insert --coupling with bi-,--

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 8

<210> SEQ ID NO 1
<211> LENGTH: 1734
<212> TYPE: DNA
<213> ORGANISM: Artificial Sequence
<220> FEATURE:
<223> OTHER INFORMATION: Expression vector CAG promoter

<400> SEQUENCE: 1
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtcgagg tgagccccac gttctgcttc actctcccca     420 tctcccccc ctccccaccc ccaatttgt atttatttat tttttaatta ttttgtgcag      480 cgatggggc gggggggggg gggggcgcg cgccaggcgg ggcggggcgg ggcgaggggc      540
ggggcggggc gaggcggaga ggtgcggcgg cagccaatca gagcggcgcg ctccgaaagt     600 ttcctttat ggcgaggcgg cggcggcggc ggccctataa aaagcgaagc gcgcggcggg      660
cggggagtcg ctgcgacgct gccttcgccc cgtgccccgc tccgccgccg cctcgcgccg     720 cccgcccgg ctctgactga ccgcgttact cccacaggtg agcgggcggg acggcccttc      780 tcctccggc tgtaattagc gcttggttta atgacggctt gtttcttttc tgtggctgcg      840
tgaaagcctt gaggggctcc gggagggccc tttgtgcggg ggagcggct cggggggtgc      900 gtgcgtgtgt gtgtgcgtgg ggagcgccgc gtgcggctcc gcgctgcccg gcggctgtga     960
gcgctgcggg cgcggcgcgg ggctttgtgc gctccgcagt gtgcgcgagg ggagcgcggc    1020 cggggggcggt gccccgcggt gcggggggg ctgcgagggg aacaaaggct gcgtgcgggg    1080
tgtgtgcgtg gggggtgag caggggtgt gggcgcgtcg gtcgggctgc aacccccccct    1140 gcaccccct ccccgagttg ctgagcacgg cccggcttcg ggtgcggggc tccgtacggg    1200
```

```
gcgtggcgcg gggctcgccg tgccgggcgg ggggtggcgg caggtggggg tgccgggcgg   1260
ggcggggccg cctcgggccg gggagggctc ggggagggg cgcggcggcc cccggagcgc    1320
cggcggctgt cgaggcgcgg cgagccgcag ccattgcctt ttatggtaat cgtgcgagag    1380
ggcgcaggga cttcctttgt cccaaatctg tgcggagccg aaatctggga ggcgccgccg    1440
caccccctct agcgggcgcg gggcgaagcg gtgcggcgcc ggcaggaagg aaatgggcgg    1500
ggagggcctt cgtgcgtcgc cgcgccgccg tccccttctc cctctccagc ctcggggctg    1560
tccgcggggg gacggctgcc ttcgggggg acggggcagg gcggggttcg gcttctggcg     1620
tgtgaccggc ggctctagag cctctgctaa ccatgttcat gccttcttct ttttcctaca    1680
gctcctgggc aacgtgctgg ttattgtgct gtctcatcat tttggcaaag aatt          1734
```

<210> SEQ ID NO 2
<211> LENGTH: 330
<212> TYPE: PRT
<213> ORGANISM: Artificial Sequence
<220> FEATURE:
<223> OTHER INFORMATION: AAVS1 ZFN-L protein sequence

<400> SEQUENCE: 2

```
Met Ala Pro Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Tyr Asn Trp His Leu Gln Arg His Ile Arg Thr His Thr Gly Glu
        35                  40                  45

Lys Pro Phe Ala Cys Asp Ile Cys Gly Arg Lys Phe Ala Arg Ser Asp
    50                  55                  60

His Leu Thr Thr His Thr Lys Ile His Thr Gly Ser Gln Lys Pro Phe
65                  70                  75                  80

Gln Cys Arg Ile Cys Met Arg Asn Phe Ser His Asn Tyr Ala Arg Asp
                85                  90                  95

Cys His Ile Arg Thr His Thr Gly Glu Lys Pro Phe Ala Cys Asp Ile
            100                 105                 110

Cys Gly Arg Lys Phe Ala Gln Asn Ser Thr Arg Ile Gly His Thr Lys
        115                 120                 125

Ile His Leu Arg Gly Ser Gln Leu Val Lys Ser Glu Leu Glu Glu Lys
    130                 135                 140

Lys Ser Glu Leu Arg His Lys Leu Lys Tyr Val Pro His Glu Tyr Ile
145                 150                 155                 160

Glu Leu Ile Glu Ile Ala Arg Asn Ser Thr Gln Asp Arg Ile Leu Glu
                165                 170                 175

Met Lys Val Met Glu Phe Phe Met Lys Val Tyr Gly Tyr Arg Gly Lys
            180                 185                 190

His Leu Gly Gly Ser Arg Lys Pro Asp Gly Ala Ile Tyr Thr Val Gly
        195                 200                 205

Ser Pro Ile Asp Tyr Gly Val Ile Val Asp Thr Lys Ala Tyr Ser Gly
    210                 215                 220

Gly Tyr Asn Leu Pro Ile Gly Gln Ala Asp Glu Met Glu Arg Tyr Val
225                 230                 235                 240

Glu Glu Asn Gln Thr Arg Asn Lys His Leu Asn Pro Asn Glu Trp Trp
                245                 250                 255

Lys Val Tyr Pro Ser Ser Val Thr Glu Phe Lys Phe Leu Phe Val Ser
            260                 265                 270
```

```
Gly His Phe Lys Gly Asn Tyr Lys Ala Gln Leu Thr Arg Leu Asn His
            275                 280                 285

Ile Thr Asn Cys Asn Gly Ala Val Leu Ser Val Glu Glu Leu Leu Ile
    290                 295                 300

Gly Gly Glu Met Ile Lys Ala Gly Thr Leu Thr Leu Glu Glu Val Arg
305                 310                 315                 320

Arg Lys Phe Asn Asn Gly Glu Ile Asn Phe
                325                 330

<210> SEQ ID NO 3
<211> LENGTH: 330
<212> TYPE: PRT
<213> ORGANISM: Artificial Sequence
<220> FEATURE:
<223> OTHER INFORMATION: AAVS1 ZFN-R protein sequence

<400> SEQUENCE: 3

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Gln Ser Ser Asn Leu Ala Arg His Ile Arg Thr His Thr Gly Glu
        35                  40                  45

Lys Pro Phe Ala Cys Asp Ile Cys Gly Arg Lys Phe Ala Arg Thr Asp
    50                  55                  60

Tyr Leu Val Asp His Thr Lys Ile His Thr Gly Ser Gln Lys Pro Phe
65                  70                  75                  80

Gln Cys Arg Ile Cys Met Arg Asn Phe Ser Tyr Asn Thr His Leu Thr
                85                  90                  95

Arg His Ile Arg Thr His Thr Gly Glu Lys Pro Phe Ala Cys Asp Ile
            100                 105                 110

Cys Gly Arg Lys Phe Ala Gln Gly Tyr Asn Leu Ala Gly His Thr Lys
        115                 120                 125

Ile His Leu Arg Gly Ser Gln Leu Val Lys Ser Glu Leu Glu Glu Lys
    130                 135                 140

Lys Ser Glu Leu Arg His Lys Leu Lys Tyr Val Pro His Glu Tyr Ile
145                 150                 155                 160

Glu Leu Ile Glu Ile Ala Arg Asn Ser Thr Gln Asp Arg Ile Leu Glu
                165                 170                 175

Met Lys Val Met Glu Phe Phe Met Lys Val Tyr Gly Tyr Arg Gly Lys
            180                 185                 190

His Leu Gly Gly Ser Arg Lys Pro Asp Gly Ala Ile Tyr Thr Val Gly
        195                 200                 205

Ser Pro Ile Asp Tyr Gly Val Ile Val Asp Thr Lys Ala Tyr Ser Gly
    210                 215                 220

Gly Tyr Asn Leu Pro Ile Gly Gln Ala Asp Glu Met Gln Arg Tyr Val
225                 230                 235                 240

Lys Glu Asn Gln Thr Arg Asn Lys His Ile Asn Pro Asn Glu Trp Trp
                245                 250                 255

Lys Val Tyr Pro Ser Ser Val Thr Glu Phe Lys Phe Leu Phe Val Ser
            260                 265                 270

Gly His Phe Lys Gly Asn Tyr Lys Ala Gln Leu Thr Arg Leu Asn His
        275                 280                 285

Lys Thr Asn Cys Asn Gly Ala Val Leu Ser Val Glu Glu Leu Leu Ile
    290                 295                 300
```

Gly Gly Glu Met Ile Lys Ala Gly Thr Leu Thr Leu Glu Glu Val Arg
305                 310                 315                 320

Arg Lys Phe Asn Asn Gly Glu Ile Asn Phe
                325                 330

<210> SEQ ID NO 4
<211> LENGTH: 993
<212> TYPE: DNA
<213> ORGANISM: Artificial Sequence
<220> FEATURE:
<223> OTHER INFORMATION: AAVS1 ZFN-L codon optimized DNA sequence

<400> SEQUENCE: 4

```
atggctccta agaaaaagag aaaagtgggg attcatggcg tgcctgccgc tatggccgag      60
agacccttcc agtgccgcat ctgtatgagg aactttttctt ataattggca cctccagcgg    120
catatcagaa ctcacaccgg cgaaaagccc tttgcctgcg catttgtgg gaggaaattc      180
gctcgctccg atcatctgac cacacacacc aagatcccata caggctctca gaaaccttt    240
cagtgccgaa tttgtatgcg gaacttctct cacaattacg ctagagactg ccacatcagg   300
acacatactg gagagaagcc atttgcatgc gatatttgtg gccggaaatt cgcccagaac    360
agtactagaa tcgggcacac caagattcat ctgcggggat ctcagctggt gaaaagtgaa    420
ctggaggaaa agaaaagtga gctgagacac aagctgaaat acgtccccca tgagtatatc    480
gaactgatcg agattgcacg caattcaacc caggacagaa tcctggagat gaaagtgatg    540
gagttctttta tgaaagtcta cggctatagg gggaagcacc tgggcgggtc acgcaaacca    600
gatgggggcca tctacaccgt gggaagcccc atcgactatg gcgtgattgt cgatacaaag    660
gcttacagcg gaggctataa cctgcctatt ggcaggcag acgagatgga acgatacgtg      720
gaggaaaacc agactcgcaa taagcacctg aaccccaatg aatggtggaa agtgtatcct    780
agctccgtca cagagttcaa gtttctgttc gtgagcggac acttcaaggg caactacaaa   840
gcccagctga cacgcctgaa tcatatcact aactgtaatg cgctgtgct gtccgtcgag    900
gaactgctga tcgggggaga gatgattaag gccggcactc tgacactgga ggaggtccgc    960
cgaaaattca acaacgggga aatcaacttc taa                                 993
```

<210> SEQ ID NO 5
<211> LENGTH: 993
<212> TYPE: DNA
<213> ORGANISM: Artificial Sequence
<220> FEATURE:
<223> OTHER INFORMATION: AAVS1 ZFN-R codon optimized DNA sequence

<400> SEQUENCE: 5

```
atggctccta aaagaaacg aaaagtcggc attcacggcg tccctgctgc tatggctgag      60
agacccttcc agtgtcgcat ttgtatgagg aactttttctc agagctccaa tctggctcgg    120
cacatcagaa cccatacagg cgaaaagccc tttgcatgcg catttgtgg gcgaaaattc      180
gcccggaccg actatctggt ggatcacacc aagatcccata cagggagtca gaaaccttt    240
cagtgcagaa tttgtatgag gaacttctca tacaatacac acctgactag gcatatccgc    300
actcacaccg gagagaagcc atttgcctgc gatatttgtg gccgaaaatt cgcccagggg    360
tataacctgg ctggacatac taagatccac ctgcgcggct cacagctggt gaaaagcgaa    420
ctggaggaaa agaaaagcga gctgagacat aagctgaaat acgtccccca cgagtatatc    480
gaactgatcg agattgcacg caattccaca caggacagaa tcctggagat gaaagtgatg    540
gagttctttta tgaaagtcta cggctatcgg gggaagcatc tgggcgggtc cagaaaacca    600
```

```
gatggcgcca tctacacagt ggggtctccc atcgactatg gagtgattgt cgatactaag    660
gcttacagcg gaggctataa cctgcctatc ggccaggcag acgaaatgca gaggtacgtg    720
aaggagaacc agacccgcaa caagcacatt aaccccaatg aatggtggaa ggtgtatcct    780
tctagtgtca cagagttcaa atttctgttc gtgtctggac atttcaaggg caactacaaa    840
gcccagctga ctcggctgaa tcacaagacc aactgcaatg cgctgtgct gagtgtcgag     900 gaactgctga tcgggggaga gatgattaag gccgggaccc tgactctgga ggaagtgagg    960
aggaagttca acaacggcga gatcaatttc taa                                 993
```

```
<210> SEQ ID NO 6
<211> LENGTH: 20
<212> TYPE: DNA
<213> ORGANISM: Artificial Sequence
<220> FEATURE:
<223> OTHER INFORMATION: corresponding coding DNA of Rosa26 gRNA for
      CRISPR

<400> SEQUENCE: 6
agtcgcttct cgattatggg                                                 20

<210> SEQ ID NO 7
<211> LENGTH: 407
<212> TYPE: PRT
<213> ORGANISM: Artificial Sequence
<220> FEATURE:
<223> OTHER INFORMATION: iCaspase9 protein

<400> SEQUENCE: 7
```

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Val Asp
            100                 105                 110

Gly Phe Gly Asp Val Gly Ala Leu Glu Ser Leu Arg Gly Asn Ala Asp
        115                 120                 125

Leu Ala Tyr Ile Leu Ser Met Glu Pro Cys Gly His Cys Leu Ile Ile
    130                 135                 140

Asn Asn Val Asn Phe Cys Arg Glu Ser Gly Leu Arg Thr Arg Thr Gly
145                 150                 155                 160

Ser Asn Ile Asp Cys Glu Lys Leu Arg Arg Arg Phe Ser Ser Leu His
                165                 170                 175

Phe Met Val Glu Val Lys Gly Asp Leu Thr Ala Lys Lys Met Val Leu
            180                 185                 190

Ala Leu Leu Glu Leu Ala Gln Gln Asp His Gly Ala Leu Asp Cys Cys
        195                 200                 205

Val Val Val Ile Leu Ser His Gly Cys Gln Ala Ser His Leu Gln Phe
    210                 215                 220

```
Pro Gly Ala Val Tyr Gly Thr Asp Gly Cys Pro Val Ser Val Glu Lys
225                 230                 235                 240

Ile Val Asn Ile Phe Asn Gly Thr Ser Cys Pro Ser Leu Gly Gly Lys
                245                 250                 255

Pro Lys Leu Phe Phe Ile Gln Ala Cys Gly Gly Glu Gln Lys Asp His
            260                 265                 270

Gly Phe Glu Val Ala Ser Thr Ser Pro Glu Asp Glu Ser Pro Gly Ser
        275                 280                 285

Asn Pro Glu Pro Asp Ala Thr Pro Phe Gln Glu Gly Leu Arg Thr Phe
    290                 295                 300

Asp Gln Leu Asp Ala Ile Ser Ser Leu Pro Thr Pro Ser Asp Ile Phe
305                 310                 315                 320

Val Ser Tyr Ser Thr Phe Pro Gly Phe Val Ser Trp Arg Asp Pro Lys
                325                 330                 335

Ser Gly Ser Trp Tyr Val Glu Thr Leu Asp Asp Ile Phe Glu Gln Trp
            340                 345                 350

Ala His Ser Glu Asp Leu Gln Ser Leu Leu Leu Arg Val Ala Asn Ala
        355                 360                 365

Val Ser Val Lys Gly Ile Tyr Lys Gln Met Pro Gly Cys Phe Asn Phe
    370                 375                 380

Leu Arg Lys Lys Leu Phe Phe Lys Thr Ser Val Asp Tyr Pro Tyr Asp
385                 390                 395                 400

Val Pro Asp Tyr Ala Leu Asp
                405

<210> SEQ ID NO 8
<211> LENGTH: 1251
<212> TYPE: DNA
<213> ORGANISM: Artificial Sequence
<220> FEATURE:
<223> OTHER INFORMATION: codon optimized DNA sequence for iCaspase9

<400> SEQUENCE: 8
agcttgccac catgctggag ggagtgcagg tcgagactat tccccccgga gacggcagaa      60
catttcctaa gagagggcag acttgcgtgg tccattacac cgggatgctg gaagacggaa     120
agaaagtgga cagctcccgc gatcgaaaca agcccttcaa gttcatgctg ggcaagcagg     180
aagtgatcag gggatgggag gaaggcgtcg cacagatgtc agtggggcag cgcgccaaac     240
tgacaatttc cccagactac gcctacggcg caactggaca ccctggaatc attccccctc     300
atgccacact ggtcttcgat gtggagctgc tgaagctgga atccgaagga ggatctggag     360
tcgacggatt tggagatgtg ggagctctgg aatctctgcg cggcaatgct gatctggcat     420
acatcctgag tatggagcct tgcggccact gtctgatcat taacaatgtg aacttctgcc     480
gggagtctgg cctgcggacc agaacaggga gtaatattga ctgtgaaaag ctgcggagaa     540
ggttctctag tctgcacttt atggtcgagg tgaaaggaga tctgaccgct aagaaaatgg     600
tgctggccct gctggaactg gctcagcagg accatggcgc actggattgc tgcgtggtcg     660
tgatcctgag ccacggctgc caggcttccc acctccagtt cccaggggca gtctatggca     720
ctgacggtgt cccgtcagc gtggagaaga tcgtgaacat cttcaacggg acctcttgcc     780
caagtctggg cggaagccc aaactgttct ttatccaggc ctgtggaggc gagcagaaag     840
atcacggctt tgaagtggct tccacatctc ccgaggacga atcacctggg agcaacccag     900
agcccgatgc aactcctttc aggaaggac tgagaacctt tgaccagctg gatgccatct     960
```

```
caagcctgcc tacccatcc gacattttcg tcagttactc aacattccct ggattcgtga    1020
gctggcggga ccccaagagc ggctcctggt acgtggagac tctggacgat atctttgagc    1080
agtgggccca tagtgaagac ctccagagcc tgctgctgcg agtggccaac gctgtctccg    1140
tgaaggggat ctacaaacag atgccaggat gcttcaattt tctgaggaaa aaactgttct    1200
tcaaaacttc cgtcgattac ccctacgatg tccccgatta tgccctggat g             1251
```